United States Patent
Tabata et al.

(10) Patent No.: US 11,557,743 B2
(45) Date of Patent: Jan. 17, 2023

(54) LUMINESCENT FILM, ORGANIC ELECTROLUMINESCENT DEVICE, AND METHOD FOR MANUFACTURING ORGANIC ELECTROLUMINESCENT DEVICE

(71) Applicant: Konica Minolta, Inc., Tokyo (JP)

(72) Inventors: Kenichi Tabata, Inagi (JP); Satoru Inoue, Kunitachi (JP); Yasuo Miyata, Yokohama (JP)

(73) Assignee: KONICA MINOLTA, INC., Tokyo (JP)

( * ) Notice: Subject to any disclaimer, the term of this patent is extended or adjusted under 35 U.S.C. 154(b) by 416 days.

(21) Appl. No.: 16/769,533

(22) PCT Filed: Dec. 13, 2018

(86) PCT No.: PCT/JP2018/045795
§ 371 (c)(1),
(2) Date: Jun. 3, 2020

(87) PCT Pub. No.: WO2019/142555
PCT Pub. Date: Jul. 25, 2019

(65) Prior Publication Data
US 2020/0388781 A1    Dec. 10, 2020

(30) Foreign Application Priority Data

Jan. 17, 2018 (JP) .............................. JP2018-005490
Feb. 13, 2018 (JP) .............................. JP2018-022674

(51) Int. Cl.
*H01L 51/50* (2006.01)
*C09K 11/06* (2006.01)
(Continued)

(52) U.S. Cl.
CPC .......... *H01L 51/5028* (2013.01); *C09K 11/06* (2013.01); *H01L 51/0055* (2013.01);
(Continued)

(58) Field of Classification Search
None
See application file for complete search history.

(56) References Cited

FOREIGN PATENT DOCUMENTS

JP    2005-310766 A    11/2005
JP    2010-530640 A    9/2010
(Continued)

OTHER PUBLICATIONS

D'Andrade et al., High-efficiency yellow double-doped organic light-emitting devices based on phosphor-sensitized fluorescence; Appl. Phys. Lett. 79, 1045-1047 (2001) (Year: 2001).*
(Continued)

*Primary Examiner* — Gregory D Clark
(74) *Attorney, Agent, or Firm* — Lucas & Mercanti, LLP

(57) ABSTRACT

The present invention provides a luminescent film containing at least a phosphorescent compound and a fluorescent compound, wherein the convolution integral value J of the emission spectrum of the phosphorescent compound and the absorption spectrum of the fluorescent compound satisfies equation (1), the light emission from the fluorescent compound accounts for at least 90% of the emission spectrum of the luminescent film, and the absolute photoluminescence quantum efficiency (PLQE) of the luminescent film is represented by equation (2). Equation (1): $J \geq 1.5 \times 10^{14}$, Equation (2): PLQE (a film composed of a phosphorescent compound and a host compound)$\times 0.9 \leq$ PLQE (a film containing a phosphorescent compound and a fluorescent compound) [The lowest triplet excited state of the host compound is higher than the lowest triplet excited state of the
(Continued)

phosphorescent compound, and does not suppress the luminescent property of the phosphorescent compound.]

14 Claims, 4 Drawing Sheets

(51) Int. Cl.
      *H01L 51/00*       (2006.01)
      *H01L 51/52*       (2006.01)
(52) U.S. Cl.
      CPC ...... *H01L 51/0056* (2013.01); *H01L 51/0058* (2013.01); *H01L 51/0085* (2013.01); *H01L 51/0094* (2013.01); *H01L 51/5016* (2013.01); *H01L 51/5253* (2013.01); *C09K 2211/1007* (2013.01); *C09K 2211/1011* (2013.01); *C09K 2211/1029* (2013.01); *C09K 2211/1033* (2013.01); *C09K 2211/1044* (2013.01); *C09K 2211/1059* (2013.01); *C09K 2211/185* (2013.01); *H01L 2251/5376* (2013.01)

(56) References Cited

FOREIGN PATENT DOCUMENTS

| JP | 4571359 B2 | 10/2010 |
|---|---|---|
| JP | 2010-270103 A | 12/2010 |
| JP | 2013-139426 A | 7/2013 |
| JP | 5905916 B2 | 4/2016 |
| JP | 2016-153173 A | 8/2016 |
| JP | 2016-225497 A | 12/2016 |
| JP | 2017-502516 A | 1/2017 |
| JP | 2017-079267 A | 4/2017 |

OTHER PUBLICATIONS

International Preliminary Report on Patentability dated Jul. 21, 2020 for corresponding application No. PCT/JP2018/045795, with English translation (23 pages).
Office Action for the corresponding Japanese Application No. 2019-565763, dated Sep. 6, 2022, with English translation.
An International Search Report dated Mar. 19, 2019 for the corresponding patent application No. PCT/JP2018/045795, with English translation.
JP 5905916 B2, referenced in the application.
JP 4571359 B2, referenced in the application.
JP 2017-502516 A, cited in (1).
JP 2005-310766 A, cited in (1).
JP 2013-139426 A, cited in (1).
JP 2010-270103 A, cited in (1).
JP 2016-225497 A, cited in (1).
JP 2017-079267 A, cited in (1).
JP 2016-153173 A, cited in (1).
D'Andrade et al., "High-efficiency yellow double-doped organic light-emitting devices based on phosphor-sensitized fluorescence", cited in (1).
Form SB08a citing items (1)-(11).
PCT, International Search Report for the corresponding application No. PCT/JP2018/045795, dated Mar. 19, 2019, with English translation (4 pages).
D'Andrade et al., "High-efficiency yellow double-doped organic light-emitting devices based on phosphor-sensitized fluorescence", Applied Letters Physics, Aug. 13, 2001, pp. 1045-1047, vol. 79, No. 7, American Institute of Physics.
JPO, Office Action for the corresponding Japanese Application No. 2019-565763, dated Mar. 8, 2022, with English translation.
Nakanotani et al., "High-efficiency fluorescence OLED by Utilizing a TADF Process", Journal of the Society of Photography and Imaging of Japan, vol. 77, 2014, pp. 296-300, with English Abstract.

* cited by examiner

LUMINESCENT FILM, ORGANIC ELECTROLUMINESCENT DEVICE, AND METHOD FOR MANUFACTURING ORGANIC ELECTROLUMINESCENT DEVICE

CROSS REFERENCE TO RELATED APPLICATION

This Application is a 371 of PCT/JP2018/045795 filed on Dec. 13, 2018, which, in turn, claimed the priority of Japanese Patent Application No. 2018-005490 filed on Jan. 17, 2018 and Japanese Patent Application No. 2018-022674 filed on Feb. 13, 2018, all of the above applications are incorporated herein by reference.

TECHNICAL FIELD

The present invention relates to a luminescent film, an organic electroluminescent element, and a method of manufacturing the organic electroluminescent element. More specifically, the present invention relates to a luminescent film having excellent luminous efficiency, chromaticity, and element lifetime.

BACKGROUND

As a light emitting type electronic display device, there is an organic electroluminescent (hereinafter also referred to as "organic EL") element.

An organic EL element has a configuration in which a light emitting layer containing a light emitting compound (hereinafter also referred to as a "light emitting material") is sandwiched between a cathode and an anode, an exciton (exciton) is generated by injecting electrons and holes into the light emitting layer and recombining the layers, and light is emitted by using light emission (fluorescence and phosphorescence) when the exciton is deactivated. Light can be emitted at a low voltage of several V to several tens of V, and further, since the organic EL element is a self-luminescent type, it has a wide viewing angle, high visibility, and is a thin-film type complete solid-state element, and is attracted attention from the viewpoint of space saving, and portability.

As the development of the organic EL element in the future, the organic EL element which further enables the good luminous efficiency, luminance and chromaticity is desired.

From the viewpoint of high luminance, phosphorescent metal complexes containing heavy atoms such as Ir, Ru, and Pt are often used as the light emitting material rather than the fluorescent compound. This is because these metal complexes are capable of spin inversion, which is inherently forbidden from the singlet excited state to the triplet excited state, by the heavy atom effect, and can theoretically achieve an internal quantum yield of up to 100%.

However, although phosphorescent compounds having high luminous efficiency have been found, they have not been found to have satisfactory levels in terms of element lifetime and chromaticity. The reason for this is that the energy level of the lowest triplet excited state of the phosphorescent compound (hereinafter, also simply referred to as "level") is higher than that of the fluorescent compound, so that both the host compound and the phosphorescent compound are liable to be deteriorated, and the energy is liable to be transferred to a quenching substance having a low level generated during electric field driving.

Phosphorescent luminescent compounds have a decay lifetime ti of several as to several tens as, which is 2 to 4 orders of magnitude longer than the fluorescence lifetime of fluorescent materials. Furthermore, as the level of the triplet excited state increases, the emission spectrum from the phosphorescent compound and the absorption spectrum of the quencher tend to overlap, the energy transfer rate increases, and the element lifetime is shortened.

Here, the quenching phenomena from the light emitting material when the quenching material is generated can be explained by STERN-VOLMER equation (Numerical Formula (A)) shown below.

$$\frac{PL(\text{with Quencher})}{PL_0(\text{without Quencher})} = \frac{1}{1 + K_q \times [Q] \times \tau_0} = \frac{1}{1 + K_q \times (K_d \times t) \times \tau_0} \quad \text{Numerical Formula (A)}$$

In the above equation (A), PL (with Quencher) is the luminescence intensity in the presence of a quenching substance, $PL_0$ (without Quencher) is the luminescence intensity in the absence of a quenching substance, $K_q$ is the energy transfer rate from a luminescent material to a quenching substance, $[Q](=K_d \times t)$ is the quenching substance concentration, $K_d$ is the generation rate of a quenching substance by aggregation or decomposition, t is the cumulative excitation time by light or current, and to is the phosphorescence half-life time of phosphorescence of a phosphorescent luminescent compound in the absence of a quenching substance.

That is, according to the formula (A), if the light emitting material has a short emission decay life to, such as a fluorescent compound, the light emitting life of the element (hereinafter, also referred to as "element lifetime") is expected to be long. However, as described above, in an organic EL element using a conventional fluorescent compound, the internal quantum yield does not exceed 25%.

Therefore, the high efficiency of the fluorescent compound was devised by the use of the triplet-triplet annihilation mechanism (hereinafter simply referred to as "TTA"). Although the triplet excited state of a general fluorescent compound is to be thermally deactivated, it is known that triplet excitons collide with each other by increasing the exciton density, and a singlet excited state is generated. The TTA mechanism is represented by the following formula (B), and one singlet exciton is generated from five triplet excitons. However, even if the TTA mechanism is used, the theoretical limit value of the external extraction quantum efficiency (EQE) is 8%, which is not as high as that of the phosphorescent compound.

$$4(T_1^* + T_1^*) \rightarrow S_1^* + 3T_1^* + 4S_0$$

$$S_1^* \rightarrow S_0 + h\nu \quad \text{Formula (B)}$$

$S_0$ in Formula (B) above represents the ground state, $S_1$ represents the singlet excitation level, $T_1$ represents the triplet excitation level, and a symbol * represents the excitation state.

In addition, for example, in Patent Document 1, by using a TADF (thermally activated delayed fluorescence) luminescent compound as an assist dopant of the fluorescent luminescent compound, a technique for producing a highly efficient organic EL element is described. However, the luminescence decay lifetime (f) of the luminescent film to which the fluorescent luminescent compound has been added is still long on the order of μ seconds, and under high luminance and high current density, roll-off and the above-mentioned acceleration coefficient become large, so that the luminescence property is lowered, and consequently, the element lifetime is lowered.

In order to express the above Formula (B) in an organic EL element, it is necessary to increase the density of excitons as described above. Therefore, the light emitting position in the light emitting layer must be biased toward the hole transport layer (HTL: hole transport layer) or the electron transport layer (ETL: electron transport layer). When the materials constituting these layers are mixed (hereinafter also referred to as "the interface is mixed"), energy transfer to the adjacent layers occurs, and a decrease in exciton density leads to a decrease in luminous efficiency.

Mixing at the interface is remarkably manifested by film formation by the coating method. It is known that when a multilayered film is formed by a coating method, the interface with the light emitting layer (EML: emitter layer) is mixed by several nanometers, and it has been confirmed that, by increasing the transfer rate of energy to the adjacent layer, a significant decrease in light emitting efficiency is caused. Therefore, the element using the TTA mechanism by densification of the exciton can be implemented only in a limited layer configuration.

In fluorescence sensitization instead of TTA, for example, Patent Document 2 proposes that a fluorescent light emitting compound and a phosphorescent light emitting compound having a higher level of the lowest triplet excited state than the level of the singlet excited state of the fluorescent compound are combined to sensitize the singlet excited state of the fluorescent compound by Förster type energy transfer from the phosphorescent compound, thereby increasing the efficiency of light emission from the fluorescent compound. However, the exciton of the phosphorescent compound does not completely sensitize the fluorescent light emitting compound, and there is room for improvement because the exciton of the phosphorescent compound does not fully sensitize the fluorescent light emitting compound, and the lifetime of the device is not sufficiently improved.

As mentioned above, the following have been found.
Phosphorescent luminescent compounds should have a luminescence decay lifetime τ as long as several μs to several tens μs.
Since the level of the lowest triplet excited state of the phosphorescent substance is high, the emission spectrum from the phosphorescent compound and the absorption spectrum of the quencher are likely to overlap, and the energy transfer rate is increased.
From the above viewpoint, the material used for the host compound also becomes higher than the level of the lowest triplet excited state of the phosphorescent compound, which causes degradation during driving.

As can be understood from the above Formula (A), the three points are combined, which is a difficult factor to prolong the lifetime of the device by using the phosphorescent compound. Also in the techniques disclosed in Patent Documents 1 and 2, the element lifetime is not sufficient, and there remains a great room for improvement.

PRIOR ART DOCUMENTS

Patent Documents

Patent Document 1: Japanese Patent No. 5,905,916
Patent Document 2: Japanese Patent No. 4,571,359

SUMMARY OF THE INVENTION

Problems to be Solved by the Invention

The present invention has been made in view of the above problems and status, and an object of the present invention is to provide a luminescent film having excellent luminous efficiency, chromaticity, and element lifetime, an organic electroluminescence element, a method of manufacturing an organic electroluminescence element.

Means to Solve the Problems

In order to solve the above-mentioned problems, the present inventor has found the following in the process of examining the cause of the above-mentioned problems. The emission spectrum of the phosphorescent compound and the absorption spectrum of the fluorescent compound have an overlap, and the overlap integral value of these light emitting compounds is made to have a relationship equal to or greater than a specific value. By this, the phosphorescent compound used as a sensitizer can transfer Förster energy from a phosphorescent compound to a fluorescent compound with higher efficiency than ever before, and can maintain the luminous efficiency of the luminescent film and improve the element lifetime. Thus, the present invention was achieved. That is, the above-mentioned problem according to the present invention is solved by the following means.

1. A luminescent film containing at least a phosphorescent compound and a fluorescent compound, wherein an overlap integral value of an emission spectrum of the phosphorescent compound and an absorption spectrum of the fluorescent compound satisfies the following Expression (1); in the emission spectrum of the luminescent film, light emission from the fluorescent compound accounts for 90% or more; and an absolute quantum yield (PLQE) of the luminescent film satisfies the following Expression (2), $$J \geq 1.5 \times 10^{14} \qquad \text{Expression (1):}$$

in expression (1), J represents an overlap integral value of the emission spectrum of the phosphorescent complex and the absorption spectrum of the fluorescent compound; and PLQE (of a film containing a phosphorescent compound and a host compound)×0.9≤PLQE (of a film containing a phosphorescent compound and a fluorescent compound)    Expression (2):

in Expression (2), a lowest triplet excited state of the host compound is higher than a lowest triplet excited state of the phosphorescent compound, and does not inhibit the luminescence of the phosphorescent compound.

2. The luminescent film according to item (1), wherein the overlap integral value of an emission spectrum of the phosphorescent compound and an absorption spectrum of the fluorescent compound satisfies the following Expression (3), $$J \geq 6.0 \times 10^{14}. \qquad \text{Expression (3):}$$

3. The luminescent film according to item (1) or item (2), wherein the host compound has the lowest triplet excited state existing at a higher energy level than the lowest triplet excited state of the phosphorescent luminescent compound.

4. The luminescent film according to item (1) or item (2), wherein the host compound has the lowest triplet excited state existing at a lower energy level than the lowest triplet excited state of the phosphorescent luminescent compound.

5. The luminescent film according to item (1) or item (2) consisting of the phosphorescent compound and the fluorescent compound.

6. The luminescent film according to any one of items (1) to (5), wherein the fluorescent compound has an absolute quantum yield (PLQE) of 10% or more in a film consisted of the fluorescent compound.

7. The luminescent film according to any one of items (1) to (6), wherein the fluorescent compound is a compound having a structure represented by the following Formula (1).

$$X—(Y)_n \quad \text{Formula (1)}$$

In Formula (1), X represents π-conjugated condensed ring of 14π electron system or more. Y represents a deuterium atom, a halogen atom, a cyano group, a nitro group, a hydroxy group, a mercapto group, an alkyl group, a cycloalkyl group, an alkenyl group, an alkynyl group, a heterocyclic group, an alkoxy group, a cycloalkoxy group, an aryloxy group, an alkylthio group, a cycloalkylthio group, an arylthio group, an alkoxycarbonyl group, an aryloxycarbonyl group, a sulfamoyl group, an acyl group, an acyloxy group, an amide group, a carbamoyl group, a ureido group, a sulfinyl group, an alkylsulfonyl group, an arylsulfonyl group, a heteroarylsulfonyl group, an amino group, a fluorinated hydrocarbon group, a triarylsilyl group, a diarylalkylsilyl group, an aryldialkylsilyl group, a trialkylsilyl group, a phosphate group, a phosphite group, phosphono group, a phenyl group, provided that these groups may further have a substituent; or a group having the structure represented by the following Formula (2) which may further have a substituent. At least one of Y is a group having a structure represented by the following Formula (2). When there are a plurality of Y, they may be different from each other. n is an integer from 1 to the maximum number that can be substituted by X.

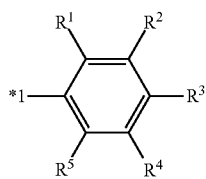

Formula (2)

In Formula (2), $R^1$ to $R^5$ each independently represent a hydrogen atom, a deuterium atom, a halogen atom, a cyano group, a nitro group, a hydroxy group, a mercapto group, an alkyl group, a cycloalkyl group, an alkenyl group, an alkynyl group, a heterocyclic group, an alkoxy group, a cycloalkoxy group, an aryloxy group, an alkylthio group, a cycloalkylthio group, an arylthio group, an alkoxycarbonyl group, an aryloxycarbonyl group, a sulfamoyl group, an acyl group, an acyloxy group, an amide group, a carbamoyl group, a ureido group, a sulfinyl group, an alkylsulfonyl group, an alylsulfonyl group, a heteroalylsulfonyl group, an amino group, a fluorinated hydrocarbon group, a triarylsilyl group, a diarylalkylsilyl group, an aryldialkylsilyl group, trialkylsilyl group, a phosphate group, a phosphite group, or a phosphono group, these may further have a substituent. At least one of $R^1$ and $R^5$ is a group having a structure represented by the following Formula (3) or (4). *1 represents a binding site to X.

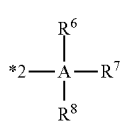

Formula (3)

In Formula (3), A represents a carbon atom or a silicon atom, $R^6$ to $R^8$ each independently represent the same group as $R^1$ to $R^5$ in Formula (2), provided that at least one of $R^6$ to $R^8$ is an alkyl group having 1 or more carbon atoms. *2 represents a bonding site with an adjacent atom.

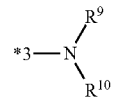

Formula (4)

In Formula (4), $R^9$ and $R^{10}$ each independently represent the same group as $R^1$ to $R^5$ in Formula (2), provided that at least one of $R^1$ to $R^5$ is an alkyl group having 1 or more carbon atoms. *3 represents a bonding site with an adjacent atom. In R1 to R10 in Formulas (2) to (4), adjacent groups may be bonded to each other to form an aliphatic ring.

8. The luminescent film according to any one of items (1) to (7), wherein the phosphorescent compound is a compound having a structure represented by the following Formula (5).

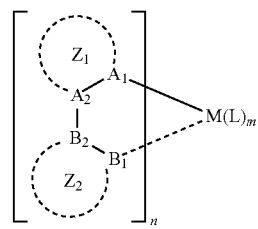

Formula (5)

In Formula (5): M represents iridium (Ir) or platinum (Pt); $A_1$, $A_2$, $B_1$ and $B_2$ each independently represent a carbon atom or a nitrogen atom; a ring $Z_1$ represents a 6-membered aromatic hydrocarbon ring, or a 5- or 6-membered aromatic heterocyclic ring formed with $A_1$ and $A_2$, or an aromatic condensed ring containing at least one of the aforesaid rings; a ring $Z_2$ represents a 5- or 6-membered aromatic heterocyclic ring formed with $B_1$ and $B_2$, or an aromatic condensed ring containing at least one of the aforesaid rings; the carbon atoms of the ring $Z_1$ and the ring $Z_2$ may be carbene carbon atoms; among a bond between $A_1$ and M, and a bond between $B_1$ and M, one is a coordinate bond and the other is a covalent bond; the ring $Z_1$ and the ring $Z_2$ each independently may have a substituent; the substituent of the ring $Z_1$ and the substituent of the ring $Z_{12}$ may be bonded to form a condensed ring structure, and ligands represented by the ring $Z_1$ and the ring $Z_2$ may be linked to each other; L represents a monoanionic bidentate ligand coordinated to M, and L may have a substituent; m represents an integer of 0 to 2, n represents an integer of 1 to 3, when M represents iridium (Ir), m+n is 3, and when m represents platinum (Pt), m+n is 2, when morn is 2 or more, the ligands represented by the ring $Z_1$ and the ring $Z_2$, or L may be the same or different; the ligands represented by the ring $Z_1$ and the ring $Z_2$ may be linked to L.

9. The luminescent film according to any one of items (1) to (7), wherein the phosphorescent compound is a compound having a structure represented by the following Formula (6).

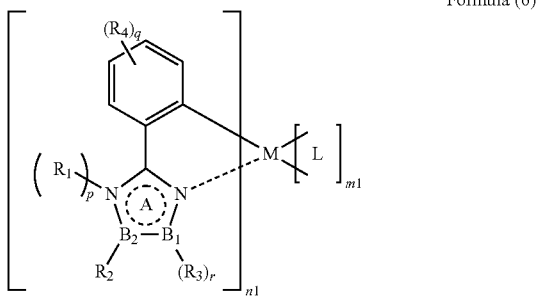

Formula (6)

In Formula (6), a ring A represents a triazole ring; $B_1$ and $B_2$ each represent a carbon atom or a nitrogen atom; $R_1$ represents a substituent, and p represents an integer of 0 or 1; $R^2$ represents a substituent; $R^3$ represents a hydrogen atom or a substituent, and r represents an integer of 0 or 1; $R^4$ represents a substituent, and q represents an integer of 1 to 4; M represents iridium (Ir) or platinum (Pt); L represents any ligand capable of coordinating with M; n1 represents an integer of 1 to 3; and m1 represents an integer of 0 to 2.

10. An organic electroluminescent element having a light emitting layer made of the luminescent film according to any one of items (1) to (9).

11. The organic electroluminescent element according to item (10), wherein a lowest triplet energy of a material used in a layer adjacent to the light emitting layer is lower than the lowest triplet excited state of the phosphorescent compound contained in the light emitting layer.

12. The organic electroluminescent element according to item (10) or (11), sealed with a gas barrier layer having a water vapor permeability in the range of 0.001 to 1 g/(m²·day) determined by a method based on JIS K 7129-1992 and an oxygen permeability in the range of 0.001 to 1 mL/(m²·day·atm) determined by a method based on JIS K 7126-1987.

13. A method of manufacturing an organic electroluminescence element according to any one of items (10) to (12), wherein the luminescent film is formed with a dry process.

14. A method of manufacturing an organic electroluminescence element according to any one of items (10) to (12), wherein the luminescent film is formed with a wet process.

Effect of the Invention

According to the above-mentioned means of the present invention, it is possible to provide a luminescent film having excellent luminous efficiency, chromaticity, and element lifetime. It is also possible to provide an organic electroluminescent element and a method of manufacturing an organic electroluminescent element. The expression mechanism or action mechanism of the effect of the present invention is not clarified, but is inferred as follows.

Advantages and Disadvantages of Fluorescent Compounds

Hereinafter, description will be made with reference to FIG. 1, FIG. 2A, FIG. 2B, and FIG. 2C. Note that reference numerals in FIG. 1 and FIGS. 2A to 2C described later are as follows. $S_0$: Ground state; $S_1$: Single state; $T_1$: Lowest triplet excited state; a: Förster-type energy transfer; b: Dexter-type energy transfer; c: Radiationless deactivation.

FIG. 1 is a schematic diagram showing energy transfer when a fluorescent compound capable of transferring energy from a phosphorescent compound is added to a luminescent film in which a host compound not contributing to light emission and a phosphorescent compound are present, which is a prior art. In the technique shown in FIG. 1, the exciton deactivation pathway of the phosphorescent compound is increased in that the phosphorescent compound undergoes a Förster-type energy transfer or a Dexter-type energy transfer from the phosphorescent compound to the fluorescing compound, which in turn undergoes fluorescence emission or radiationless deactivation. Therefore, it is known that the luminescent film to which the fluorescent luminescent compound is added can shorten the luminescence decay lifetime τ of the phosphorescent luminescent compound itself when compared with the luminescent film to which the fluorescent luminescent compound is not added.

However, the present inventors have found that shortening the luminescence decay (luminescence decay lifetime τ) of the phosphorescent compound by adding the fluorescent compound has the following drawbacks.

Generally, since the triplet excited state of the fluorescent compound is a low energy level equal to or lower than the energy corresponding to the wavelength of red light, it is considered that the energy level is lower than the energy level of the lowest triplet excited state of the phosphorescent compound, and radiationless deactivation occurs predominantly That is, as shown in FIG. 1, the luminescent film to which the fluorescent luminescent compound is added can shorten the luminescence decay lifetime τ of the phosphorescent luminescent compound. On the other hand, when the addition amount is increased in order to sufficiently sensitize the fluorescent compound, the energy transfer (Dexter-type energy transfer) to $T_1$ level of the fluorescent compound whose energy level is lower than the lowest triplet excited state ($T_1$ level) of the phosphorescent compound is also increased, so that the luminescence characteristics sufficiently obtained in the luminescent film to which the fluorescent compound is not added are lowered, and as a result, the luminescence amount obtained from the luminescent film is reduced. When the exciton is deactivated from $T_1$ level of the phosphorescent compound to $T_1$ level of the added fluorescent compound in this manner, the exciton generated is deactivated by a radiationless deactivation mechanism such as thermal deactivation mechanism, which causes a decrease in luminescence luminance, and as a result, the life of the element using the luminescent film in the same luminance conversion mechanism is shortened.

Accordingly, it is considered that the distance between the phosphorescent compound and the fluorescent compound is separated by the added concentration in order to suppress the energy transfer (Dexter-type energy transfer) to $T_1$ level of the fluorescent compound lower than $T_1$ level of the phosphorescent compound. However, since the Förster transfer efficiency is also lowered at the same time, the amount of excitons that can be transferred from $T_1$ level of the phosphorescent compound to $S_1$ level of the fluorescent compound decreases, and the luminescence of the phosphorescent compound that is used as the sensitizer of the fluorescent compound remains, so that the fluorescent compound is not completely sensitized.

Incidentally, it is considered that the reason why the desired element lifetime cannot be obtained by the addition of the known fluorescent compound is based on the disadvantage of the addition of the fluorescent compound as described above.

<Investigation and Solving Means of Drawbacks of Addition of Fluorescent Compound>

In general, as shown in FIG. 1, when a phosphorescent compound and a fluorescent compound are used, the triplet exciton of the phosphorescent compound is deactivated without radiation deactivation by Dexter-type energy transfer to the triplet excited state of the fluorescent compound, and the exciton does not contribute to light emission.

Therefore, the present inventors focused on first improving the Förster-type energy transfer from the triplet excited state of the phosphorescent compound to the singlet excited state of the fluorescent compound in order to extend the element lifetime of the element using the luminescent film to which the fluorescent compound has been added. As a result, it was found that the Förster-type energy transfer from $T_1$ level of the phosphorescent compound to $S_1$ level of the fluorescent compound can be sufficiently increased by increasing the overlap (overlap integral value) between the emission spectrum of the phosphorescent compound and the absorption spectrum of the fluorescent compound by a prescribed value or more, and only the fluorescence emission can be expressed without decreasing the emission intensity (see FIG. 2A).

Furthermore, by increasing the overlap (integral overlap) between the emission spectrum of the phosphorescent compound and the absorption spectrum of the fluorescent compound by more than a specified value, it has been found that even if the host compound used until now for dispersing the phosphorescent compound is at a level lower than the triplet excitation level of the phosphorescent compound, it is possible to maintain luminescence by predominantly transferring Förster energy from the triplet excited state of the phosphorescent compound to the singlet excited state of the fluorescent compound instead of the triplet excited state to the host compound, and thus the host compound having a low $T_1$ level, which has not been used until now, can be applied. As a result, it is possible to greatly suppress the deterioration caused by the host (see FIG. 2B).

Furthermore, by increasing the overlap (integral overlap) between the emission spectrum of the phosphorescent compound and the absorption spectrum of the fluorescent compound by more than a specified value, it has been found that the concentration quenching can be suppressed by transferring the Förster energy to the singlet excited states of the phosphorescent compound before deactivation on the phosphorescent compound, even if a host compound which has been used as a dispersing agent for suppressing the concentration quenching of the phosphorescent compound is not completely used (see FIG. 2). By the above mechanism, it is presumed that it was possible to realize an unprecedented longer element lifetime.

EMBODIMENTS TO CARRY OUT THE INVENTION

Figure 1:
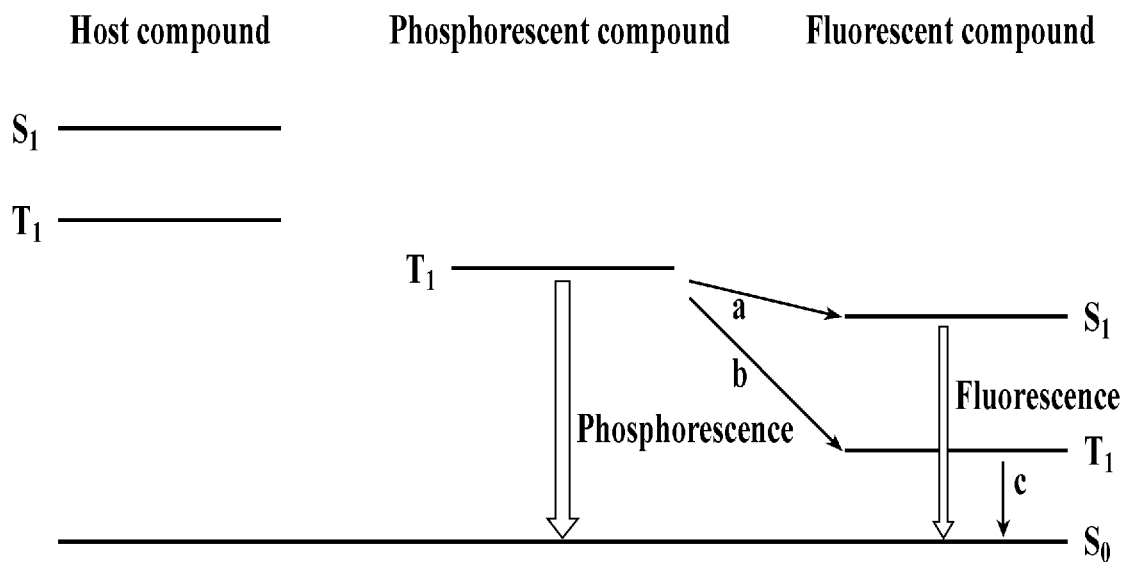
FIG. 1 is a schematic diagram showing energy transfer between luminescent compounds in the prior art
Figure 2A:
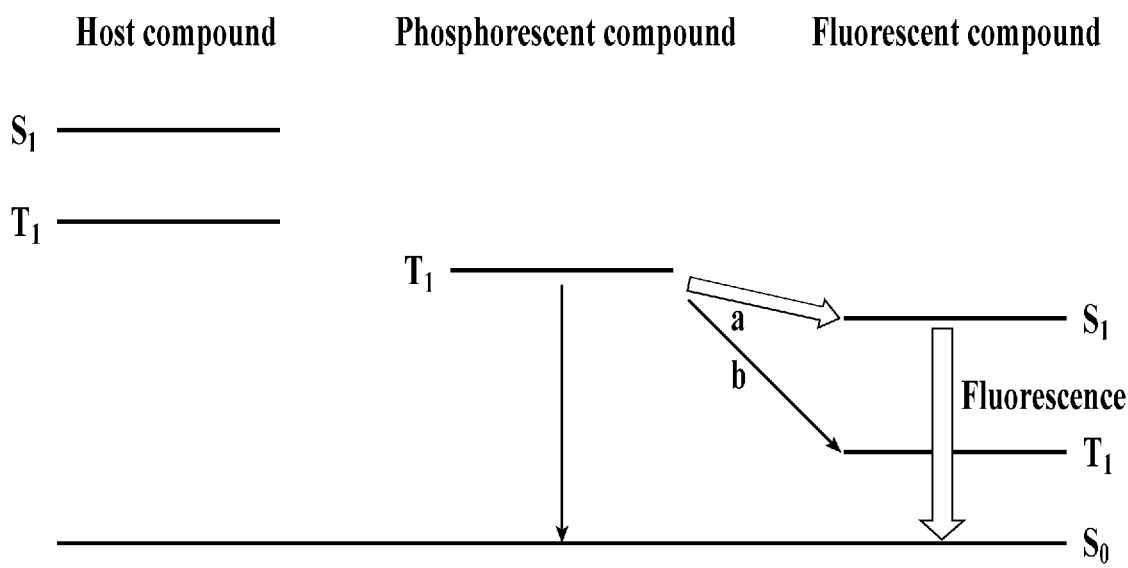
FIG. 2A is a schematic diagram showing energy transfer between luminescent compounds according to the present invention
Figure 2B:
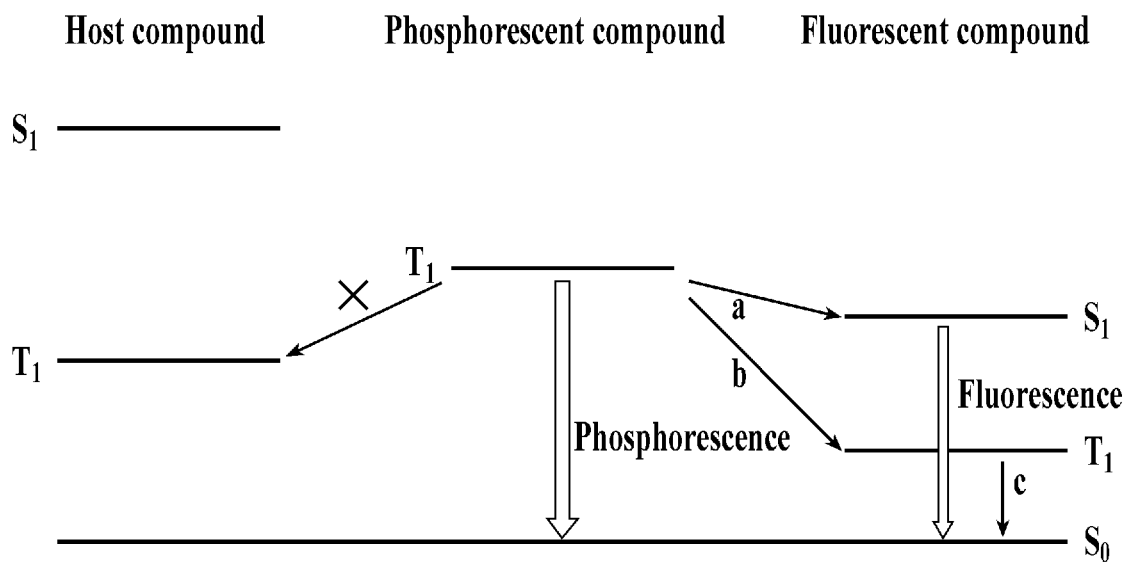
FIG. 2B is a schematic diagram showing energy transfer between luminescent compounds according to the present invention
Figure 2C:
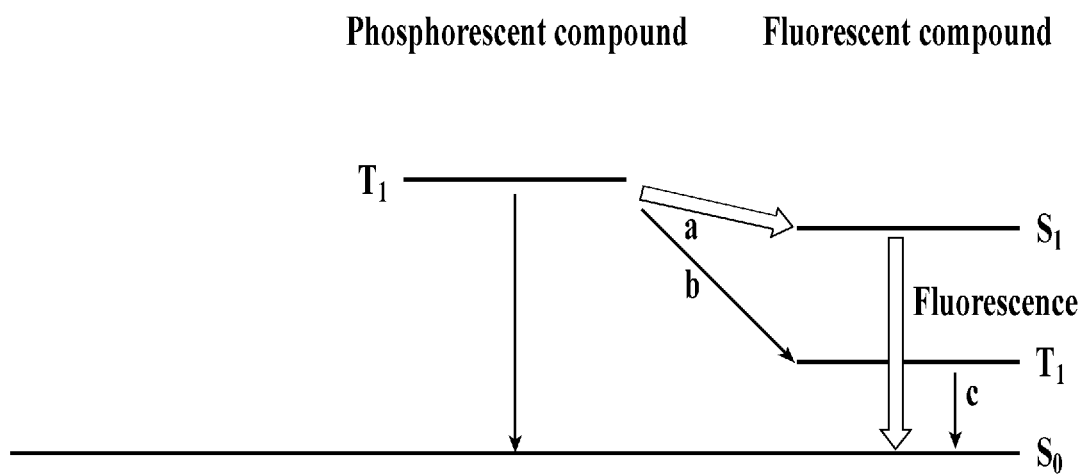
FIG. 2C is a schematic diagram showing energy transfer between luminescent compounds according to the present invention

The luminescent film of the present invention is a luminescent film containing at least a phosphorescent compound and a fluorescent compound, in which the overlap integral value of the emission spectra of the phosphorescent compound and the absorption spectra of the fluorescent compound satisfies Expression (1); in the emission spectrum of the luminescent film, light emission from the fluorescent compound accounts for 90% or more; and an absolute quantum yield (PLQE) of the luminescent film satisfies the following expression (2). This feature is a technical feature common to or corresponding to each of the following embodiments.

In an embodiment of the present invention, it is preferable that the overlap integral value between the emission spectrum of the phosphorescent compound and the absorption spectrum of the fluorescent compound satisfies the formula (3) in terms of improvement in the Förster-type energy transfer from the triplet excited state of the phosphorescent compound to the singlet excited state of the fluorescent compound, and improvement in the emission intensity and the element lifetime.

It is preferable to contain a host compound having a lowest triplet excited state at a higher energy level than the lowest triplet excited state of the phosphorescent compound. This is because the element lifetime can be improved by adjusting the distance of the fluorescent compound without inhibiting exciton transfer from the phosphorescent compound.

In addition, it is preferable to contain a host compound in which the lowest triplet excited state exists at a lower energy than the lowest triplet excited state of the phosphorescent compound in terms of suppressing the degradation of the host compound to a large extent and improving the element lifetime as compared with a material in which the lowest triplet excited state is relatively high.

Further, as another embodiment of the luminescent film of the present invention, it is preferable that the luminescent film is composed of only the phosphorescent compound and the fluorescent compound without containing a host compound, in that deterioration of the host compound which is liable to be deteriorated can be eliminated and the element lifetime is improved.

In addition, it is preferable that the emission spectrum of the phosphorescent compound and the absorption spectrum of the fluorescent compound overlap in that the Förster-type energy transfer from the triplet excited state of the phosphorescent compound to the singlet excited state of the fluorescent compound is improved, and the emission intensity and the element lifetime are improved.

It is preferable that the fluorescent compound has an absolute quantum yield of 10% or more of the single film composed of the fluorescent compound because the addition amount of the fluorescent compound can be increased and the element lifetime can be improved by improving the Förster transfer efficiency.

In addition, it is preferable that the fluorescent compound is a compound having a structure represented by Formula (1) because concentration quenching is suppressed, the addition amount of the fluorescent compound can be increased, and the Förster transfer efficiency is improved, thereby improving the element lifetime.

It is preferable that the phosphorescent compound is a compound having the structure represented by Formula (5) because the overlap integral value between the absorption of the fluorescent compound and the phosphorescent compound can be increased, and the element lifetime can be improved by improving the Förster transfer efficiency.

It is preferable that the phosphorescent compound is a compound having the structure represented by Formula (6) because the overlap integral value between the absorption of the fluorescent compound and the phosphorescent compound can be increased, and the element lifetime can be improved by improving the Förster transfer efficiency.

The organic electroluminescent element of the present invention has a light emitting layer formed of the luminescent film. This makes it possible to provide an organic electroluminescent element having excellent luminous efficiency, chromaticity, and lifetime.

In addition, it is preferable that the lowest triplet energy of the material used in the layer adjacent to the light emitting layer is lower than the lowest triplet excited state of the phosphorescent compound contained in the light emitting layer from the viewpoint of suppressing deterioration of the adjacent layer and improving the element lifetime.

It is preferable from the viewpoint of reducing the cost that the organic electroluminescent element is sealed with a gas barrier layer having a water vapor permeability in the range of 0.001 to 1 g/(m$^2$·day) determined by a method based on JIS K 7129-1992 and an oxygen permeability in the range of 0.001 to 1 mL/(m$^2$·day·atm) determined by a method based on JIS K 7126-1987.

In the method for manufacturing an organic electroluminescent element of the present invention, the luminescent film is manufactured by a dry process. Thereby, a homogeneous film can be easily obtained, and mixing with the adjacent layer can be suppressed.

In the method for manufacturing an organic electroluminescent element of the present invention, the luminescent film is manufactured by a wet process. Thereby, a uniform film is easily obtained, and pinholes are hardly generated.

The present invention and the constitution elements thereof, as well as configurations and embodiments, will be detailed in the following. In the present description, when two figures are used to indicate a range of value before and after "to", these figures are included in the range as a lowest limit value and an upper limit value.

[Luminescent Film]

The luminescent film of the present invention is a luminescent film containing at least a phosphorescent compound and a fluorescent compound, wherein an overlap integral value of an emission spectra of the phosphorescent compound and an absorption spectra of the fluorescent compound satisfies the following Expression (1); in the emission spectrum of the luminescent film, light emission from the fluorescent compound accounts for 90% or more; and an absolute quantum yield (PLQE) of the luminescent film satisfies the following Expression (2).

$$J \geq 1.5 \times 10^{14} \quad \text{Expression (1):}$$

in Expression (1), J represents an overlap integral value of the emission spectrum of the phosphorescent complex and the absorption spectrum of the fluorescent compound; and $$\text{PLQE (of a film containing a phosphorescent compound and a host compound)} \times 0.9 \leq \text{PLQE (of a film containing a phosphorescent compound and a fluorescent compound)} \quad \text{Expression (2):}$$

in Expression (2), a lowest triplet excited state of the host compound is higher than a lowest triplet excited state of the phosphorescent compound, and does not inhibit the luminescence of the phosphorescent compound.

That is, Expression (2) means that, with respect to the reference film composed of (phosphorescent compound+ high T1 host compound) before addition of the fluorescent compound, the PLQE of the luminescent film to which the phosphorescent compound and the fluorescent compound are added is 90% or more.

In the luminescent film of the present invention, it is preferable that the overlap integral value of the emission spectrum of the phosphorescent compound and the absorption spectrum of the fluorescent compound satisfies the following Expression (3).

$$J \geq 6.0 \times 10^{14}. \quad \text{Expression (3):}$$

It is considered that, by satisfying Expression (3), the Förster-type energy transfer from the triplet excited state of the phosphorescent compound to the singlet excited state of the fluorescence compound is improved, and as a result, the exciton of the phosphorescent compound can be immediately transferred to the fluorescent compound, and the emission intensity and the element lifetime are improved.

As an embodiment of the present invention, the focus is made on the sensitization of the singlet excited state of the fluorescent compound by Förster-type energy transfer from the lowest triplet excited state of the phosphorescent compound to the singlet excited state of the fluorescent compound. Here, we describe the process by which a phosphorescent compound converts all excitons from a host compound into their triplet excited state, and then transfers that triplet excited state to a fluorescent compound. The following formula relates to a luminescent film containing a host compound, a phosphorescent compound and a fluorescent compound, and it is a description of exciton transfer when the host compound is mainly photoexcited.

$$^1D^* + {}^1X \rightarrow {}^1D + {}^1X^*$$

$$^1X^* \rightarrow {}^3X^*$$

$$^3X^* + {}^1A \rightarrow {}^1X + {}^1A^*$$

$$^1A^* \rightarrow {}^1A + h\nu \quad \text{Formula (C):}$$

In Formula (C), D represents a host compound, X represents an intersystem crossing agent (phosphorescent compound), and A represents an energy acceptor (fluorescence compound). Superscript 1 indicates singlet spin multiplicity, superscript 3 indicates triplet spin multiplicity, and * indicates excitation state.

In order to facilitate the understanding of the above mechanism, the underlying mechanistic theory of energy transfer will be described.

«Dexter-Type Energy Transfer and Förster-Type Energy Transfer»

<Dexter-Type Energy Transfer>

Dexter-type energy transfer is a short-range process that depends on the overlap of molecular orbitals of adjacent molecules. It also preserves the symmetry of the pair of energy donor and energy acceptor. Thus, the energy transfer of Formula (C) is not possible with the Dexter mechanism.

<Förster-type Energy Transfer>

In the Förster-type energy transfer mechanism, the energy transfer of Formula (C) is possible. In Förster-type energy transfer, similar to transmitters and antennas, it is caused by allowed transitions in molecules of both the energy donor and the energy acceptor. This typically limits the Förster-type energy transfer to the transfer between singlet states.

However, in an embodiment of the present invention, a phosphorescent compound that allows the transfer of the energy donor ($^3X^* \rightarrow {}^1A$) is considered. However, due to the difference in symmetry between the excited triplet state and the ground singlet state, this transfer probability is low.

Nevertheless, it can also serve as an energy donor in Förster-type energy transfer as long as the phosphorescent compound can phosphoresce with some perturbation of the state, such as by spin orbital interactions introduced by heavy metal atoms.

In addition, a major factor in efficiently expressing Förster-type energy transfer is the presence of an overlap of the emission spectrum of the energy donor (phosphorescent compound) and the absorption spectrum of the energy acceptor (fluorescence compound). Therefore, in the present invention, it is essential that the emission spectrum of the phosphorescent compound and the absorption spectrum of the fluorescent compound overlap.

The respective energy-transfer efficiencies can be obtained from the absolute quantum yield (hereinafter, also simply referred to as "PLQE") and the luminescence decay lifetime τ (hereinafter, also simply referred to as "τ") of the luminescent film before and after the addition of the luminescent compound. For example, PLQE measurement can be measured by using an absolute quantum yield measurement device C9920-02 (manufactured by Hamamatsu Photonics K.K.) and the luminescence decay lifetime measurement device (for example, a streak camera C4334 or a small fluorescence lifetime measurement device C11367-03 (manufactured by Hamamatsu Photonics K.K.).

The calculation method of each energy transfer efficiency is as shown in the following Numerical Formula (D).

$$P_F = \frac{Kf}{Kr + Knr + Kf + Kd}$$ Numerical Formula (D)

$$P_D = \frac{Kd}{Kr + Knr + Kf + Kd}$$

$$Kf = \frac{PLQE}{\tau} - Kr$$

$$Kd = \frac{1}{\tau} - (kr + Knr + Kf)$$

$$PLQE = \frac{Kr + Kf}{Kr + Knr + Kf + Kd}$$

$$\tau = \frac{1}{Kr + Knr + Kf + Kd}$$

$$PLQE_0 = \frac{Kr}{Kr + Knr}$$

$$\tau_0 = \frac{1}{Kr + Knr}$$

In Numerical Formula (D) above, to represents the light-attenuation lifetime of the luminescent film in which no fluorescence compound is added (hereinafter, referred to as "the 1 luminescent film before adding the fluorescent compound"), and ti represents the light-attenuation lifetime (unit: sec) after the addition of the fluorescent compound. $PLQE_0$ is the absolute quantum yield in the luminescent film prior to addition of the fluorescence compound, and PLQE is the absolute quantum yield in the luminescent film to which the fluorescing compound has been added (hereinafter also referred to as "luminescent film after addition of the fluorescing compound"). Kr is the radiation rate (unit: 1/sec) of the phosphorescent compound, Knr is the non-radiation rate (unit: 1/sec) of the phosphorescent compound, Kf is the Förster energy transfer rate (unit: 1/sec) from the triplet excited state of the phosphorescent compound to the fluorescent compound $S_1$ excited state, and Kd is the Dexter energy transfer rate (unit: 1/sec) from the triplet excited state of the phosphorescent compound to the fluorescent compound $T_1$ excited state. PD shows a Dexter-type energy transfer efficiency from the triplet excited state of the phosphorescent compound to the triplet excited state of the fluorescent compound. PF indicates a Förster-type energy transfer efficiency from the triplet excited state of the phosphorescent compound to the singlet excited state of the fluorescence compound.

«Overlap Integral Value»

As described above, the main factor for efficiently expressing the Förster-type energy transfer is the overlap of the emission spectrum of the phosphorescent compound and the absorption spectrum of the fluorescent compound. It is known that the magnitude of the overlap of the spectrum is called an overlap integral value, and is calculated by the following Numerical Formula (OI).

$$J = \int f_D(\lambda) \varepsilon_A(\lambda) \lambda^4 d\lambda$$ Numerical Formula (OI)

$f_D$ in Numerical Formula (OI) represents the emission spectrum of standardized donors (energy donor, phosphorescent compound), and the $\varepsilon_A$ represents the molar extinction coefficients of acceptors (energy acceptor, fluorescence compound). λ represents the wavelength. Note that J represents an overlap integral value.

(Measure of Emission Spectrum)

The emission spectrum can be measured by a known method. For example, it can be performed using a fluorometer (HITACHI F-7000 spectrofluorometer).

(Measure of Absorption Spectrum)

The absorption spectrum can be measured by a known method. For example, it can be performed using a fluorometer (HITACHI U-3300 spectrophotometer). The overlap integral value is calculated on the basis of the result of the solution absorption spectrum and the solution molar extinction coefficient.

(Measure of Molar Extinction Coefficient)

The molar extinction coefficients can be determined by measuring a sample dissolved in 2-methyltetrahydrofuran (2Me-THF) with a spectrophotometer. Specifically, a sample prepared by 2Me-THF to a density of $1 \times 10^{-5}$ mol/L may be measured by a spectrophotometer U-3000 (manufactured by Hitachi High Technologies, Ltd.).

(Measuring Method of Chromaticity)

Figure 4:
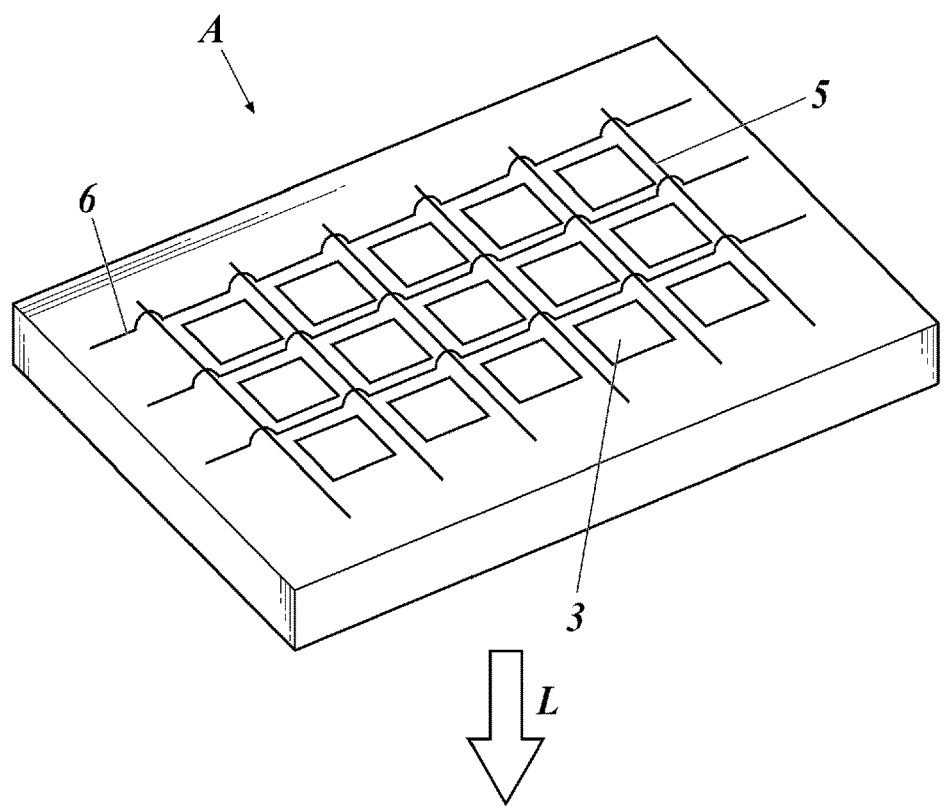
FIG. 4 is a schematic view of a display section A shown in FIG. 3

Color of light emitted by an organic EL element or a luminescent film of the present invention is specified as follows. In FIG. 4.16 on page 108 of "New Edition Color Science Handbook" (edited by The Color Science Association of Japan, University of Tokyo Press, 1985), values determined via Spectroradiometer CS-1000 (produced by Konica Minolta, Inc.) are applied to the CIE chromaticity coordinate, whereby the color is specified. The method for detecting the chromaticity of each compound is not particularly limited. For example, the compounds may be separated and purified by HPLC (High Performance Liquid Chromatography), and then measurement may be done with the above-described spectral radiance meter.

It is preferable that the luminescent film of the present invention further contains a host compound in addition to the phosphorescent compound and the fluorescent compound, the luminescence spectrum of the phosphorescent compound and the absorption spectrum of the fluorescent compound overlap, and the lowest triplet excited state of the host compound exists at a level on the higher energy side than the lowest triplet excited state of the phosphorescent compound, in that the distance of the fluorescent compound can be adjusted without inhibiting the exciton transfer from the phosphorescent compound, so that the element lifetime can be improved.

In addition, as another embodiment of the luminescent film of the present invention, it is preferable that the luminescent film further contain a host compound in addition to the phosphorescent compound and the fluorescent compound, the emission spectrum of the phosphorescent compound and the absorption spectrum of the fluorescent compound overlap, and the lowest triplet excited state of the host compound exists at a level on the lower energy side than the lowest triplet excited state of the phosphorescent compound, from the viewpoint of greatly suppressing deterioration of the host compound and improving the element lifetime, as compared with a material in which the lowest triplet excited state is relatively high.

Further, as another embodiment of the luminescent film of the present invention, it is preferable that the luminescent film does not contain a host compound, but contains only a phosphorescent compound and a fluorescent compound, and that the emission spectrum of the phosphorescent compound and the absorption spectrum of the fluorescent compound overlap with each other, in that deterioration of the host compound, which is liable to be deteriorated, can be eliminated and the element lifetime can be improved.

The content of the phosphorescent compound, the fluorescent compound, and the host compound in the luminescent film of the present invention can be arbitrarily determined based on the conditions required for the product to be applied, and may be contained at a uniform concentration in the film thickness direction, or may have an arbitrary concentration distribution. The content of the phosphorescent compound in the luminescent film of the present invention is preferably in the range of 1 to 50% by mass and more preferably in the range of 1 to 30% by mass when the mass of the luminescent film is 100% in order to suitably develop the luminescence phenomenon in the past, but is not particularly defined. The content of the host compound in the luminescent film of the present invention is also conventionally within the range of 50 to 99% by mass when the mass of the luminescent film is 100% by mass, and more preferably within the range of 70 to 99% by mass, but may not be particularly defined and may be included. The content of the fluorescent compound in the luminescent film of the present invention is preferably equal to or less than that of the phosphorescent compound, and more preferably within the range of 0.1 to 20.0% by mass, from the viewpoint of suitably expressing the sensitization phenomenon from the phosphorescent compound and suppressing the direct recombination on the fluorescent compound at the time of electric field driving.

«Relationship Between Contents of Phosphorescent Compound and Fluorescent Compound: (Expression (4))»

The content (mass %) of the phosphorescent compound and the content (mass %) of the fluorescent compound may satisfy the following Expression (4). This makes it possible to more efficiently sensitize the fluorescent compound via the phosphorescent compound.

Content of phosphorescent compound (mass %)≥
Content of fluorescent compound (mass %)    Expression (4):

«Fluorescent Compound»

The fluorescent compound used in the present invention is a compound capable of emitting light from a singlet excited state and is not particularly limited as long as light emission from a singlet excited state is observed.

It is preferable that the fluorescent compound according to the present invention has an absolute quantum yield in the fluorescent compound alone film consisted of the fluorescent compound is 10% or more from the viewpoint of enabling to increase an amount of the fluorescent compound added, the lifetime of the element is improved by improving the Förster moving efficiency.

Examples of the fluorescent compound usable in the present invention are: an anthracene derivative, a pyrene derivative, a chrysene derivative, a fluoranthene derivative, a perylene derivative, a fluorene derivative, an arylacetylene derivative, a styrylafylene derivative, a styfylamine derivative, an arylamine derivative, a boron complex, a coumarin derivative, a pyran derivative, a cyanine derivative, a croconium derivative, a squarylium derivative, an oxobenzanthracene derivative, a fluorescein derivative, a rhodamine derivative, a pyrylium derivative, a perylene derivative, a polythiophene derivative, and a rare earth complex compound. There is no particular limitation as long as light emission can be obtained. Above all, it is more preferable to use a fluorescent compound having a small Stokes shift from the viewpoint of increasing the overlap integral value of the emission spectrum of the phosphorescent compound and the absorption spectrum of the fluorescent compound.

In recent years, light emitting dopants utilizing delayed fluorescence were developed. These dopants may be used.

Specific examples of a light emitting dopant utilizing delayed fluorescence are compounds described in: WO 2011/156793, JP-A 2011-213643, and JP-A 2010-93181. However, the present invention is not limited to them.

In particular, the fluorescent compound according to the present invention is preferably a fluorescent compound having a structure represented by the following Formula (1).

$$X—(Y)_n \qquad \text{Formula (1)}$$

In Formula (1), X represents π-conjugated condensed ring of 14π electron system or more. Y represents a deuterium atom, a halogen atom, a cyano group, a nitro group, a hydroxy group, a mercapto group, a alkyl group, a cycloalkyl group, an alkenyl group, an alkynyl group, a heterocyclic group, an alkoxy group, a cycloalkoxy group, an aryloxy group, an alkylthio group, a cycloalkylthio group, an arylthio group, an alkoxycarbonyl group, an aryloxycarbonyl group, a sulfamoyl group, an acyl group, an acyloxy group, an amide group, a carbamoyl group, a ureido group, a sulfinyl group, an alkylsulfonyl group, an arylsulfonyl group, a heteroarylsulfonyl group, an amino group, a fluorinated hydrocarbon group, a triarylsilyl group, diarylalkylsilyl group, aryldialkylsilyl group, a trialkylsilyl group, a phosphate group, a phosphite group, a phosphono group, a phenyl group, provide that these groups may further have a substituent; or a group having the structure represented by the following Formula (2) which may further have a substituent. At least one of Y is a group having a structure represented by the following Formula (2). When there are a plurality of Y, they may be different from each other. n is an integer from 1 to the maximum number that can be substituted by X.

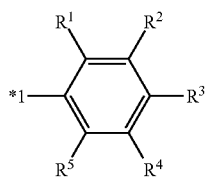

Formula (2)

In Formula (2), $R^1$ to $R^5$ each independently represent a hydrogen atom, a deuterium atom, a halogen atom, a cyano group, a nitro group, a hydroxy group, a mercapto group, an alkyl group, a cycloalkyl group, an alkenyl group, an alkynyl group, a heterocyclic group, an alkoxy group, a cycloalkoxy group, an aryloxy group, an alkylthio group, a group, an aryloxycarbonyl group, a sulfamoyl group, an acyl group, an acyloxy group, an amide group, a carbamoyl group, a ureido group, a sulfinyl group, an alkylsulfonyl group, an arylsulfonyl group, a heteroalylsulfonyl group, an amino group, a fluorinated hydrocarbon group, a triarylsilyl group, a diaryalkylsilyl group, an aryldialkylsilyl group, a trialkylsilyl group, a phosphate group, a a phosphite group, or a phosphono group, these may further have a substituent. At least one of $R^1$ and $R^5$ is a group having a structure represented by the following Formula (3) or (4). *1 represents a binding site to X.

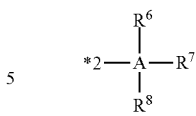

Formula (3)

In Formula (3), A represents a carbon atom or a silicon atom, $R^6$ to $R^8$ each independently represent the same group as $R^1$ to $R^5$ in Formula (2), provided that at least one of $R^6$ to $R^8$ is an alkyl group having 1 or more carbon atoms. *2 represents a bonding site with an adjacent atom.

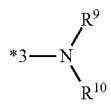

Formula (4)

In Formula (4), $R^9$ and $R^{10}$ each independently represent the same group as $R^1$ to $R^5$ in Formula (2), provided that at least one of $R^1$ to $R^5$ is an alkyl group having 1 or more carbon atoms. *3 represents a bonding site with an adjacent atom. In R1 to R10 in Formulas (2) to (4), adjacent groups may be bonded to each other to form an aliphatic ring.

Hereinafter, specific examples of the fluorescent compound according to the present invention (including compounds other than a fluorescent compound having a structure represented by Formula (1)) will be described, but the present invention is not particularly limited thereto.

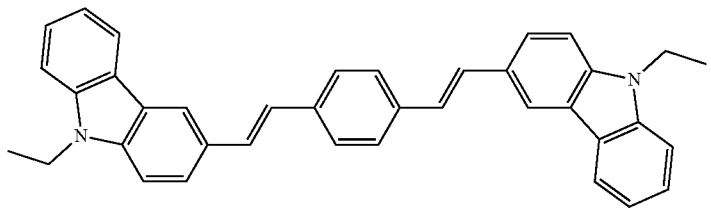

A-1

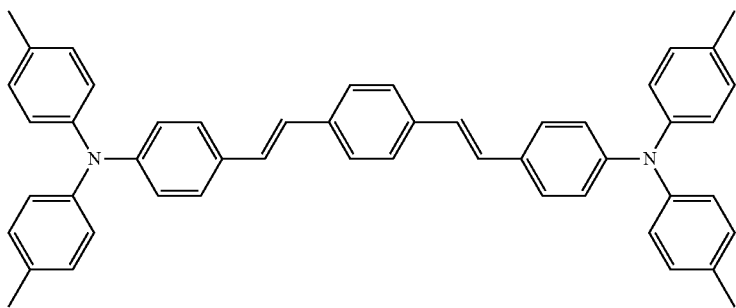

A-2

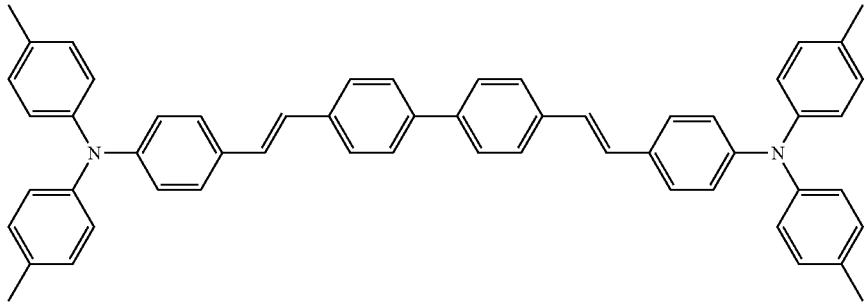

A-3

-continued
A-4
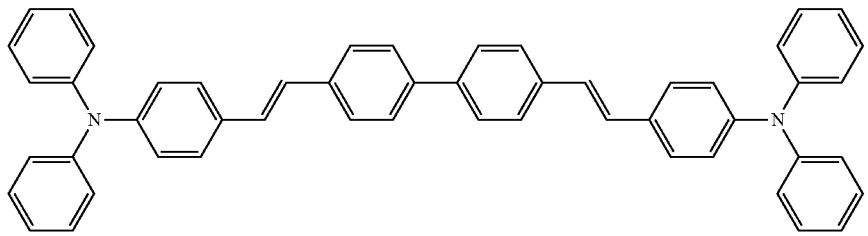
A-5
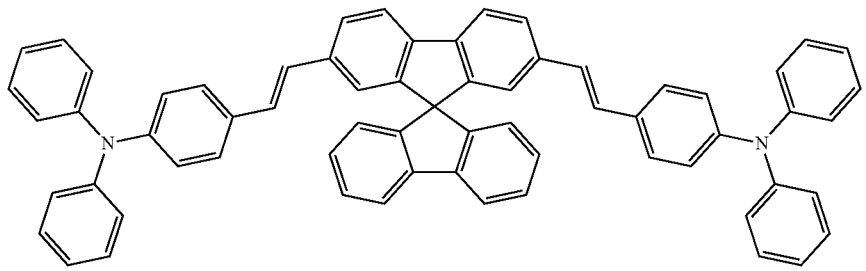
A-6
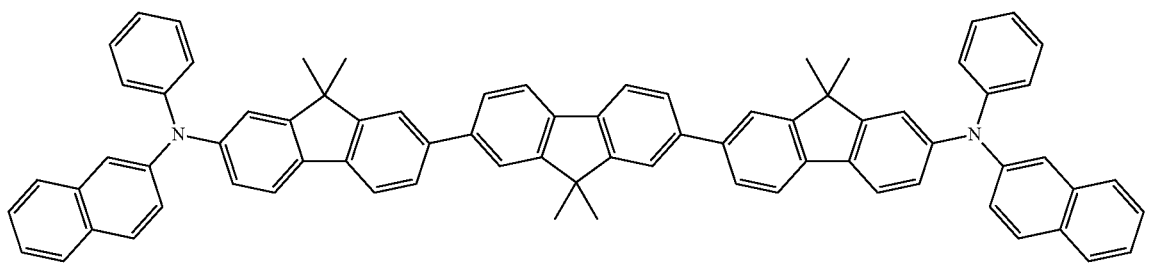
A-7
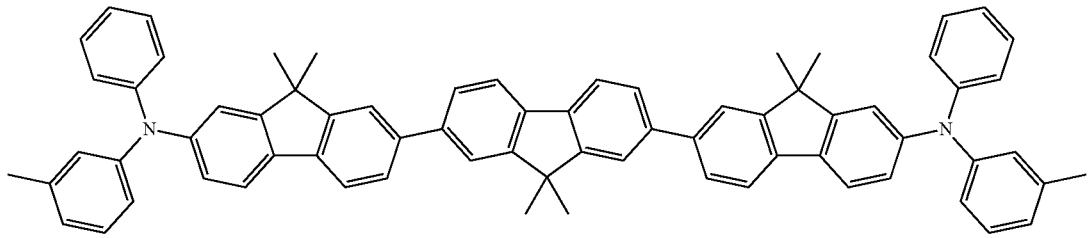
A-8
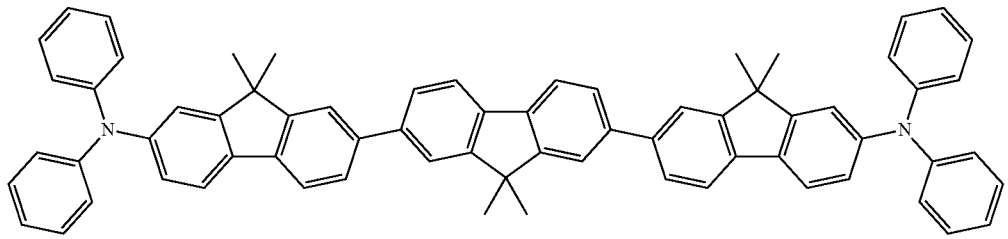
A-9
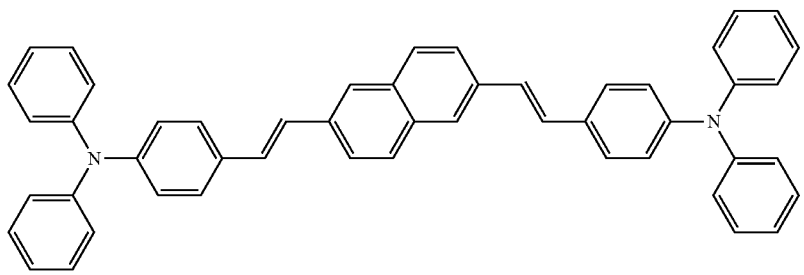

-continued
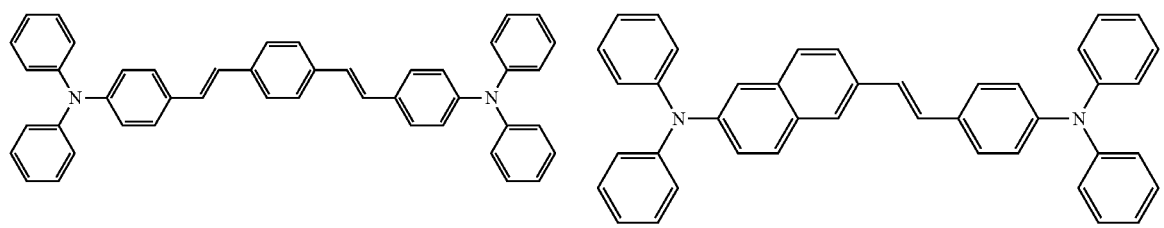
A-10  A-11
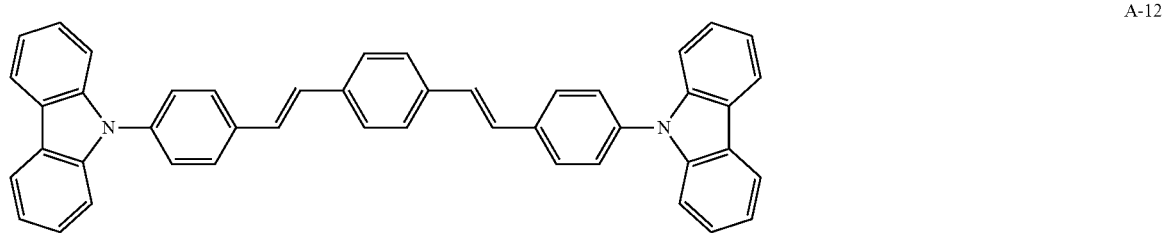
A-12
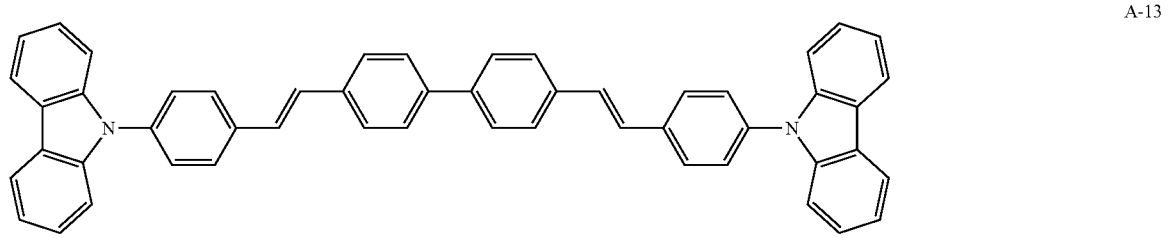
A-13
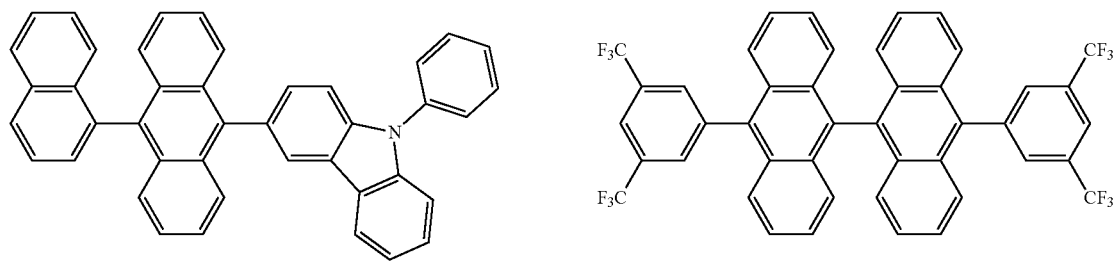
A-14  A-15
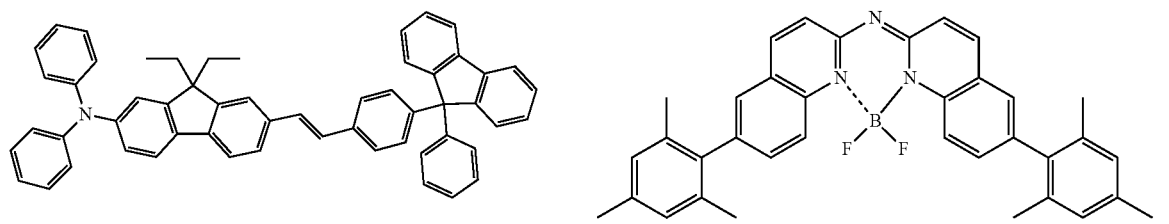
A-16  A-17
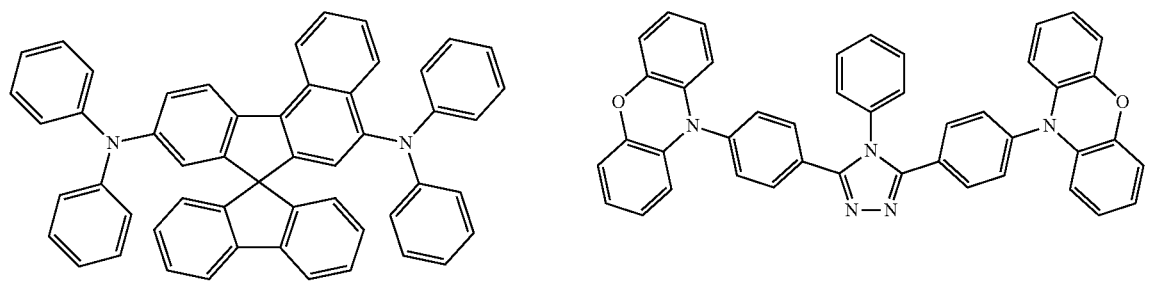
A-18  A-19

-continued
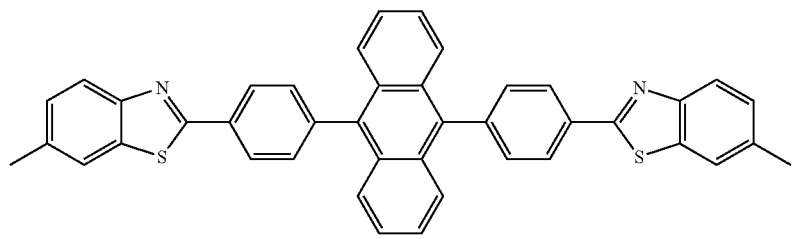
A-20
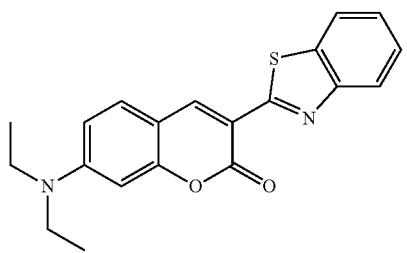
A-21
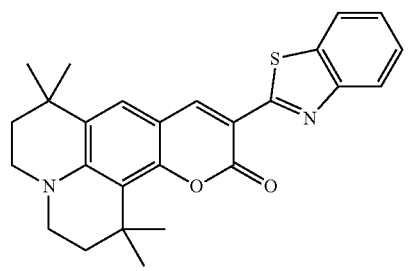
A-22
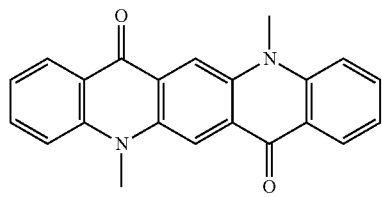
A-23
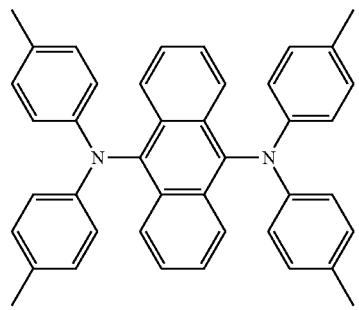
A-24
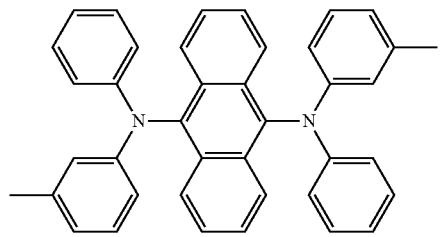
A-25
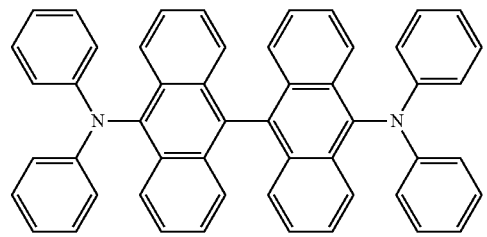
A-26
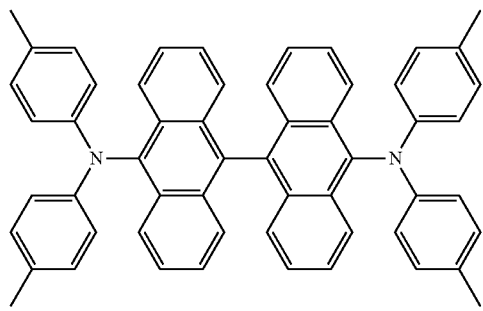
A-27
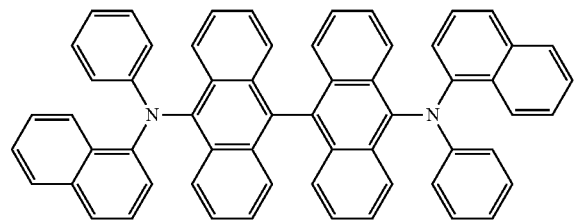
A-28

-continued
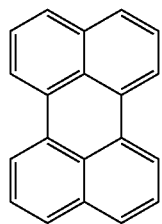
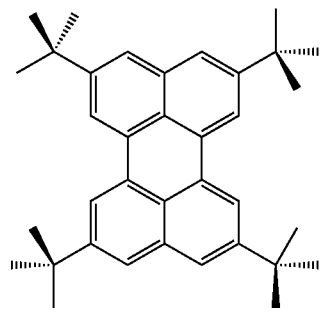
A-29
A-30
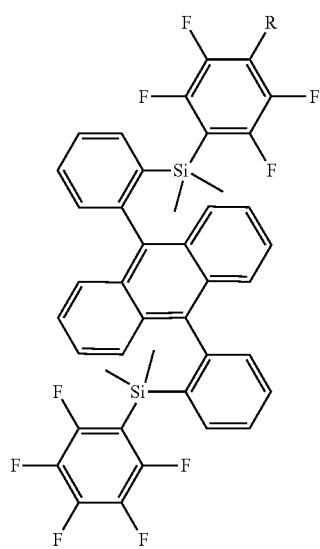
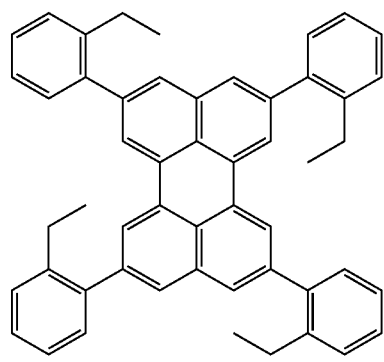
A-31
Example compound 1
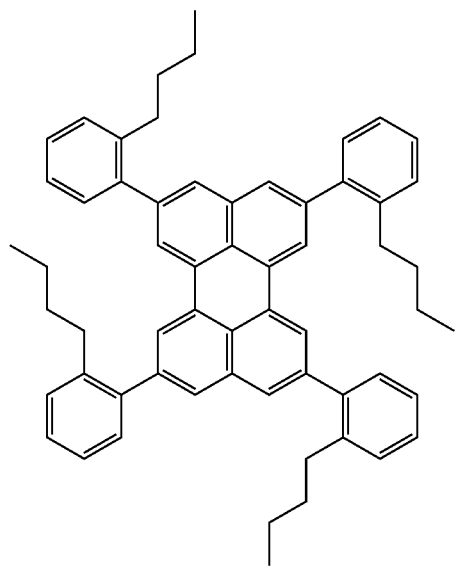
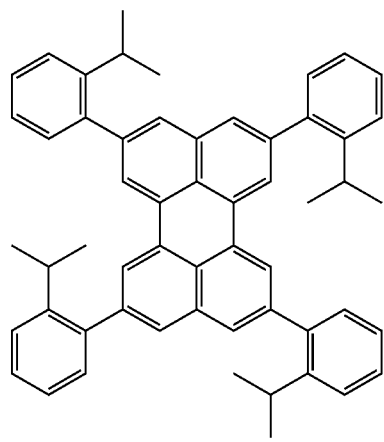
Example compound 2
Example compound 3

-continued
Example compound 4
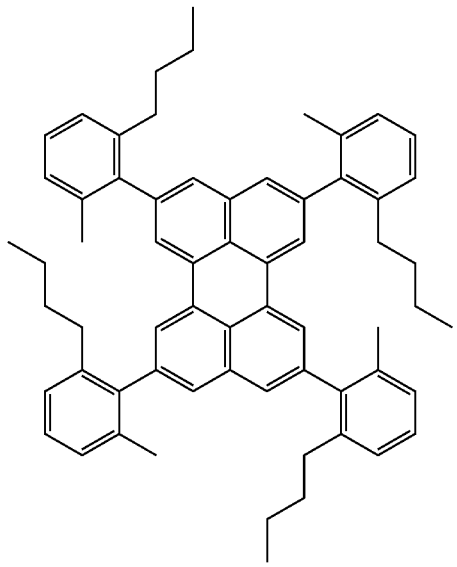
Example compound 5
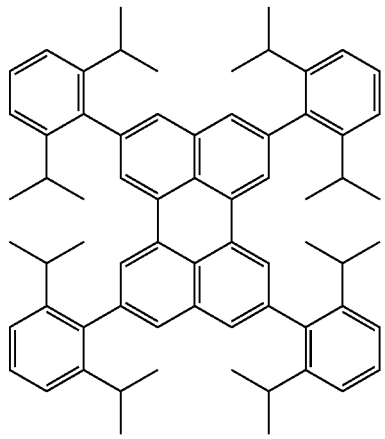
Example compound 6 (F-2)
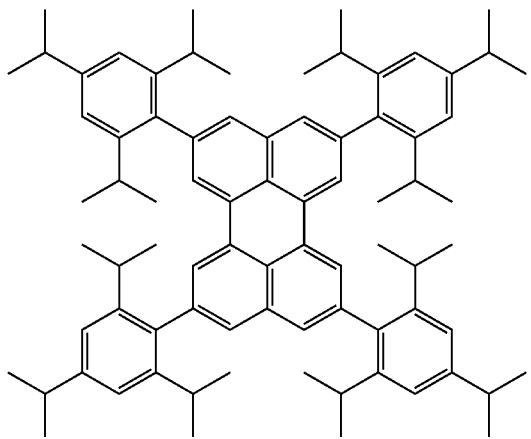
Example compound 7
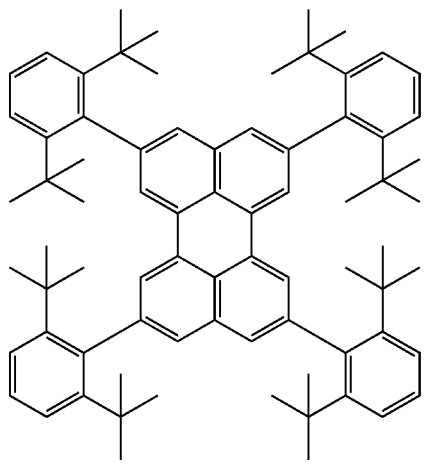
Example compound 8
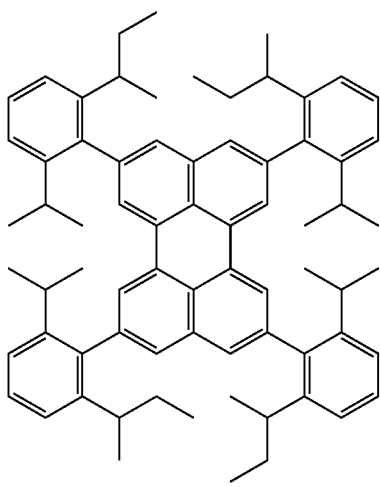
Example compound 9
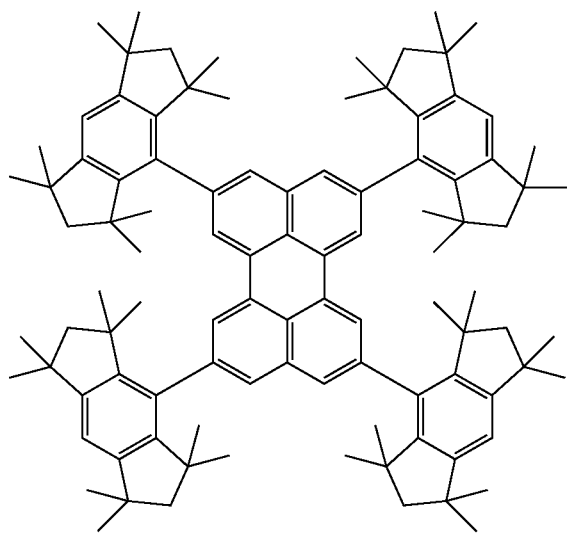

-continued
Example compound 10
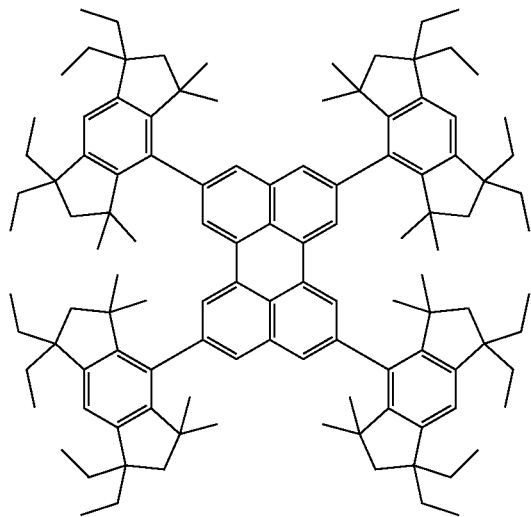
Example compound 11 (F-1)
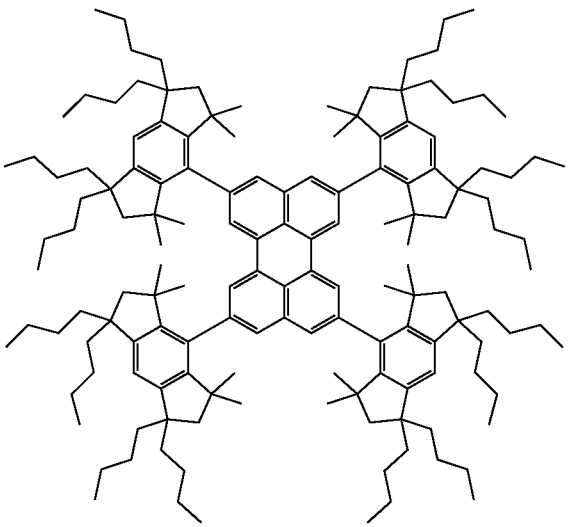
Example compound 12
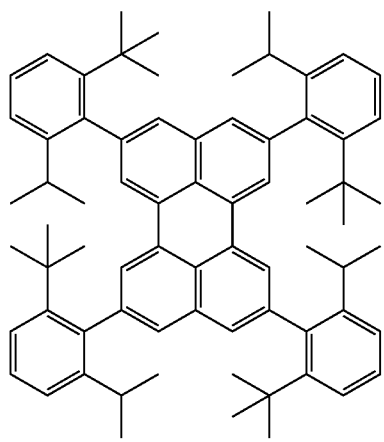
Example compound 13
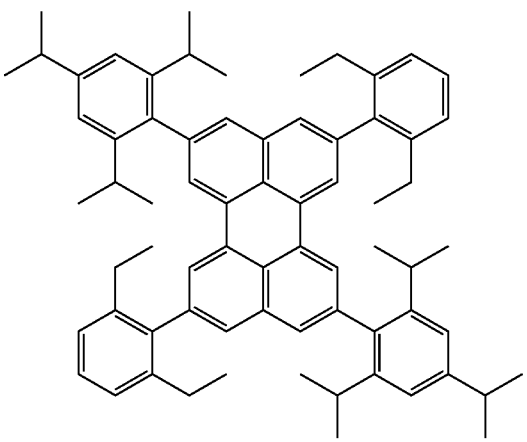
Example compound 14
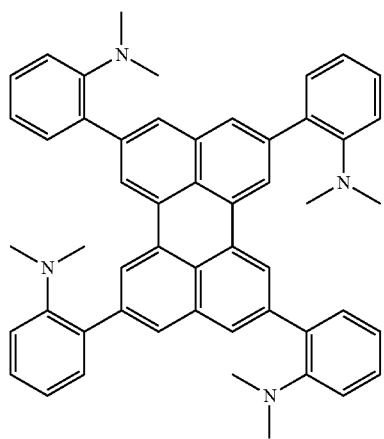
Example compound 15
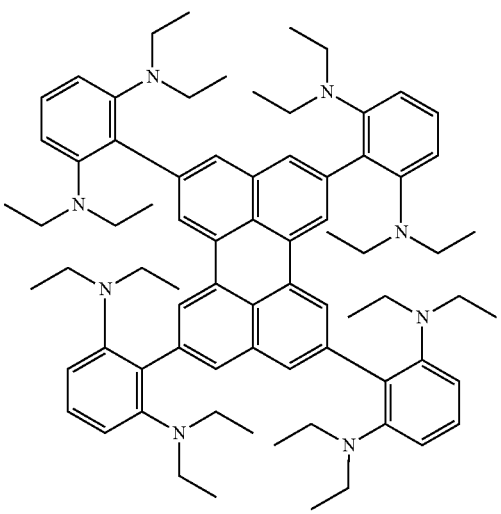

-continued
Example compound 16
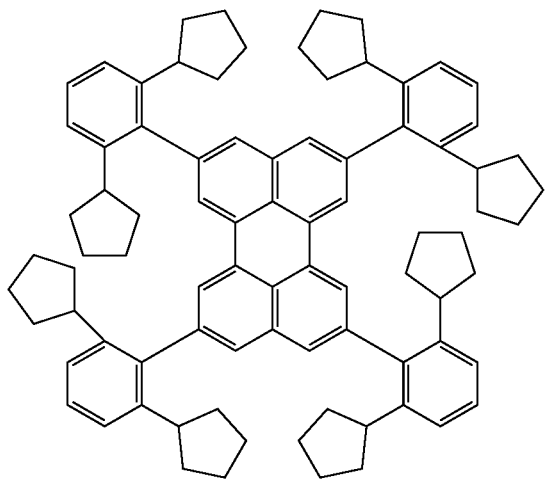
Example compound 17
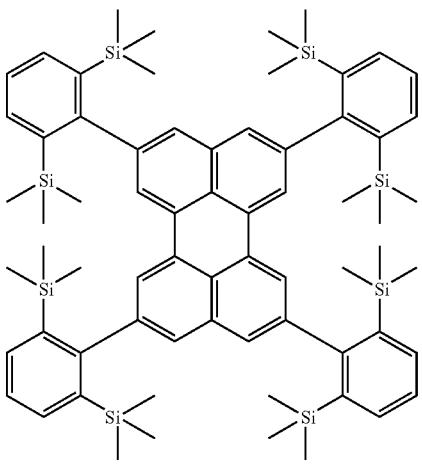
Example compound 18
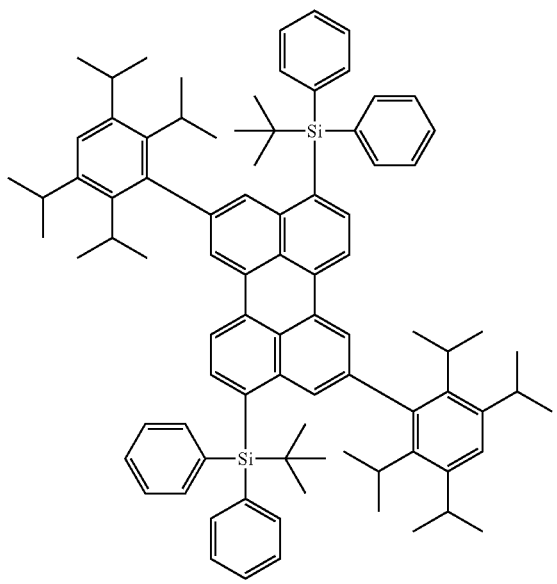
Example compound 19
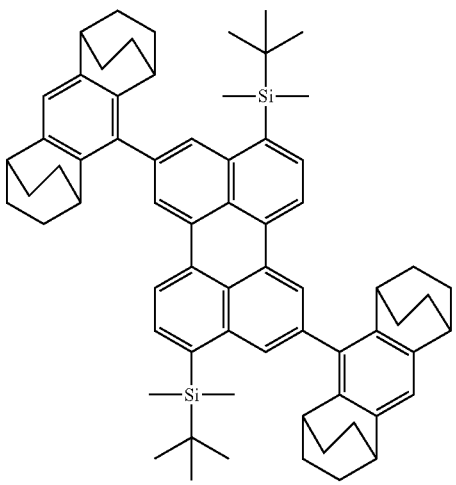
Example compound 20
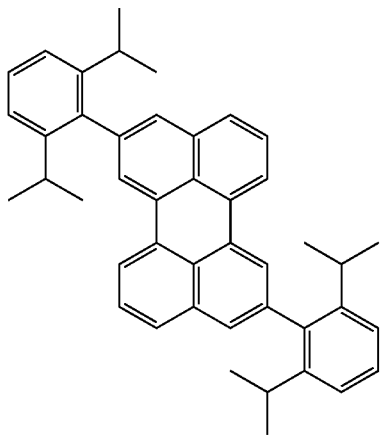
Example compound 21
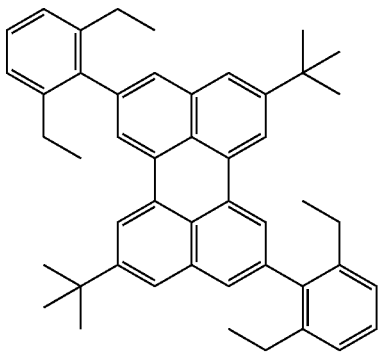

-continued
Example compound 22
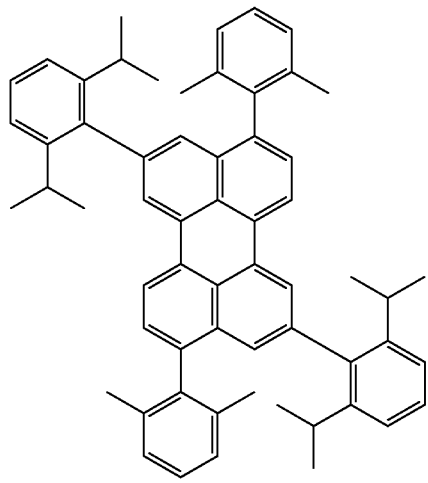
Example compound 23 (F-3)
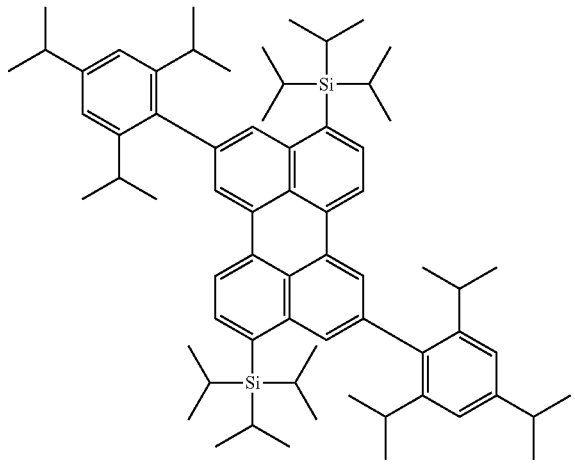
Example compound 24
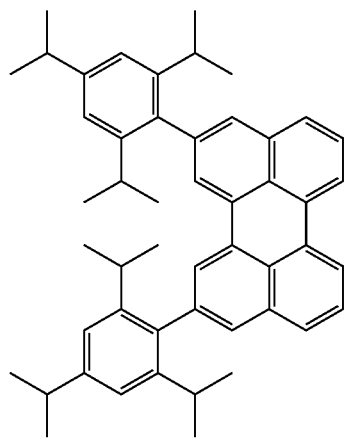
Example compound 25
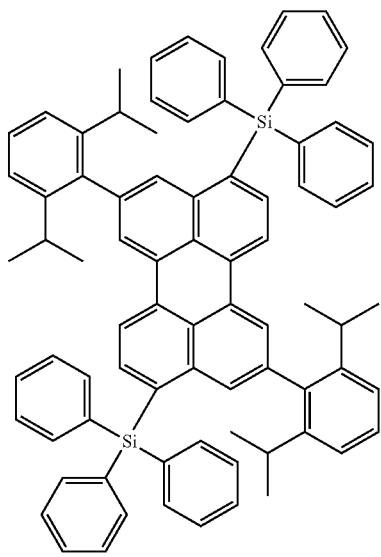
Example compound 26
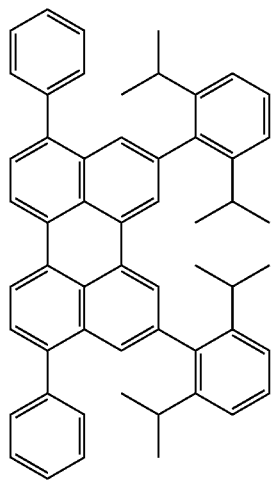
Example compound 27
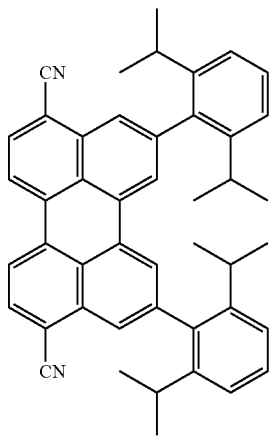

-continued
Example compound 28
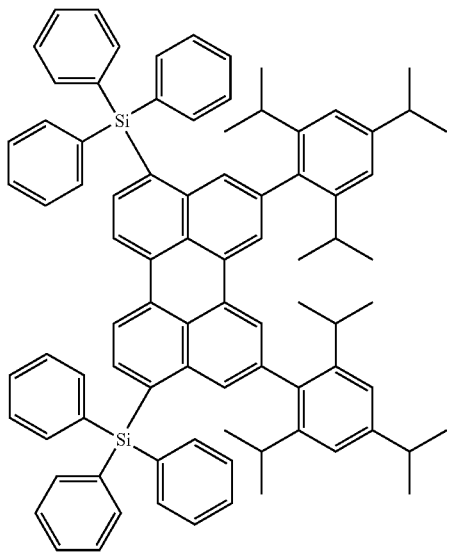
Example compound 29
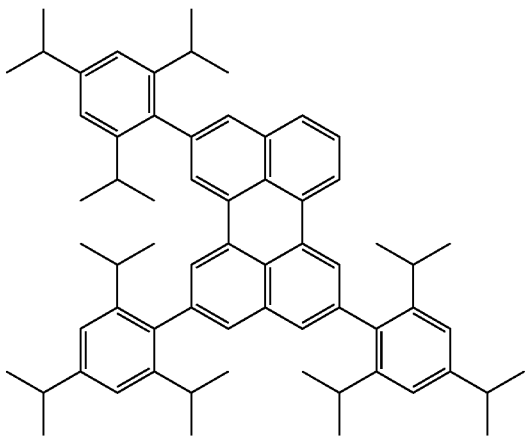
Example compound 30
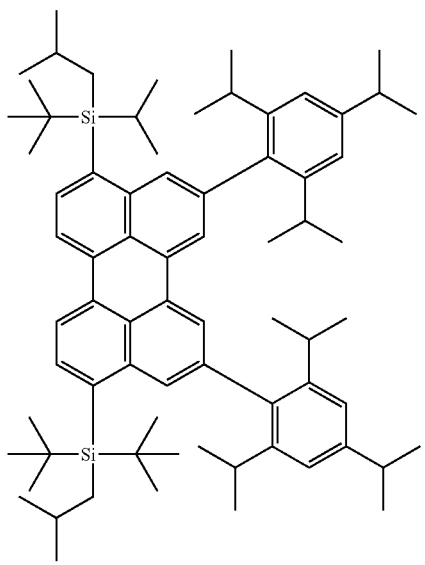
Example compound 31
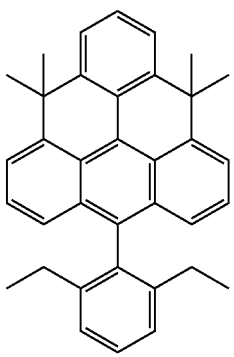
Example compound 32
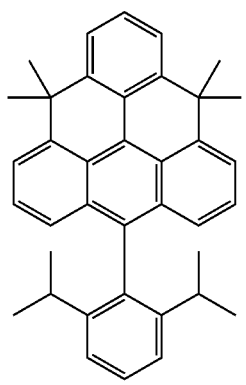
Example compound 33
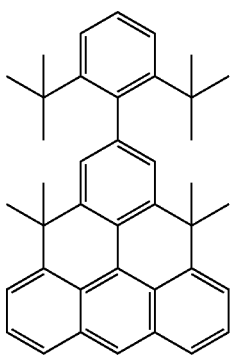

-continued
Example compound 34 (F-4)
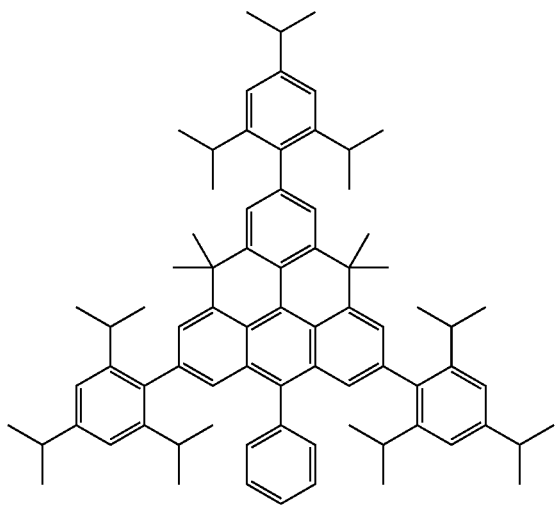
Example compound 35
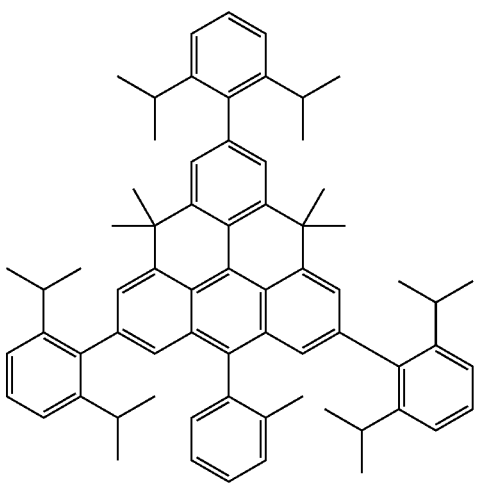
Example compound 36
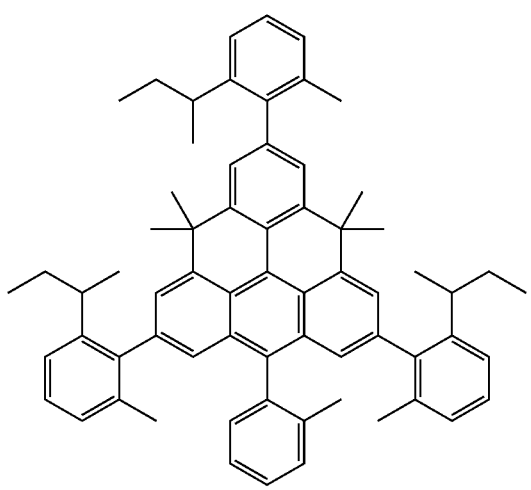
Example compound 37
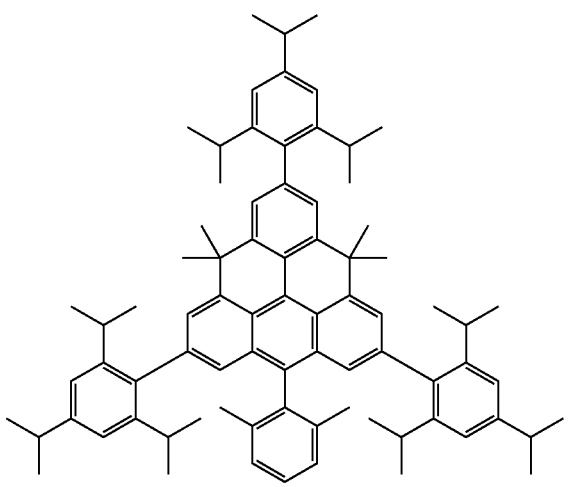
Example compound 38
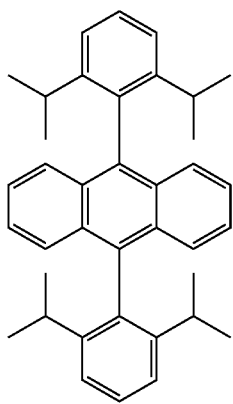
Example compound 39
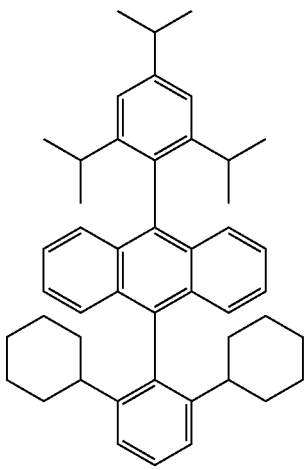

-continued
Example compound 40
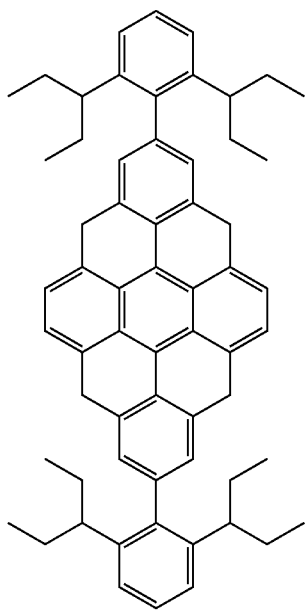
Example compound 41
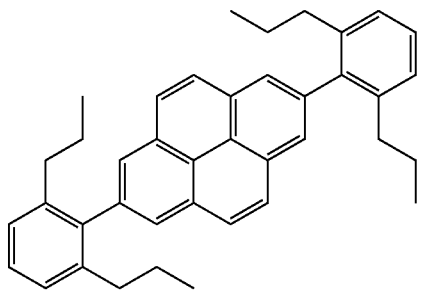
Example compound 42
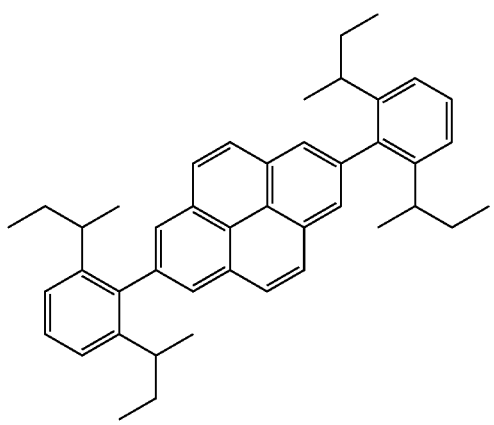
Example compound 43
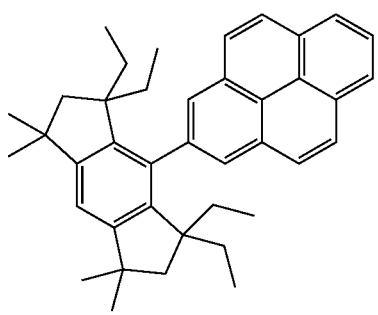
Example compound 44
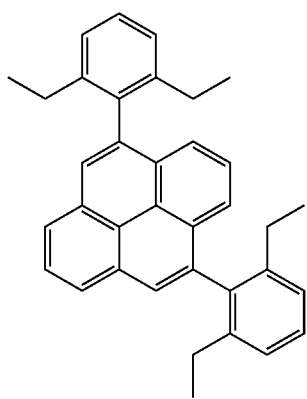
Example compound 45
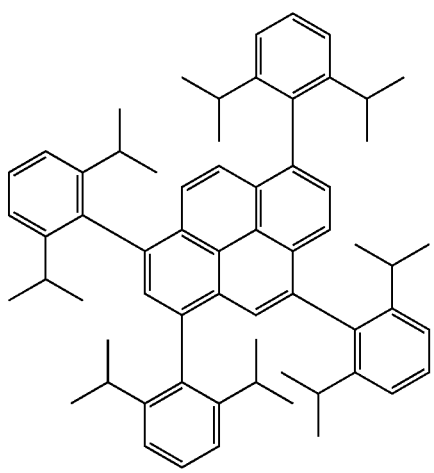

-continued
Example compound 46
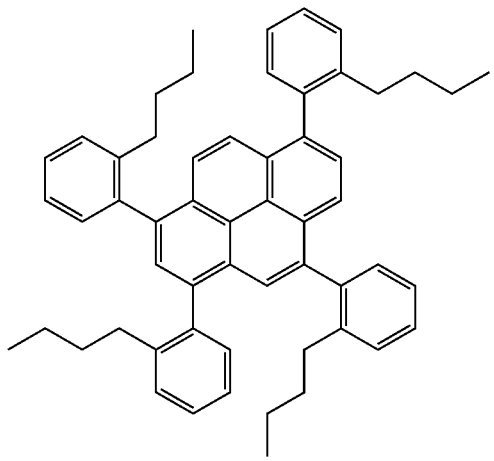
Example compound 47
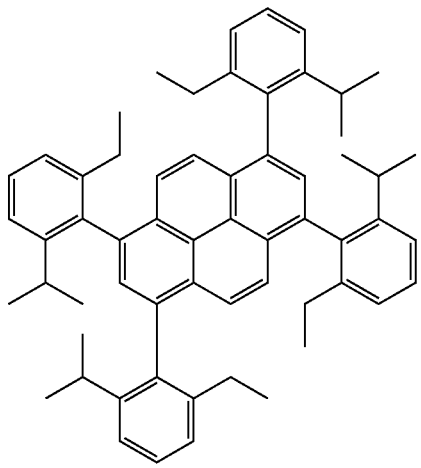
Example compound 48
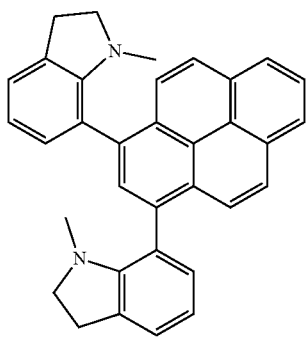
Example compound 49
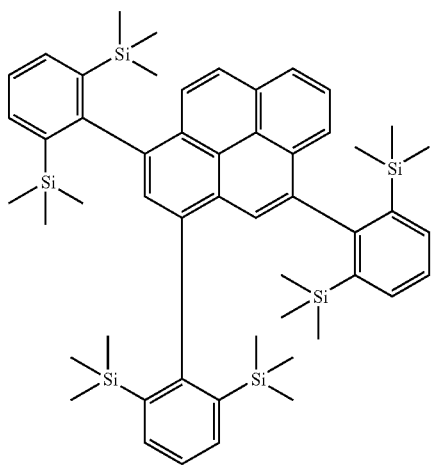
Example compound 50
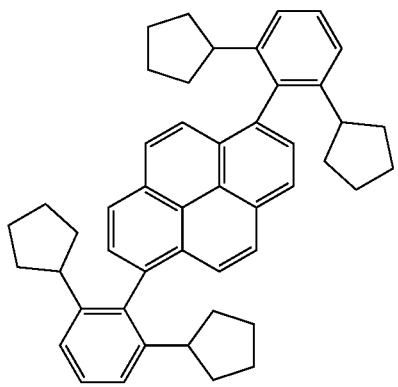
Example compound 51
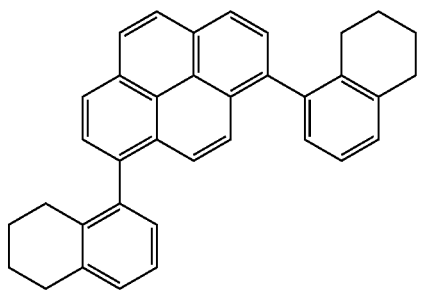

Example compound 52
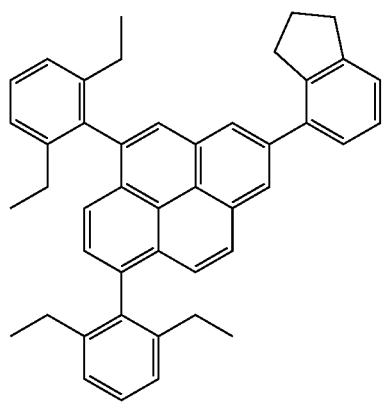
Example compound 53
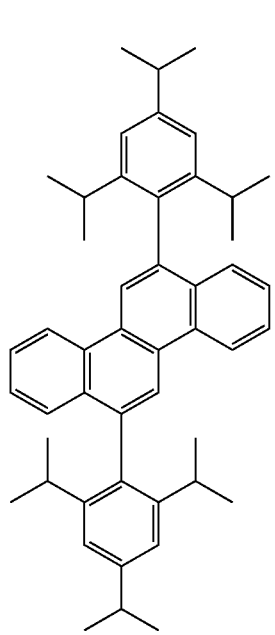
Example compound 54
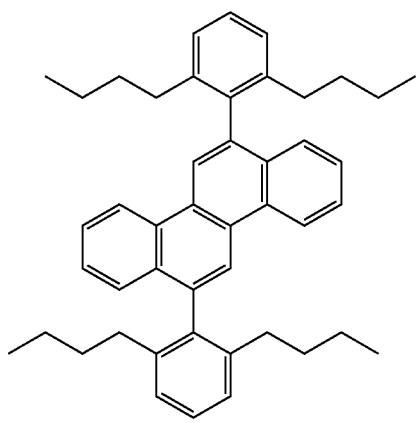
Example compound 55
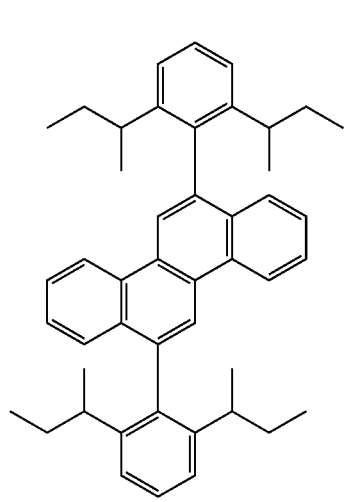
Example compound 56
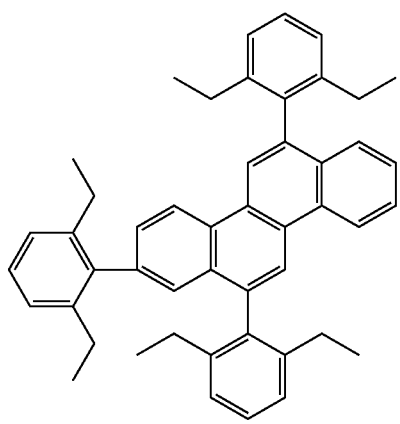

-continued
Example compound 57
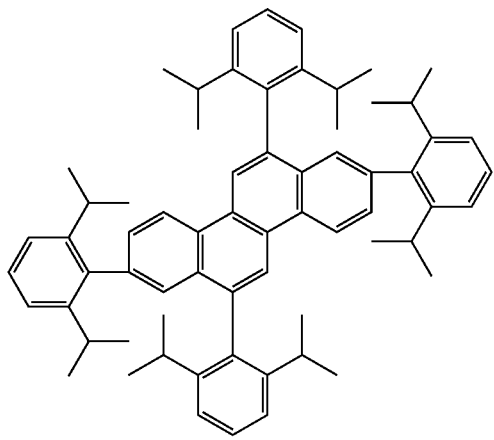
Example compound 58
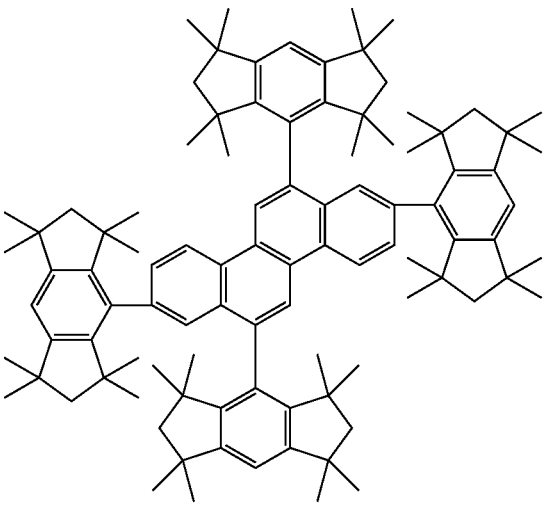
Example compound 59
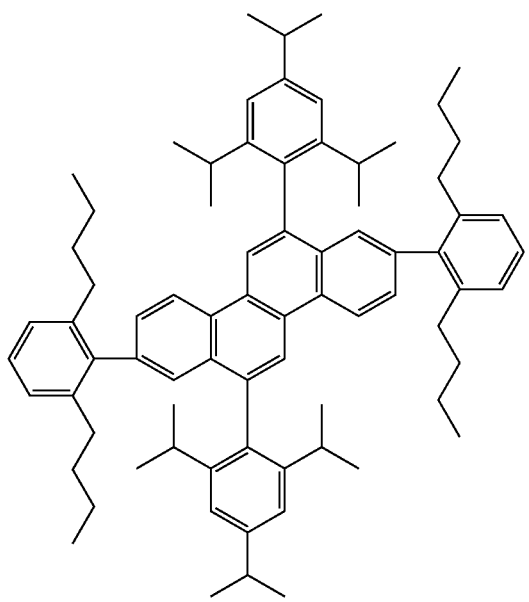
Example compound 60
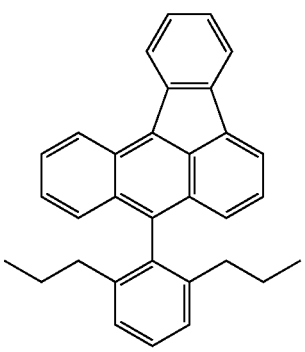
Example compound 61
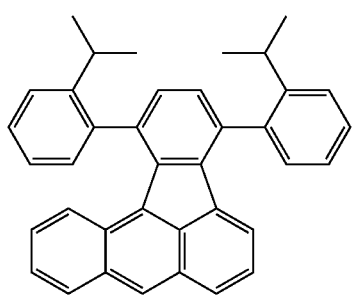
Example compound 62
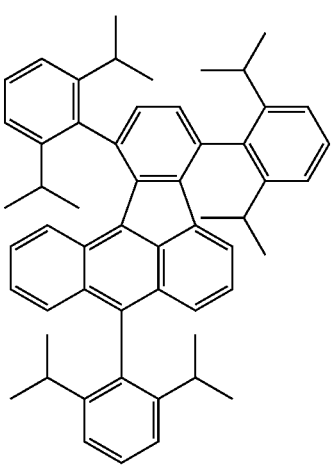

-continued
Example compound 63
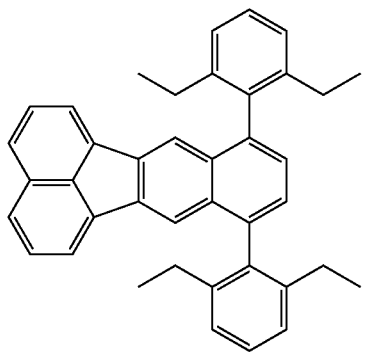
Example compound 64
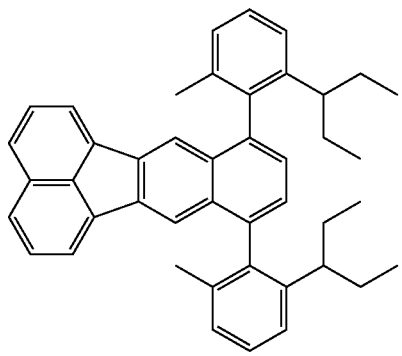
Example compound 65
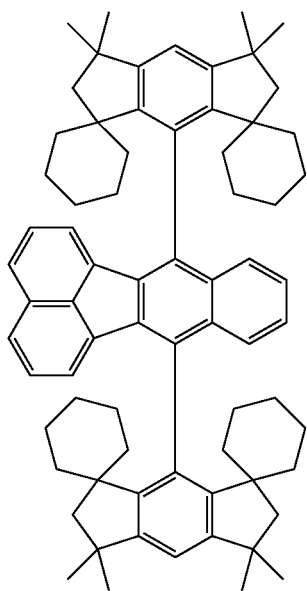
Example compound 66
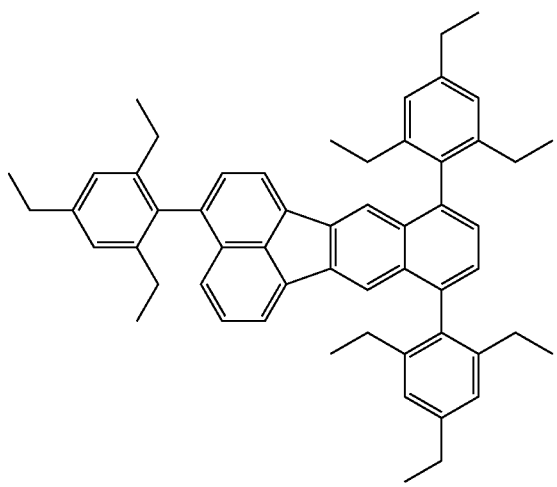
Example compound 67
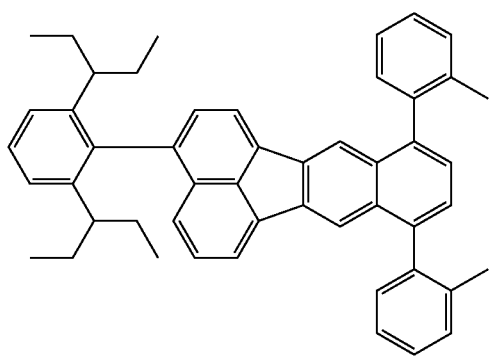
Example compound 68
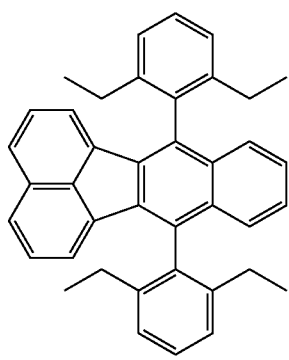

-continued
Example compound 69
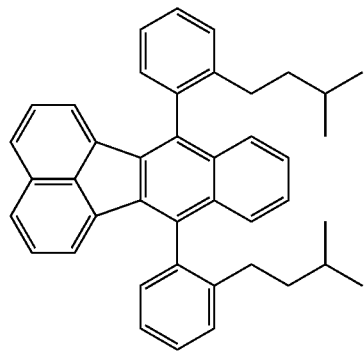
Example compound 70
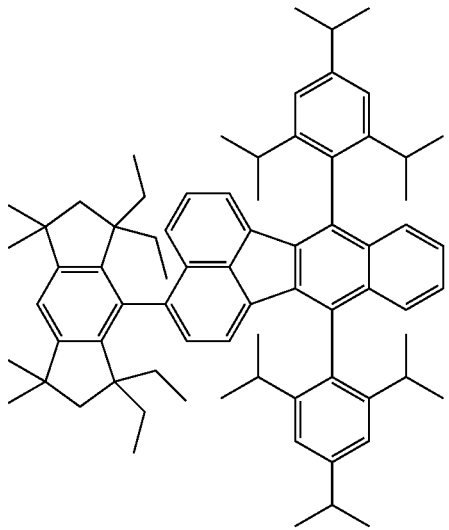
Ezample compound 71
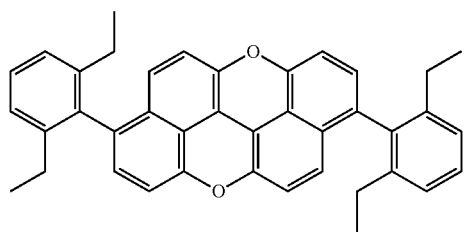
Example compound 72
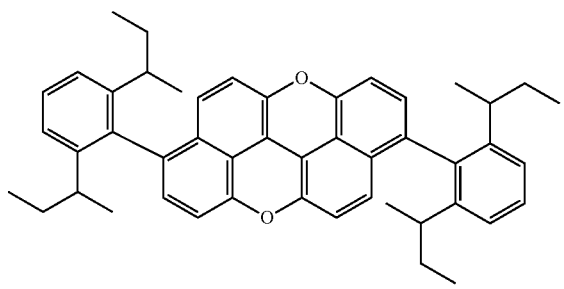
Example compound 73
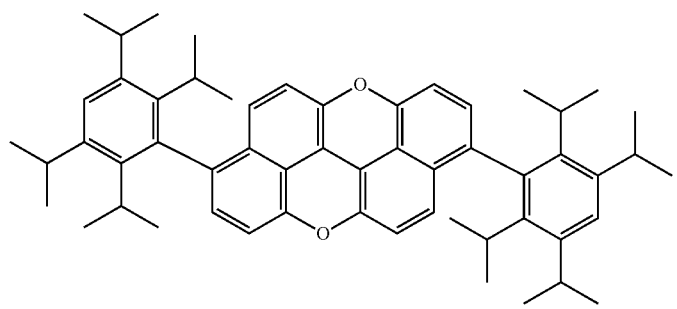
Example compound 74
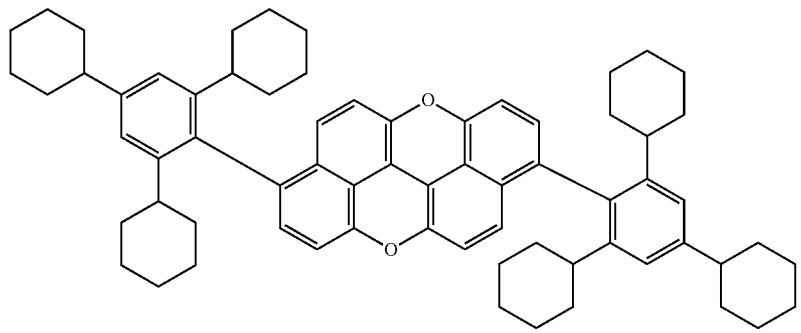

-continued
Example compound 75
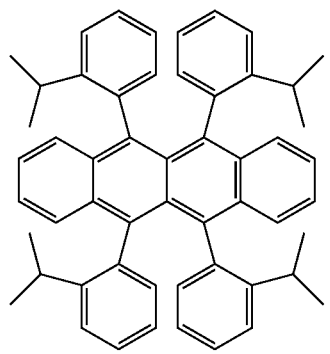
Example compound 76
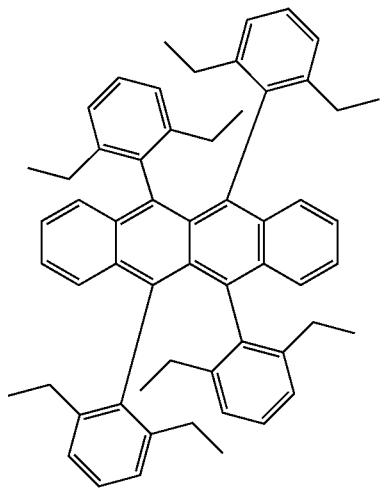
Example compound 77
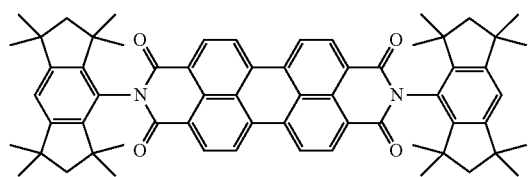
Example compound 78 (F-6)
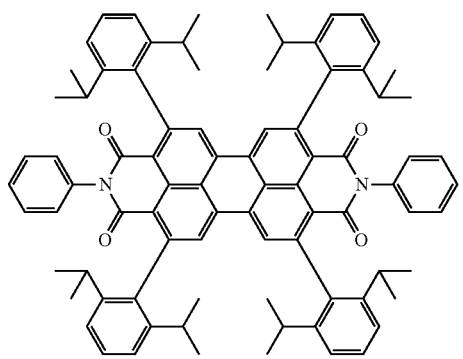
Example compound 79
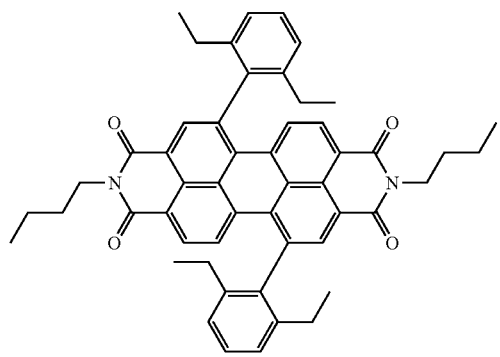
Example compound 80
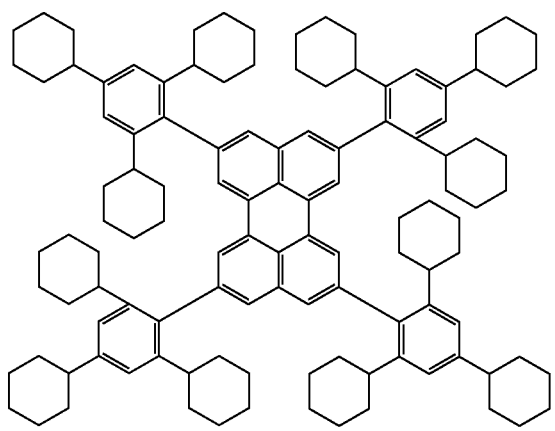

-continued
Example compound 81
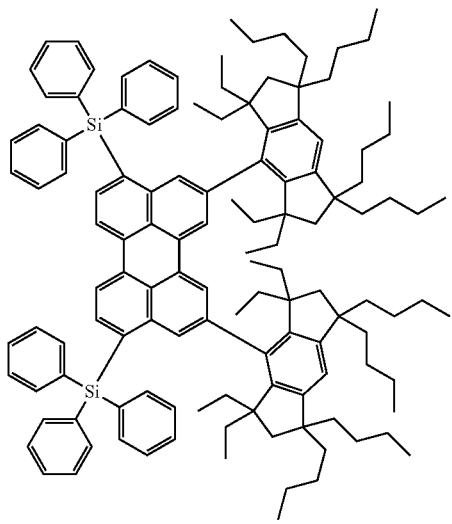
Example compound 82
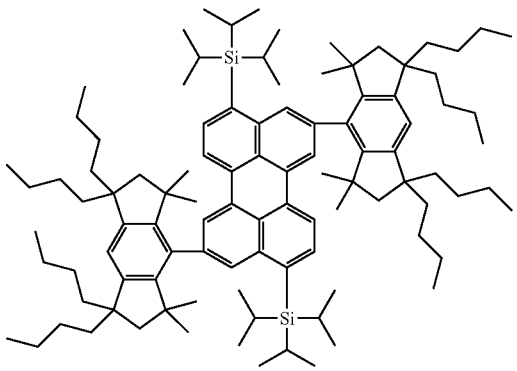
Example compound 83
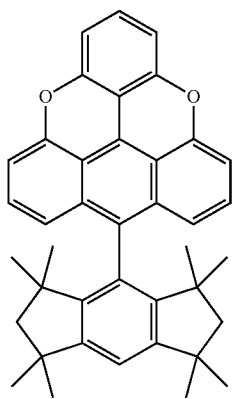
Example compound 84
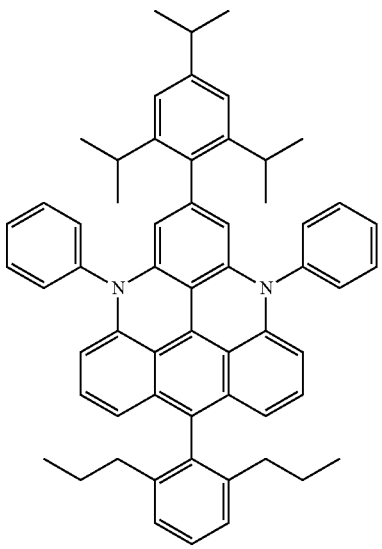
Example compound 85
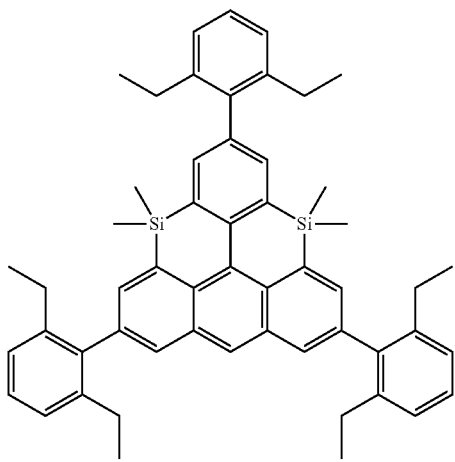
Example compound 86
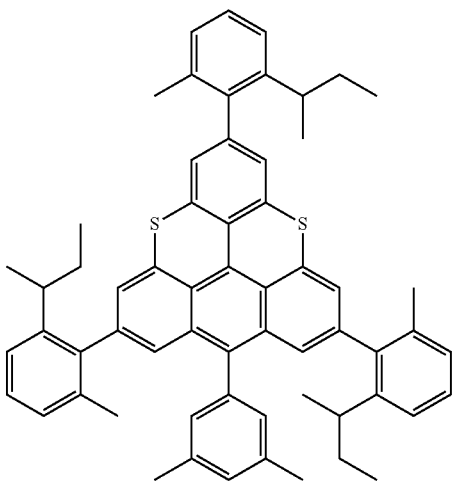

Example compound 87
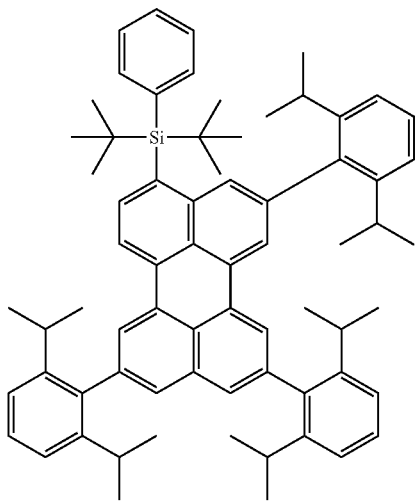
Example compound 88
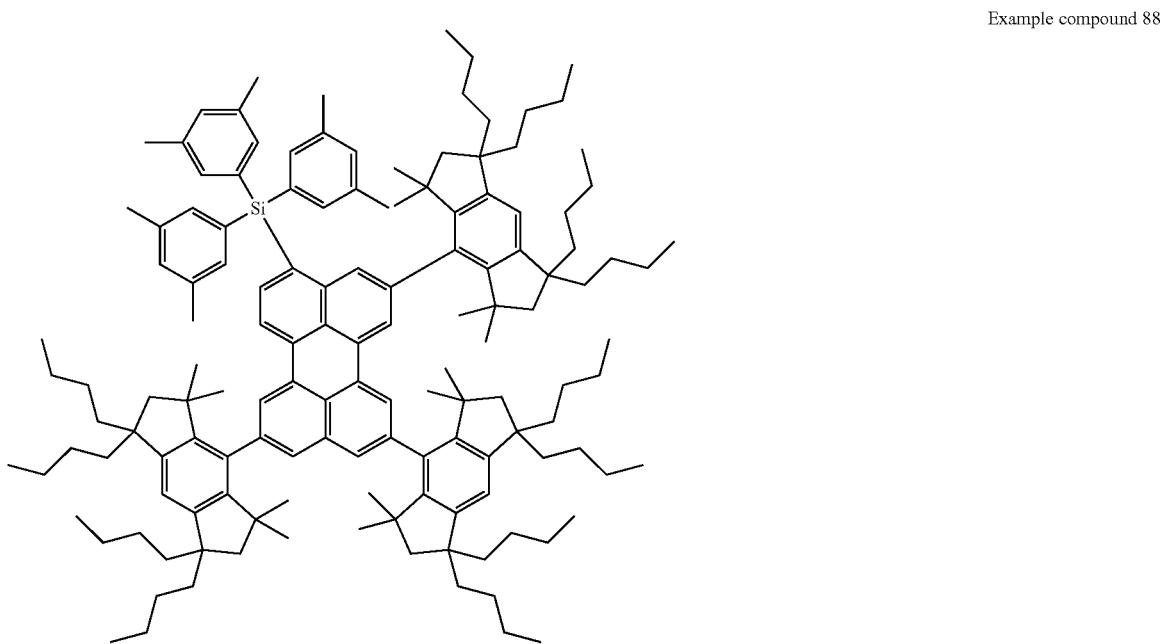
Example compound 89
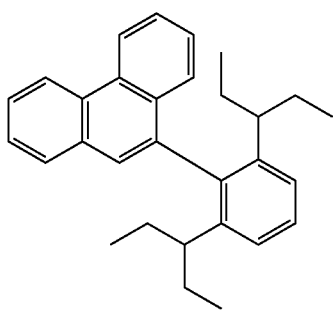
Example compound 90
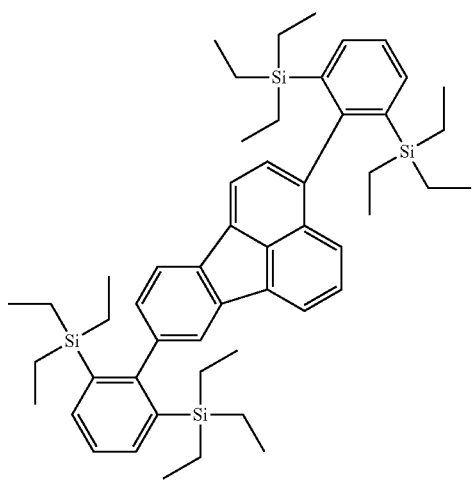

-continued
Example compound 91
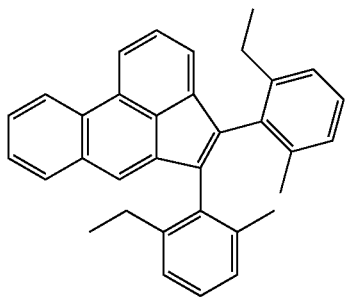
Example compound 92
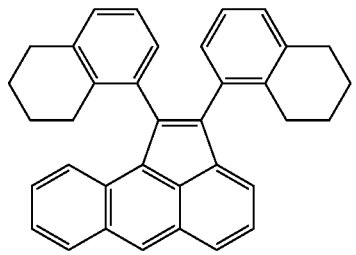
Example compound 93
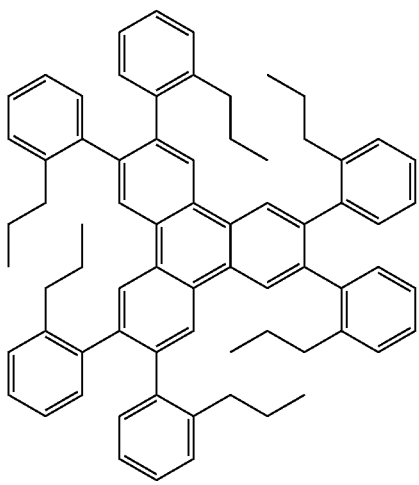
Example compound 94
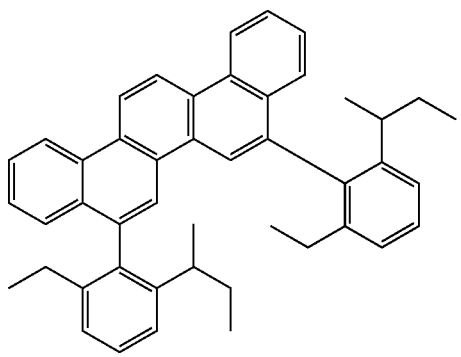
Example compound 95
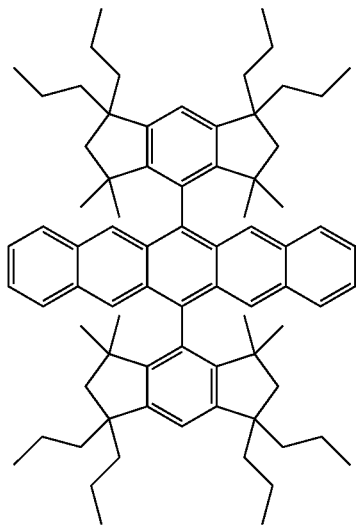
Example compound 97
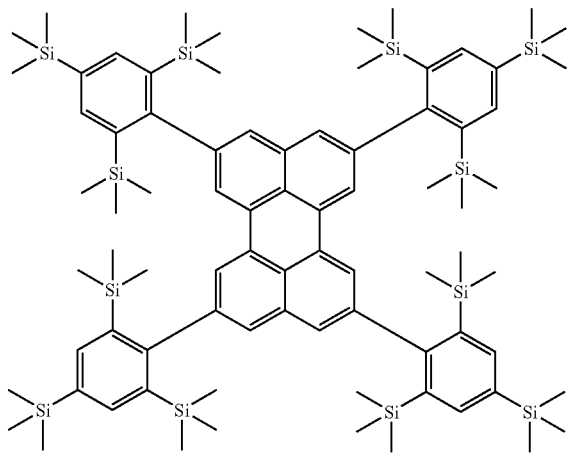

-continued
Example cmpound 99
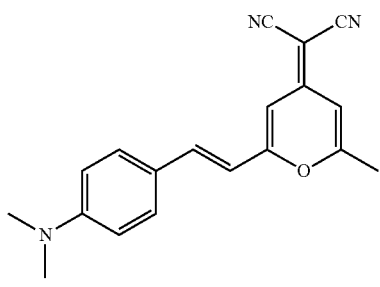
Example compound 100
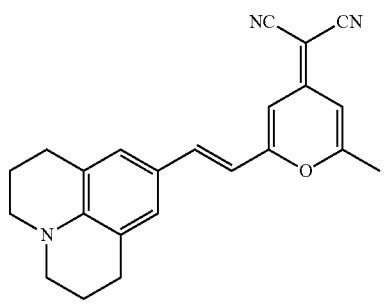
Example compound 101
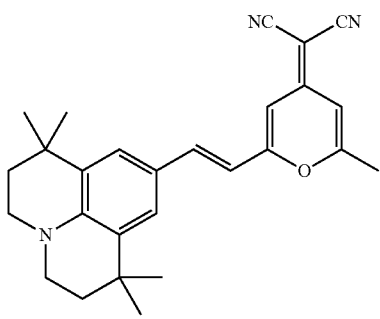
Example compound 102 (F-8)
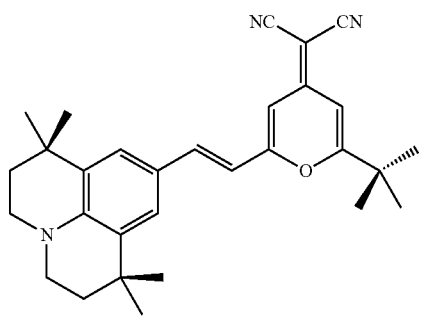
Example compound 103
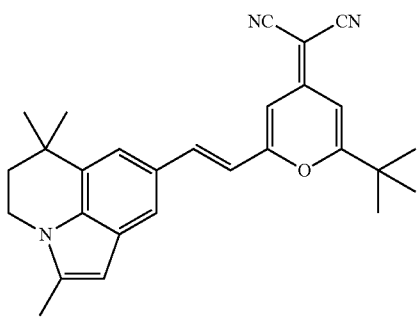
Example compound 104
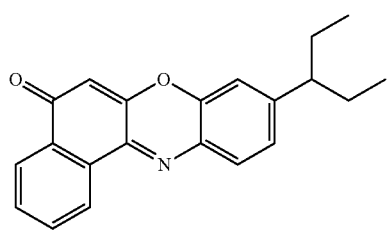
Example compound 105
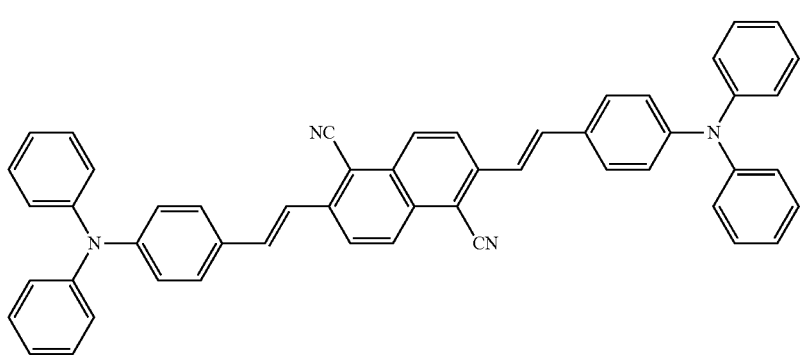

-continued
Example compound 106
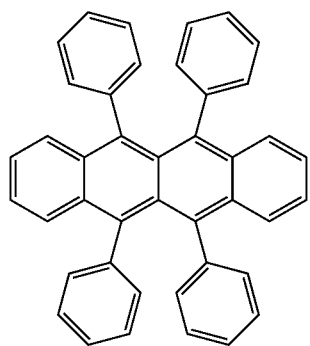
Example compound 107
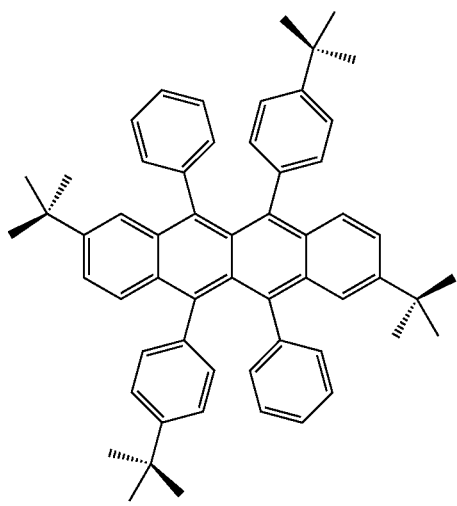
F-1 (Example compound 11)
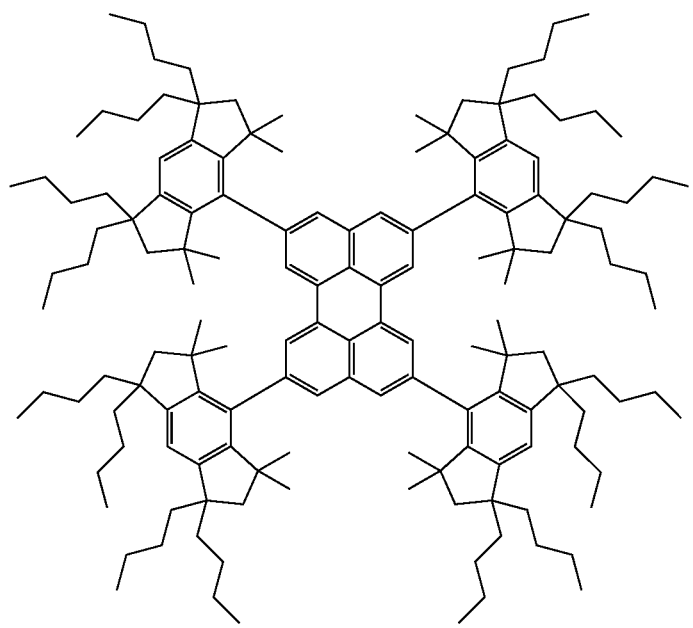
F-2 (Example compound 6)
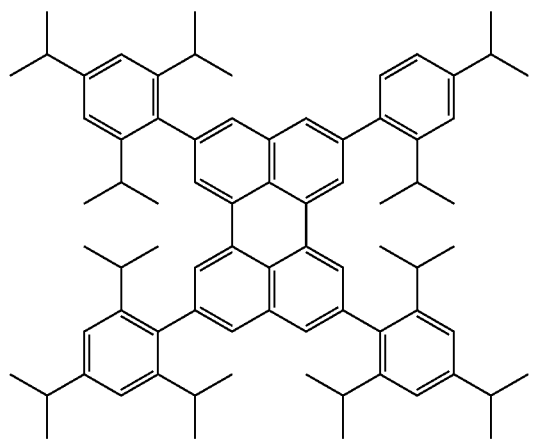
F-3 (Example compound 23)
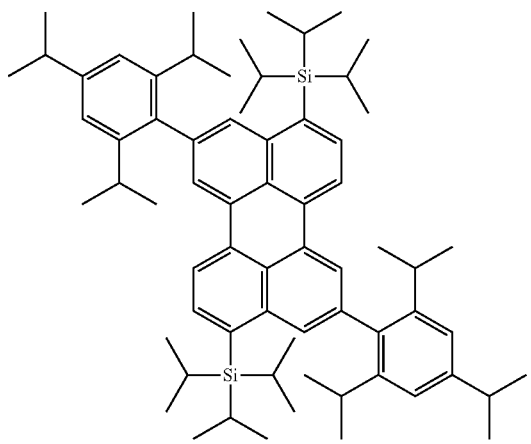

F-4 (Example compound 34)

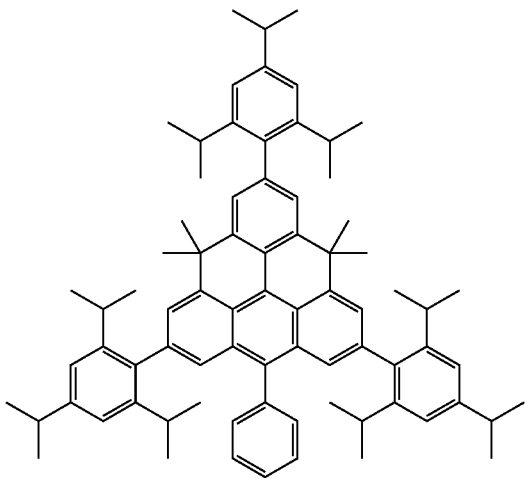

F-5

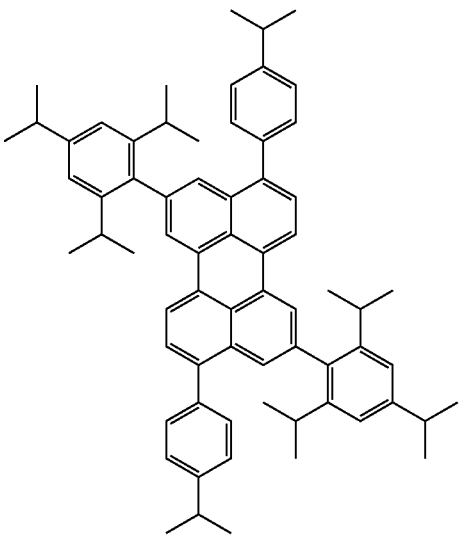

F-6 (Example compound 78)

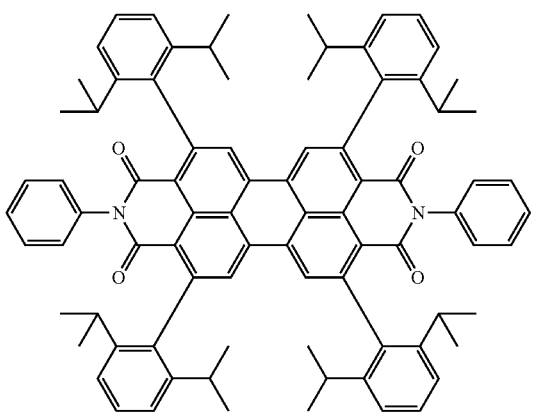

F-7

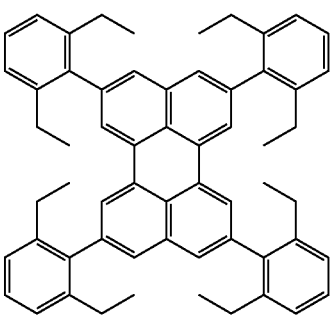

F-8 (Example compound 102)

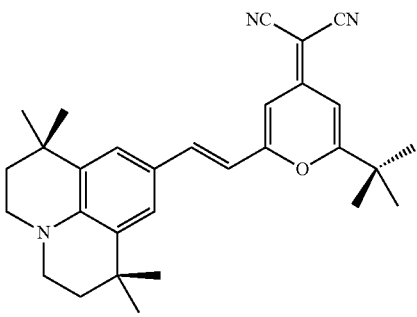

«Phosphorescent Compound»

The phosphorescent compound according to the present invention is a compound containing a heavy atom and capable of emitting light from triplet excitation, and is not particularly limited as long as light emission from triplet excitation is observed. The phosphorescent compound according to the present invention is preferably a compound having a structure represented by the following Formula (5).

This makes it possible not only to produce a phosphorescent compound having a more stable exciton, but also to increase the overlap integral value between the emission spectrum of the phosphorescent compound and the absorption spectrum of the fluorescent compound, and as a result, it is possible to obtain a luminescent film which can more effectively use the exciton for light emission and, consequently, can extend the lifetime of the element.

Formula (5)

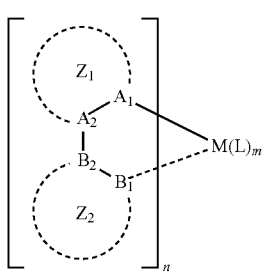

In Formula (5): M represents iridium (Ir) or platinum (Pt); $A_1$, $A_2$, $B_1$ and $B_2$ each independently represent a carbon atom or a nitrogen atom; a ring $Z_1$ represents a 6-membered aromatic hydrocarbon ring, or a 5- or 6-membered aromatic heterocyclic ring formed with $A_1$ and $A_2$, or an aromatic condensed ring containing at least one of the aforesaid rings; a ring $Z_2$ represents a 5- or 6-membered aromatic heterocyclic ring formed with $B_1$ and $B_2$, or an aromatic condensed ring containing at least one of the aforesaid rings; the carbon atoms of the ring $Z_1$ and the ring $Z_2$ may be carbene carbon atoms; among a bond between $A_1$ and M, and a bond between $B_1$ and M, one is a coordinate bond and the other is a covalent bond; the ring $Z_1$ and the ring $Z_2$ each independently may have a substituent; the substituent of the ring $Z_1$ and the substituent of the ring $Z_{12}$ may be bonded to form a condensed ring structure, and ligands represented by the ring $Z_1$ and the ring $Z_2$ may be linked to each other; L represents a monoanionic bidentate ligand coordinated to M, and L may have a substituent; m represents an integer of 0 to 2, n represents an integer of 1 to 3, when M represents iridium (Ir), m+n is 3, and when m represents platinum (Pt), m+n is 2, when morn is 2 or more, the ligands represented by the ring $Z_1$ and the ring $Z_2$, or L may be the same or different; the ligands represented by the ring $Z_1$ and the ring $Z_2$ may be linked to L.

The ring $Z_2$ is preferably a 5-membered aromatic heterocyclic ring, and at least one of $B_1$ and $B_2$ is preferably a nitrogen atom. The compound having the structure represented by Formula (5) is preferably a compound having the structure represented by the following Formula (DP-1).

Formula (DP-1)

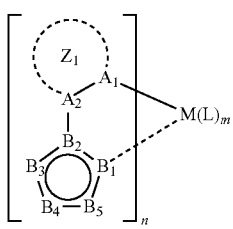

In Formula (DP-1), M, $A_1$, $A_2$, $B_1$, $B_2$, ring $Z_1$, L, m, and n are synonyms for M, $A_1$, $A_2$, $B_1$, $B_2$, ring $Z_1$, L, m, and n in Formula (5).

$B_3$ to $B_5$ are a group of atoms forming an aromatic heterocycle, each independently representing a carbon atom, a nitrogen atom, an oxygen atom or a sulfur atom which may have a substituent. Substitution groups in $B_3$ to $B_5$ include those synonymous with those of the ring $Z_1$ and ring $Z_2$ in Formula (5) described above.

The aromatic heterocycle formed of $B_1$ to $B_5$ in the Formula (DP-1) is preferably represented by any one of the following Formulas (DP-1a), (DP-1b) and (DP-1c).

Formula (DP-1a)

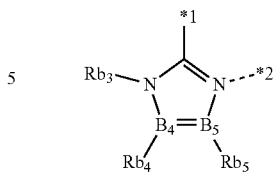

Formula (DP-1b)

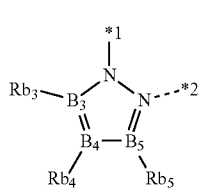

Formula (DP-1c)

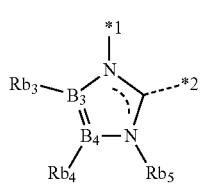

In Formulas (DP-1a), (DP-1b) and (DP-1c), *1 represents a bond site with $A_2$ of Formula (DP-1), and *2 represents a binding site with M. $Rb_3$ to $Rb_5$ represent a hydrogen atom or a substituent, and the substituent represented by $Rb_3$ to $Rb_5$ is a group that is synonymous with the substituent of the ring $Z_1$ and ring $Z_2$ in Formula (5) described above. $B_4$ and $B_5$ in Formula (DP-1a) are a carbon atom or a nitrogen atom, more preferably, at least one of $B_4$ and $B_5$ is a carbon atom. $B_3$ to $B_5$ in Formula (DP-1b) are a carbon atom or a nitrogen atom, and more preferably, at least one of $B_3$ to $B_5$ is a carbon atom. $B_3$ and $B_4$ in Formula (DP-1c) are a carbon atom or a nitrogen atom, more preferably, at least one of $B_3$ and $B_4$ is a carbon atom, it is more preferable that a substituent represented by $Rb_3$ and $Rb_4$ is further bonded to each other to form a condensed ring structure, it is preferable that the condensed ring structure newly formed in Formula (DP-1c) is an aromatic ring, and any one of a benzimidazopyridine ring, an imidazopyrazine ring, and a purine ring is preferable. $Rb_5$ is preferably an alkyl group or an aryl group, and more preferably $Rb_5$ is a phenyl group.

The phosphorescent compound according to the present invention may be a compound having a structure represented by the following Formula (6).

Formula (6)

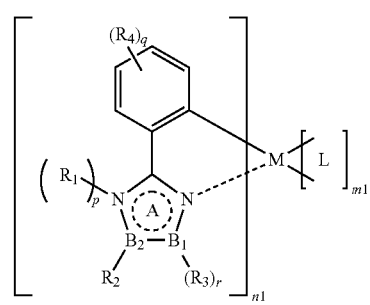

In Formula (6), a ring A represents a triazole ring; $B_1$ and $B_2$ each represent a carbon atom or a nitrogen atom; $R_1$ represents a substituent, and p represents an integer of 0 or 1; $R^2$ represents a substituent; $R^3$ represents a hydrogen atom or a substituent, and r represents an integer of 0 or 1; $R^4$ represents a substituent, and q represents an integer of 1 to 4; M represents iridium (Ir) or platinum (Pt); L represents any ligand capable of coordinating with M; n1 represents an integer of 1 to 3; and m1 represents an integer of 0 to 2.

In Formula (6), a ring A represents a triazole ring, and $B_1$ and $B_2$ each represent a carbon atom or a nitrogen atom. However, when $B_1$ is a nitrogen atom, $B_2$ represents a carbon atom, and when $B_2$ is a nitrogen atom, $B_1$ represents a carbon atom.

Examples of the substituent represented by $R_1$ in Formula (6) include: an alkyl group (for example, a methyl group, an ethyl group, a propyl group, an isopropyl group, a tert-butyl group, a pentyl group, a hexyl group, an octyl group, a dodecyl group, a tridecyl group, a tetradecyl group, and a pentadecyl group); a cycloalkyl group (for example, a cyclopentyl group, and a cyclohexyl group); an alkenyl group (for example, a vinyl group, an allyl group); an alkynyl group (for example, an ethynyl group and a propargyl group); an aromatic hydrocarbon group (also called an aromatic hydrocarbon ring, an aromatic carbon ring group or an aryl group, for example, a phenyl group, a p-chlorophenyl group, a mesityl group, a tolyl group, a xylyl group, a naphthyl group, an anthryl group, an azulenyl group, an acenaphthenyl group, a fluorenyl group, a phenantolyl group, an indenyl group, a pyrenyl group, and a biphenyl group); an aromatic heterocyclic group (for example, a pyridyl group, a pyrazyl group, a pyrimidinyl group, a triazyl a group, a furyl group, a pyrrolyl group, an imidazolyl group, a benzimidazolyl group, a pyrazolyl group, a pyrazinyl group, a triazolyl group (for example, 1,2,4-triazol-1-yl group, and 1,2,3-triazol-1-yl group), an oxazolyl group, a benzoxazolyl group, a thiazolyl group, an isoxazolyl group, an isothiazolyl group, a furazanyl group, a thienyl group, a quinolyl group, a benzofuryl group, a dibenzofuryl group, a benzothienyl group, a dibenzothienyl group, an indolyl group, a carbazolyl group, an azacarbazolyl group (indicating a ring structure in which one of the carbon atoms constituting the carbazole ring of the carbazolyl group is replaced with nitrogen atoms), a quinoxalinyl group, a pyridazinyl group, a triazinyl group, a quinazolinyl group, and a phthalazinyl group); a heterocyclic group (for example, a pyrrolidyl group, an imidazolidyl group, a morpholyl group, and an oxazolidyl group); an alkoxy group (for example, a methoxy group, an ethoxy group, a propyloxy group, a pentyloxy group, an hexyloxy group, an octyloxy group, and a dodecyloxy group); a cycloalkoxy group (for example, a cyclopentyloxy group and a cyclohexyloxy group); an aryloxy group (for example, a phenoxy group and a naphthyloxy group); an alkylthio group (for example, a methylthio group, an ethylthio group, a propylthio group, a pentylthio group, hexylthio group, an octylthio group, and a dodecylthio group); a cycloalkylthio group (for example, a cyclopentylthio group and a cyclohexylthio group); an arylthio group (for example, a phenylthio group and a naphthylthio group); an alkoxycarbonyl group (for example, a methyloxycarbonyl group, an ethyloxycarbonyl group, a butyloxycarbonyl group, an octyloxycarbonyl group, and a dodecyloxycarbonyl group); an aryloxycarbonyl group (for example, a phenyloxycarbonyl group and a naphthyloxycarbonyl group); a sulfamoyl group (for example, an aminosulfonyl group, a methylaminosulfonyl group, a dimethylaminosulfonyl group, a butylaminosulfonyl group, a hexylaminosulfonyl group, a cyclohexylaminosulfonyl group, an octylaminosulfonyl group, a dodecylaminosulfonyl group, a phenylaminosulfonyl group, a naphthylaminosulfonyl group, and a 2-pyridylaminosulfonyl group); an acyl group (for example, an acetyl group, an ethyl carbonyl group, a propylcarbonyl group, a pentylcarbonyl group, a cyclohexylcarbonyl group, an octylcarbonyl group, a 2-ethylhexylcarbonyl group, a dodecylcarbonyl group, a phenylcarbonyl group, a naphthylcarbonyl group, and a pyridylcarbonyl group); an acyloxy group (for example, an acetyloxy group, an ethylcarbonyloxy group, a butylcarbonyloxy group, an octylcarbonyloxy group, a dodecylcarbonyloxy group, and a phenylcarbonyloxy group); an amido group (for example, a methylcarbonylamino group, an ethylcarbonylamino group, a dimethylcarbonylamino group, a propylcarbonylamino group, a pentylcarbonylamino group, a cyclohexylcarbonylamino group, a 2-ethylhexylcarbonylamino group, an octylcarbonylamino group, a dodecylcarbonylamino group, a phenylcarbonylamino group, and a naphthylcarbonylamino group); a carbamoyl group (for example, an aminocarbonyl group, a methylaminocarbonyl group, a dimethylaminocarbonyl group, a propylaminocarbonyl group, a pentylaminocarbonyl group, a cyclohexylaminocarbonyl group, an octylaminocarbonyl group, a 2-ethymexylaminocarbonyl group, a dodecylaminocarbonyl group, a phenylaminocarbonyl group, a naphthylaminocarbonyl group, and a 2-pyridylaminocarbonyl group); a ureido group (for example, a methylureido group, an ethylureido group, a pentylureido group, a cyclohexylureido group, an octylureido group, a dodecylureido group, a phenylureido group, a naphthylureido group, and a 2-pyridylaminoureido group); a sulfinyl group (for example, a methylsulfinyl group, an ethylsufinyl group, a butylsulfinyl group, a cyclohexylsulfinyl group, a 2-ethylhexylsulfinyl group, a dodecylsulfinyl group, a phenylsulfinyl group, a naphthylsulfinyl group, and a 2-pyridylsulfinyl group); an alkylsulfonyl group (for example, a methylsulfonyl group, an ethylsulfonyl group, a butylsulfinyl group, a cyclohexylsulfonyl group, a 2-ethylhexylsulfonyl group, and a dodecylsulfonyl group); an arylsulfonyl group or a heteroarylsulfonyl group (for example, a phenylsulfonyl group, a naphthylsulfonyl group, and a 2-pyridylsulfonyl group); an amino group (for example, an amino group, an ethylamino group, a dimethylamino group, a butylamino group, a cyclopentylamino group, a dodecylamino group, an anilino group, a naphthylamino group, and a 2-pyridylamino group); a halogen atom (for example, a fluorine atom, a chlorine atom and a bromine atom); a fluorinated hydrocarbon group (for example, a fluoromethyl group, trifluoromethyl group, a pentafluoroethyl group and a pentafluorophenyl group); a cyano group; a nitro group; a hydroxyl group; a mercapto group; and a silyl group (for example, a trimethylsilyl group, a triisopropylsilyl group, a triphenylsilyl group, and a phenyldiethylsilyl group). These substituents may be further substituted by the above-mentioned substituents. A plurality of these substituents may be bonded to each other to form a ring.

In Formula (6), p represents an integer of 0 or 1. That is, when $B_2$ in Formula (6) is a nitrogen atom, p is 0 or 1, and when $B_2$ in Formula (6) is a carbon atom, p is 1.

In the compound represented by Formula (6), the substituent represented by $R^2$ has the same meaning as $R_1$ in Formula (6).

In Formula (6), $R^3$ represents a hydrogen atom or a substituent, and a substituent represented by $R^2$ has the same meaning as $R_1$ in Formula (6).

In Formula (6), r represents an integer of 0 or 1. That is, r is 0 when $B_1$ in Formula (6) is a nitrogen atom, and r is 1 when $B_1$ in Formula (6) is a carbon atom.

In Formula (6), $R^3$ represents a hydrogen atom or a substituent, and a substituent represented by $R^3$ has the same meaning as $R_1$ in Formula (6).

In Formula (6), $R^4$ represents a hydrogen atom or a substituent, and a substituent represented by $R^4$ has the same meaning as $R_1$ in the Formula (6).

In the compound represented by Formula (6), q represents an integer of 1 to 4. Each $R^4$ may be identical or may be different. Furthermore, when more than one $R^4$ is present, they may be bonded to each other to form a ring.

In Formula (6), L represents any ligand capable of coordinating with M, and it is a ligand well known to those skilled in the art. Ligands used in conventionally known metal complexes include various known ligands, for example, ligands (e g, halogen ligands (preferably chlorine ligands), nitrogen-containing heterocyclic ligands (e.g., bipyridyl, phenanthroline), and diketone ligands) as described in "Photochemistry and Photophysics of Coordination Compounds" published by Springer-Verlag, H. Yersin, 1987, and "Organometallic chemistry-Basics and Applications" by Akio Yamamoto, published by Shokabou in 1982. Further, a substituted or unsubstituted phenylpyridine, phenylpyrazole, phenylimidazole, phenyltriazole, phenyltetrazole, pyrazabole, picolinic acid, and carbene can be used in combination as preferable ligands.

In Formula (6), n1 represents an integer of 1 to 3, and m1 represents an integer of 0 to 2.

Specific examples of the compound having the structure represented by Formula (5) or Formula (6) of the present invention are shown below, but the compounds which can be used in the present application are not limited thereto.

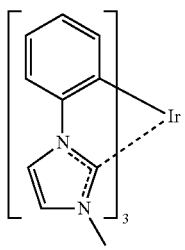

C-1

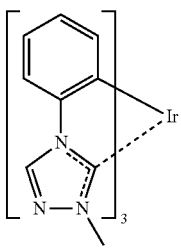

C-2

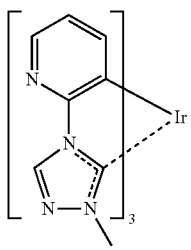

C-3

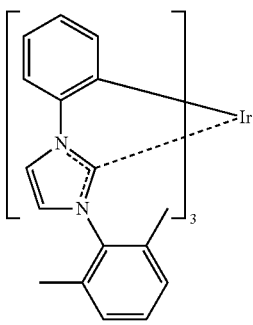

C-4

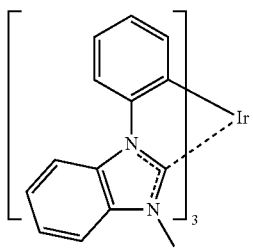

C-5

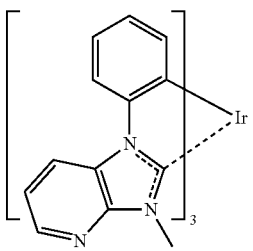

C-6

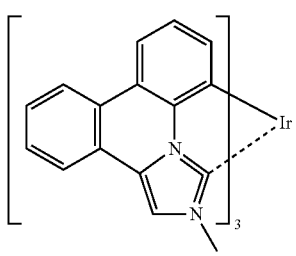

C-7

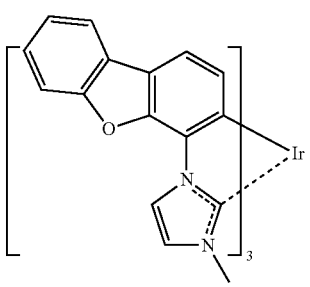

C-8

-continued
C-9
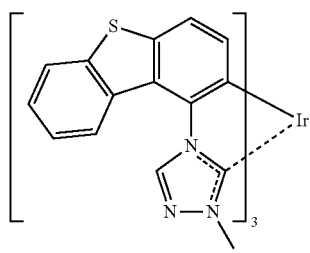
C-10
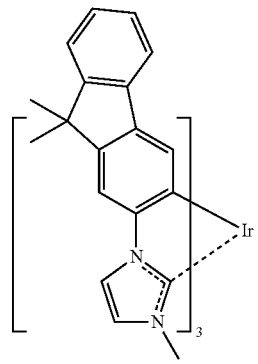
C-11 (Dp-5)
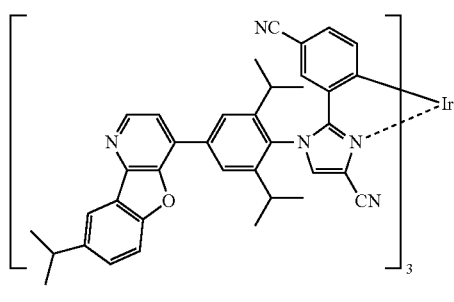
C-12
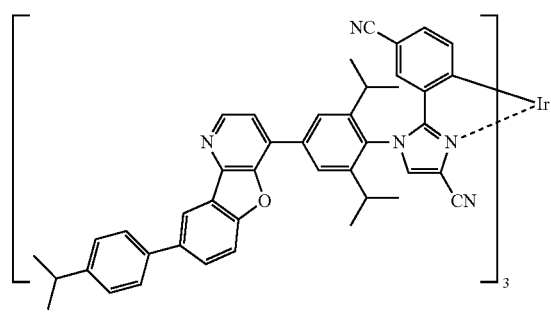
C-13
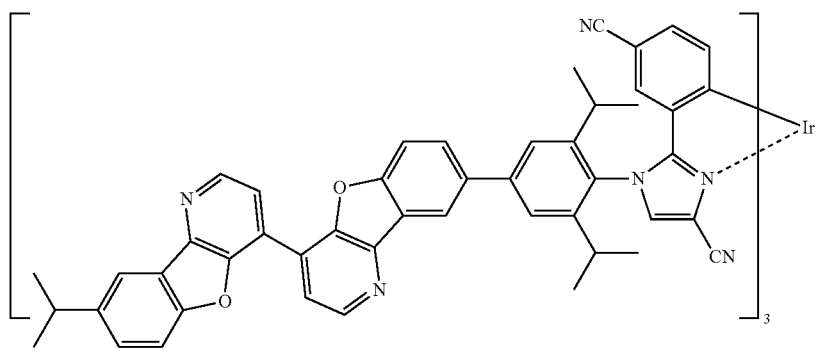
C-14
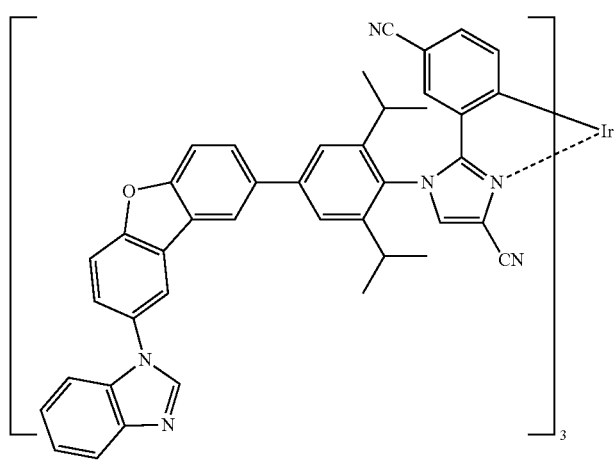

-continued
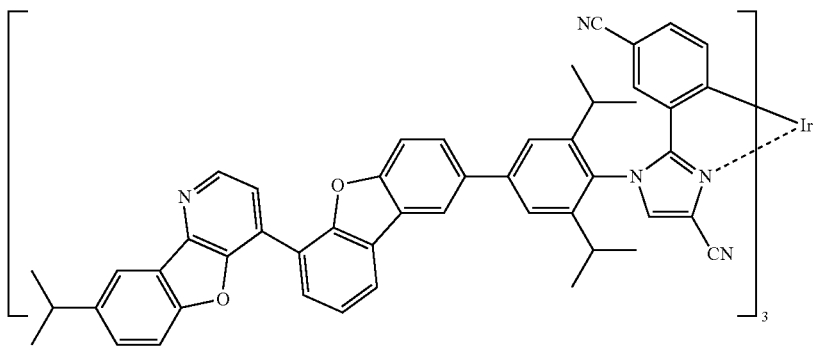
C-15
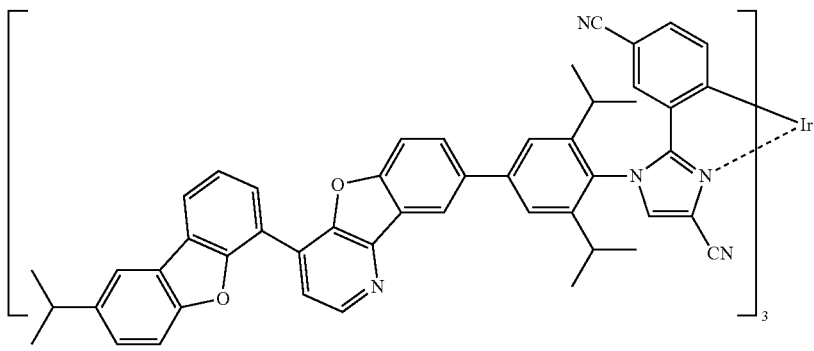
C-16
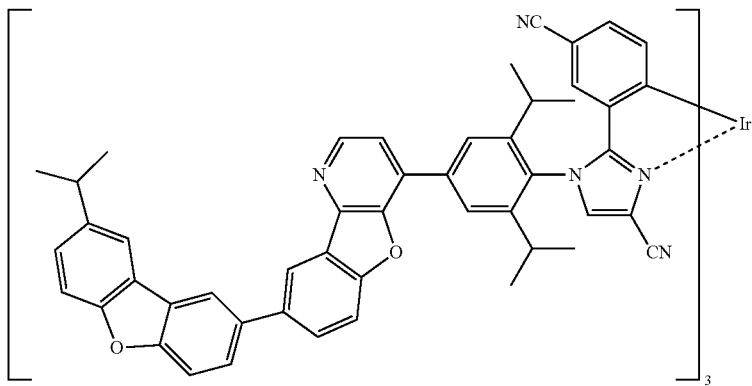
C-17
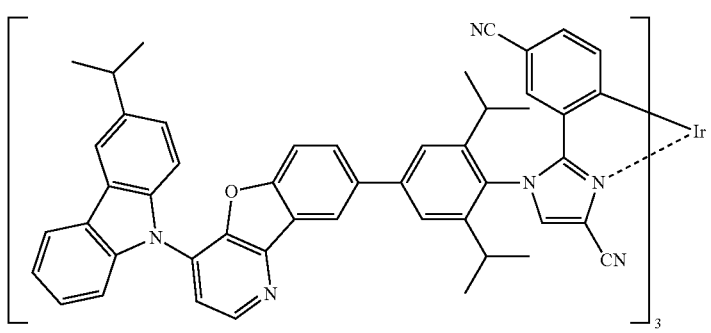
C-18

-continued
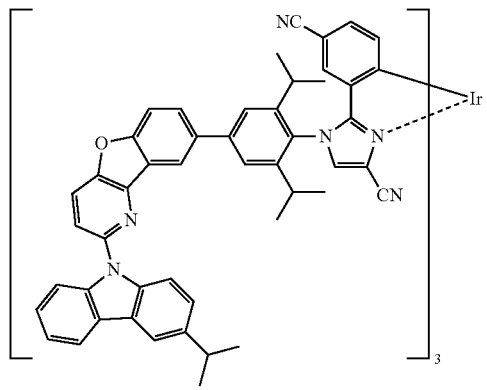
C-19
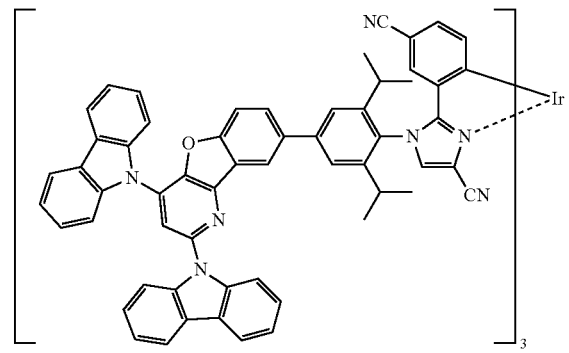
C-20
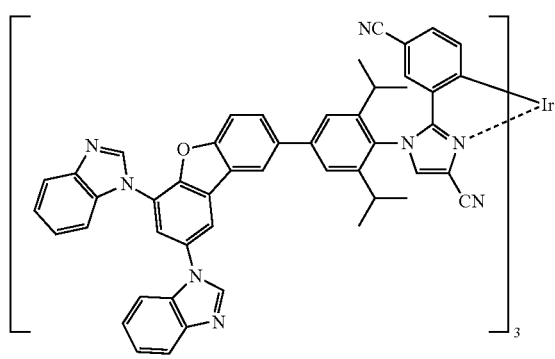
C-21
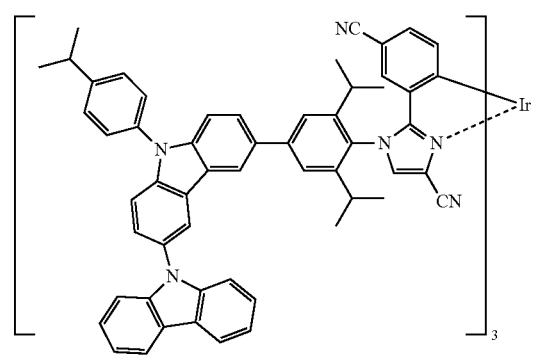
C-22
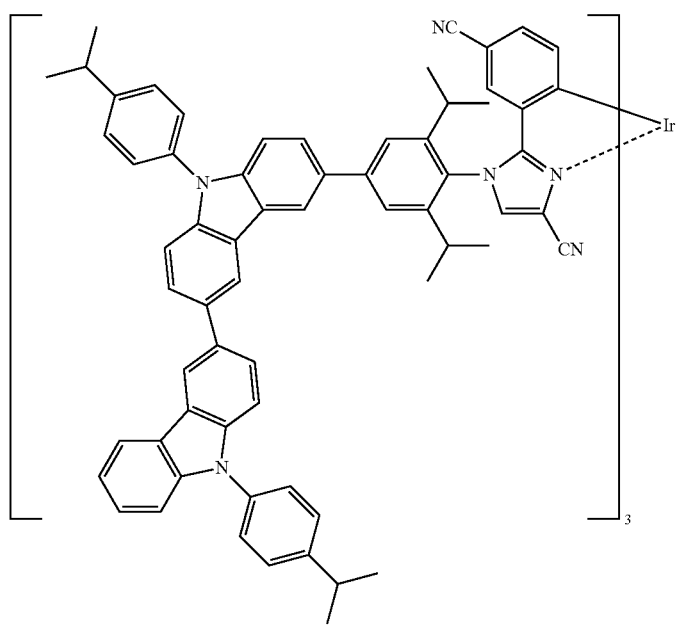
C-23

-continued
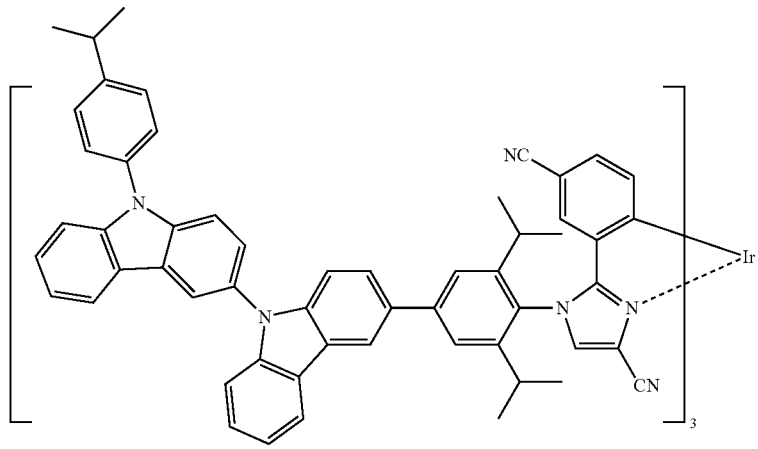
C-24
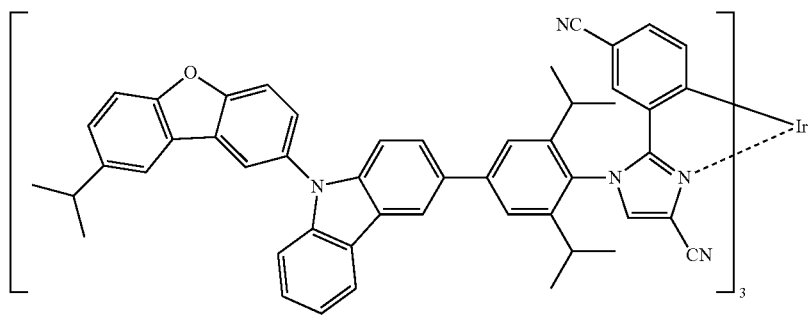
C-25
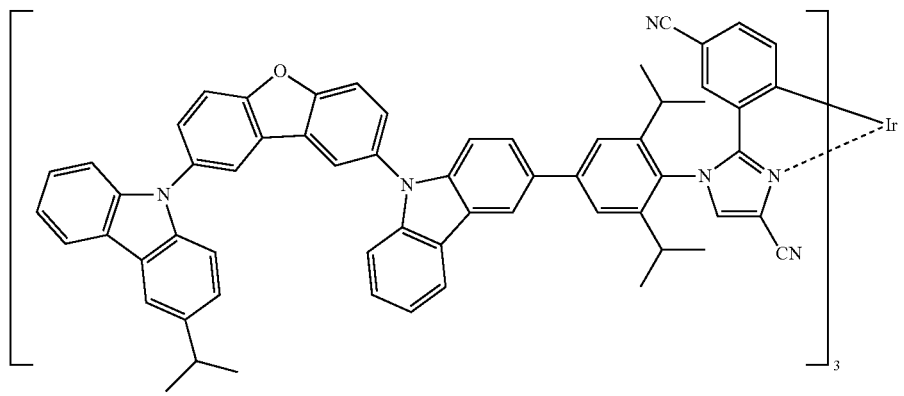
C-26
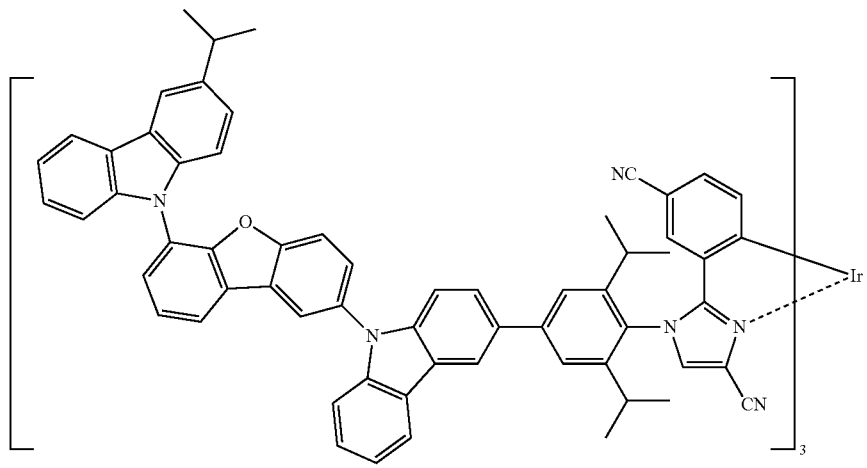
C-27

-continued
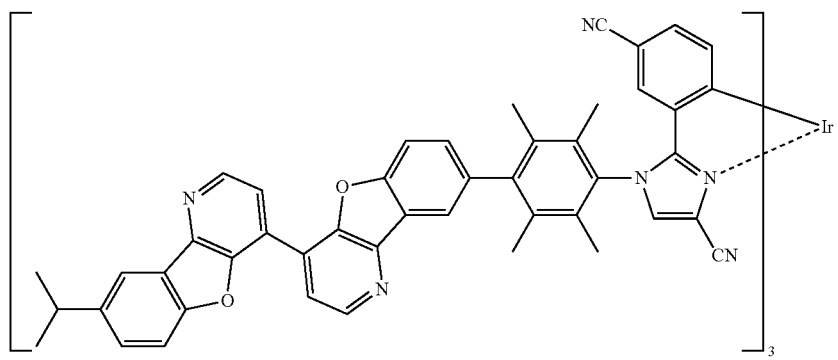
C-28 (Dp-6)
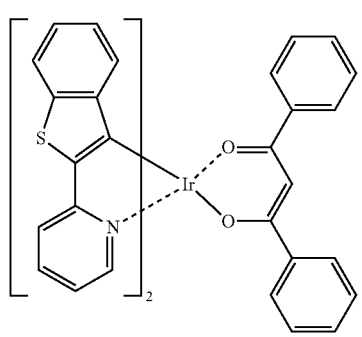
C-29
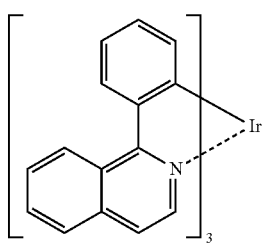
C-30
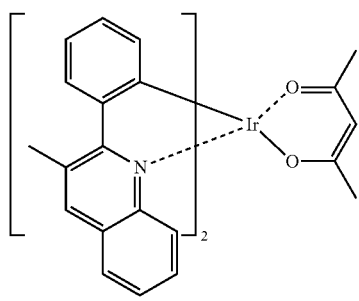
C-31
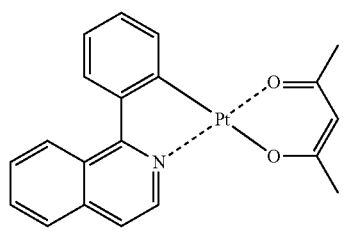
C-33
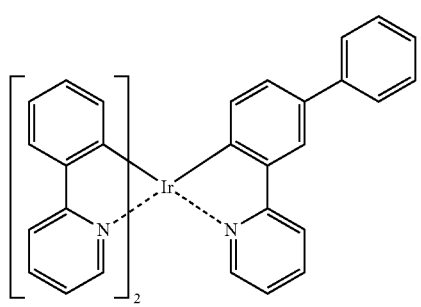
C-35
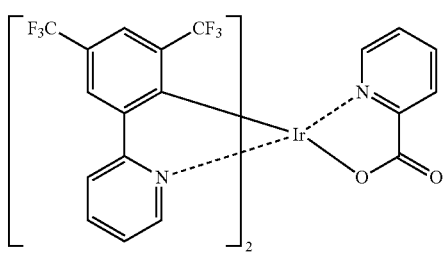
C-36

-continued
C-37
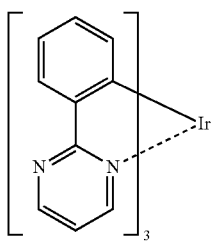
C-38
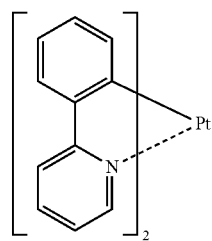
C-39
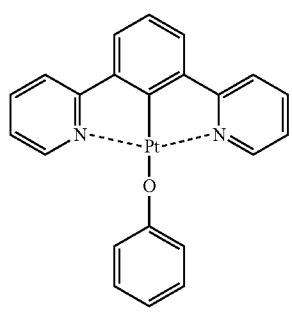
C-40
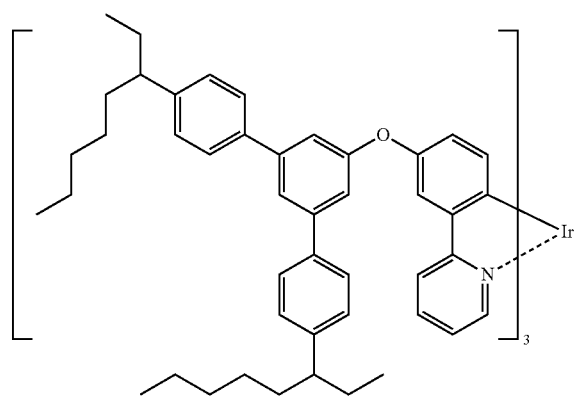
C-41
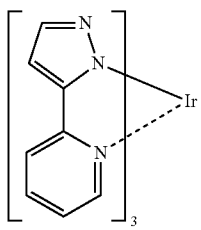
C-42
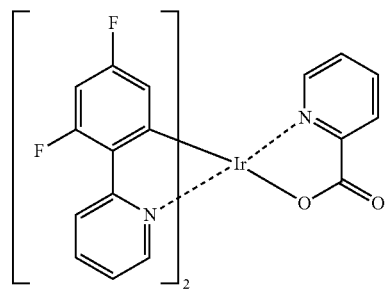
C-43
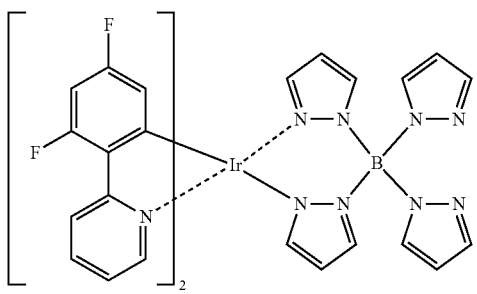
C-44
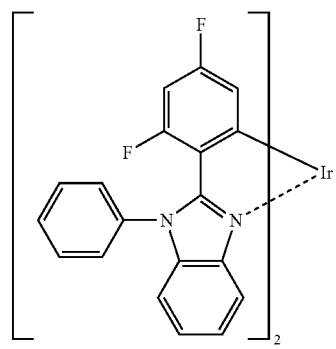
C-45
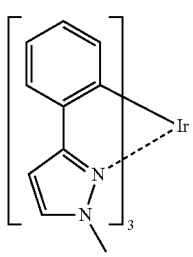
C-46
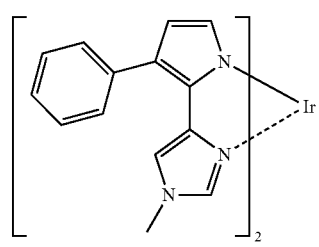

-continued
C-47
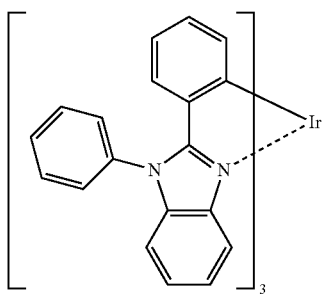
C-48
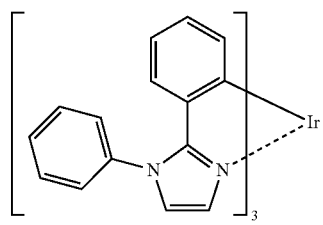
C-49
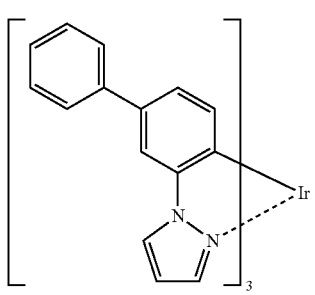
C-50
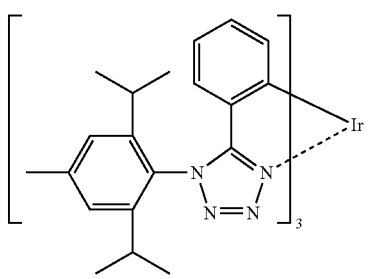
Dp-1
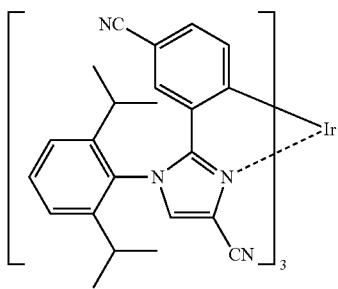
Dp-2
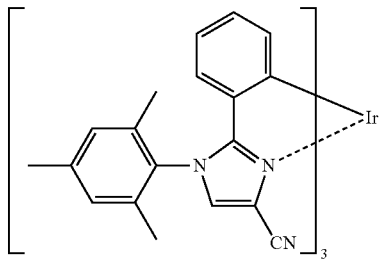
Dp-3
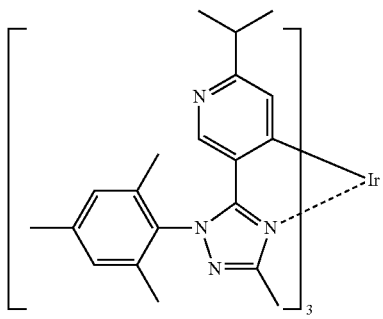
Dp-4
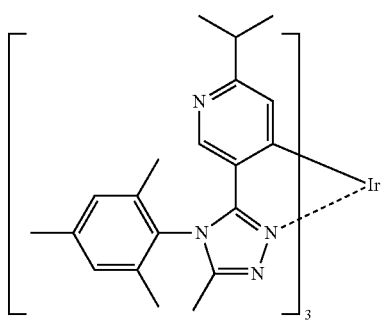
Dp-5 (C-11)
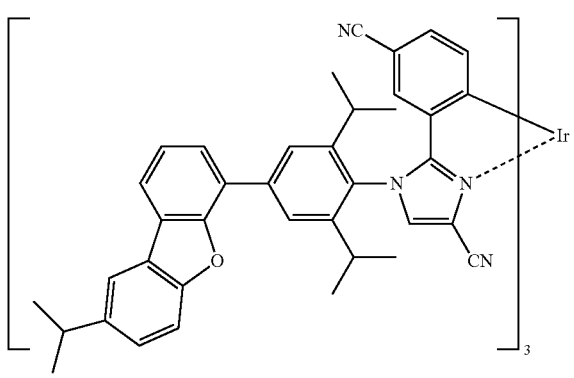

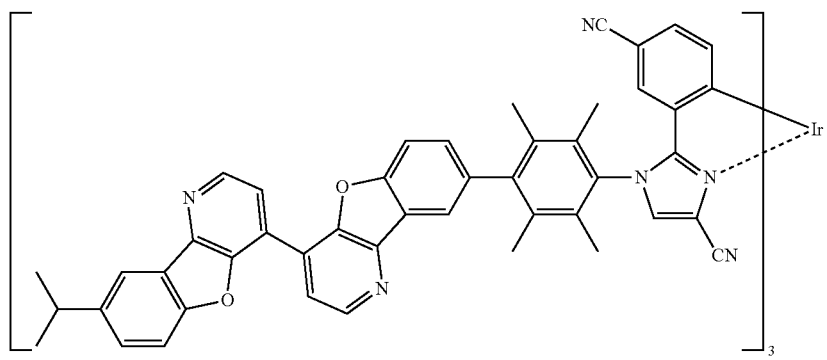

Dp-6 (C-28)

A phosphorescent compound usable in the present invention may be suitably selected and employed from the known materials used for a light emitting layer for an organic EL element.

Specific examples of a known phosphorescent compound usable in the present invention are compounds described in the following publications. However, the present invention is not limited to them.

Nature 395, 151 (1998), Appl. Phys. Lett. 78, 1622 (2001), Adv. Mater. 19, 739 (2007), Chem. Mater. 17, 3532 (2005), Adv. Mater. 17, 1059 (2005), WO 2009/100991, WO 2008/101842, WO 2003/040257, US 2006/835469, US 2006/0202194, US 2007/0087321, US 2005/0244673, Inorg. Chem. 40, 1704 (2001), Chem. Mater. 16, 2480 (2004), Adv. Mater. 16, 2003 (2004), Angew. Chem. Int. Ed. 2006, 45, 7800, Appl. Phys. Lett. 86, 153505 (2005), Chem. Lett. 34, 592 (2005), Chem. Commun. 2906 (2005), Inorg. Chem. 42, 1248 (2003), WO 2009/050290, WO 2002/015645, WO 2009/000673, US 2002/0034656, U.S. Pat. No. 7,332,232, US 2009/0108737, US 2009/0039776, U.S. Pat. Nos. 6,921,915, 6,687,266, US 2007/0190359, US 2006/0008670, US 2009/0165846, US 2008/0015355, U.S. Pat. Nos. 7,250,226, 7,396,598, US 2006/0263635, US 2003/0138657, US 2003/0152802, U.S. Pat. No. 7,090,928, Angew. Chem. Int. Ed. 47, 1 (2008), Chem. Mater. 18, 5119 (2006), Inorg. Chem. 46, 4308 (2007), Organometallics 23, 3745 (2004), Appl. Phys. Lett. 74, 1361 (1999), WO 2002/002714, WO 2006/009024, WO 2006/056418, WO 2005/019373, WO 2005/123873, WO 2005/123873, WO 2007/004380, WO 2006/082742, US 2006/0251923, US 2005/0260441, U.S. Pat. Nos. 7,393,599, 7,534,505, 7,445,855, US 2007/0190359, US 2008/0297033, U.S. Pat. No. 7,338,722, US 2002/0134984, and U.S. Pat. No. 7,279,704, US 2006/098120, US 2006/103874, WO 2005/076380, WO 2010/032663, WO 2008/140115, WO 2007/052431, WO 2011/134013, WO 2011/157339, WO 2010/086089, WO 2009/113646, WO 2012/020327, WO 2011/051404, WO 2011/004639, WO 2011/073149, US 2012/228583, US 2012/212126, JP-A 2012-069737, JP-A 2012-195554, JP-A 2009-114086, JP-A 2003-81988, JP-A 2002-302671 and JP-A 2002-363552.

Further, when the carbon atoms of the ring $Z_1$ and the ring $Z_2$ are cathene carbon atoms (specifically, when it is a cathene complexe), the carbene complexes described in the following publications are suitably used: WO 2005/019337, WO 2006/056418, WO 2005/113704, WO 2007/115970, WO 2007/115981, and WO 2008/000727.

«Host Compound»

The luminescent film of the present invention may contain a host compound in addition to the fluorescent compound and the phosphorescent compound. The host compound according to the present invention is a compound mainly responsible for charge injection and transport in the light emitting layer, and substantially no light emission itself is observed in the organic EL element of the present invention.

Preferably, the host compound is a compound exhibiting a phosphorescent emission yield of less than 0.1 at a room temperature (25° C.), more preferably a compound exhibiting a phosphorescent emission yield of less than 0.01. It is preferable that the excited energy level of the host compound is higher than the excited energy level of the phosphorescent metal complex contained in the same layer.

Host compounds may be used singly or may be used alone, or in combination of two or more compounds. By using a plurality of host compounds, it is possible to adjust transfer of charge, thereby it is possible to achieve an organic EL element of high efficiency. A host compound used in the present invention is not specifically limited. A known compound previously used in an organic EL element may be used. It may be a compound having a low molecular weight, or a polymer having a high molecular weight. Further, it may be a compound having a reactive group such as a vinyl group or an epoxy group.

As a known host compound, preferably, it has a hole transporting ability or an electron transporting ability, as well as preventing elongation of an emission wavelength. In addition, from the viewpoint of stably driving an organic EL element at high temperature, it is preferable that a host compound has a high glass transition temperature (Tg) of 90° C. or more, more preferably, has a Tg of 120° C. or more. Here, a glass transition temperature (Tg) is a value obtained using DSC (Differential Scanning Colorimetry) based on the method in conformity to JIS-K-7121.

The host compound according to the present invention is preferably a compound having a structure represented by the following Formula (HA) or (HB).

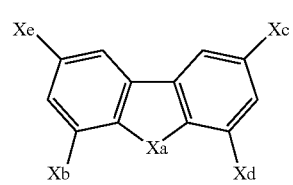

Formula (HA)

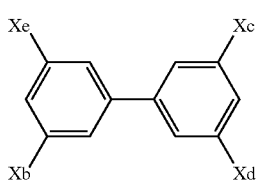

Formula (HB)

In Formula (HA) and Formula (HB), Xa represents O or S. Xb, Xc, Xd and Xe each independently represent a hydrogen atom, a substituent or a group having a structure represented by the following Formula (HC). At least one of Xb, Xc, Xd and Xe represents a group having a structure represented by the following Formula (HC), and at least one of groups having a structure represented by the following Formula (HC). It is preferred that Ar represents a carbazolyl group.

Ar-(L')$_n$-*  Formula (HC)

In Formula (HC), L' represents a divalent linking group derived from an aromatic hydrocarbon ring or an aromatic heterocyclic ring. n represents an integer of 0 to 3, and when n is 2 or more, plural L's may be the same or different. A symbol * represents a linking site with Formula (HA) or Formula (HB). Ar represents a group having a structure represented by the following Formula (HD).

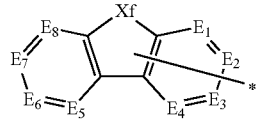

Formula (HD)

In Formula (HD), Xf represents N(R$^1$), O or S. $E_1$ to $E_8$ represents C(R") or N. R' and R" represent a hydrogen atom, a substituent or a linking site with L' in Formula (HC). A symbol * represents a linking site with L' in Formula (HC).

In the compound having a structure represented by the Formula (HA), at least two of Xb, Xc, Xd and Xe are preferably represented by Formula (HC), more preferably Xc is represented by Formula (HC), and Ar in Formula (HC) represents a carbazolyl group which may have a substituent.

As the substituents represented by Xb, Xc, Xd and Xe in the Formulas (HA) and (HB) and the substituents represented by R' and R" in Formula (HD), it may be cited the same substituents which may be held by the ring $Z_1$ and the ring $Z_2$ in Formula (DP).

Examples of the aromatic hydrocarbon ring represented by L' in Formula (HC) include: a benzene ring, a p-chlorobenzene ring, a mesitylene ring, a toluene ring, a xylene ring, a naphthalene ring, an anthracene ring, an azulene ring, an acenaphthene ring, a fluorene ring, a phenanthrene ring, an indene ring, a pyrene ring, and a biphenyl ring.

Examples of the aromatic heterocyclic ring represented by L' in Formula (HC) include: a furan ring, a thiophene ring, a pyridine ring, a pyridazine ring, a pyrimidine ring, a pyrazine ring, a triazole ring, an imidazole ring, a pyrazole ring, a thiazole ring, a quinazoline ring, a carbazole ring, a carboline ring, a diazacarbazole ring (indicating a ring structure in which an arbitral carbon atom constituting the carboline ring is replaced with a nitrogen atom), and a phthalazine ring.

Specific examples of the host compound according to the present invention include compounds applicable to the present invention besides the compound having the structure represented by Formula (HA) or Formula (HB), but the present invention is not particularly limited to these compounds.

OC-1

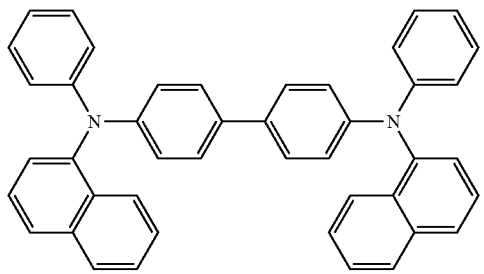

OC-2

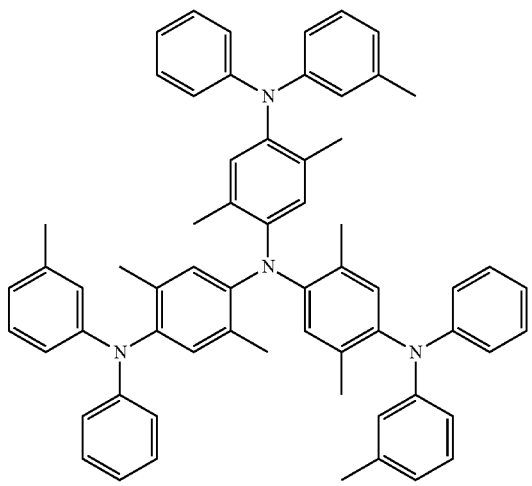

OC-3

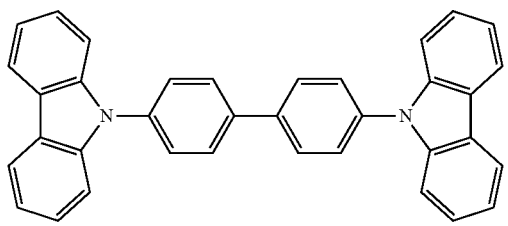

OC-4

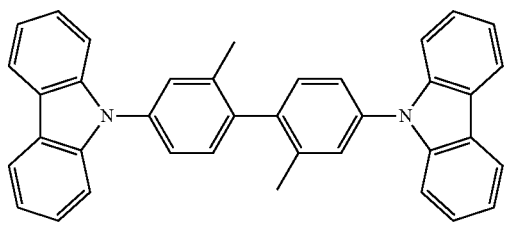

-continued
OC-5
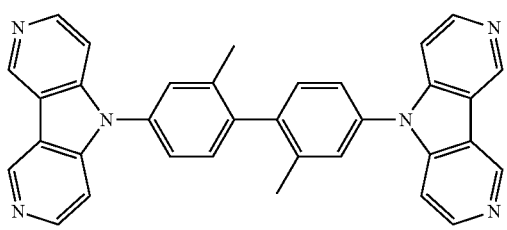
OC-6
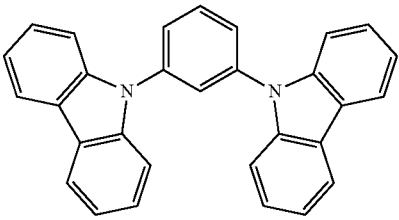
OC-7
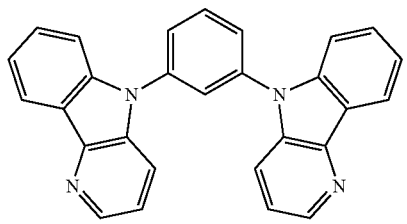
OC-8
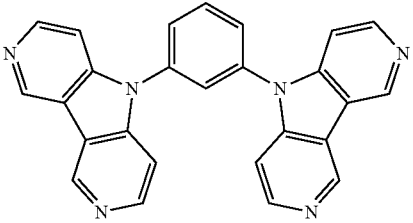
OC-9
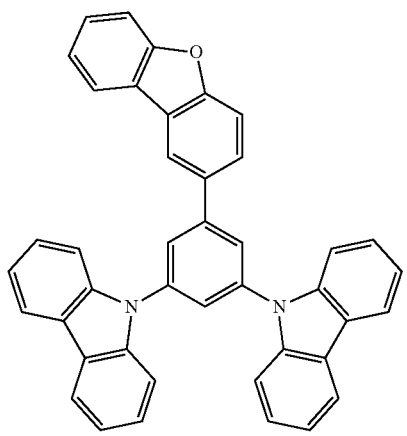
OC-10
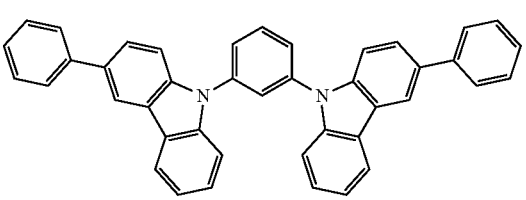
OC-11
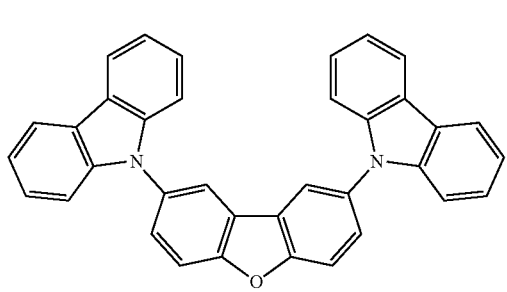
OC-12
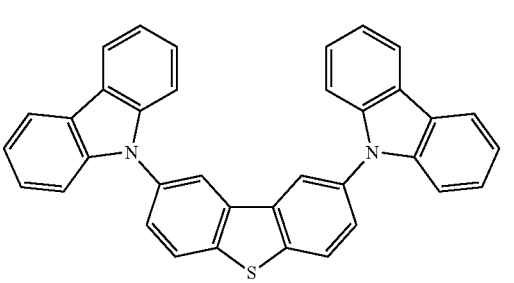
OC-13
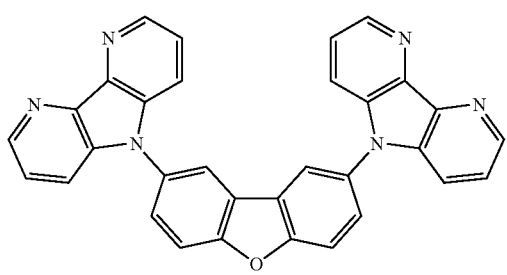

OC-14
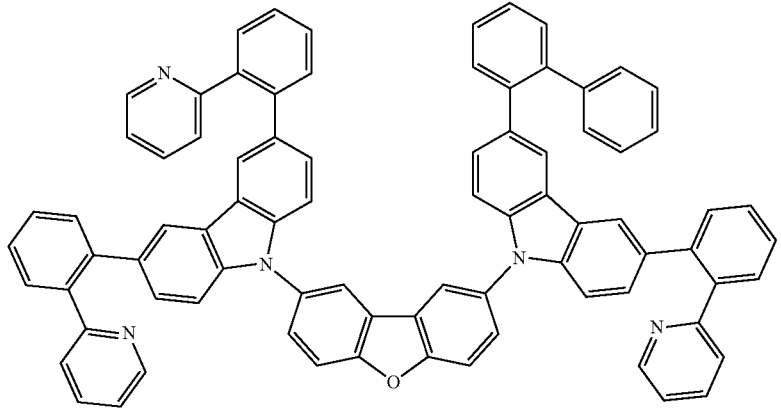
OC-15
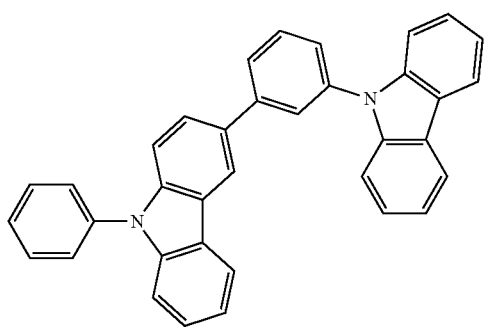
OC-16
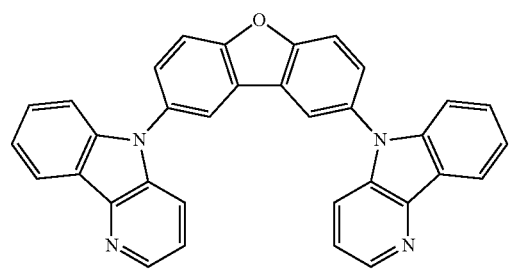
OC-17
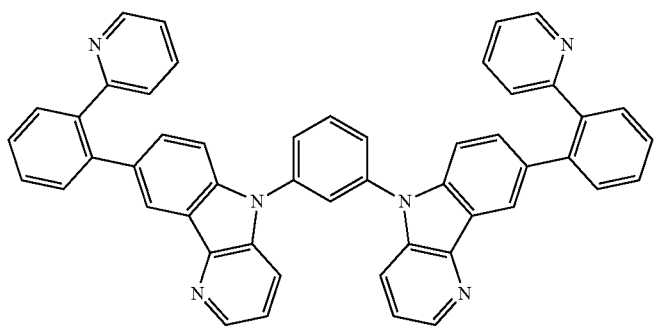
OC-18
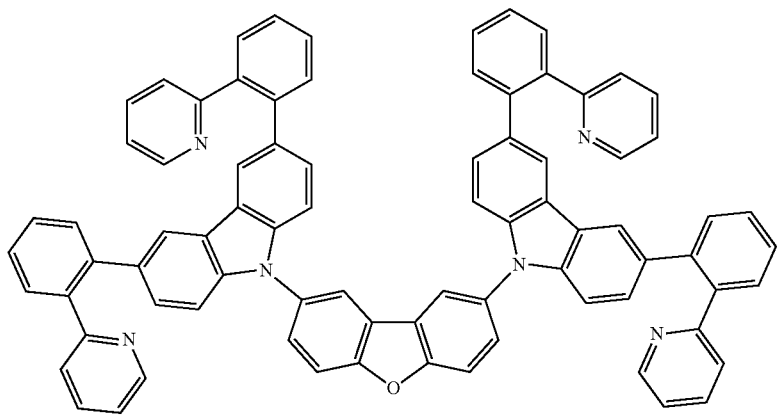

-continued
OC-19
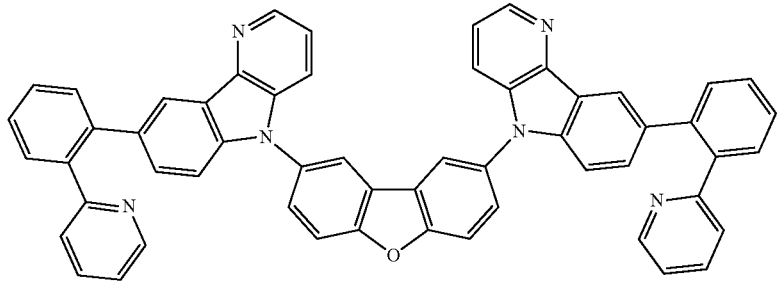
OC-20
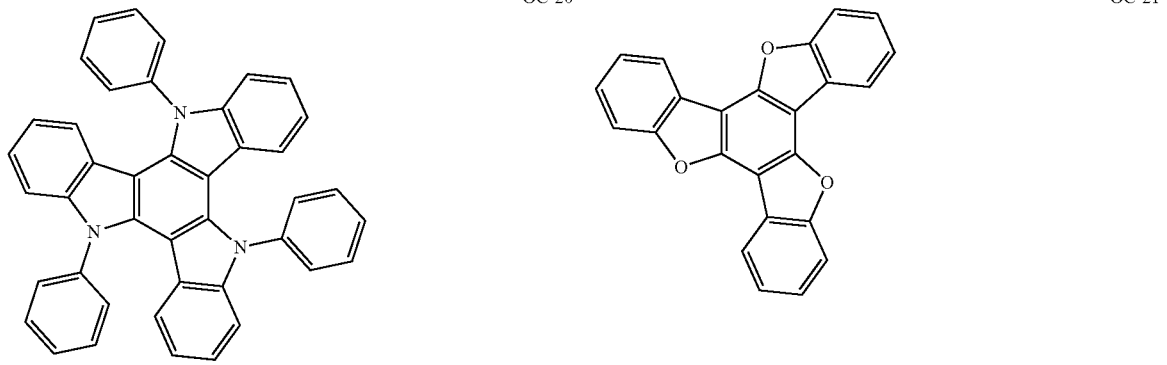
OC-21
OC-22
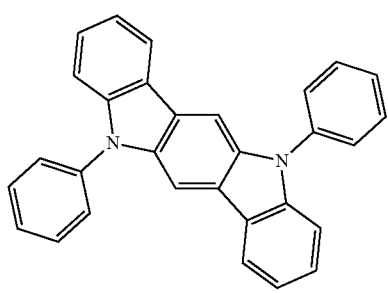
OC-23
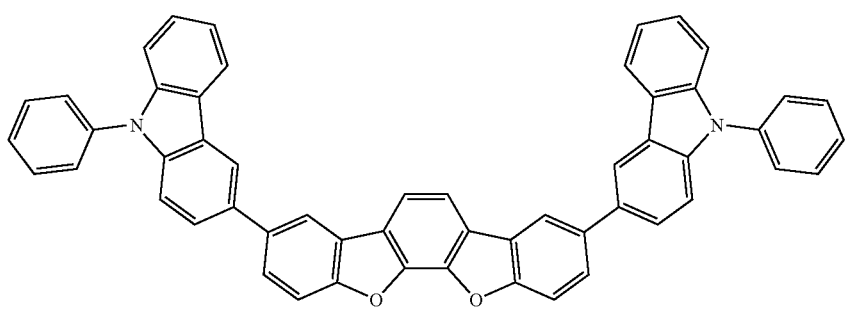
OC-24
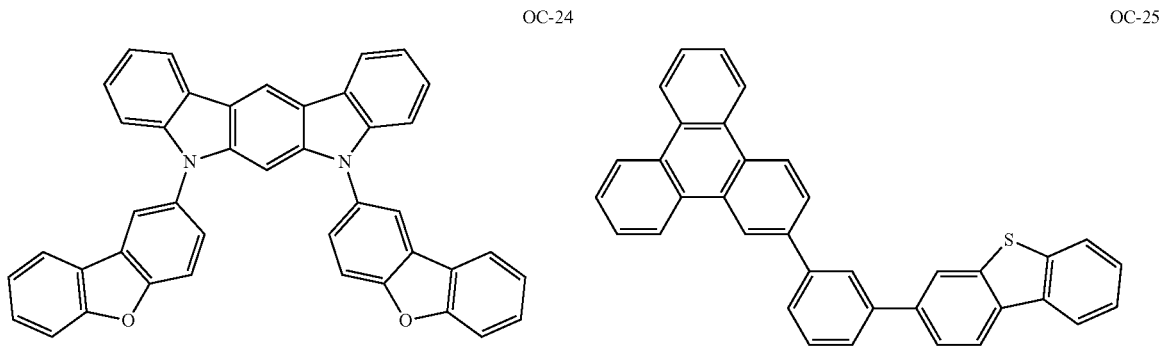
OC-25
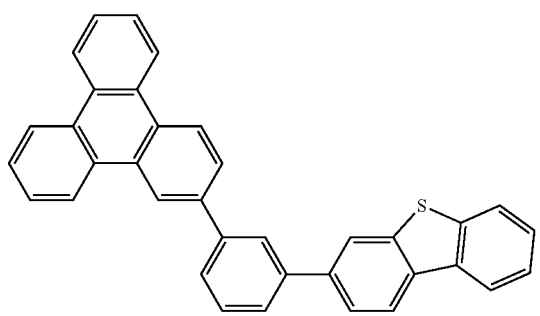

-continued
OC-26
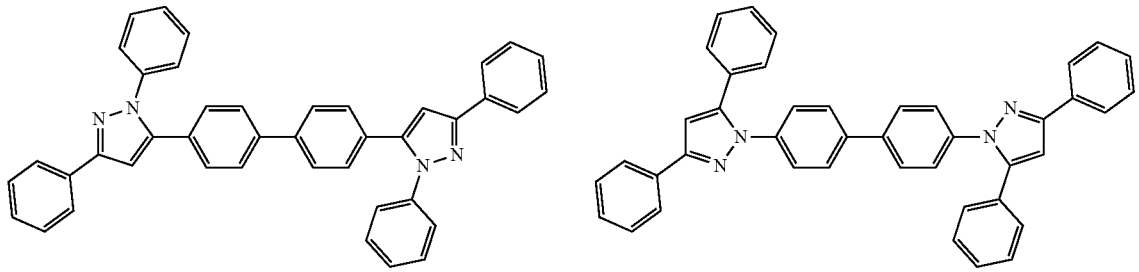
OC-27
OC-28
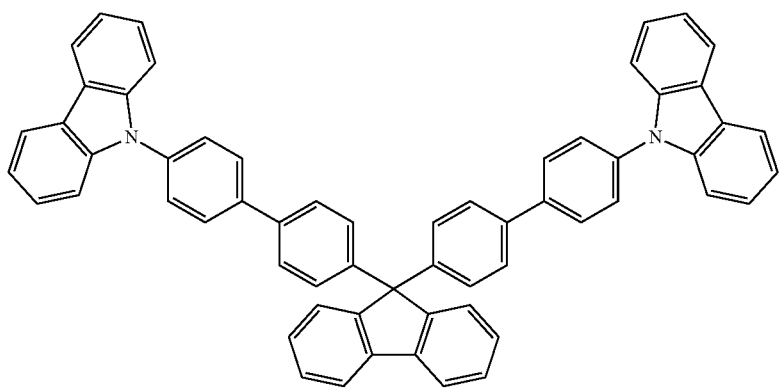
OC-29 (H-1)
OC-30
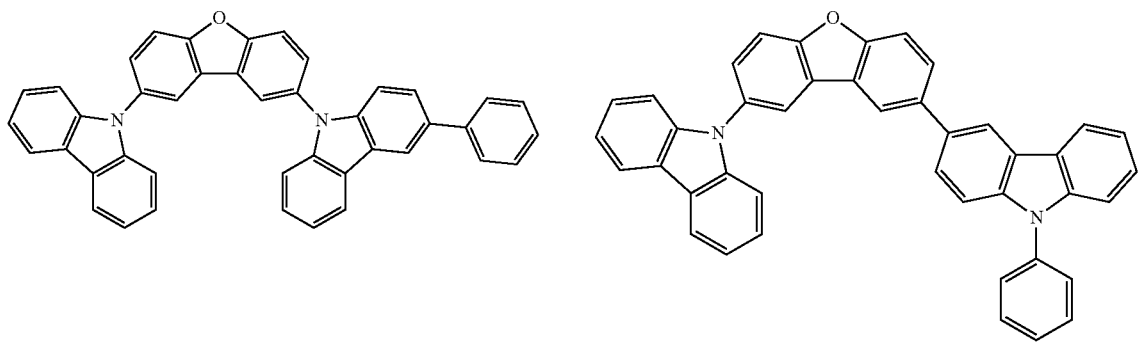
OC-31
OC-32
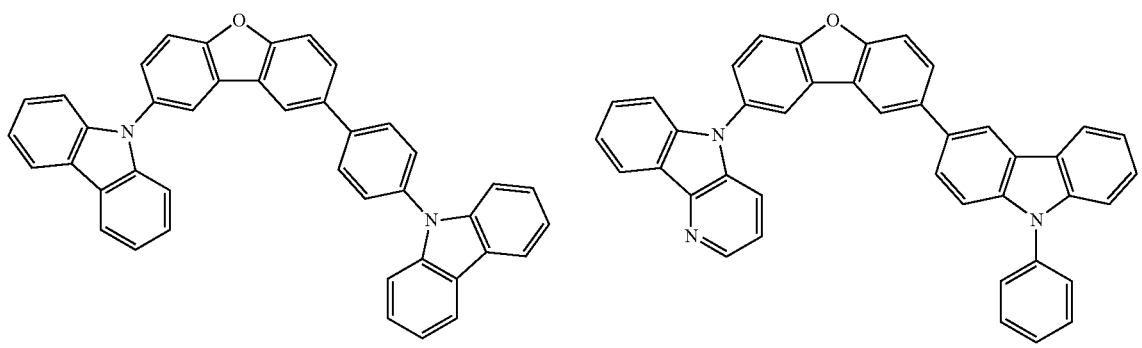

-continued
OC-33
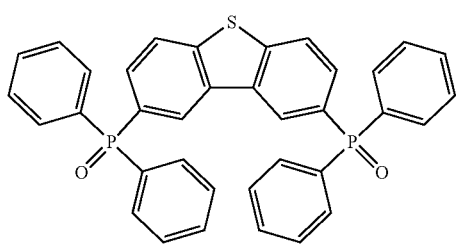
OC-34
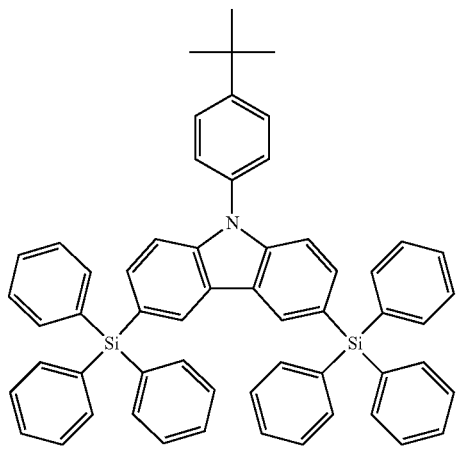
OC-35
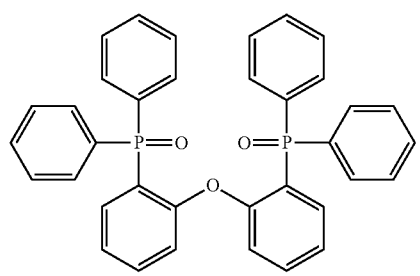
OC-36
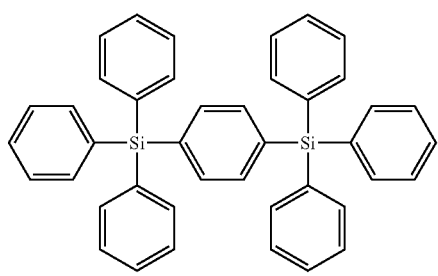
H1
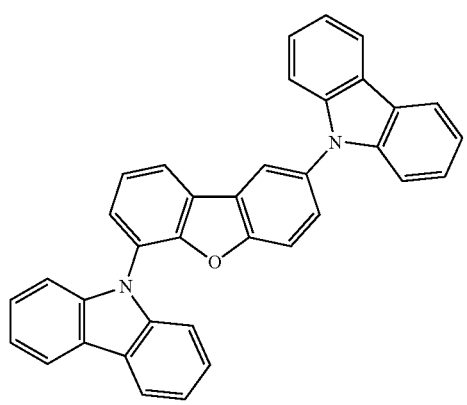
H2
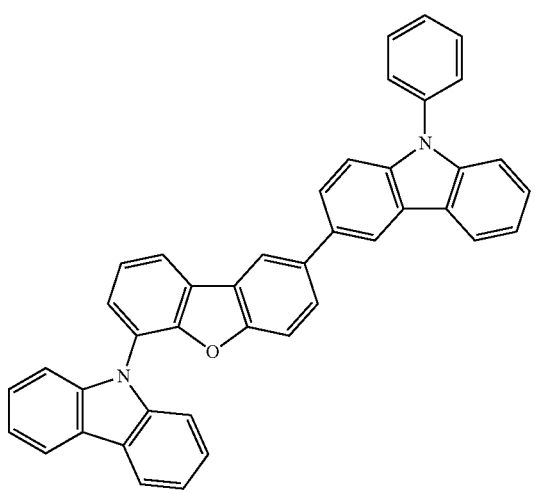

-continued
H3
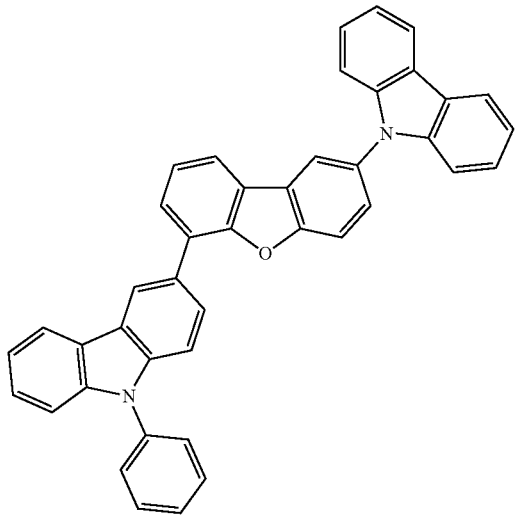
H4
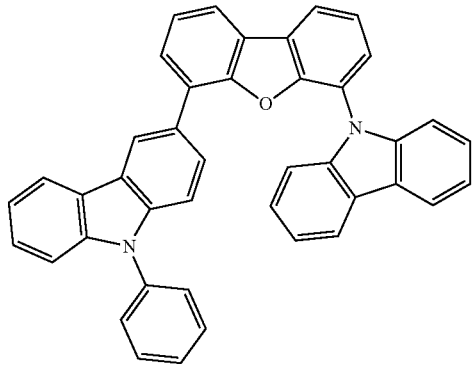
H5
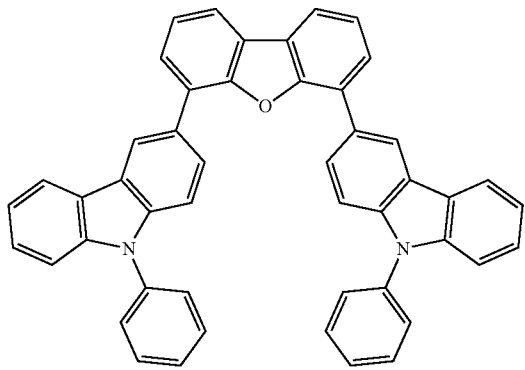
H6
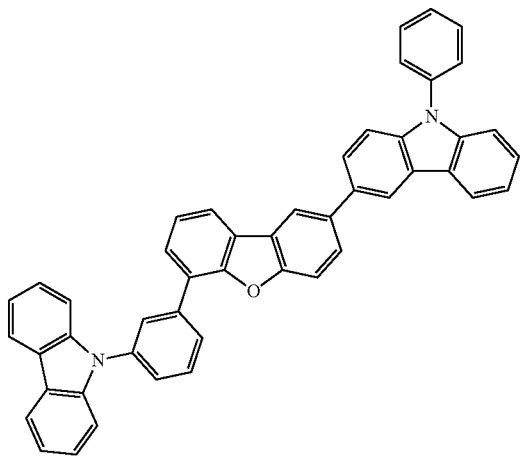
H7
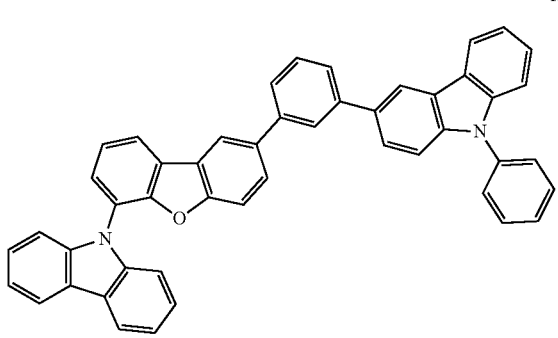
H8
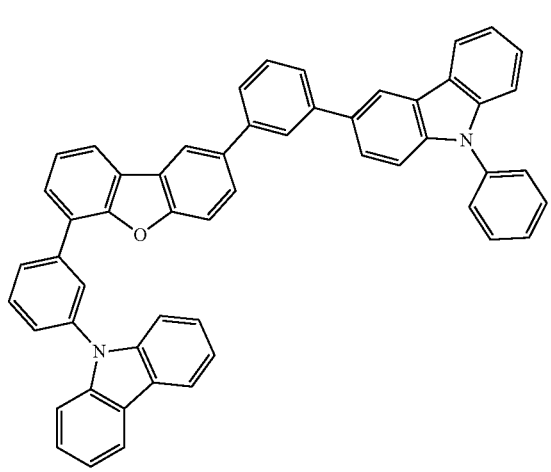

-continued
H9
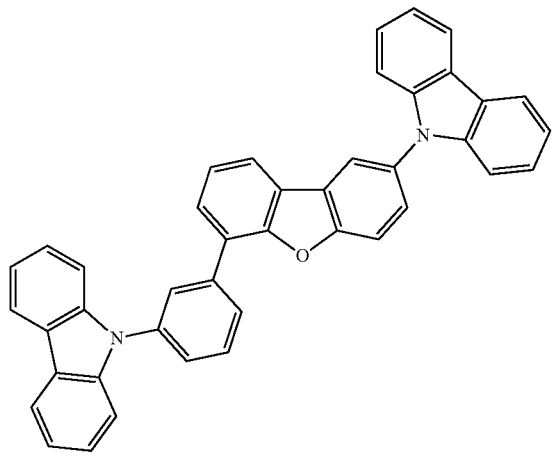
H10
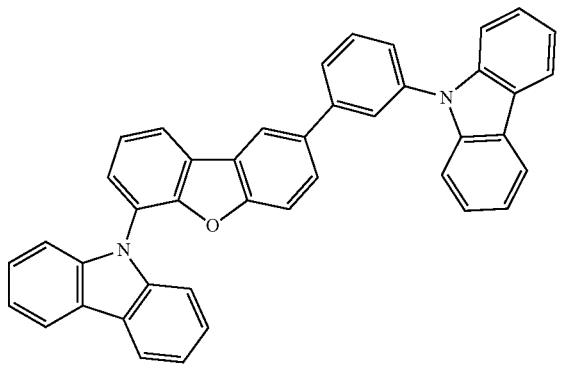
H11
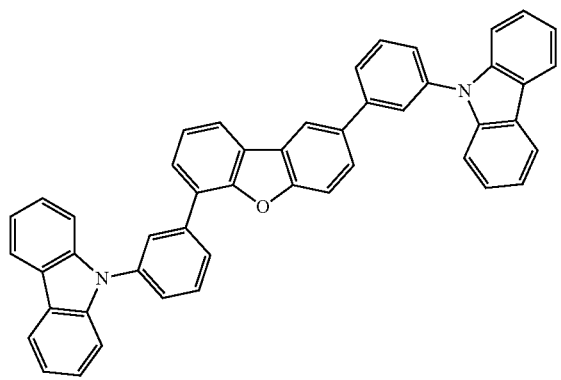
H12
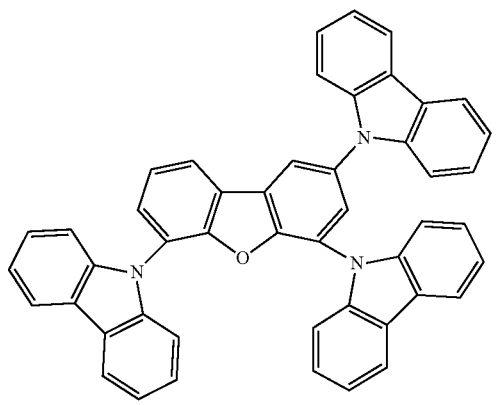
H13
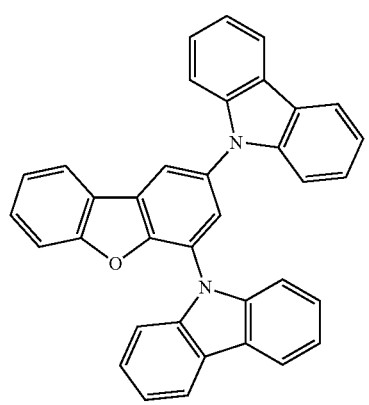
H14
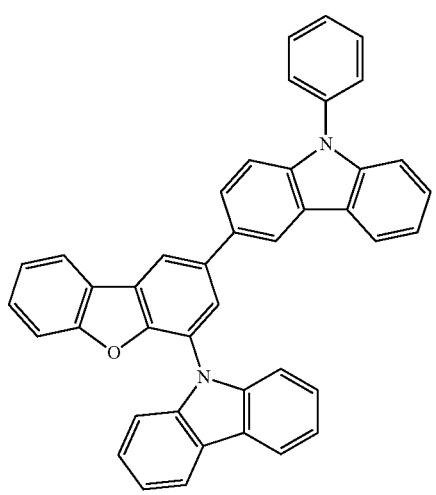

-continued
H15
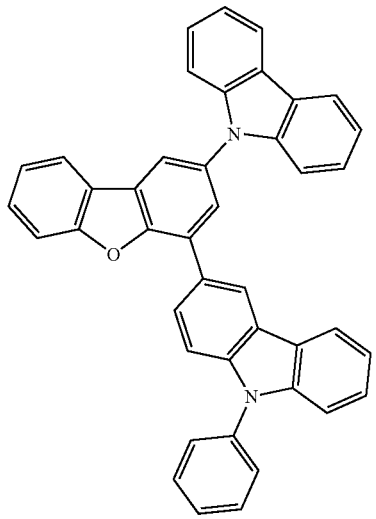
H16
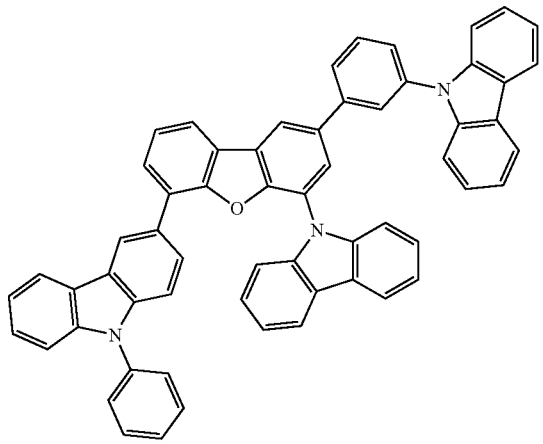
H17
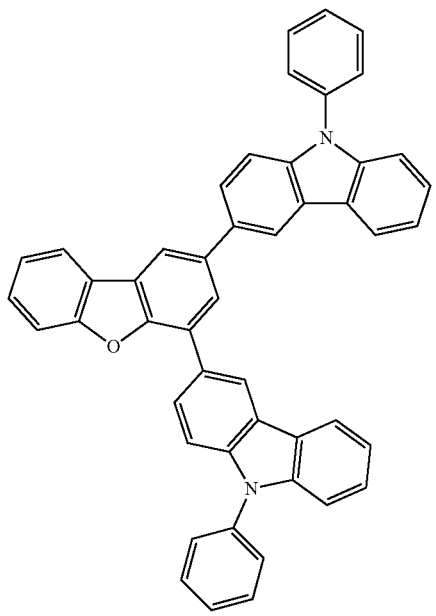
H18
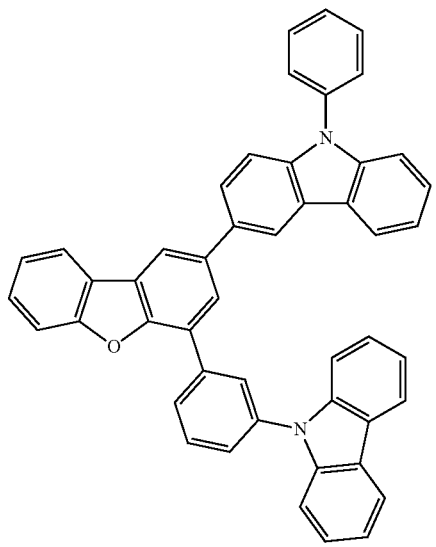
H19
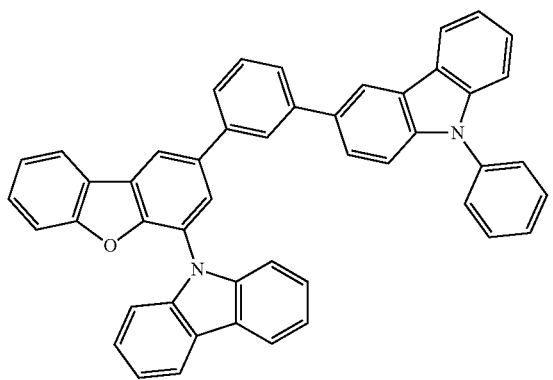
H20
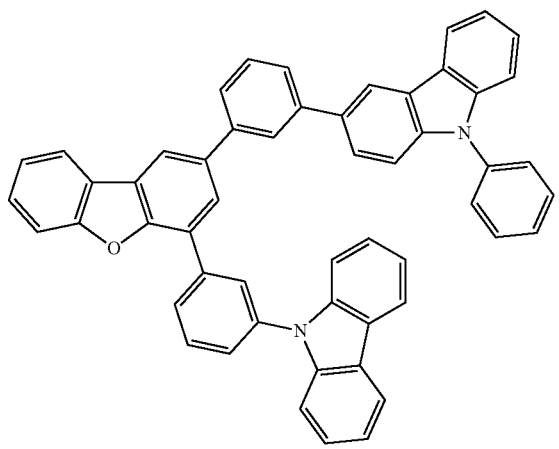

105 106
-continued
H21 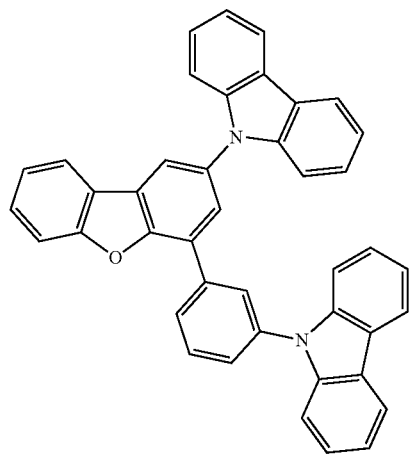
H22 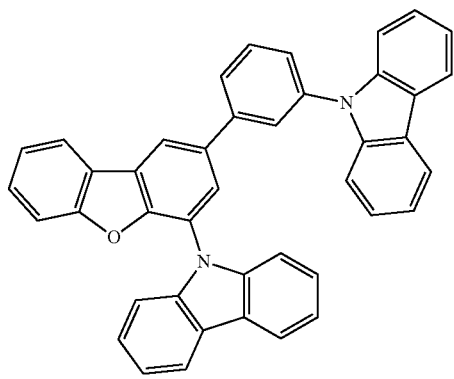
H23 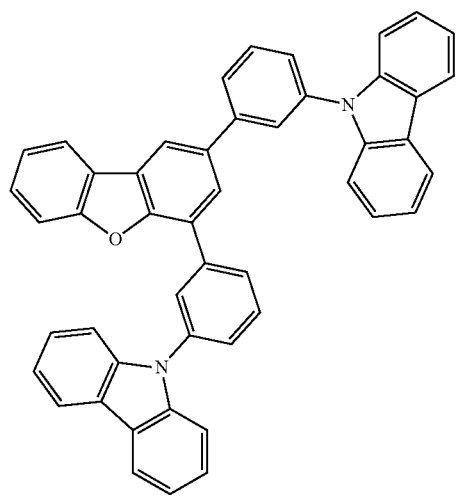
H24 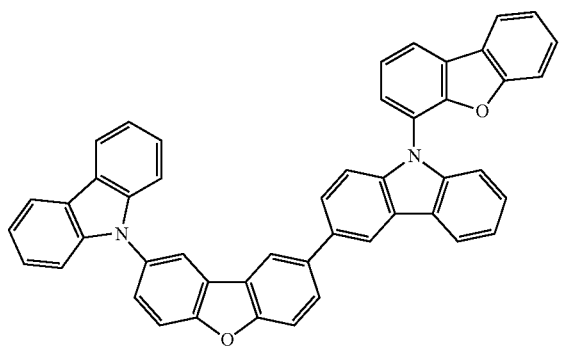
H25 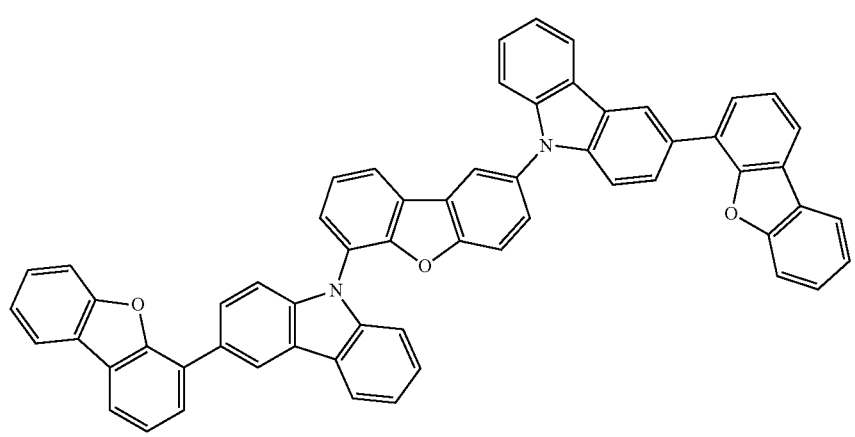

H26
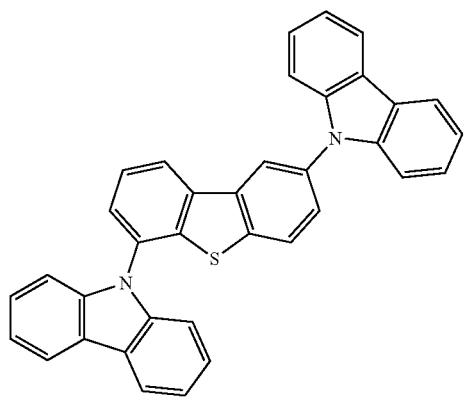
H27
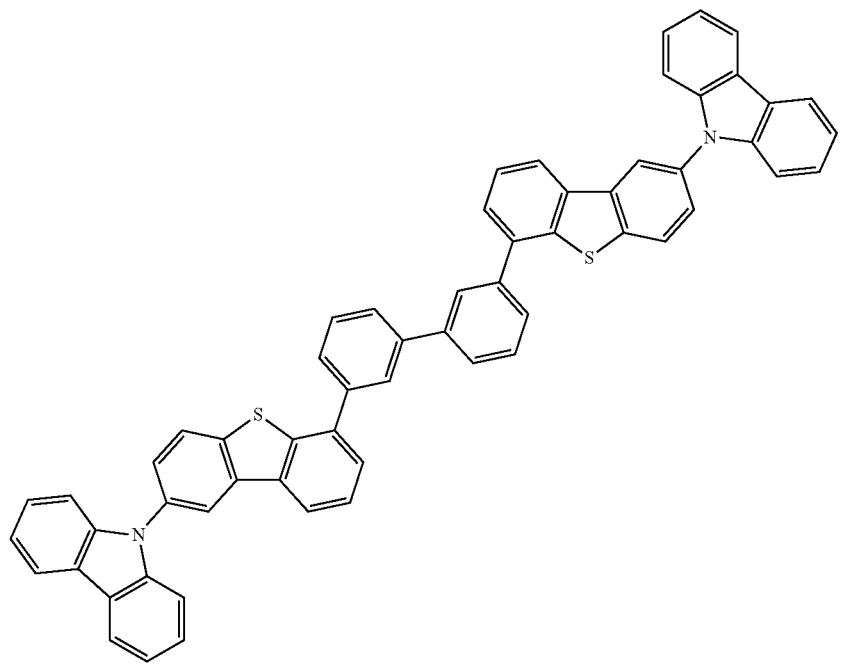
H28
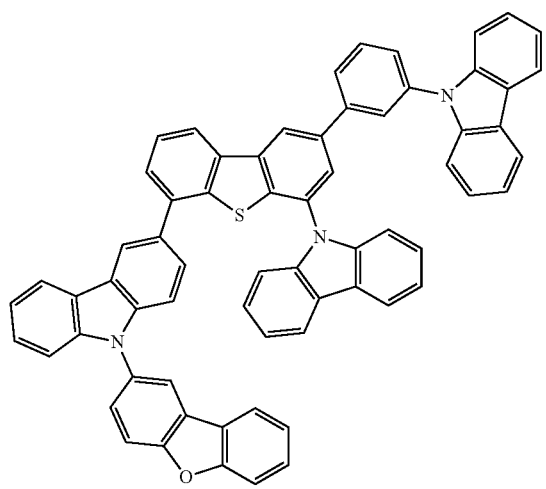
H29
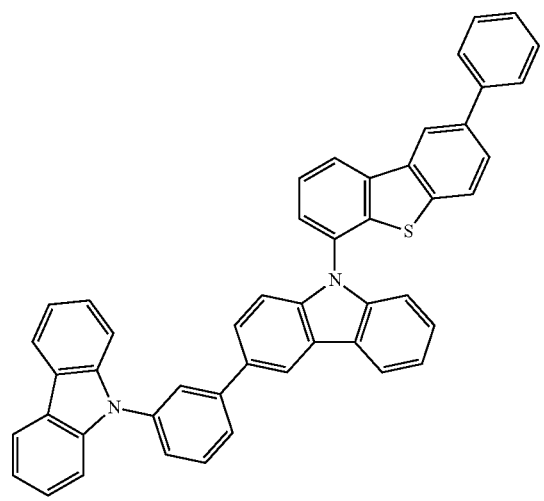

H30
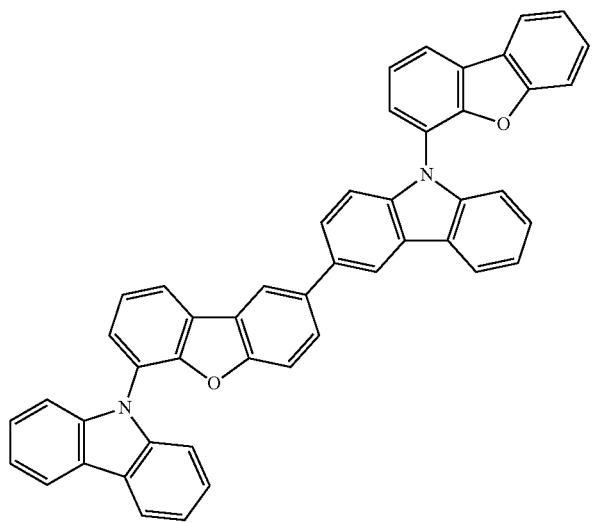
H31
H32
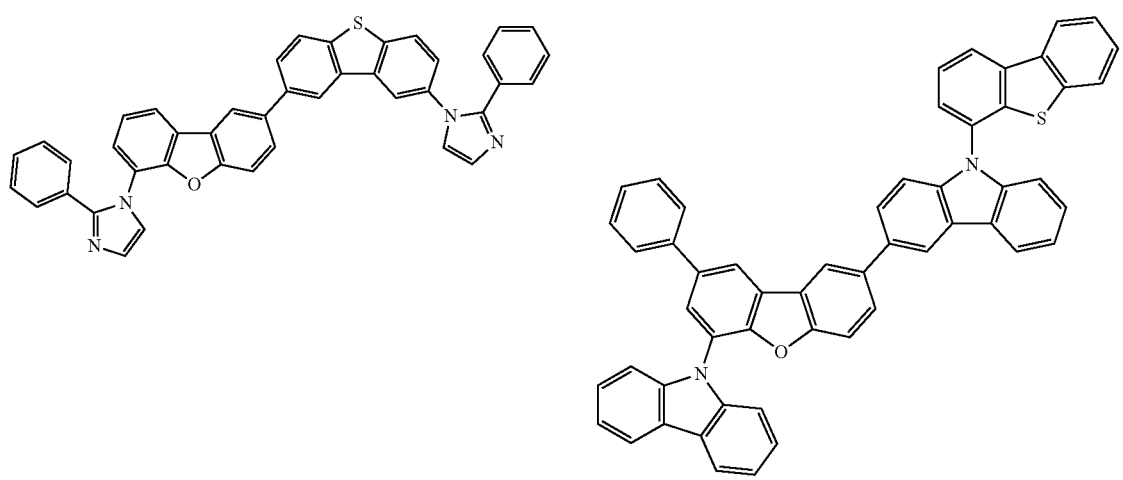
H33
H34
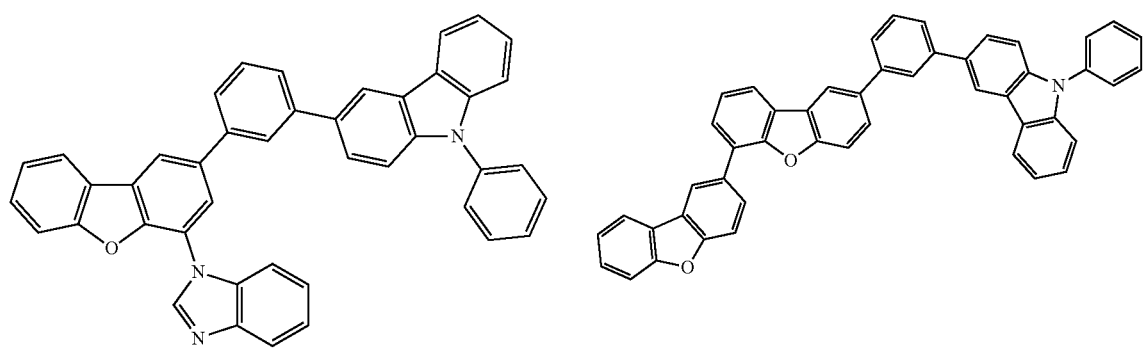

-continued
111
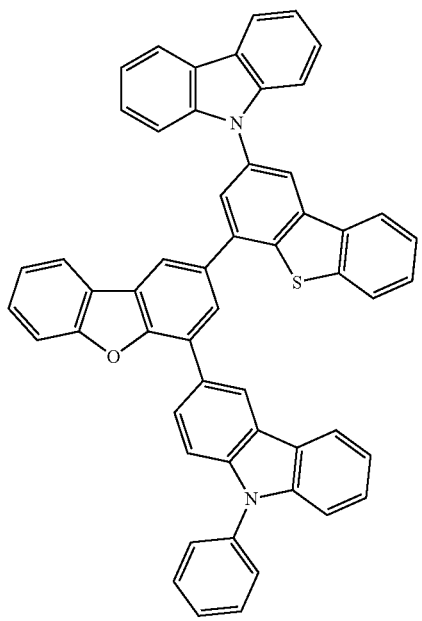
H35
112
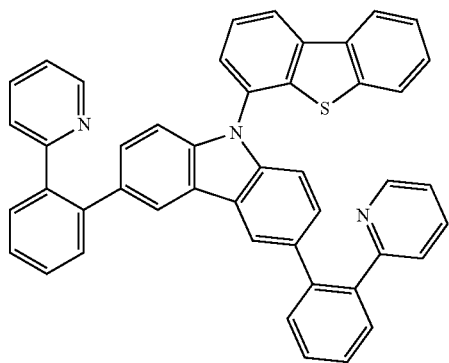
H36
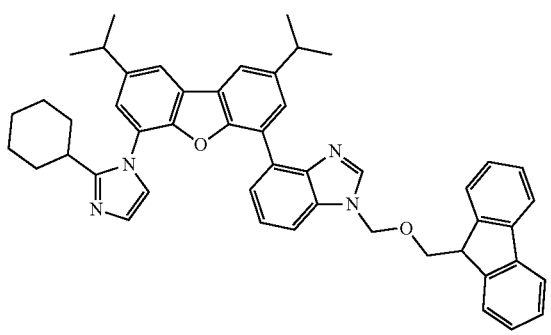
H37
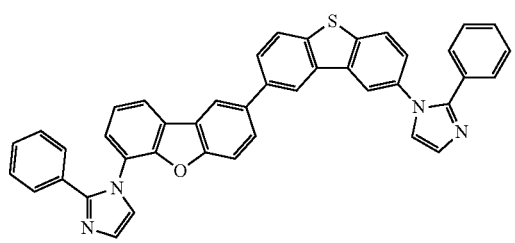
H31
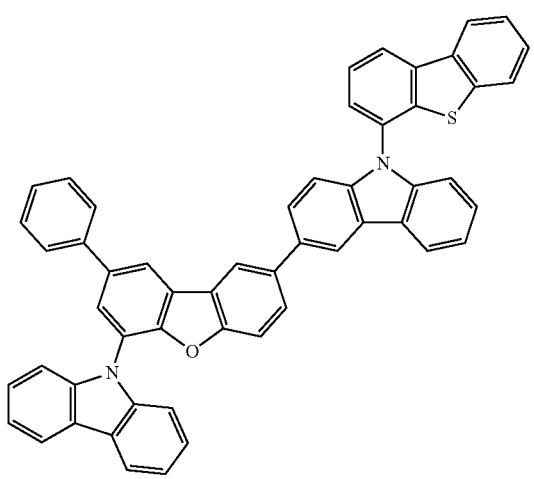
H32
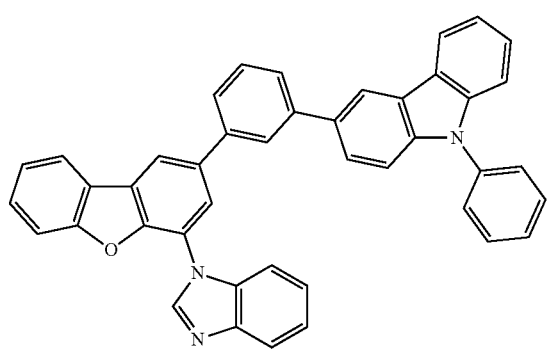
H33

-continued
| H34 | H35 |
|---|---|
| 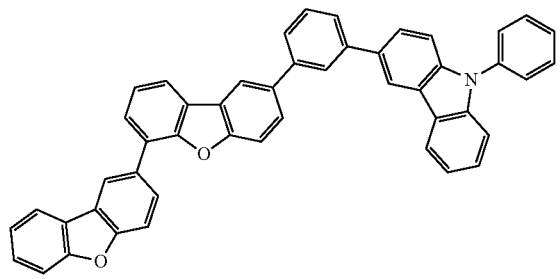 | 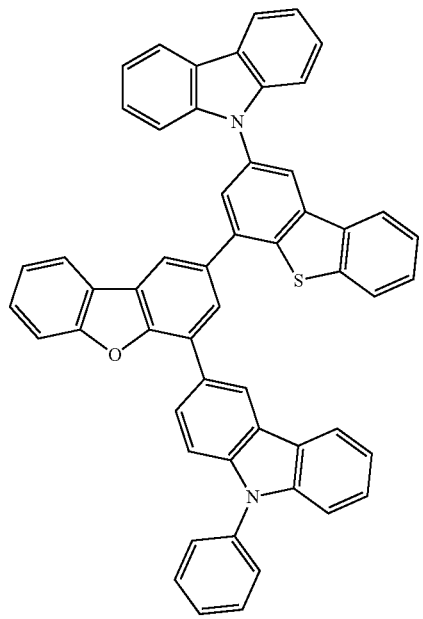 |
| H36 | H37 |
|---|---|
| 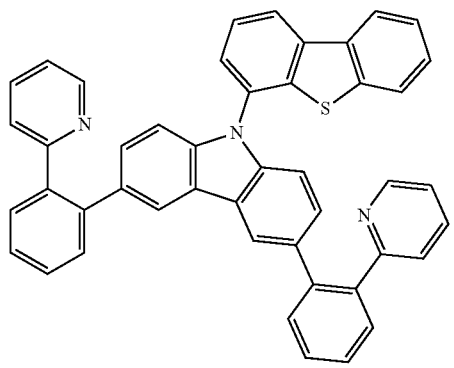 | 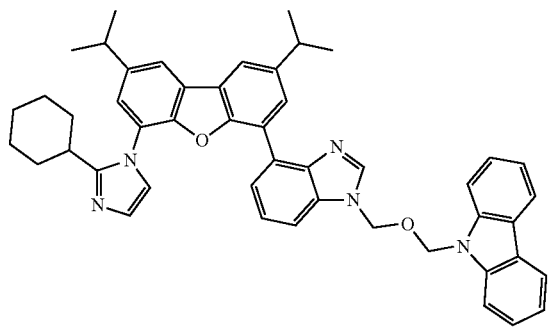 |
| H41 | H42 |
|---|---|
| 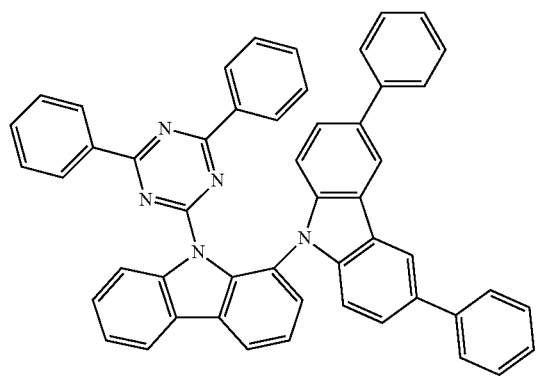 | 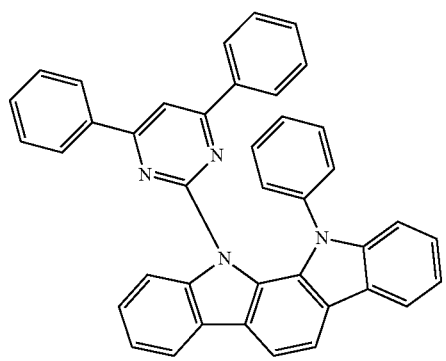 |

-continued
H43
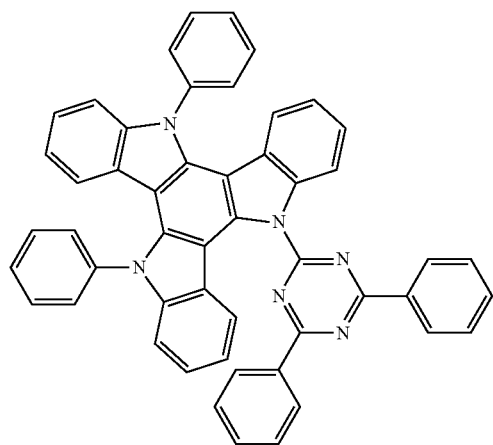
H44
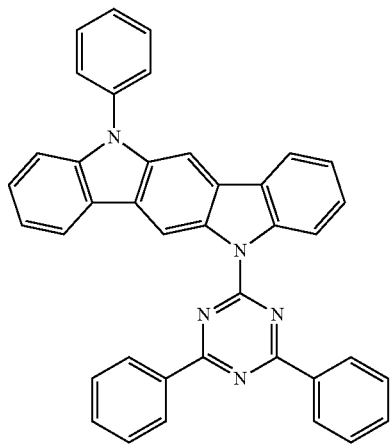
H45
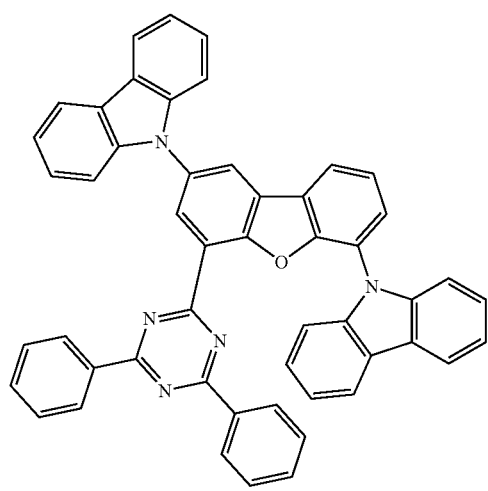
H46
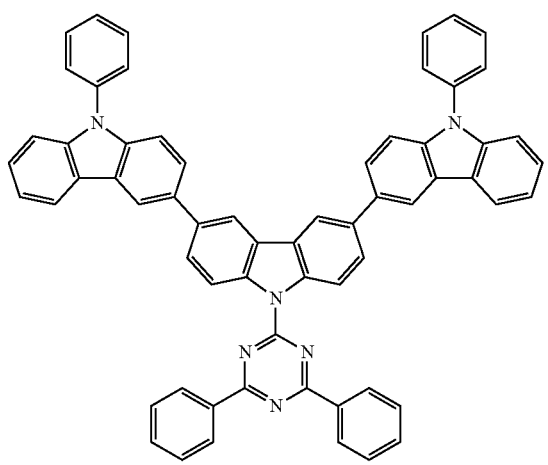
H47
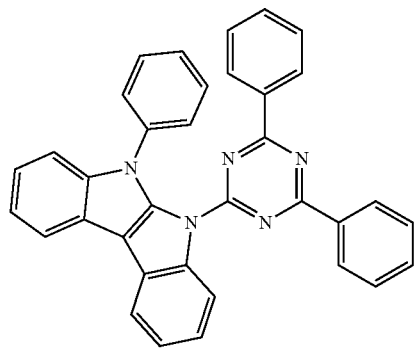
H48
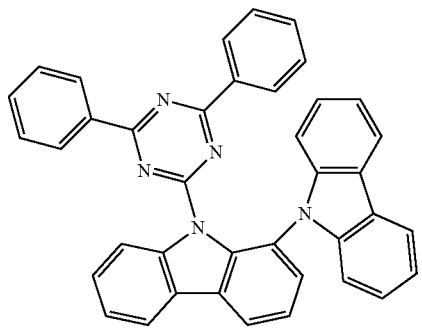

-continued
H49
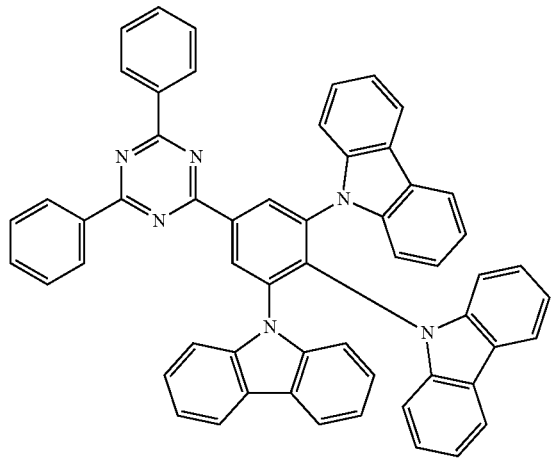
H50
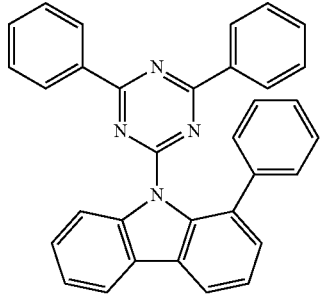
H51
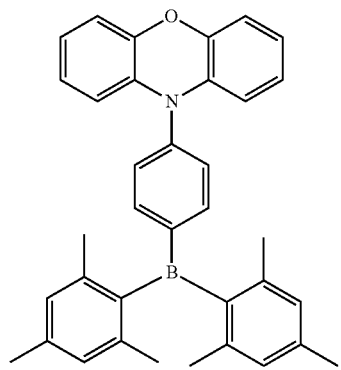
H52
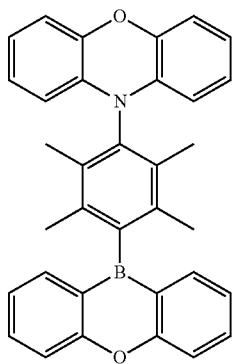
H53
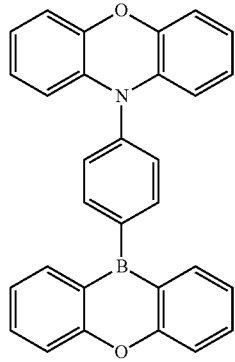
H54
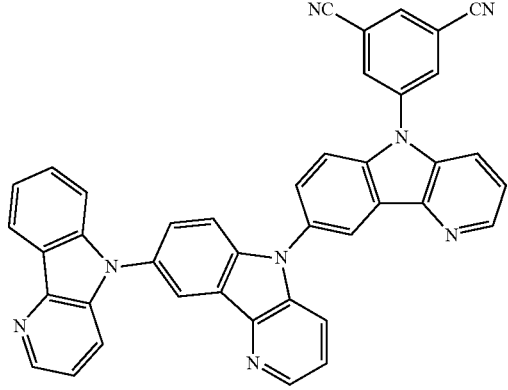
H55
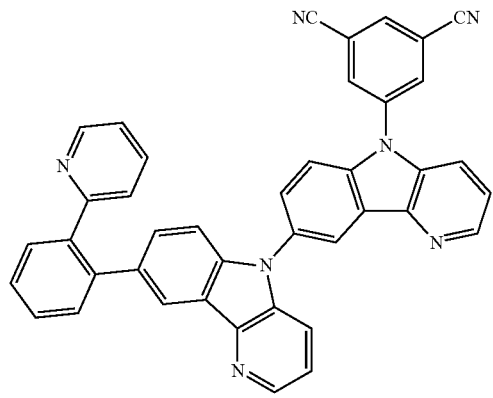
H56
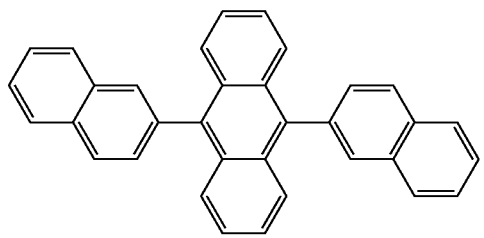

-continued
H57
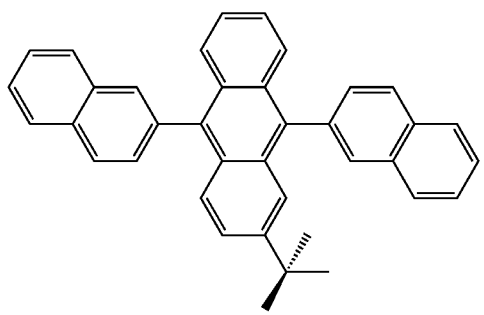
H58
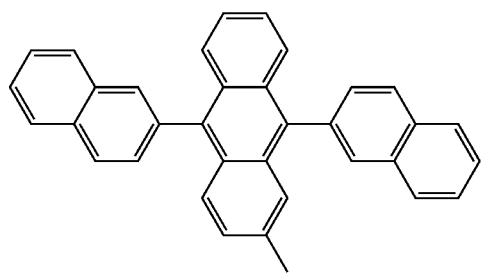
H59
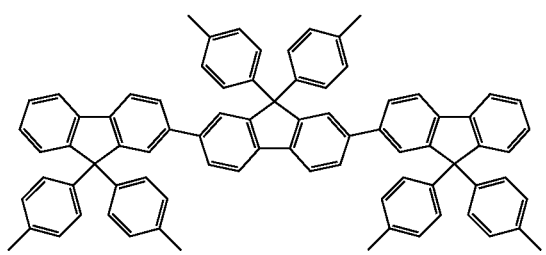
H60
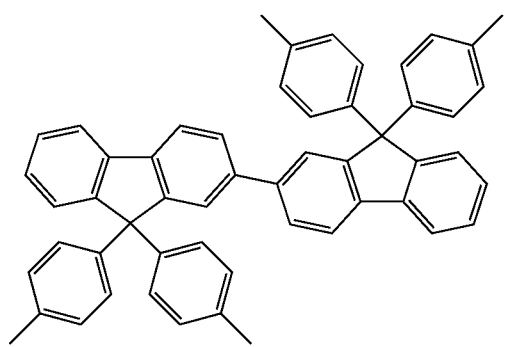
H61
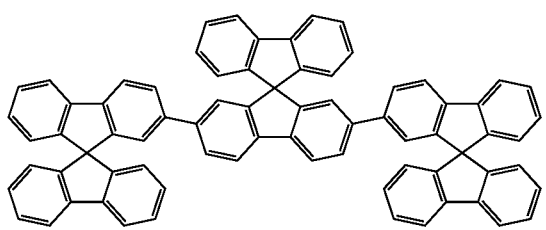
H62
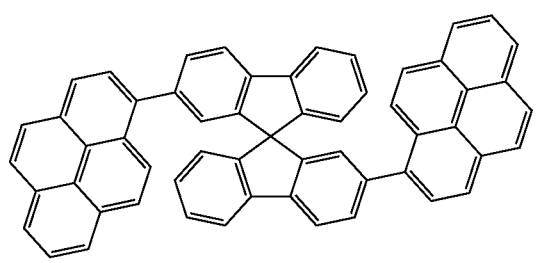
H63
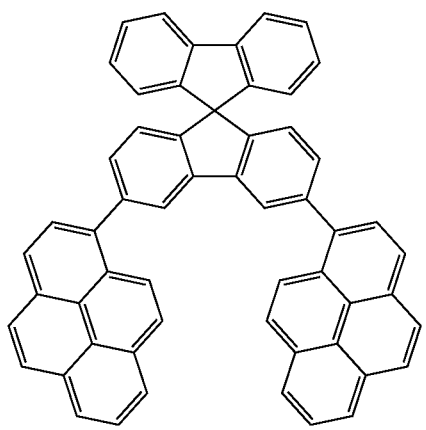
H64
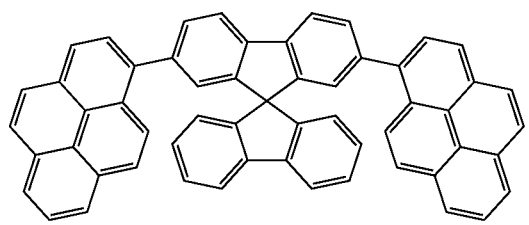

-continued
H65
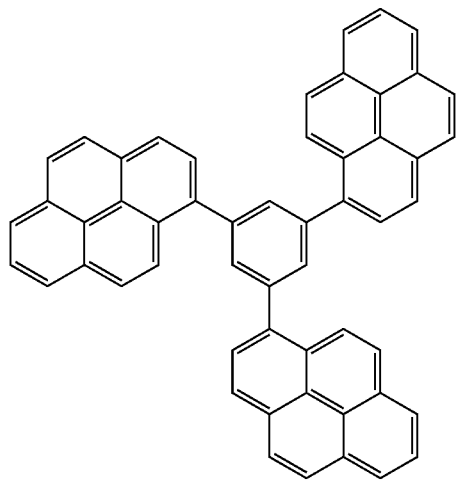
H66
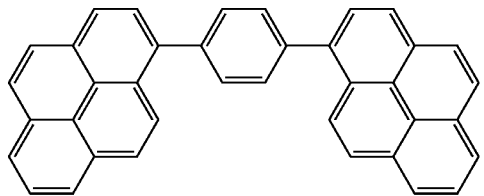
H67
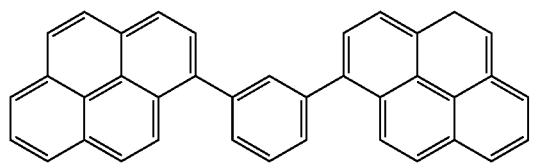
H68
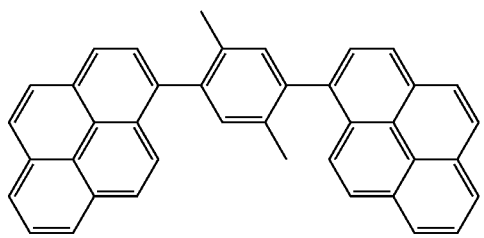
H69
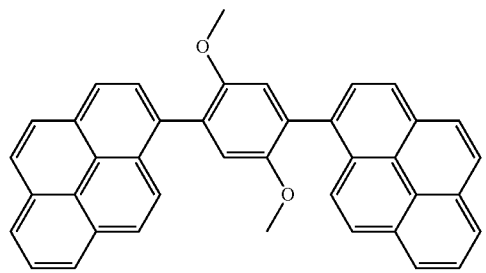
H70
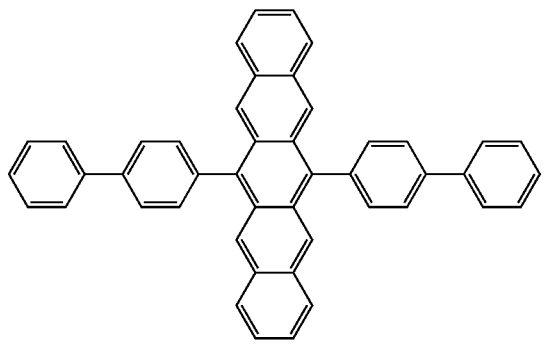
H71
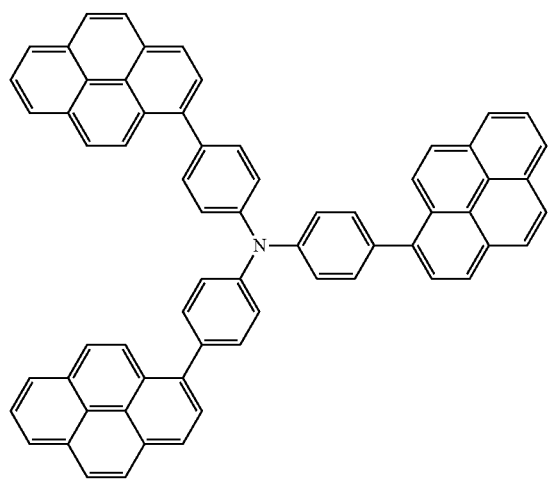
H72
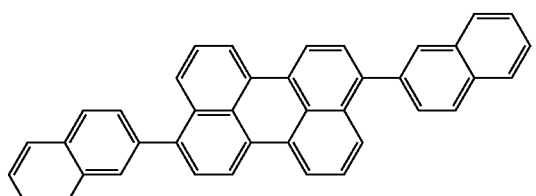

-continued
H73
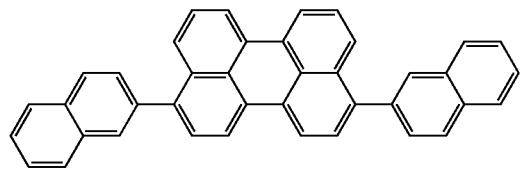
H74
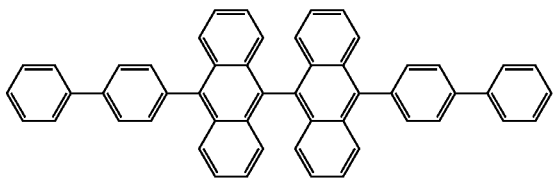
H75
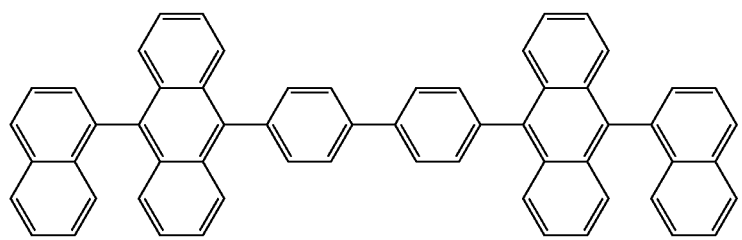
H76
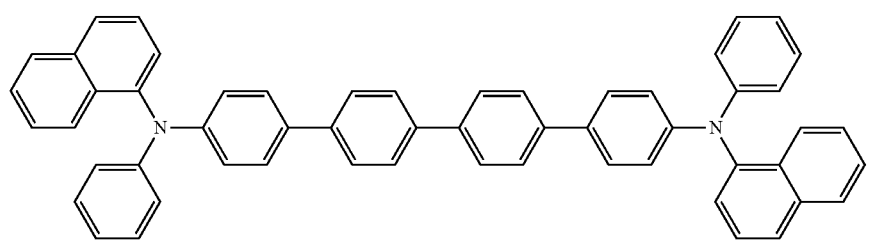
H77
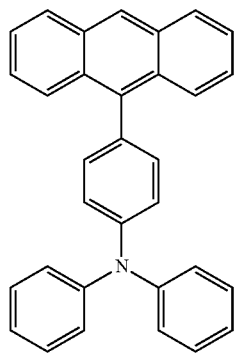
H78
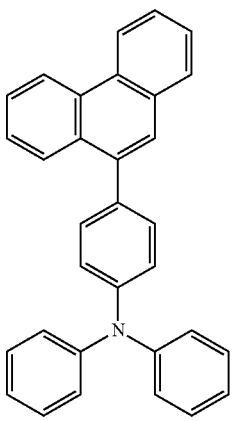
H79
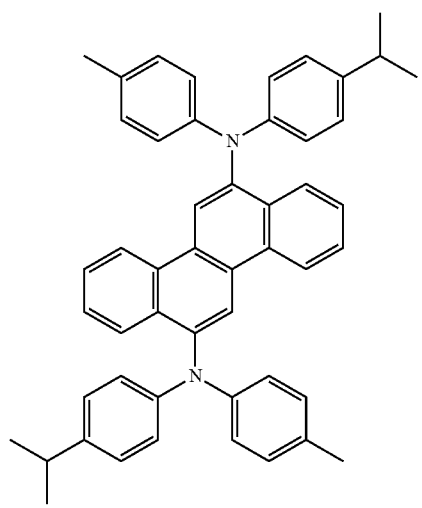
H80
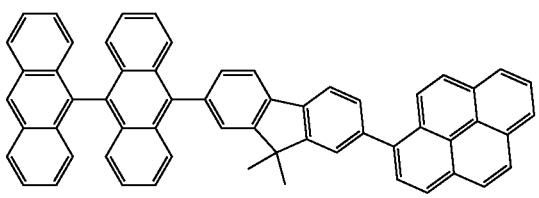

-continued
H81
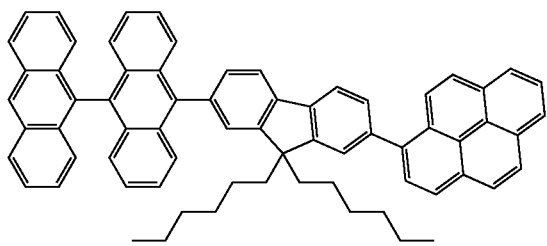
H82
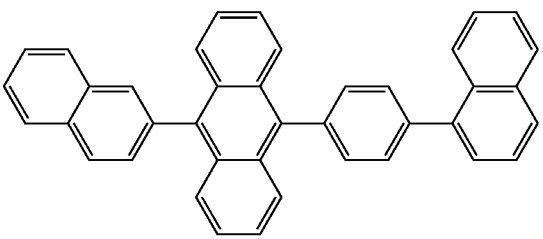
H83
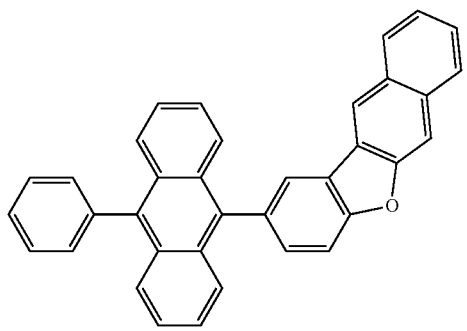
H84
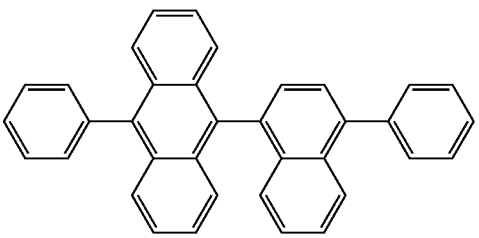
H85
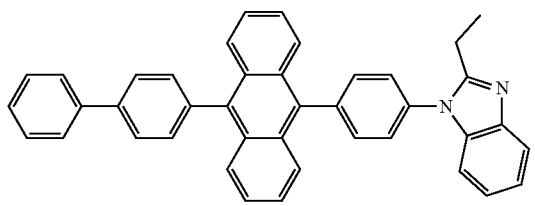
H-1 (OC-29)
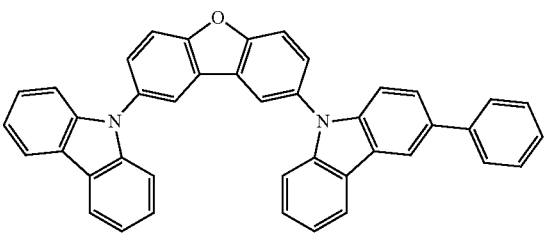
H-2
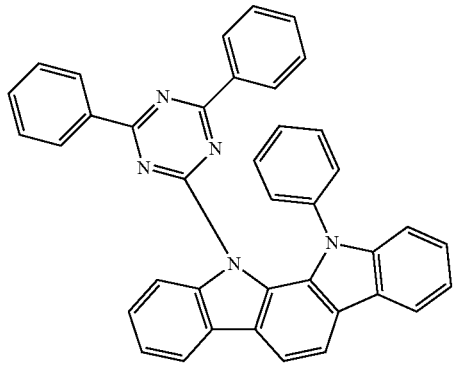
H-3
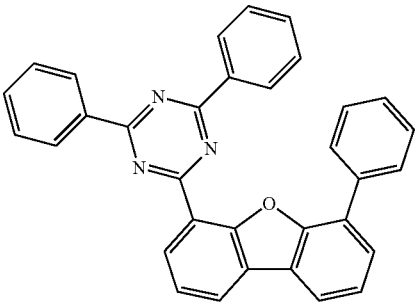
H-4 (H84)
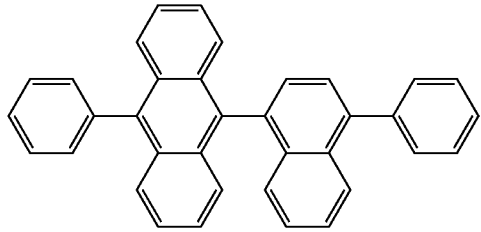
As specific examples of a known host compound used in an organic EL element of the present invention, the compounds described in the following Documents are cited. However, the present invention is not limited to them.
Japanese patent application publication (JP-A) Nos. 20010-257076, 2002-308855, 2001-313179, 2002-319491, 2001-357977, 2002-334786, 2002-8860, 2002-334787, 2002-15871, 2002-334788, 2002-43056, 2002-334789, 2002-75645, 2002-338579, 2002-105445, 2002-343568, 2002-141173, 2002-352957, 2002-203683, 2002-363227, 2002-231453, 2003-3165, 2002-234888, 2003-27048, 2002-255934, 2002-260861, 2002-280183, 2002-299060, 2002-

302516, 2002-305083, 2002-305084 and 2002-308837; US Patent Application Publication (US) Nos. 2003/0175553, 2006/0280965, 2005/0112407, 2009/0017330, 2009/0030202, 2005/0238919; WO 2001/039234, WO 2009/021126, WO 2008/056746, WO 2004/093 207, WO 2005/089025, WO 2007/063796, WO 2007/063754, WO 2004/107822, WO 2005/030900, WO 2006/114966, WO 2009/086028, WO 2009/003898, WO 2012/023947, JP-A 2008-074939, JP-A 2007-254297, and EP 2034538. Further, the compounds H-1 to H-230 described in paragraphs [0255] to [0293] of JP-A No. 2015-38941 can also be suitably used.

Note that the host compound used in the present invention may be used in an adjacent layer adjacent to the light emitting layer.

As described above, the "fluorescent compound", the "phosphorescent compound" and the "host compound" contained in the luminescent film of the present invention have been described separately. However, any combination of "phosphorescent compound" and "host compound" may be used.

In addition, the plurality of "phosphorescent compounds" may be used in combination, and the plurality of "host compounds" may be used in combination. The luminescent film according to the present invention can be applied to various products, and can be applied to, for example, an organic electroluminescent element and an organic luminescent film solar cell described later. In addition, the luminescent film according to the present invention, besides the above-mentioned "phosphorescent compound" and "host compound", may further contain a known substance that is generally used when applied to each product.

[Organic Electroluminescent Element]

The luminescent film of the present invention can be suitably used as a light emitting layer of an organic electroluminescent element having a light emitting layer between an anode and a cathode. In the organic EL element of the present invention, it is preferable that the material used for the layer adjacent to the light emitting layer has a lowest triplet energy lower than the lowest triplet excited state of the phosphorescent compound contained in the light emitting layer. As the layer adjacent to the light emitting layer, for example, an electron transport layer is preferable.

«Constitution Layers of Organic Electroluminescent Element»

Representative element constitutions used for an organic EL element of the present invention are as follows, however, the present invention is not limited to these. (1) Anode/light emitting layer/cathode
(2) Anode/light emitting layer/electron transport layer/cathode
(3) Anode/hole transport layer/light emitting layer/cathode
(4) Anode/hole transport layer/light emitting layer/electron transport layer/cathode
(5) Anode/hole transport layer/light emitting layer/electron transport layer/electron injection layer/cathode
(6) Anode/hole injection layer/hole transport layer/light emitting layer/electron transport layer/cathode
(7) Anode/hole injection layer/hole transport layer/(electron blocking layer/) light emitting layer/(hole blocking layer/) electron transport layer/electron injection layer/cathode Among these, the embodiment (7) is preferably used. However, the present invention is not limited to this.

The light emitting layer of the present invention is composed of one or a plurality of layers. When a plurality of layers are employed, it may be placed a non-light emitting intermediate layer between the light emitting layers.

According to necessity, it may be provided with a hole blocking layer (it is also called as a hole barrier layer) or an electron injection layer (it is also called as a cathode buffer layer) between the light emitting layer and the cathode. Further, it may be provided with an electron blocking layer (it is also called as an electron barrier layer) or an hole injection layer (it is also called as an anode buffer layer) between the light emitting layer and the anode.

An electron transport layer according to the present invention is a layer having a function of transporting an electron. An electron transport layer includes an electron injection layer, and a hole blocking layer in a broad sense. Further, an electron transport layer unit may be composed of plural layers.

A hole transport layer according to the present invention is a layer having a function of transporting a hole. A hole transport layer includes a hole injection layer, and an electron blocking layer in a broad sense. Further, a hole transport layer unit may be composed of plural layers.

In the above-described typical element configuration, a layer excluding an anode and a cathode is also referred to as an "organic layer".

«Tandem Structure»

An organic EL element of the present invention may be so-called a tandem structure element in which plural light emitting units each containing at least one light emitting layer are laminated.

A representative example of an element constitution having a tandem structure is as follows.

Anode/first light emitting unit/second light emitting unit/third light emitting unit/cathode; and Anode/first light emitting unit/intermediate layer/second light emitting unit/intermediate layer/third light emitting unit/cathode.

Here, the above-described first light emitting unit, second light emitting unit, and third light emitting unit may be the same or different. It may be possible that two light emitting units are the same and the remaining one light emitting unit is different.

In addition, the third light emitting unit may not be provided. Otherwise, a further light emitting unit or a further intermediate layer may be provided between the third light emitting unit and the electrode.

The plural light emitting units each may be laminated directly or they may be laminated through an intermediate layer. Examples of an intermediate layer are: an intermediate electrode, an intermediate conductive layer, a charge generating layer, an electron extraction layer, a connecting layer, and an intermediate insulating layer. Known composing materials may be used as long as it can form a layer which has a function of supplying an electron to an adjacent layer to the anode, and a hole to an adjacent layer to the cathode.

Examples of a material used in an intermediate layer are: conductive inorganic compounds such as ITO (indium tin oxide), IZO (indium zinc oxide), $ZnO_2$, TiN, ZrN, HfN, $TiO_X$, $VO_X$, CuI, InN, GaN, $CuAlO_2$, $CuGaO_2$, $SrCu_2O_2$, $LaB_6$, $RuO_2$, and Al; a two-layer film such as $Au/Bi_2O_3$; a multi-layer film such as $SnO_2/Ag/SnO_2$, ZnO/Ag/ZnO, $Bi_2O_3/Au/Bi_2O_3$, $TiO_2/TiN/TiO_2$, and $TiO_2/ZrN/TiO_2$; fullerene such as $C_{60}$; and a conductive organic layer such as oligothiophene, metal phthalocyanine, metal-free phthalocyanine, metal porphyrin, and metal-free porphyrin. The present invention is not limited to them.

Examples of a preferable constitution in the light emitting unit are the constitutions of the above-described (1) to (7) from which an anode and a cathode are removed. However, the present invention is not limited to them.

Examples of a tandem type organic EL element are described in: U.S. Pat. Nos. 6,337,492, 7,420,203, 7,473,923, 6,872,472, 6,107,734, 6,337,492, WO 2005/009087, JP-A 2006-228712, JP-A 2006-24791, JP-A 2006-49393, JP-A 2006-49394, JP-A 2006-49396, JP-A 2011-96679, JP-A 2005-340187, JP Patent 4711424, JP Patent 3496681, JP Patent 3884564, JP Patent 4213169, JP-A 2010-192719, JP-A 2009-076929, JP-A 2008-078414, JP-A 2007-059848, JP-A 2003-272860, JP-A 2003-045676, and WO 2005/094130. The constitutions of the elements and the composing materials are described in these documents, however, the present invention is not limited to them.

Each layer that constitutes an organic EL element of the present invention will be described in the following.

«Light Emitting Layer»

A light emitting layer used in the present invention is a layer which provide a place of emitting light via an exciton produce by recombination of electrons and holes injected from an electrode or an adjacent layer. The light emitting portion may be either within the light emitting layer or at an interface between the light emitting layer and an adjacent layer thereof. The light emitting layer according to the present invention may have a configuration having the above-described "luminescent film" of the present invention. Specifically, the light emitting layer according to the present invention may be the "luminescent film" of the present invention, but is not particularly limited, and includes, for example, other light emitting layers and films made of other compounds and the like. The configuration of the light emitting layer according to the present invention is not particularly limited as long as the requirements for the luminescent film defined in the present invention are satisfied.

The total thickness of the light emitting layer is not particularly limited, but from the viewpoint of achieving homogeneity of the film to be formed and preventing application of unnecessary high voltage at the time of light emission and improvement of stability of luminescent color with respect to driving current, it is preferable to adjust in the range of 2 nm to 5 μm, more preferably in the range of 2 nm to 500 nm, and further preferably in the range of 5 to 200 nm.

In the present invention, the thickness of each light emitting layer is preferably adjusted in the range of 2 nm to 1 μm, more preferably adjusted in the range of 2 to 200 nm, further preferably in the range of 3 to 150 nm.

(Other Light Emitting Dopant and Host Compound)

Since the light emitting layer according to the present invention contains the luminescent film of the present invention as described above, it comprises the above-mentioned "phosphorescent compound" and "fluorescent compound" and, if necessary, "host compound". Further, in the organic EL element of the present invention, the luminescent film of the present invention may contain a material of a layer adjacent to the luminescent film. The material of the adjacent layer is not particularly limited as long as it is a material of the layer adjacent to the luminescent film (light emitting layer), and examples thereof include a compound contained in the hole transport layer. Thereby, as described above, the luminescent film of the present invention can stably provide an organic electroluminescence element that is hardly affected by an external environment. Further, the light emitting layer according to the present invention may contain a compound described below separately as long as the effects of the present invention are not impaired: (1) Light emitting dopant (hereinafter, also referred to as "other light emitting dopant"): (1.1) Phosphorescent compound (hereinafter, also referred to as "other phosphorescent compound"), (1. 2) Fluorescent compound (hereinafter, also referred to as "other fluorescent compound")" or "(2) Host compound (hereinafter, also referred to as "other host compound").

(1) Other Light Emitting Dopant

As the other light emitting dopant according to the present invention, it is preferable to use other phosphorescence emitting compounds (also referred to as other phosphorescent dopants or other phosphorescent compounds) in combination with other fluorescence emitting compounds (other fluorescent dopants or other fluorescent compounds).

The phosphorescent compound and other phosphorescent compounds according to the present invention may be used in combination of a plurality of kinds, or a combination of dopants having different structures may be used. As a result, an arbitrary luminescent color can be obtained.

In the present invention, it is also preferable that one or a plurality of light emitting layers contain a plurality of light emitting dopants having different emission colors and exhibit white light emission.

The combination of the light emitting dopants exhibiting white color is not particularly limited, and for example, a combination of blue and orange, and a combination of blue, green and red can be cited.

(Other Phosphorescent Compound)

The other phosphorescent compound (hereinafter, it may be called as "other phosphorescent dopant") will be described.

The other phosphorescent dopant according to the present invention is a compound which is observed emission from an excited triplet state thereof. Specifically, it is a compound which emits phosphorescence at room temperature (25° C.) and exhibits a phosphorescence quantum yield of at least 0.01 at 25° C. The phosphorescence quantum yield is preferably at least 0.1.

The phosphorescence quantum yield will be determined via a method described in page 398 of "Spectroscopy II of 4th Edition Lecture of Experimental Chemistry 7" (1992, published by Maruzen Co. Ltd.). The phosphorescence quantum yield in a solution will be determined using appropriate solvents. However, it is only necessary for the phosphorescent dopant of the present invention to exhibit the above phosphorescence quantum yield (0.01 or more) using any of the appropriate solvents.

Two kinds of principles regarding emission of the other phosphorescent dopant are cited. One is an energy transfer-type, wherein carriers recombine on a host compound on which the carriers are transferred to produce an excited state of the host compound, and then via transfer of this energy to the other phosphorescent dopant, emission from the phosphorescent dopant is realized. The other is a carrier trap-type, wherein the other phosphorescent dopant serves as a carrier trap and then the carriers recombine on the other phosphorescent dopant to generate emission from the other phosphorescent dopant. In each case, the excited state energy level of the other phosphorescent dopant is required to be lower than that of the host compound.

The other phosphorescent dopant usable in the present invention may be suitably selected and employed from the known materials used for a light emitting layer for an organic EL element.

Specific examples of other phosphorescent dopants that can be used in the present invention include known compounds described in the literature exemplified as the phosphorescent compound according to the present invention.

Among them, preferable other phosphorescent dopants are organic metal complexes containing Ir as a center metal.

More preferable are complexes containing at least one coordination mode selected from a metal-carbon bond, a metal-nitrogen bond, a metal-oxygen bond and a metal-sulfur bond.

(1.2) Other Fluorescent Dopant

The other fluorescent dopant (hereinafter, it may be called as "other fluorescent dopant") will be described.

The other fluorescent dopant is a compound capable of emitting light from a singlet excited state, and is not particularly limited as long as light emission from a singlet excited state is observed.

Examples of the other fluorescent dopant are: an anthracene derivative, a pyrene derivative, a chrysene derivative, a fluoranthene derivative, a perylene derivative, a fluorene derivative, an arylacetylene derivative, a styrylarylene derivative, a styfylamine derivative, an arylamine derivative, a boron complex, a coumarin derivative, a pyran derivative, a cyanine derivative, a croconium derivative, a squarylium derivative, an oxobenzanthracene derivative, a fluorescein derivative, a rhodamine derivative, a pyrylium derivative, a perylene derivative, a polythiophene derivative, and a rare earth complex compound.

In recent years, light emitting dopants utilizing delayed fluorescence were developed. These dopants may be used.

Specific examples of a light emitting dopant utilizing delayed fluorescence are compounds described in: WO 2011/156793, JP-A 2011-213643, and JP-A 2010-93181. However, the present invention is not limited to them.

(2) Other Host Compound

The other host compound is a compound which mainly plays a role of injecting or transporting a charge in the light emitting layer. In an organic EL element, an emission from the host compound itself is substantially not observed.

Preferably, the other host compound is a compound exhibiting a phosphorescent emission yield of less than 0.1 at a room temperature (25° C.), more preferably a compound exhibiting a phosphorescent emission yield of less than 0.01.

It is preferable that the excited energy level of the other host compound is higher than the excited energy level of the phosphorescent metal complex contained in the same layer.

The other host compounds may be used singly or may be used in combination of two or more compounds. By using a plurality of the other host compounds, it is possible to adjust transfer of charge, thereby it is possible to achieve an organic EL element of high efficiency.

The other host compound is not specifically limited. A known compound previously used in an organic EL element may be used. It may be a compound having a low molecular weight, or a polymer having a high molecular weight. Further, it may be a compound having a reactive group such as a vinyl group or an epoxy group.

As a known host compound, preferably, it has a hole transporting ability or an electron transporting ability, as well as preventing elongation of an emission wavelength. In addition, from the viewpoint of stably driving an organic EL element at high temperature, it is preferable that a host compound has a high glass transition temperature (Tg) of 90° C. or more, more preferably, has a Tg of 120° C. or more.

Specific examples of the other host compounds used in the organic EL element according to the present invention include, but are not limited to, known compounds described in the literature exemplified as the host compound according to the present invention.

Further, the other host compounds according to the present invention may be used in an adjacent layer adjacent to the light emitting layer.

«Electron Transport Layer»

An electron transport layer of the present invention is composed of a material having a function of transferring an electron. It is only required to have a function of transporting an injected electron from a cathode to a light emitting layer. Further, with respect to the material used for the electron transport layer according to the present invention, it is preferable that the lowest triplet energy of the material is lower than the lowest triplet excited state of the phosphorescent compound contained in the light emitting layer. This is preferable in that deterioration is suppressed and the life of the element is improved.

A total layer thickness of the electron transport layer is not specifically limited, however, it is generally in the range of 2 nm to 5 µm, and preferably, it is in the range of 2 to 500 nm, and more preferably, it is in the range of 5 to 200 nm.

In an organic EL element, it is known that there occurs interference between the light directly taken from the light emitting layer and the light reflected at the electrode located at the opposite side of the electrode from which the light is taken out at the moment of taking out the light which is produced in the light emitting layer. When the light is reflected at the cathode, it is possible to use effectively this interference effect by suitably adjusting the total thickness of the electron transport layer in the range of 5 nm to 1 µm.

On the other hand, the voltage will be increased when the layer thickness of the electron transport layer is made thick. Therefore, especially when the layer thickness is large, it is preferable that the electron mobility in the electron transport layer is $10^{-5}$ cm$^2$/Vs or more.

As a material used for an electron transport layer (hereinafter, it is called as "an electron transport material"), it is only required to have either a property of ejection or transport of electrons, or a barrier to holes. Any of the conventionally known compounds may be selected and they may be employed.

Cited examples thereof include: a nitrogen-containing aromatic heterocyclic derivative (a carbazole derivative, an azacarbazole derivative (a compound in which one or more carbon atoms constituting the carbazole ring are substitute with nitrogen atoms), a pyridine derivative, a pyrimidine derivative, a pyrazine derivative, a pyridazine derivative, a triazine derivative, a quinoline derivative, a quinoxaline derivative, a phenanthroline derivative, an azatriphenylene derivative, an oxazole derivative, a thiazole derivative, an oxadiazole derivative, a thiadiazole derivative, a triazole derivative, a benzimidazole derivative, a benzoxazole derivative, and a benzothiazole derivative); a dibenzofuran derivative, a dibenzothiophene derivative, a silole derivative; and an aromatic hydrocarbon ring derivative (a naphthalene derivative, an anthracene derivative and a triphenylene derivative).

Further, metal complexes having a ligand of a 8-quinolinol structure or dibnenzoquinolinol structure such as tris(8-quinolinol)aluminum (Alq$_3$), tris(5,7-dichloro-8-quinolinol)aluminum, tris(5,7-dibromo-8-quinolinol)aluminum, tris(2-methyl-8-quinolinol)aluminum, tris(5-methyl-8-quinolinol)aluminum and bis(8-quinolinol)zinc (Znq); and metal complexes in which a central metal of the aforesaid metal complexes is substituted by In, Mg, Cu, Ca, Sn, Ga or Pb, may be also utilized as an electron transport material.

Further, a metal-free or metal phthalocyanine, or a compound whose terminal is substituted by an alkyl group or a sulfonic acid group, may be preferably utilized as an electron transport material. A distyrylpyrazine derivative, which is exemplified as a material for a light emitting layer, may be used as an electron transport material. Further, in the same manner as used for a hole injection layer and a hole transport layer, an inorganic semiconductor such as an n-type Si and an n-type SiC may be also utilized as an electron transport material.

A polymer material which is introduced these compounds in the polymer side-chain or a polymer main chain may be used.

In an electron transport layer according to the present invention, it is possible to employ an electron transport layer of a higher n property (electron rich) which is doped with impurities as a guest material. As examples of a dope material, listed are those described in each of JP-A Nos. 4-297076, 10-270172, 2000-196140, 2001-102175, as well as in J. Appl. Phys., 95, 5773 (2004).

Although the present invention is not limited thereto, preferable examples of a known electron transport material used in an organic EL element of the present invention are compounds described in the following publications.

U.S. Pat. Nos. 6,528,187, 7,230,107, US 2005/0025993, US 2004/0036077, US 2009/0115316, US 2009/0101870, US 2009/0179554, WO 2003/060956, WO 2008/132085, Appl. Phys. Lett. 75, 4 (1999), Appl. Phys. Lett. 79, 449 (2001), Appl. Phys. Lett. 81, 162 (2002), Appl. Phys. Lett. 81, 162 (2002), Appl. Phys. Lett. 79, 156 (2001), U.S. Pat. No. 7,964,293, US 2009/030202, WO 2004/080975, WO 2004/063159, WO 2005/085387, WO 2006/067931, WO 2007/086552, WO 2008/114690, WO 2009/069442, WO 2009/066779, WO 2009/054253, WO 2011/086935, WO 2010/150593, WO 2010/047707, EP 2311826, JP-A 2010-251675, JP-A 2009-209133, JP-A 2009-124114, JP-A 2008-277810, JP-A 2006-156445, JP-A 2005-340122, JP-A 2003-45662, JP-A 2003-31367, JP-A 2003-282270, and WO 2012/115034.

Examples of a preferable electron transport material are: a pyridine derivative, a pyrimidine derivative, a pyrazine derivative, a triazine derivative, a dibenzofuran derivative, a dibenzothiophene derivative, a carbazole derivative, an azacarbazole derivative, and a benzimidazole derivative.

An electron transport material may be used singly, or may be used in combination of plural kinds of compounds.

«Hole Blocking Layer»

A hole blocking layer is a layer provided with a function of an electron transport layer in a broad meaning. Preferably, it contains a material having a function of transporting an electron, and having very small ability of transporting a hole. It will improve the recombination probability of an electron and a hole by blocking a hole while transporting an electron.

Further, a composition of an electron transport layer described above may be appropriately utilized as a hole blocking layer of the present invention when needed.

A hole blocking layer placed in an organic EL element of the present invention is preferably arranged at a location in the light emitting layer adjacent to the cathode side.

A thickness of a hole blocking layer according to the present invention is preferably in the range of 3 to 100 nm, and more preferably, in the range of 5 to 30 nm.

With respect to a material used for a hole blocking layer, the material used in the aforesaid electron transport layer is suitably used, and further, the material used as the aforesaid host compound is also suitably used for a hole blocking layer.

«Electron Injection Layer»

An electron injection layer (it is also called as "a cathode buffer layer") according to the present invention is a layer which is arranged between a cathode and a light emitting layer to decrease an operating voltage and to improve an emission luminance An example of an electron injection layer is detailed in volume 2, chapter 2 "Electrode materials" (pp. 123-166) of "Organic EL Elements and Industrialization Front thereof (Nov. 30, 1998, published by N.T.S. Co. Ltd.)".

In the present invention, an electron injection layer is provided according to necessity, and as described above, it is placed between a cathode and a light emitting layer, or between a cathode and an electron transport layer.

An electron injection layer is preferably a very thin layer. The layer thickness thereof is preferably in the range of 0.1 to 5 nm depending on the materials used.

An election injection layer is detailed in JP-A Nos. 6-325871, 9-17574, and 10-74586. Examples of a material preferably used in an election injection layer include: a metal such as strontium and aluminum; an alkaline metal compound such as lithium fluoride, sodium fluoride, or potassium fluoride; an alkaline earth metal compound such as magnesium fluoride; a metal oxide such as aluminum oxide; and a metal complex such as lithium 8-hydroxyquinolate (Liq). It is possible to use the aforesaid electron transport materials.

The above-described materials may be used singly or plural kinds may be used together in an election injection layer.

«Hole Transport Layer»

In the present invention, a hole transport layer contains a material having a function of transporting a hole. A hole transport layer is only required to have a function of transporting a hole injected from an anode to a light emitting layer.

The total layer thickness of a hole transport layer of the present invention is not specifically limited, however, it is generally in the range of 5 nm to 5 μm, preferably in the range of 2 to 500 nm, and more preferably in the range of 5 nm to 200 nm.

A material used in a hole transport layer (hereinafter, it is called as "a hole transport material") is only required to have any one of properties of injecting and transporting a hole, and a barrier property to an electron. A hole transport material may be suitably selected from the conventionally known compounds.

Examples of a hole transport material include: a porphyrin derivative, a phthalocyanine derivative, an oxazole derivative, an oxadiazole derivative, a triazole derivative, an imidazole derivative, a pyrazoline derivative, a pyrazolone derivative, a phenylenediamine derivative, a hydrazone derivative, a stilbene derivative, a polyarylalkane derivative, a triarylamine derivative, a carbazole derivative, an indolocarbazole derivative, an isoindole derivative, an acene derivative of anthracene or naphthalene, a fluorene derivative, a fluorenone derivative, polyvinyl carbazole, a polymer or an oligomer containing an aromatic amine in a side chain or a main chain, polysilane, and a conductive polymer or an oligomer (e.g., PEDOT: PSS, an aniline type copolymer, polyaniline and polythiophene).

Examples of a triarylamine derivative include: a benzidine type represented by α-NPD, a star burst type represented by MTDATA, a compound having fluorenone or anthracene in a triarylamine bonding core.

A hexaazatriphenylene derivative described in JP-A Nos. 2003-519432 and 2006-135145 may be also used as a hole transport material.

In addition, it is possible to employ an electron transport layer of a higher p property which is doped with impurities. As its example, listed are those described in each of JP-A Nos. 4-297076, 2000-196140, and 2001-102175, as well as in J. Appl. Phys., 95, 5773 (2004).

Further, it is possible to employ so-called p-type hole transport materials, and inorganic compounds such as p-type Si and p-type SiC, as described in JP-A No. 11-251067, and J. Huang et al. reference (Applied Physics Letters 80 (2002), p. 139). Moreover, an orthometal compounds having Ir or Pt as a center metal represented by $Ir(ppy)_3$ are also preferably used.

Although the above-described compounds may be used as a hole transport material, preferably used are: a triarylamine derivative, a carbazole derivative, an indolocarbazole derivative, an azatriphenylene derivative, an organic metal complex, a polymer or an oligomer incorporated an aromatic amine in a main chain or in a side chain.

Specific examples of a known hole transport material used in an organic EL element of the present invention are compounds in the aforesaid publications and in the following publications. However, the present invention is not limited to them.

Examples of the publication are: Appl. Phys. Lett. 69, 2160(1996), J. Lumin. 72-74, 985(1997), Appl. Phys. Lett. 78, 673(2001), Appl. Phys. Lett. 90, 183503(2007), Appl. Phys. Lett. 51, 913(1987), Synth. Met. 87, 171(1997), Synth. Met. 91, 209(1997), Synth. Met. 111, 421(2000), SID Symposium Digest, 37, 923(2006), J. Mater. Chem. 3, 319(1993), Adv. Mater. 6, 677(1994), Chem. Mater. 15, 3148(2003), US 2003/0162053, US 2002/0158242, US 2006/0240279, US 2008/0220265, U.S. Pat. No. 5,061,569, WO 2007/002683, WO 2009/018009, EP 650955, US 2008/0124572, US 2007/0278938, US 2008/0106190, US 2008/0018221, WO 2012/115034, JP-A 2003-519432, JP-A 2006-135145, and U.S. patent application Ser. No. 13/585,981.

A hole transport material may be used singly or may be used in combination of plural kinds of compounds.

«Electron Blocking Layer»

An electron blocking layer is a layer provided with a function of a hole transport layer in a broad meaning. Preferably, it contains a material having a function of transporting a hole, and having very small ability of transporting an electron. It will improve the recombination probability of an electron and a hole by blocking an electron while transporting a hole.

Further, a composition of a hole transport layer described above may be appropriately utilized as an electron blocking layer of an organic EL element when needed.

An electron blocking layer placed in an organic EL element is preferably arranged at a location in the light emitting layer adjacent to the anode side.

A thickness of an electron blocking layer is preferably in the range of 3 to 100 nm, and more preferably, it is in the range of 5 to 30 nm.

With respect to a material used for an electron blocking layer, the material used in the aforesaid hole transport layer is suitably used, and further, the material used as the aforesaid host compound is also suitably used for an electron blocking layer.

«Hole Injection Layer»

A hole injection layer (it is also called as "an anode buffer layer") is a layer which is arranged between an anode and a light emitting layer to decrease an operating voltage and to improve an emission luminance An example of a hole injection layer is detailed in volume 2, chapter 2 "Electrode materials" (pp. 123-166) of "Organic EL Elements and Industrialization Front thereof (Nov. 30, 1998, published by N.T.S. Co. Ltd.)".

A hole injection layer of the present invention is provided according to necessity, and as described above, it is placed between an anode and a light emitting layer, or between an anode and a hole transport layer.

A hole injection layer is also detailed in JP-A Nos. 9-45479, 9-260062 and 8-288069. As materials used in the hole injection layer, it is cited the same materials used in the aforesaid hole transport layer.

Among them, preferable materials are: a phthalocyanine derivative represented by copper phthalocyanine; a hexaazatriphenylene derivative described in JP-A Nos. 2003-519432 and 2006-135145; a metal oxide represented by vanadium oxide; a conductive polymer such as amorphous carbon, polyaniline (or called as emeraldine) and polythiophene; an orthometalated complex represented by tris(2-phenylpyridine) iridium complex; and a triarylamine derivative.

The above-described materials used in a hole injection layer may be used singly or plural kinds may be co-used.

«Other Additive»

The above-described organic layer of the present invention may further contain other additive.

Examples of an ingredient are: halogen elements such as bromine, iodine and chlorine, and a halide compound; and a compound, a complex and a salt of an alkali metal, an alkaline earth metal and a transition metal such as Pd, Ca and Na.

Although a content of an ingredient may be arbitrarily decided, preferably, it is 1,000 ppm or less based on the total mass of the layer containing the ingredient, more preferably, it is 500 ppm or less, and still more preferably, it is 50 ppm or less.

In order to improve a transporting property of an electron or a hole, or to facilitate energy transport of an exciton, the content of the ingredient is not necessarily within these range, and other range of content may be used.

«Forming Method of Organic Layer»

The method for producing an organic electroluminescence element having a luminescent film of the present invention can be suitably selected from known methods. In particular, it is preferable that the luminescent film is formed using a wet process or a dry process. In the following, a method of forming each organic layer (a hole injection layer, a hole transport layer, an electron blocking layer, a light emitting layer, a hole blocking layer, an electron transport layer, and an electron injection layer) will be described.

The method for forming the organic layer according to the present invention is not particularly limited, and a conventionally known method such as a vacuum deposition method such as a dry process or a formation method based on a wet process can be used. A method may be used in which a wet process or a dry process is selectively used and laminated to form an organic layer according to the material. Here, the organic layer is preferably a layer formed by a wet process. That is, it is preferable to manufacture an organic EL element by a wet process. By manufacturing an organic EL element by a wet process, it is possible to obtain effects such as easy formation of a uniform film (coating) and hardly generation of pinholes. Here, the film (coating) is a film that has been dried after being applied by a wet process.

Examples of a wet process include: a spin coating method, a cast method, an inkjet method, a printing method, a die coating method, a blade coating method, a roll coating method, a spray coating method, a curtain coating method, and a LB method (Langmuir Blodgett method). From the viewpoint of getting a uniform thin layer with high productivity, preferable are method highly appropriate to a roll-toroll method such as a die coating method, a roll coating method, an inkjet method, and a spray coating method.

Examples of the dry process include an evaporation method (resistance heating and an EB method), a sputtering method, and a CVD method.

Examples of a liquid medium to dissolve or to disperse materials according to the present invention include: ketones such as methyl ethyl ketone and cyclohexanone; aliphatic esters such as ethyl acetate; halogenated hydrocarbons such as dichlorobenzene; aromatic hydrocarbons such as toluene, xylene, mesitylene, and cyclohexylbenzene; aliphatic hydrocarbons such as cyclohexane, decalin, and dodecane; organic solvents such as DMF and DMSO.

These will be dispersed with a dispersion method such as an ultrasonic dispersion method, a high shearing dispersion method and a media dispersion method.

A different film forming method may be applied to every organic layer. When a vapor deposition method is adopted for forming each layer, the vapor deposition conditions may be changed depending on the compounds used. Generally, the following ranges are suitably selected for the conditions, heating temperature of boat: 50 to 450° C., level of vacuum: $10^{-6}$ to $10^{-2}$ Pa, vapor deposition rate: 0.01 to 50 nm/sec, temperature of substrate: −50 to 300° C., and layer thickness: 0.1 nm to 5 μm, preferably 5 to 200 nm.

Formation of each organic layer according to the present invention is preferably continuously carried out from a hole injection layer to a cathode with one time vacuuming. It may be taken out on the way, and a different layer forming method may be employed. In that case, the operation is preferably done under a dry inert gas atmosphere.

«Anode»

As an anode of an organic EL element, a metal having a large work function (4 eV or more, preferably, 4.5 eV or more), an alloy, and a conductive compound and a mixture thereof are utilized as an electrode substance. Specific examples of an electrode substance are: metals such as Au, and an alloy thereof; transparent conductive materials such as CuI, indium tin oxide (ITO), $SnO_2$, and ZnO. Further, a material such as IDIXO ($In_2O_3$—ZnO), which may form an amorphous and transparent electrode, may also be used.

As for an anode, these electrode substances may be made into a thin layer by a method such as a vapor deposition method or a sputtering method; followed by making a pattern of a desired form by a photolithography method. Otherwise, when the requirement of pattern precision is not so severe (about 100 μm or more), a pattern may be formed through a mask of a desired form at the time of layer formation with a vapor deposition method or a sputtering method using the above-described material.

Alternatively, when a coatable substance such as an organic conductive compound is employed, it is possible to employ a wet film forming method such as a printing method or a coating method. When emitted light is taken out from the anode, the transmittance is preferably set to be 10% or more. A sheet resistance of the anode is preferably a few hundred Ω/sq or less.

Further, although a layer thickness of the anode depends on a material, it is generally selected in the range of 10 nm to 1 μm, and preferably in the range of 10 to 200 nm.

«Cathode»

As a cathode, a metal having a small work function (4 eV or less) (it is called as an electron injective metal), an alloy, a conductive compound and a mixture thereof are utilized as an electrode substance. Specific examples of the aforesaid electrode substance includes: sodium, sodium-potassium alloy, magnesium, lithium, a magnesium/copper mixture, a magnesium/silver mixture, a magnesium/aluminum mixture, a magnesium/indium mixture, an aluminum/aluminum oxide ($Al_2O_3$) mixture, indium, a lithium/aluminum mixture, aluminum, and a rare earth metal. Among them, with respect to an electron injection property and durability against oxidation, preferable are: a mixture of election injecting metal with a second metal which is stable metal having a work function larger than the electron injecting metal. Examples thereof are: a magnesium/silver mixture, a magnesium/aluminum mixture, a magnesium/indium mixture, an aluminum/aluminum oxide ($Al_2O_3$) mixture, a lithium/aluminum mixture and aluminum.

A cathode may be made by using these electrode substances with a method such as a vapor deposition method or a sputtering method to form a thin film. A sheet resistance of the cathode is preferably a few hundred Ω/sq or less. A layer thickness of the cathode is generally selected in the range of 10 nm to 5 μm, and preferably in the range of 50 to 200 nm.

In order to transmit emitted light, it is preferable that one of an anode and a cathode of an organic EL element is transparent or translucent for achieving an improved luminescence.

Further, after forming a layer of the aforesaid metal having a thickness of 1 to 20 nm on the cathode, it is possible to prepare a transparent or translucent cathode by providing with a conductive transparent material described in the description for the anode thereon. By applying this process, it is possible to produce an element in which both an anode and a cathode are transparent.

«Support Substrate»

A support substrate which may be used for an organic EL element of the present invention is not specifically limited with respect to types such as glass and plastics. Hereinafter, the support substrate may be also called as substrate body, substrate, substrate substance, or support. They may be transparent or opaque. However, a transparent support substrate is preferable when the emitting light is taken from the side of the support substrate. Support substrates preferably utilized includes such as glass, quartz and transparent resin film. A specifically preferable support substrate is a resin film capable of providing an organic EL element with a flexible property.

Examples of a resin film include: polyesters such as polyethylene terephthalate (PET) and polyethylene naphthalate (PEN), polyethylene, polypropylene, cellophane, cellulose esters and their derivatives such as cellulose diacetate, cellulose triacetate (TAC), cellulose acetate butyrate, cellulose acetate propionate (CAP), cellulose acetate phthalate, and cellulose nitrate, polyvinylidene chloride, polyvinyl alcohol, polyethylene vinyl alcohol, syndiotactic polystyrene, polycarbonate, norbornene resin, polymethyl pentene, polyether ketone, polyimide, polyether sulfone (PES), polyphenylene sulfide, polysulfones, polyether imide, polyether ketone imide, polyimide, fluororesin, Nylon, polymethyl methacrylate, acrylic resin, polyallylates and cycloolefin resins such as ARTON (trade name, made by JSR Co. Ltd.) and APEL (trade name, made by Mitsui Chemicals, Inc.).

On a surface of a resin film, it may be formed a film incorporating an inorganic or an organic compound or a hybrid film incorporating both compounds. It is preferable that the film is a barrier film having a water vapor permeability of 0.01 g/($m^2$·day) or less (25±0.5° C., humidity 90±2% RH) determined by the method based on JIS K 7129-1992. It is more preferable that the film is a high barrier film having an oxygen permeability of $10^{-3}$ mL/

($m^2 \cdot day \cdot atm$) or less determined by the method based on JIS K 7126-1987, and a water vapor permeability of $10^{-5}$ mL/($m^2 \cdot day$) or less.

As materials that form a barrier film, employed may be those which retard penetration of moisture and oxygen, which deteriorate the element. For example, it is possible to employ silicon oxide, silicon dioxide, and silicon nitride. Further, in order to improve the brittleness of the aforesaid film, it is more preferable to achieve a laminated layer structure of inorganic layers and organic layers. The laminating order of the inorganic layer and the organic layer is not particularly limited, but it is preferable that both are alternatively laminated a plurality of times.

Barrier film forming methods are not particularly limited. Examples of employable methods include a vacuum deposition method, a sputtering method, a reactive sputtering method, a molecular beam epitaxy method, a cluster ion beam method, an ion plating method, a plasma polymerization method, a plasma CVD method, a laser CVD method, a thermal CVD method, and a coating method. Of these, specifically preferred is a method employing an atmospheric pressure plasma polymerization method, described in JP-A No. 2004-68143.

Examples of opaque support substrates include metal plates such aluminum or stainless steel films, opaque resin substrates, and ceramic substrates.

An external extraction quantum efficiency of light emitted by the organic EL element of the present invention is preferably 1% or more at a room temperature, but is more preferably 5% or more.

External extraction quantum efficiency (%)=(Number of photons emitted by the organic EL element to the exterior/Number of electrons fed to organic EL element)×100.

Further, it may be used simultaneously a color hue improving filter such as a color filter, or it may be used simultaneously a color conversion filter which convert emitted light color from the organic EL element to multicolor by employing fluorescent materials.

«Sealing»

As sealing means employed in the present invention, listed may be, for example, a method in which sealing members, electrodes, and a support substrate are subjected to adhesion via adhesives. The sealing members may be arranged to cover the display region of an organic EL element, and may be a concave plate or a flat plate. Neither transparency nor electrical insulation is limited.

Specifically listed are glass plates, polymer plate-films, metal plate-films. Specifically, it is possible to list, as glass plates, soda-lime glass, barium-strontium containing glass, lead glass, aluminosilicate glass, borosilicate glass, barium borosilicate glass, and quartz. Further, listed as polymer plates may be polycarbonate, polyethylene terephthalate, polyether sulfide, and polysulfone. As a metal plate, listed are those composed of at least one metal selected from the group consisting of stainless steel, iron, copper, aluminum magnesium, nickel, zinc, chromium, titanium, molybdenum, silicon, germanium, and tantalum, or alloys thereof.

In the present invention, since it is possible to achieve a thin organic EL element, it is preferable to employ a polymer film or a metal film. Further, it is preferable that the polymer film has a water vapor permeability (WVTR) of 0.001 to 1 g/($m^2 \cdot day$) determined by the method based on JIS K 7129-1992 and an oxygen permeability (OTR) of 0.001 to 1 mL/($m^2 \cdot day \cdot atm$) determined by the method based on JIS K 7126-1987. More preferably, the polymer film has WVTR in the range of 0.01 to 1 g/($m^2 \cdot day$) and OTR in the range of 0.01 to 1 mL/($m^2 \cdot day \cdot atm$).

Conversion of the sealing member into concave is carried out by employing a sand blast process or a chemical etching process.

In practice, as adhesives, listed may be photo-curing and heat-curing types having a reactive vinyl group of acrylic acid based oligomers and methacrylic acid, as well as moisture curing types such as 2-cyanoacrylates. Further listed may be thermal and chemical curing types (mixtures of two liquids) such as epoxy based ones. Still further listed may be hot-melt type polyamides, polyesters, and polyolefins. Yet further listed may be cationically curable type UV curable epoxy resin adhesives.

In addition, since an organic EL element is occasionally deteriorated via a thermal process, preferred are those which enable adhesion and curing between a room temperature and 80° C. Further, desiccating agents may be dispersed into the aforesaid adhesives. Adhesives may be applied onto sealing portions via a commercial dispenser or printed on the same in the same manner as screen printing.

Further, it is appropriate that on the outside of the aforesaid electrode which interposes the organic layer and faces the support substrate, the aforesaid electrode and organic layer are covered, and in the form of contact with the support substrate, inorganic and organic material layers are formed as a sealing film. In this case, as materials that form the aforesaid film may be those which exhibit functions to retard penetration of moisture or oxygen which results in deterioration. For example, it is possible to employ silicon oxide, silicon dioxide, and silicon nitride.

Still further, in order to improve brittleness of the aforesaid film, it is preferable that a laminated layer structure is formed, which is composed of these inorganic layers and layers composed of organic materials. Methods to form these films are not particularly limited. It is possible to employ, for example, a vacuum deposition method, a sputtering method, a reactive sputtering method, a molecular beam epitaxy method, a cluster ion beam method, an ion plating method, a plasma polymerization method, an atmospheric pressure plasma polymerization method, a plasma CVD method, a thermal CVD method, and a coating method.

It is preferable to inject a gas phase and a liquid phase material of inert gases such as nitrogen or argon, and inactive liquids such as fluorinated hydrocarbon or silicone oil into the space formed between the sealing member and the display region of the organic EL element. Further, it is possible to form vacuum in the space. Still further, it is possible to enclose hygroscopic compounds in the interior of the space.

Examples of a hygroscopic compound include: metal oxides (for example, sodium oxide, potassium oxide, calcium oxide, barium oxide, magnesium oxide, and aluminum oxide); sulfates (for example, sodium sulfate, calcium sulfate, magnesium sulfate, and cobalt sulfate); metal halides (for example, calcium chloride, magnesium chloride, cesium fluoride, tantalum fluoride, cerium bromide, magnesium bromide, barium iodide, and magnesium iodide); perchlorates (for example, barium perchlorate and magnesium perchlorate). In sulfates, metal halides, and perchlorates, suitably employed are anhydrides. For sulfate salts, metal halides and perchlorates, suitably used are anhydrous salts.

«Protective Film and Protective Plate»

On the aforesaid sealing film which interposes the organic layer and faces the support substrate or on the outside of the aforesaid sealing film, a protective or a protective plate may be arranged to enhance the mechanical strength of the element. Specifically, when sealing is achieved via the aforesaid sealing film, the resulting mechanical strength is not always high enough, therefore it is preferable to arrange the protective film or the protective plate described above. Usable materials for these include glass plates, polymer plate-films, and metal plate-films which are similar to those employed for the aforesaid sealing. However, from the viewpoint of reducing weight and thickness, it is preferable to employ a polymer film.

«Improving Method of Light Extraction»

It is generally known that an organic EL element emits light in the interior of the layer exhibiting the refractive index (being about 1.6 to 2.1) which is greater than that of air, whereby only about 15% to 20% of light generated in the light emitting layer is extracted. This is due to the fact that light incident to an interface (being an interlace of a transparent substrate to air) at an angle of 0 which is at least critical angle is not extracted to the exterior of the element due to the resulting total reflection, or light is totally reflected between the transparent electrode or the light emitting layer and the transparent substrate, and light is guided via the transparent electrode or the light emitting layer, whereby light escapes in the direction of the element side surface.

Means to enhance the efficiency of the aforesaid light extraction include, for example: a method in which roughness is formed on the surface of a transparent substrate, whereby total reflection is minimized at the interface of the transparent substrate to air (U.S. Pat. No. 4,774,435), a method in which efficiency is enhanced in such a manner that a substrate results in light collection (JP-A No. 63-314795), a method in which a reflection surface is formed on the side of the element (JP-A No. 1-220394), a method in which a flat layer of a middle refractive index is introduced between the substrate and the light emitting body and an antireflection film is formed (JP-A No. 62-172691), a method in which a flat layer of a refractive index which is equal to or less than the substrate is introduced between the substrate and the light emitting body (JP-A No. 2001-202827), and a method in which a diffraction grating is formed between the substrate and any of the layers such as the transparent electrode layer or the light emitting layer (including between the substrate and the outside) (JP-A No. 11-283751).

In the present invention, it is possible to employ these methods while combined with the organic EL element of the present invention. Of these, it is possible to appropriately employ the method in which a flat layer of a refractive index which is equal to or less than the substrate is introduced between the substrate and the light emitting body and the method in which a diffraction grating is formed between any layers of a substrate, and a transparent electrode layer and a light emitting layer (including between the substrate and the outside space).

By combining these means, the present invention enables the production of elements which exhibit higher luminance or excel in durability.

When a low refractive index medium having a thickness, greater than the wavelength of light is formed between the transparent electrode and the transparent substrate, the extraction efficiency of light emitted from the transparent electrode to the exterior increases as the refractive index of the medium decreases.

As materials of the low refractive index layer, listed are, for example, aerogel, porous silica, magnesium fluoride, and fluorine based polymers. Since the refractive index of the transparent substrate is commonly about 1.5 to 1.7, the refractive index of the low refractive index layer is preferably approximately 1.5 or less. More preferably, it is 1.35 or less.

Further, thickness of the low refractive index medium is preferably at least two times of the wavelength in the medium. The reason is that, when the thickness of the low refractive index medium reaches nearly the wavelength of light so that electromagnetic waves escaped via evanescent enter into the substrate, effects of the low refractive index layer are lowered.

The method in which the interface which results in total reflection or a diffraction grating is introduced in any of the media is characterized in that light extraction efficiency is significantly enhanced. The above method works as follows. By utilizing properties of the diffraction grating capable of changing the light direction to the specific direction different from diffraction via so-called Bragg diffraction such as primary diffraction or secondary diffraction of the diffraction grating, of light emitted from the light entitling layer, light, which is not emitted to the exterior due to total reflection between layers, is diffracted via introduction of a diffraction grating between any layers or in a medium (in the transparent substrate and the transparent electrode) so that light is extracted to the exterior.

It is preferable that the introduced diffraction grating exhibits a two-dimensional periodic refractive index. The reason is as follows. Since light emitted in the light emitting layer is randomly generated to all directions, in a common one-dimensional diffraction grating exhibiting a periodic refractive index distribution only in a certain direction, light which travels to the specific direction is only diffracted, whereby light extraction efficiency is not sufficiently enhanced.

However, by changing the refractive index distribution to a two-dimensional one, light, which travels to all directions, is diffracted, whereby the light extraction efficiency is enhanced.

A position to introduce a diffraction grating may be between any layers or in a medium (in a transparent substrate or a transparent electrode). However, a position near the organic light emitting layer, where light is generated, is preferable. In this case, the cycle of the diffraction grating is preferably from about ½ to 3 times of the wavelength of light in the medium. The preferable arrangement of the diffraction grating is such that the arrangement is two-dimensionally repeated in the form of a square lattice, a triangular lattice, or a honeycomb lattice.

«Light Collection Sheet»

Via a process to arrange a structure such as a micro-lens array shape on the light extraction side of the organic EL element of the present invention or via combination with a so-called light collection sheet, light is collected in the specific direction such as the front direction with respect to the light emitting element surface, whereby it is possible to enhance luminance in the specific direction.

In an example of the micro-lens array, square pyramids to realize a side length of 30 μm and an apex angle of 90 degrees are two-dimensionally arranged on the light extraction side of the substrate. The side length is preferably 10 to 100 μm. When it is less than the lower limit, coloration occurs due to generation of diffraction effects, while when it exceeds the upper limit, the thickness increases undesirably.

It is possible to employ, as a light collection sheet, for example, one which is put into practical use in the LED backlight of liquid crystal display devices. It is possible to employ, as such a sheet, for example, the luminance enhancing film (BEF), produced by Sumitomo 3M Limited. As shapes of a prism sheet employed may be, for example, A shaped stripes of an apex angle of 90 degrees and a pitch of 50 μm formed on a substrate, a shape in which the apex angle is rounded, a shape in which the pitch is randomly changed, and other shapes.

Further, in order to control the light radiation angle from the light emitting element, simultaneously employed may be a light diffusion plate-film. For example, it is possible to employ the diffusion film (LIGHT-UP), produced by Kimoto Co., Ltd.

«Applications»

It is possible to employ the organic EL element of the present invention as display devices, displays, and various types of light emitting sources.

Examples of light emitting sources include: lighting apparatuses (home lighting and car lighting), clocks, backlights for liquid crystals, sign advertisements, signals, light sources of light memory media, light sources of electrophotographic copiers, light sources of light communication processors, and light sources of light sensors. The present invention is not limited to them. It is especially effectively employed as a backlight of a liquid crystal display device and a lighting source.

If needed, the organic EL element of the present, invention may undergo patterning via a metal mask or an ink-jet printing method during film formation. When the patterning is carried out, only an electrode may undergo patterning, an electrode and a light emitting layer may undergo patterning, or all element layers may undergo patterning. During preparation of the element, it is possible to employ conventional methods.

[Display Device]

Hereinafter, one example of a display device provided with an organic EL element of the present invention will be explained with reference to figures.

Figure 3:
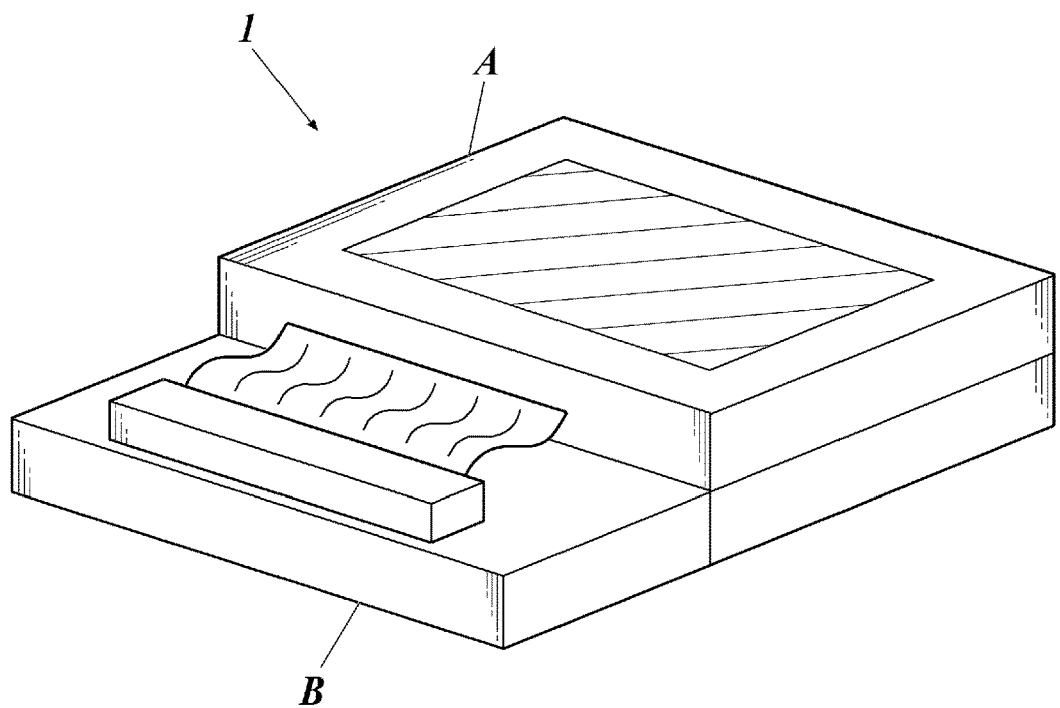
FIG. 3 is a schematic perspective view showing an example of a configuration of a display device according to the present invention

FIG. 3 is a schematic perspective drawing to show an example of a display device constituted of an organic EL element of the present invention. It displays image information by emission of an organic EL element. An example is a mobile phone. As illustrated in FIG. 3, a display 1 is constituted of a display section A having plural number of pixels and a control section B which performs image scanning of the display section A based on image information.

The control section B, which is electrically connected to the display section A, sends a scanning signal and an image data signal to plural number of pixels based on image information from the outside and pixels of each scanning line successively emit depending on the image data signal by a scanning signal to perform image scanning, whereby image information is displayed on the display section A.

FIG. 4 is a schematic drawing of the display section A illustrated in FIG. 3.

The display section A is provided with a wiring part, which contains plural scanning lines 5 and data lines 6, and plural pixels 3 on a substrate.

Primary members of the display section A will be explained in the following.

In FIG. 4, it is illustrated the case that light emitted by a pixel 3 is taken out along a white arrow (downward). Scanning lines 5 and plural data lines 6 in a wiring part each are composed of a conductive material, and the scanning lines 5 and the data lines 6 are perpendicular in a grid form and are connected to the pixels 3 at the right-angled crossing points (details are not shown in the drawing).

The pixel 3 receives an image data from the data line 6 when a scanning signal is applied from the scanning line 5 and emits according to the received image data.

A full-color display device is achieved by appropriately arranging pixels each having an emission color in a red region, in a green region, and in a blue region, being placed side by side on the same substrate.

[Lighting Device]

One embodiment of a lighting device according to the present invention including the organic EL element of the present invention will be described.

The non-light emitting surface of the organic EL element of the present invention was covered with a glass case, and a 300 μm thick glass substrate was employed as a sealing substrate. An epoxy based light curable type adhesive (LUXTRACK LC0629B produced by Toagosei Co., Ltd.) was employed in the periphery as a sealing material. The resulting one was superimposed on the aforesaid cathode to be brought into close contact with the aforesaid transparent support substrate, and curing and sealing were carried out via exposure of UV radiation onto the glass substrate side, whereby the lighting device shown in FIG. 5 and FIG. 6 was formed.

Figure 5:
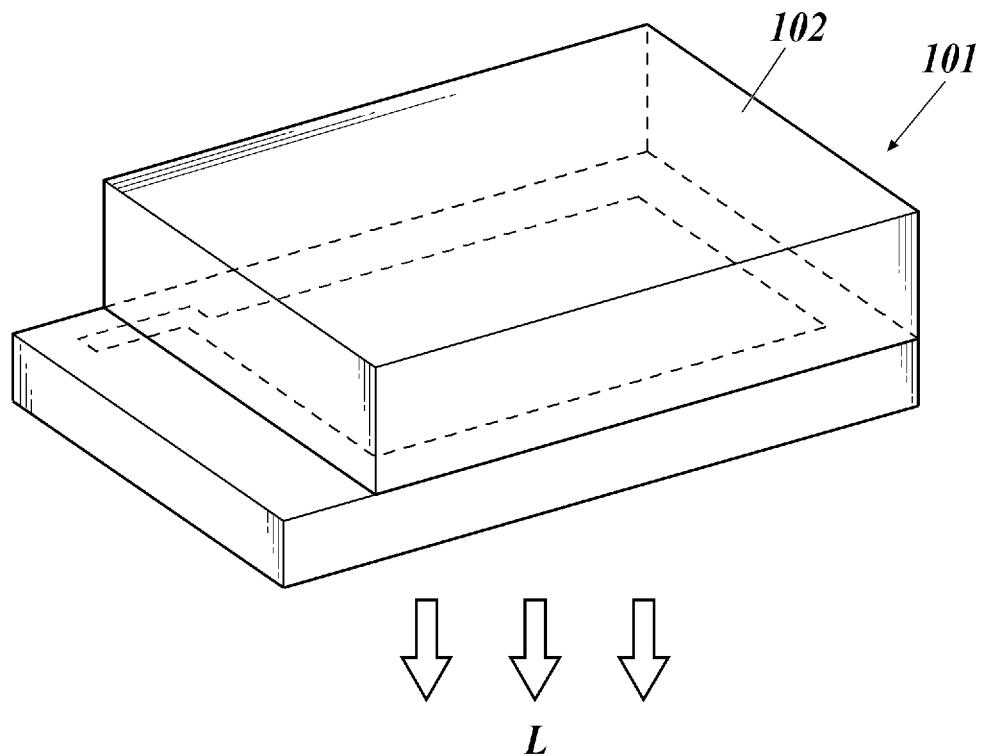
FIG. 5 is a schematic diagram of a lighting apparatus according to the present invention

FIG. 5 is a schematic view of a lighting device. An organic EL element 101 of the present invention is covered with a glass cover 102 (incidentally, sealing by the glass cover was carried out in a globe box under nitrogen ambience (under air ambience of high purity nitrogen gas at a purity of at least 99.999%) so that the organic EL Element 101 was not brought into contact with atmosphere.

Figure 6:
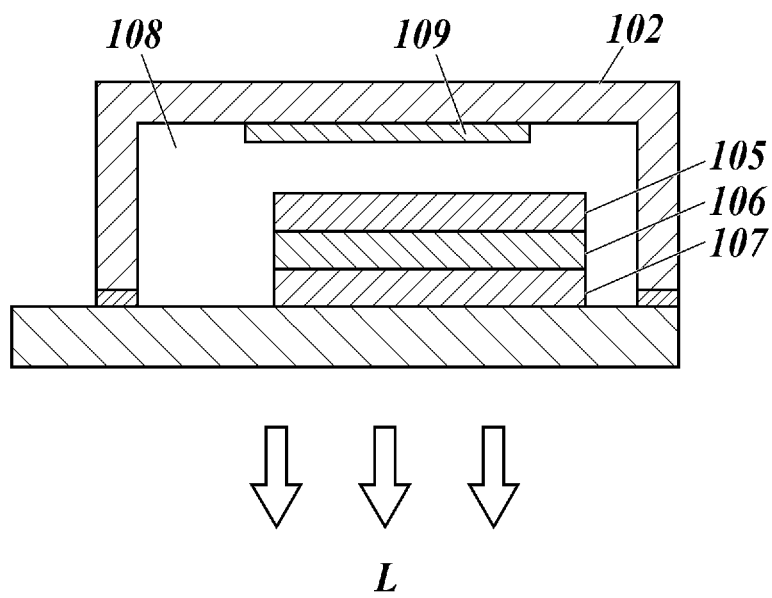
FIG. 6 is a cross-sectional view of a lighting apparatus according to the present invention

FIG. 6 is a cross-sectional view of a lighting device. In FIG. 6, 105 represents a cathode, 106 represents an organic EL layer, and 107 represents a glass substrate having a transparent electrode. Further, the interior of glass cover 102 is filled with nitrogen gas 108 and a water catching agent 109 is provided.

EXAMPLES

Hereafter, the present invention will be described specifically by referring to examples, however, the present invention is not limited to them. In examples, the indication of "part" or "%" is used. Unless particularly mentioned, it represents "part by mass" or "% by mass" The compounds used in Examples are indicated below.

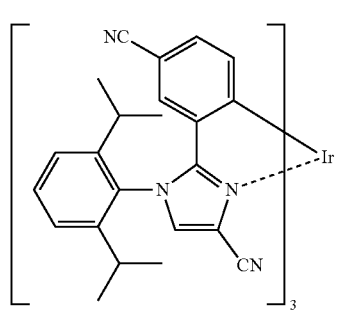

Dp-1

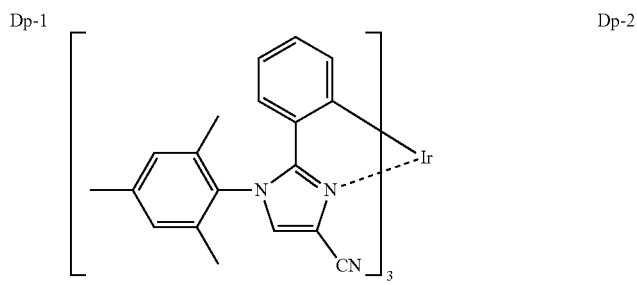

Dp-2

-continued
Dp-3
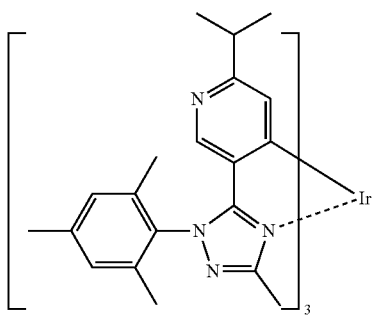
Dp-4
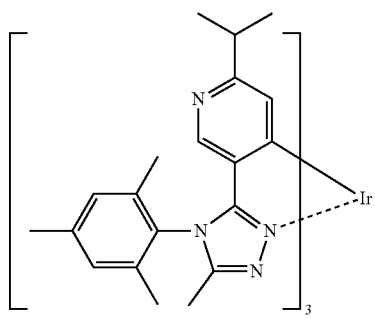
Dp-5 (C-11)
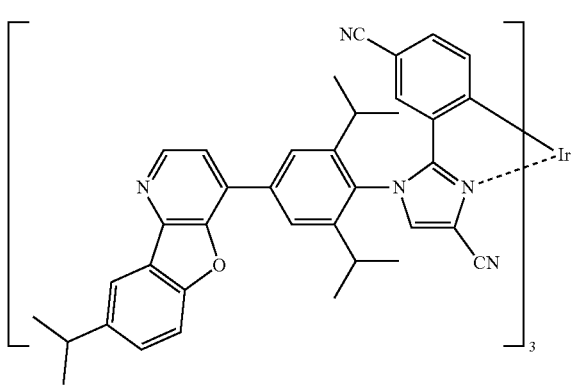
Dp-6 (C-28)
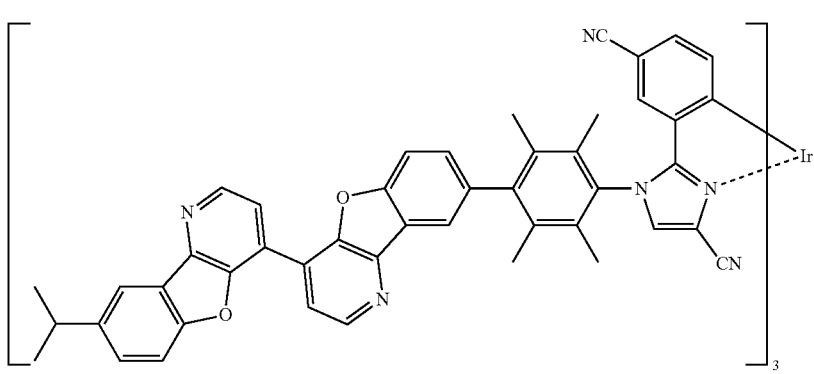
H-1 (OC-29)
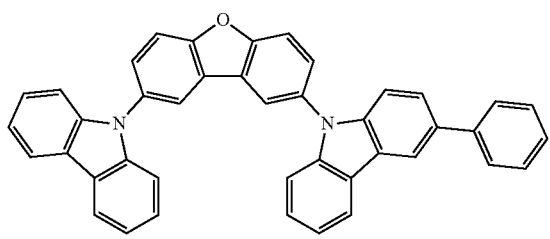
H-2
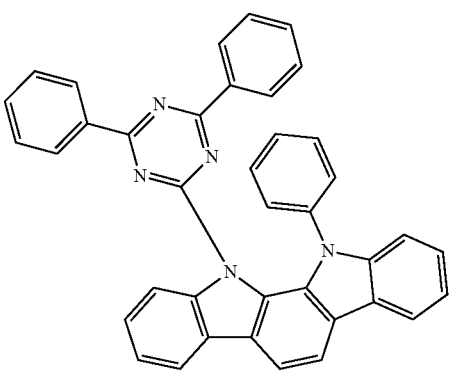

-continued
H-3
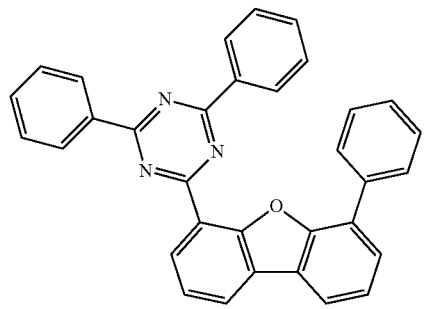
H-4 (H84)
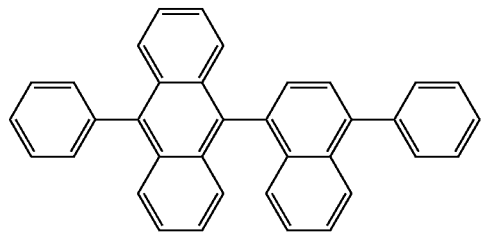
F-1 (Example compound 11)
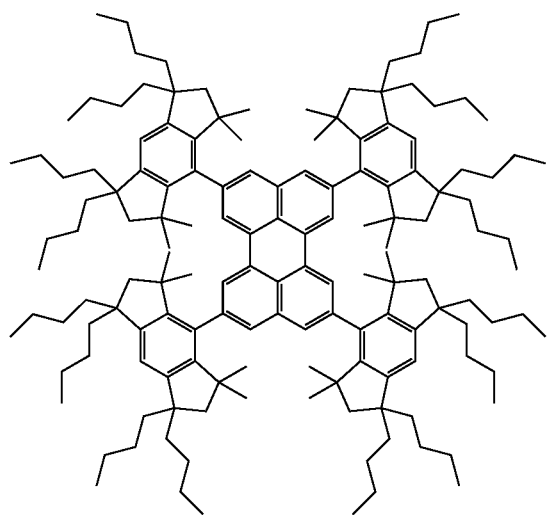
F-2 (Example compound 6)
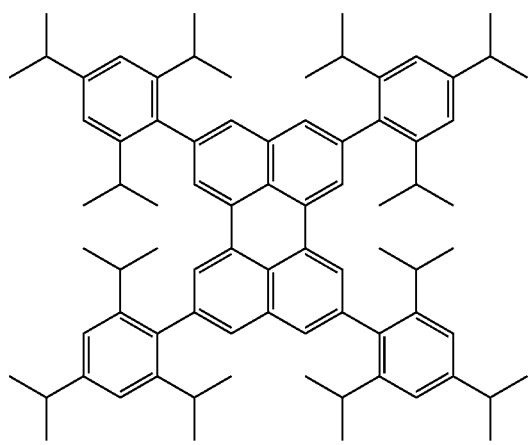
F-3 (Example compound 23)
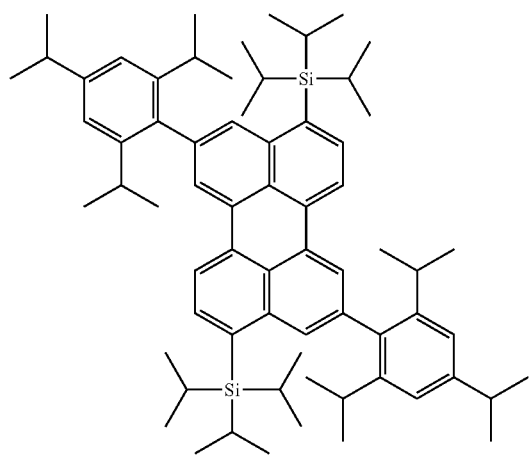
F-4 (Example compound 34)
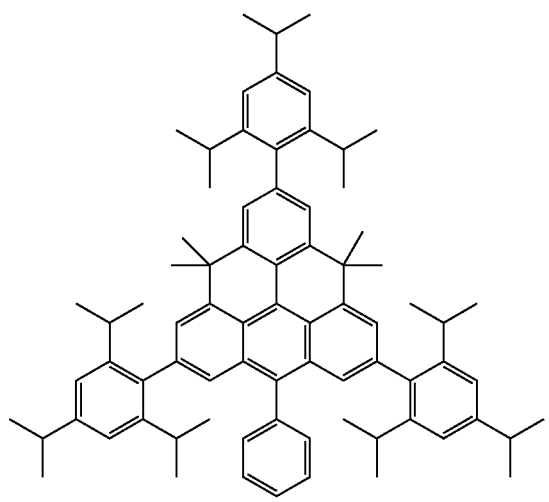

-continued
F-5
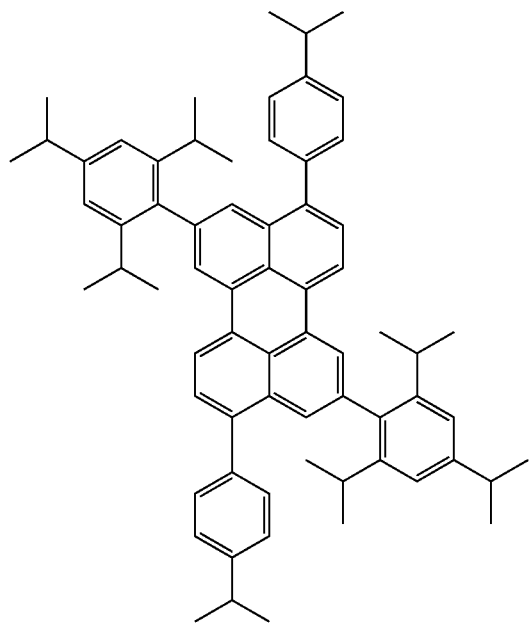
F-6 (Example compound 78)
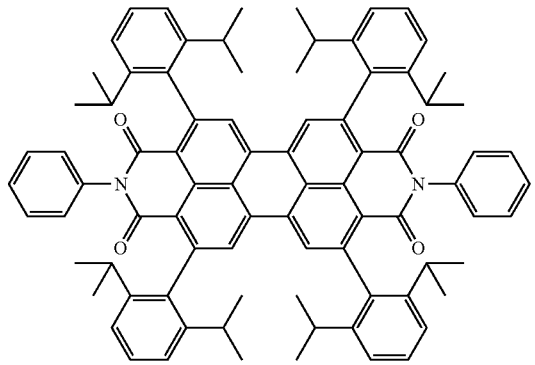
F-7
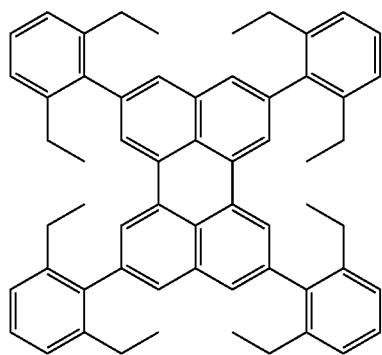
F-8 (Example compound 102)
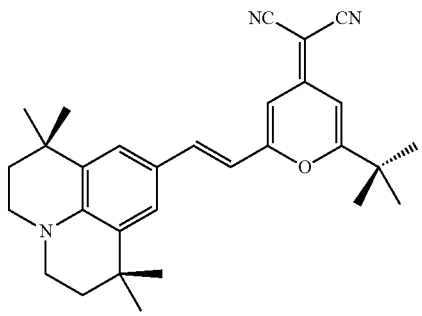
A-22
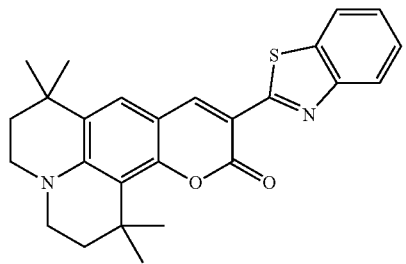
HI-1
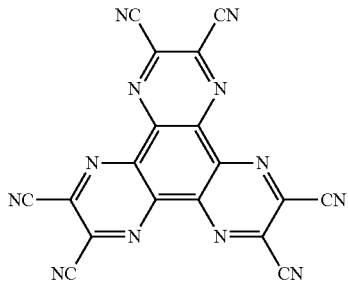
HT-1
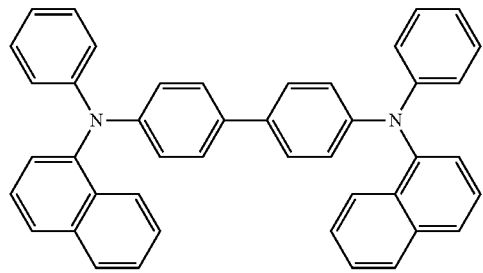
HT-2
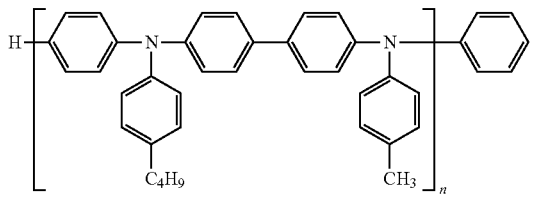

-continued

ET-1
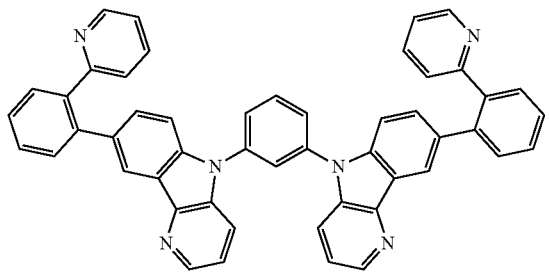

HB-1
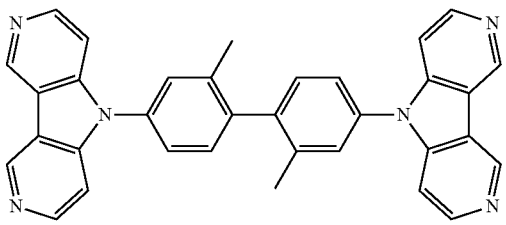
3.28eV

HB-2
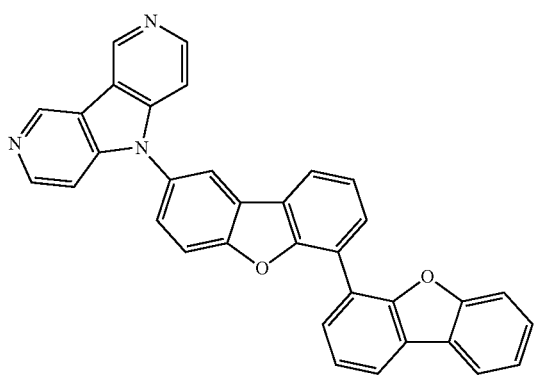
2.86eV

HB-3
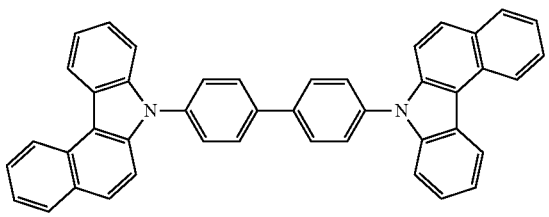
2.63eV

HS-1
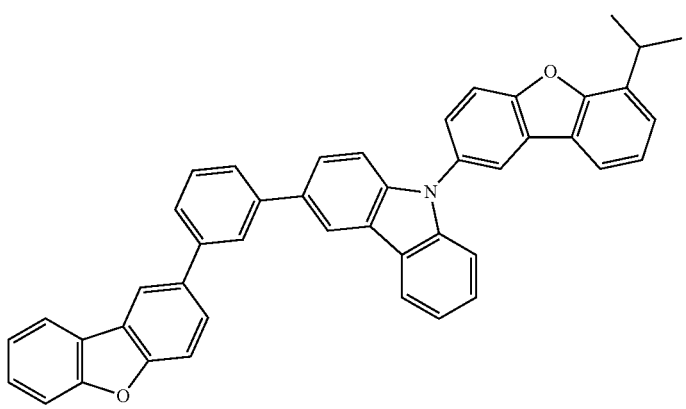

Example 1

Example 1 describes a luminescent film using a host compound having a relatively higher triplet energy level than a phosphorescent compound. In this example, the luminescent film was formed by an evaporation method.

«Preparation of Luminescent Films (1-2) to (1-5) and (1-7) to (1-10)»

A quartz substrate of 50 mm×50 mm having a thickness of 0.7 mm was subjected to ultrasonic washing with isopropyl alcohol, followed by drying with desiccated nitrogen gas, and was subjected to UV ozone washing for 5 minutes. The resulting transparent substrate was fixed to a substrate holder of a commercial vacuum deposition apparatus. In each of the vapor deposition heating boat of the vacuum vapor deposition apparatus, "a host compound, hereinafter, it may be simply called as a host", "a phosphorescent compound", or "a fluorescent compound" as indicated in Table 1 was filled so as to be an optimum amount for each element fabrication. As a resistance heating boat for vapor deposition, a resistance heating boat made of molybdenum was used.

After the inside of the vacuum deposition apparatus was evacuated to a degree of vacuum of $1 \times 10^{-4}$ Pa, evaporation was performed in a way that the host compound, the host compound, the phosphorescent compound and the fluorescent compound were adjusted to 82% by volume, 15% by volume, and 3% by volume, respectively. The host compound was deposited at a deposition rate of 1.0 Å/sec, the phosphorescent compound was deposited at a rate of 0.2 Å/sec, and the fluorescent compound was deposited at a deposition rate of 0.04 Å/sec. In this way, each luminescent film having a thickness of 30 nm was produced.

«Preparation of Luminescent Films (1-1) and (1-6)»

Each luminescent film was produced in the same manner as used for the preparation of the luminescent film (1-2), except that the phosphorescent compound and the host compound were replaced with the compounds shown in Table I below, and the fluorescent compound was set at 0% by volume, and the host compound was 85% by volume.

«Evaluation»

The methods of evaluation are as follows. The results are as shown in Table I.

«Calculation of Energy Transfer Efficiency from Phosphorescent Compound to Fluorescent Compound»

Kf/Kr was calculated from each energy transfer efficiency using the above formula (D) from the change in PLQE and the τ of the luminescent film before and after the addition of the fluorescent compound. The unit of Kr and Kf is 1/sec. The above Kf/Kr is the ratio of the transferred energy of the excited phosphorescent compound to the fluorescent compound in the emission spectrum obtained by exciting the phosphorescent compound contained in the luminescent film. That is, it represents the ratio of light emission from the fluorescent compound in the obtained emission spectrum when the phosphorescent compound contained in the luminescent film is excited. The fact that Kf/Kr is 0.9 or more means that 90% or more of the emission spectrum obtained from the luminescent film is light emission from the fluorescent compound, in other words, this means that the emission ratio from the fluorescent compound occupies 90% or more of the whole light emission.

(Measurement of Emission Decay Lifetime τ)

The emission decay lifetime τ (unit: sec) in the above formula (D) was determined by measuring transient PL characteristics. For measurement of the transient PL characteristic, a small fluorescence lifetime measuring device C11367-03 (manufactured by Hamamatsu Photonics K.K.) was used. The attenuation component was measured in a TCC900 mode using a 280 nm LED as an excitation light source. The relative value was calculated from the measured value of the luminescence decay lifetime τ and is shown in the following table.

(Measurement of Absolute Quantum Yield (PLQE))

The absolute quantum yield was measured using an absolute quantum yield measuring device C9920-02 (manufactured by Hamamatsu Photonics K.K.), and the relative value was calculated from the measured value. The criteria for the relative values of the emission decay lifetime τ and the absolute quantum yield (PLQE) are as follows.

Criterion of luminescent films (1-2) to (1-5): luminescent film (1-1)

Criterion of luminescent films (1-7) to (1-10): luminescent film (1-6)

(Calculation of Overlap Integral Value (J))

The overlap integral value (J) was calculated from Formula (OI). Specifically, the emission spectrum was measured using a fluorometer (HITACHI F-7000 spectrofluorometer), and the absorption spectrum was measured using a fluorometer (HITACHI U-3300 spectrophotometer). The assumed molar extinction coefficient was measured with a spectrophotometer U-3000 (manufactured by Hitachi High-Technologies Corporation) using a sample prepared at a concentration of $1 \times 10^{-5}$ mol/L with 2 m-THF.

As described above, as the overlap integral becomes larger, the Förster transfer becomes more dominant. In particular, when a luminescent film having a combination of the compounds where the overlap integral exceeds $6.0 \times 10^{14}$, the luminescent film emits light while maintaining the deactivation rate and the light emitting property of several tens of nanoseconds, which is close to the emission lifetime of the fluorescent light emission. Therefore, it is expected that the element is hardly affected by the quencher, and the life of the element is improved.

Example 2

Example 2 describes a luminescent film using a host compound having a relatively higher triplet energy level than that of a phosphorescent compound. In this example, the luminescent film was formed by a coating method.

«Preparation of Luminescent Films (2-2), (2-3), (2-5) to (2-10), (2-12) to (2-17), (2-19) to (2-24), (2-26) to (2-31) and (2-33)»

A quartz substrate of 50 mm×50 mm having a thickness of 0.7 mm was subjected to ultrasonic washing with isopropyl alcohol, followed by drying with desiccated nitrogen gas, and was subjected to UV ozone washing for 5 minutes. Each material dissolved in isopropyl acetate was applied by a spin coat method, and dried at 120° C. for 30 minutes to form a light emitting layer having a thickness of 50 nm. A single film was prepared at mol % in terms of analysis, and the compounds shown in Table II were used as a host compound, a phosphorescent compound and a fluorescent compound, and each had a concentration of 87% by mole, 10% by mole, and 33% by mole, respectively. Thus, each luminescent film having a thickness of 30 nm was produced.

«Preparation of Luminescent Films (2-1), (2-4), (2-11), (2-18), (2-25) and (2-32)»

Each luminescent film was produced in the same manner as used for the preparation of the luminescent film (2-2), except that the phosphorescent compound and the host compound were replaced with the compounds shown in Table II below, and the fluorescent compound was set at 0% by mole, and the host compound was 90% by mole.

«Evaluation»

Evaluation was performed in the same manner as in Example 1 above. The criteria for the relative values of the emission decay lifetime τ and the absolute quantum yield (PLQE) are as follows.

Criterion of luminescent films (2-2) to (2-3): luminescent film (2-1)

TABLE I

| Luminescent film No. | Phosphorescent compound Kind | Phosphorescent compound Concentration (volume %) | Host compound Kind | Host compound Concentration (volume %) | Fluorescent compound Kind | Fluorescent compound Concentration (volume %) | J | PLQE (Relative value) | τ (Relative value) | Kf/Kr | Remarks |
|---|---|---|---|---|---|---|---|---|---|---|---|
| 1-1 | Dp-1 | 15 | H-1 | 85 | — | — | — | 1.00 | 1.00 | — | Comparative example |
| 1-2 | Dp-1 | 15 | H-1 | 82 | F-2 | 3 | $2.5 \times 10^{14}$ | 1.12 | 0.11 | 9.5 | Present invention |
| 1-3 | Dp-1 | 15 | H-1 | 82 | F-3 | 3 | $3.5 \times 10^{14}$ | 1.01 | 0.06 | 16.2 | Present invention |
| 1-4 | Dp-1 | 15 | H-1 | 82 | F-4 | 3 | $4.3 \times 10^{14}$ | 1.04 | 0.06 | 15.7 | Present invention |
| 1-5 | Dp-1 | 15 | H-1 | 82 | F-5 | 3 | $6.1 \times 10^{14}$ | 1.15 | 0.02 | 75.5 | Present invention |
| 1-6 | Dp-2 | 15 | H-1 | 85 | — | — | — | 1.00 | 1.00 | — | Comparative example |
| 1-7 | Dp-2 | 15 | H-1 | 82 | F-2 | 3 | $1.4 \times 10^{14}$ | 0.62 | 0.06 | 8.3 | Comparative example |
| 1-9 | Dp-2 | 15 | H-1 | 82 | F-3 | 3 | $2.3 \times 10^{14}$ | 1.04 | 0.09 | 10.5 | Present invention |
| 1-9 | Dp-2 | 15 | H-1 | 82 | F-4 | 3 | $4.1 \times 10^{14}$ | 1.00 | 0.06 | 14.0 | Present invention |
| 1-10 | Dp-2 | 15 | H-1 | 82 | F-5 | 3 | $5.1 \times 10^{14}$ | 1.06 | 0.05 | 18.4 | Present invention |

Criterion of luminescent films (2-5) to (2-10): luminescent film (2-4)
Criterion of luminescent films (2-12) to (2-17): luminescent film (2-11)
Criterion of luminescent films (2-19) to (2-24): luminescent film (2-18)
Criterion of luminescent films (2-26) to (2-31): luminescent film (2-25)
Criterion of luminescent film (2-33): luminescent film (2-32)

«Preparation of Luminescent Films (3-3) to (3-6) and (3-9) and (3-10)»

In the same manner as in Example 1, the compounds shown in Table III were used as the host compound, the phosphorescent compound and the fluorescent compound, and the host compound, the phosphorescent compound and the fluorescent compound each respectively set to 75% by volume, 15% by volume and 10% by volume. In this manner, each luminescent film having a thickness of 30 nm was produced.

TABLE II

| Luminescent film No. | Phosphorescent compound Kind | Concentration (mol %) | Host compound Kind | Concentration (mol %) | Fluorescent compound Kind | Concentration (mol %) | J | PLQE (Relative value) | τ (Relative value) | Kf/Kr | Remarks |
|---|---|---|---|---|---|---|---|---|---|---|---|
| 2-1 | Dp-1 | 10 | H-1 | 90 | — | — | — | 1.00 | 1.00 | — | Comparative example |
| 2-2 | Dp-1 | 10 | H-1 | 87 | F-1 | 3 | $2.4 \times 10^{14}$ | 1.19 | 0.12 | 9.0 | Present invention |
| 2-3 | Dp-1 | 10 | H-1 | 87 | F-6 | 3 | $7.2 \times 10^{14}$ | 1.06 | 0.02 | 55.5 | Present invention |
| 2-4 | Dp-3 | 10 | PMMA | 90 | — | — | — | 1.00 | 1.00 | — | Comparative example |
| 2-5 | Dp-3 | 10 | PMMA | 87 | F-1 | 3 | $4.5 \times 10^{14}$ | 0.95 | 0.10 | 9.3 | Present invention |
| 2-6 | Dp-3 | 10 | PMMA | 87 | F-2 | 3 | $4.6 \times 10^{14}$ | 0.96 | 0.06 | 15.1 | Present invention |
| 2-7 | Dp-3 | 10 | PMMA | 87 | F-3 | 3 | $4.9 \times 10^{14}$ | 0.95 | 0.06 | 14.1 | Present invention |
| 2-8 | Dp-3 | 10 | PMMA | 87 | F-4 | 3 | $5.6 \times 10^{14}$ | 0.96 | 0.06 | 16.6 | Present invention |
| 2-9 | Dp-3 | 10 | PMMA | 87 | F-5 | 3 | $7.1 \times 10^{14}$ | 1.02 | 0.01 | 95.7 | Present invention |
| 2-10 | Dp-3 | 10 | PMMA | 87 | F-6 | 3 | $1.3 \times 10^{14}$ | 0.32 | 0.02 | 17. | Comparative example |
| 2-11 | Dp-4 | 10 | PMMA | 90 | — | — | — | 1.00 | 1.00 | — | Comparative example |
| 2-12 | Dp-4 | 10 | PMMA | 87 | F-1 | 3 | $2.8 \times 10^{14}$ | 1.03 | 0.10 | 9.3 | Present invention |
| 2-13 | Dp-4 | 10 | PMMA | 87 | F-2 | 3 | $2.9 \times 10^{14}$ | 0.97 | 0.07 | 13.0 | Present invention |
| 2-14 | Dp-4 | 10 | PMMA | 87 | F-3 | 3 | $4.1 \times 10^{14}$ | 0.99 | 0.05 | 20.4 | Present invention |
| 2-15 | Dp-4 | 10 | PMMA | 87 | F-4 | 3 | $5.0 \times 10^{14}$ | 0.96 | 0.04 | 21.6 | Present invention |
| 2-16 | Dp-4 | 10 | PMMA | 87 | F-5 | 3 | $6.7 \times 10^{14}$ | 1.04 | 0.02 | 51.1 | Present invention |
| 2-17 | Dp-4 | 10 | PMMA | 87 | F-6 | 3 | $7.3 \times 10^{14}$ | 0.99 | 0.01 | 74.4 | Present invention |
| 2-18 | Dp-5 | 10 | H-1 | 90 | — | — | — | 1.00 | 1.00 | — | Comparative example |
| 2-19 | Dp-5 | 10 | H-1 | 87 | F-1 | 3 | $2.3 \times 10^{14}$ | 1.15 | 0.11 | 9.4 | Present invention |
| 2-20 | Dp-5 | 10 | H-1 | 87 | F-2 | 3 | $2.3 \times 10^{14}$ | 1.08 | 0.08 | 13.3 | Present invention |
| 2-21 | Dp-5 | 10 | H-1 | 87 | F-3 | 3 | $3.8 \times 10^{14}$ | 1.02 | 0.05 | 18.4 | Present invention |
| 2-22 | Dp-5 | 10 | H-1 | 87 | F-4 | 3 | $4.4 \times 10^{14}$ | 1.03 | 0.05 | 21.8 | Present invention |
| 2-23 | Dp-5 | 10 | H-1 | 87 | F-5 | 3 | $6.1 \times 10^{14}$ | 1.00 | 0.03 | 32.7 | Present invention |
| 2-24 | Dp-5 | 10 | H-1 | 87 | F-6 | 3 | $7.8 \times 10^{14}$ | 1.08 | 0.02 | 57.2 | Present invention |
| 2-25 | Dp-6 | 10 | H-1 | 90 | — | — | — | 1.00 | 1.00 | — | Comparative example |
| 2-26 | Dp-6 | 10 | H-1 | 87 | F-1 | 3 | $2.3 \times 10^{14}$ | 1.06 | 0.11 | 9.1 | Present invention |
| 2-27 | Dp-6 | 10 | H-1 | 87 | F-2 | 3 | $2.3 \times 10^{14}$ | 1.03 | 0.08 | 11.4 | Present invention |
| 2-28 | Dp-6 | 10 | H-1 | 87 | F-3 | 3 | $3.8 \times 10^{14}$ | 0.98 | 0.05 | 17.7 | Present invention |
| 2-29 | Dp-6 | 10 | H-1 | 87 | F-4 | 3 | $4.4 \times 10^{14}$ | 0.95 | 0.05 | 19.7 | Present invention |
| 2-30 | Dp-6 | 10 | H-1 | 87 | F-5 | 3 | $6.1 \times 10^{14}$ | 1.01 | 0.04 | 27.1 | Present invention |
| 2-31 | Dp-6 | 10 | H-1 | 87 | F-6 | 3 | $7.8 \times 10^{14}$ | 0.98 | 0.02 | 42.2 | Present invention |
| 2-32 | Dp-2 | 10 | H-1 | 90 | — | — | — | 1.00 | 1.00 | — | Comparative example |
| 2-33 | Dp-2 | 10 | H-1 | 87 | F-6 | 3 | $9.1 \times 10^{14}$ | 1.04 | 0.03 | 33.5 | Present invention |

As described above, even in the coating process, the larger the overlap integral, the more the Förster transfer works. In particular, a luminescent film having a combination of overlap integrals exceeding $6.0 \times 10^{14}$ emits light at a deactivation rate of several tens of nanoseconds, which is close to the emission lifetime of fluorescence emission, and maintains light emission. Therefore, it is less likely to be affected by the quencher, and the element lifetime may be improved. The reason why the Förster transfer speed is slightly reduced when F-1 is used as the fluorescent compound is as follows. This is because the substituent that substitutes the light emitting site is bulky, and the physical distance from the phosphorescent compound increases.

Example 3

Example 3 describes a luminescent film using a host compound having a relatively higher triplet energy level than that of a phosphorescent compound. In this example, the luminescent film was formed by an evaporation method.

«Preparation of Luminescent Films (3-1), (3-2), (3-7) and (3-8)»

Each luminescent film was produced in the same manner as used for the preparation of the luminescent film (3-3), except that the compounds shown in Table III below were used as the phosphorescent compound and the host compound, the fluorescent compound was set to 0% by volume, and the host compound was 85% by volume.

«Evaluation»

As for the evaluation, the measurement of the absolute quantum yield (PLQE) and the calculation of the overlap integral value (J) were performed in the same manner as in Example 1 described above. The criterion for the relative value of the absolute quantum yield (PLQE) is as follows.

Criterion of luminescent films (3-2) to (3-6): luminescent film (3-1)
Criterion of luminescent films (3-8) to (3-10): luminescent film (3-7)

The luminescent films (3-2) and (3-8) are reference values when a low $T_1$ host compound is used.

TABLE III

| Luminescent film No. | Phosphorescent compound Kind | Phosphorescent compound Concentration (volume %) | Host compound Kind | Host compound Concentration (volume %) | Fluorescent compound Kind | Fluorescent compound Concentration (volume %) | J | PLQE (Relative value) | Remarks |
|---|---|---|---|---|---|---|---|---|---|
| 3-1 | Dp-1 | 15 | H-1 | 85 | — | — | — | 1.00 | *1 |
| 3-2 | Dp-1 | 15 | H-4 | 85 | — | — | — | 0.21 | *1 |
| 3-3 | Dp-1 | 15 | H-4 | 75 | F-2 | 10 | $2.5 \times 10^{14}$ | 0.44 | *1 |
| 3-4 | Dp-1 | 15 | H-2 | 75 | F-5 | 10 | $6.1 \times 10^{14}$ | 1.01 | *2 |
| 3-5 | Dp-1 | 15 | H-3 | 75 | F-5 | 10 | $6.1 \times 10^{14}$ | 0.95 | *2 |
| 3-6 | Dp-1 | 15 | H-4 | 75 | F-5 | 10 | $6.1 \times 10^{14}$ | 1.00 | *2 |
| 3-7 | Dp-2 | 15 | H-1 | 85 | — | — | — | 1.00 | *1 |
| 3-8 | Dp-2 | 15 | H-2 | 85 | — | — | — | 0.29 | *1 |
| 3-9 | Dp-2 | 15 | H-2 | 75 | F-3 | 10 | $2.3 \times 10^{14}$ | 0.37 | *1 |
| 3-10 | Dp-2 | 15 | H-2 | 75 | F-5 | 10 | $6.1 \times 10^{14}$ | 0.90 | *2 |

*1: Comparative example
*2: Present invention

As described above, if it is conventional, it is difficult to maintain the luminescent property because the exciton is deactivated to the triplet excited state of the host compound. However, in a combination in which the overlap integral is $6.0 \times 10^{14}$ or more, the Förster transfer is dominant, the light emission can be maintained, and the effect of deterioration of the host is less likely to occur, so that element that life may be improved.

Example 4

Example 4 describes a luminescent film using a host compound whose triplet energy level is relatively lower than that of a phosphorescent compound. In this example, the luminescent film was formed by a coating method.

«Preparation of Luminescent Films (4-1), (4-2), (4-4), (4-5), (4-8), (4-9), (4-12) and (4-13)»

Each luminescent film was produced in the same manner as used for the preparation of the luminescent film (2-2), except that the compounds shown in Table IV below were used as the phosphorescent compound and the host compound, the fluorescent compound was set to 0% by mole, and the host compound was set to 90% by mole.

«Evaluation»

As for the evaluation, the measurement of the absolute quantum yield (PLQE) and the calculation of the overlap integral value (J) were performed in the same manner as in Example 1 described above. The criterion for the relative value of the absolute quantum yield (PLQE) is as follows.

Criterion of luminescent films (4-2) to (4-3): luminescent film (4-1)
Criterion of luminescent films (4-5) to (4-8): luminescent film (4-4)
Criterion of luminescent films (4-9) to (4-11): luminescent film (4-8)
Criterion of luminescent films (4-13) to (4-15): luminescent film (4-12)

The luminescent films (4-2), (4-5), (4-9) and (4-13) are reference values when a low $T_1$ host compound is used.

TABLE IV

| Luminescent film No. | Phosphorescent compound Kind | Phosphorescent compound Concentration (mole %) | Host compound Kind | Host compound Concentration (mole %) | Fluorescent compound Kind | Fluorescent compound Concentration (mole %) | J | PLQE (Relative value) | Remarks |
|---|---|---|---|---|---|---|---|---|---|
| 4-1 | Dp-3 | 10 | PMMA | 90 | — | — | — | 1.00 | *1 |
| 4-2 | Dp-3 | 10 | H-1 | 90 | — | — | — | 0.14 | *1 |
| 4-3 | Dp-3 | 10 | H-1 | 80 | F-5 | 10 | $6.7 \times 10^{14}$ | 0.90 | *2 |
| 4-4 | Dp-4 | 10 | PMMA | 90 | — | — | — | 1.00 | *1 |
| 4-5 | Dp-4 | 10 | H-1 | 90 | — | — | — | 0.18 | *1 |
| 4-6 | Dp-4 | 10 | H-1 | 80 | F-5 | 10 | $6.7 \times 10^{14}$ | 0.90 | *2 |
| 4-7 | Dp-4 | 10 | H-1 | 80 | F-6 | 10 | $7.3 \times 10^{14}$ | 0.92 | *2 |
| 4-8 | Dp-5 | 10 | H-1 | 90 | — | — | — | 1.00 | *1 |
| 4-9 | Dp-5 | 10 | H-4 | 90 | — | — | — | 0.21 | *1 |
| 4-10 | Dp-5 | 10 | H-4 | 80 | F-5 | 10 | $6.1 \times 10^{14}$ | 0.98 | *2 |
| 4-11 | Dp-5 | 10 | H-4 | 80 | F-6 | 10 | $7.8 \times 10^{14}$ | 1.02 | *2 |
| 4-12 | Dp-6 | 10 | H-1 | 90 | — | — | — | 1.00 | *1 |
| 4-13 | Dp-6 | 10 | H-4 | 90 | — | — | — | 0.33 | *1 |
| 4-14 | Dp-6 | 10 | H-4 | 80 | F-5 | 10 | $6.1 \times 10^{14}$ | 0.98 | *2 |
| 4-15 | Dp-6 | 10 | H-4 | 80 | F-6 | 10 | $7.8 \times 10^{14}$ | 1.00 | *2 |

*1: Comparative example
*2: Present invention

As described above, if it is conventional, even in a process such as coating, it is difficult to maintain the luminescent property because the exciton is deactivated to the triplet excited state of the host compound. However, in a combination in which the overlap integral is $6.0 \times 10^{14}$ or more, the Förster transfer is dominant, the light emission can be maintained, and the effect of deterioration of the host is reduced, so that the element lifetime may be improved.

Example 5

Example 5 describes a luminescent film that does not use a host compound. Note that, in this example, the luminescent film was formed by an evaporation method.

«Evaluation»

As for the evaluation, the measurement of the absolute quantum yield (PLQE) and the calculation of the overlap integral value (J) were performed in the same manner as in Example 1 described above. The criterion for the relative value of the absolute quantum yield (PLQE) is as follows.

Criterion of luminescent films (5-4) to (5-6): luminescent film (5-1)

Criterion of luminescent film (5-7): luminescent film (5-2)

Criterion of luminescent film (5-8): luminescent film (5-3)

TABLE V

| Luminescent film No. | Phosphorescent compound | | Host compound | | Fluorescent compound | | J | PLQE (Relative value) | Remarks |
| --- | --- | --- | --- | --- | --- | --- | --- | --- | --- |
| | Kind | Concentration (volume %) | Kind | Concentration (volume %) | Kind | Concentration (volume %) | | | |
| 5-1 | Dp-1 | 15 | H-1 | 85 | — | — | — | 1.00 | *1 |
| 5-2 | Dp-3 | 15 | H-1 | 85 | — | — | — | 1.00 | *1 |
| 5-3 | Dp-4 | 15 | H-1 | 85 | — | — | — | 1.00 | *1 |
| 5-4 | Dp-1 | 90 | — | — | F-5 | 10 | $6.1 \times 10^{14}$ | 1.06 | *2 |
| 5-5 | Dp-1 | 90 | — | — | F-5 | 5 | $6.1 \times 10^{14}$ | 1.00 | *2 |
| 5-6 | Dp-1 | 90 | — | — | F-5 | 3 | $6.1 \times 10^{14}$ | 0.96 | *2 |
| 5-7 | Dp-3 | 90 | — | — | F-5 | 10 | $7.1 \times 10^{14}$ | 0.93 | *2 |
| 5-8 | Dp-4 | 90 | — | — | F-5 | 10 | $6.7 \times 10^{14}$ | 0.90 | *2 |

*1: Comparative example
*2: Present invention

«Preparation of Luminescent Films (5-4) to (5-8)»

A quartz substrate of 50 mm×50 mm having a thickness of 0.7 mm was subjected to ultrasonic washing with isopropyl alcohol, followed by drying with desiccated nitrogen gas, and was subjected to UV ozone washing for 5 minutes. The resulting transparent substrate was fixed to a substrate holder of a commercial vacuum deposition apparatus. In each of the vapor deposition heating boat of the vacuum vapor deposition apparatus, "a phosphorescent compound", or "a fluorescent compound" as indicated in Table V was filled so as to be an optimum amount for each element fabrication. As a resistance heating boat for vapor deposition, a resistance heating boat made of molybdenum was used.

After the inside of the vacuum deposition apparatus was evacuated to a degree of vacuum of $1 \times 10^{-4}$ Pa, evaporation was performed in a way that the phosphorescent compound and the fluorescent compound were adjusted to the volume % as indicated in Table V. The phosphorescent compound was deposited at a rate of 0.2 Å/sec, and the fluorescent compound was deposited at a deposition rate of 0.02 Å/sec. In this way, an evaluation luminescent film having a thickness of 30 nm was produced.

«Preparation of Luminescent Films (5-1) to (5-3)»

Each luminescent film was produced in the same manner as used for the preparation of the luminescent film (5-4), except that the compounds shown in Table IV below were used as the phosphorescent compound and the host compound, the fluorescent compound was set to 0% by volume, and the host compound was set to 85% by volume.

Example 6

Example 6 describes a luminescent film that does not use a host compound. Note that, in this example, the luminescent film was formed by a coating method.

«Preparation of Luminescent Films (6-4) to (6-8)»

A quartz substrate of 50 mm×50 mm having a thickness of 0.7 mm was subjected to ultrasonic washing with isopropyl alcohol, followed by drying with desiccated nitrogen gas, and was subjected to UV ozone washing for 5 minutes. Each material dissolved in isopropyl acetate was applied by a spin coat method, and dried at 120° C. for 30 minutes to form a light emitting layer having a thickness of 50 nm. A single film was prepared at mol % in terms of analysis, and the compounds shown in Table VI were used as a phosphorescent compound and a fluorescent compound, and each had a concentration of 90% by mole and 10% by mole, respectively. Thus, each luminescent film having a thickness of 30 nm was produced.

«Preparation of Luminescent Films (6-1) to (6-3)»

Each luminescent film was produced in the same manner as used for the preparation of the luminescent film (6-4), except that the phosphorescent compound and the host compound were replaced with the compounds shown in Table II below, and the fluorescent compound was set to 0% by mole, the phosphorescent compound was set to 10% by mole, and the host compound was set to 90% by mole.

«Evaluation»

As for the evaluation, the measurement of the absolute quantum yield (PLQE) and the calculation of the overlap integral value (J) were performed in the same manner as in Example 1 described above. The criterion for the relative value of the absolute quantum yield (PLQE) is as follows.

Criterion of luminescent film (6-4): luminescent film (6-1)

Criterion of luminescent films (6-5) to (6-6): luminescent film (6-2)

Criterion of luminescent films (6-7) to (6-8): luminescent film (6-3)

TABLE VI

| Luminescent film No. | Phosphorescent compound | | Host compound | | Fluorescent compound | | J | PLQE (Relative value) | Remarks |
|---|---|---|---|---|---|---|---|---|---|
| | Kind | Concentration (mol %) | Kind | Concentration (mol %) | Kind | Concentration (mol %) | | | |
| 6-1 | Dp-1 | 10 | H-1 | 90 | — | — | — | 1.00 | *1 |
| 6-2 | Dp-5 | 10 | H-1 | 90 | — | — | — | 1.00 | *1 |
| 6-3 | Dp-6 | 10 | H-1 | 90 | — | — | — | 1.00 | *1 |
| 6-4 | Dp-1 | 90 | — | — | F-6 | 10 | $7.2 \times 10^{14}$ | 0.96 | *2 |
| 6-5 | Dp-5 | 90 | — | — | F-5 | 10 | $6.1 \times 10^{14}$ | 1.03 | *2 |
| 6-6 | Dp-5 | 90 | — | — | F-6 | 10 | $7.8 \times 10^{14}$ | 1.08 | *2 |
| 6-7 | Dp-6 | 90 | — | — | F-5 | 10 | $6.1 \times 10^{14}$ | 1.00 | *2 |
| 6-8 | Dp-6 | 90 | — | — | F-6 | 10 | $7.8 \times 10^{14}$ | 1.08 | *2 |

*1: Comparative example
*2: Present invention

As described above, conventionally, the host compound is required as a dispersant for a phosphorescent compound, but in a combination having an overlap integral of $6.0 \times 10^{14}$ or more, Förster transfer works predominantly By making exciton transfer to the singlet excited state of the fluorescence without concentration quenching, it was found that the light emitting property could be maintained And improvement of element lifetime may be expected.

Example 7

«Preparation of Luminescent Films (7-1) to (7-5)»

A quartz substrate of 50 mm×50 mm having a thickness of 0.7 mm was subjected to ultrasonic washing with isopropyl alcohol, followed by drying with desiccated nitrogen gas, and was subjected to UV ozone washing for 5 minutes. Each material indicated in Table VII (a phosphorescent compound, a host compound, and a fluorescent compound) dissolved in isopropyl acetate was applied by a spin coat method, and dried at 120° C. for 30 minutes to form luminescent films (dope films) (7-1) to (7-5) having a thickness of 50 nm. On the other hand, a single film of a fluorescent compound alone corresponding to each luminescent film was prepared. The compounds shown in Table VII were used as a phosphorescent compound to be a concentration of 100% by mole. Thus, each single film having a thickness of 30 nm was produced.

«Evaluation»

As for the evaluation, the measurement of the absolute quantum yield (PLQE) and the calculation of the overlap integral value (J) were performed in the same manner as in Example 1 described above. The criterion for the relative value of the absolute quantum yield (PLQE) is as follows.

Criterion of luminescent films (7-2) to (7-5): luminescent film (7-1)

TABLE VII

| Luminescent film No. | Phosphorescent compound | | Host compound | | Fluorescent compound | | J | PLQE of dope film (Relative value) | PLQE of single film | Remarks |
|---|---|---|---|---|---|---|---|---|---|---|
| | Kind | Concentration (mol %) | Kind | Concentration (mol %) | Kind | Concentration (mol %) | | | | |
| 7-1 | Dp-1 | 10 | H-1 | 90 | — | — | — | 1.00 | — | *1 |
| 7-2 | Dp-1 | 10 | H-1 | 87 | A-22 | 3 | $6.2 \times 10^{14}$ | 0.61 | 0.08 | *1 |
| 7-3 | Dp-1 | 10 | H-1 | 87 | F-7 | 3 | $2.2 \times 10^{14}$ | 0.90 | 0.13 | *2 |
| 7-4 | Dp-1 | 10 | H-1 | 87 | F-2 | 3 | $2.5 \times 10^{14}$ | 1.12 | 0.36 | *2 |
| 7-5 | Dp-1 | 10 | H-1 | 87 | F-1 | 3 | $2.4 \times 10^{14}$ | 1.19 | 0.50 | *2 |

*1: Comparative example
*2: Present invention

In the fluorescent compound A-22 in which PLQE decrease is observed in the single film, the 7E conjugate plane involved in the light emission is largely opened, and even if the overlap integration is sufficiently performed, the exciton is deactivated by Dexter transfer from the triplet excited state of the phosphorescent compound. On the other hand, with respect to the fluorescent compound capable of maintaining PLQE of 10% or more in the single film, by covering the π conjugate plane involved in light emission with a bulky substituent, Dexter transfer was suppressed, and maintaining of PLQE was achieved. This means that even when the element is formed, carriers are hardly loaded on the fluorescent compound, and this contributes to suppression of direct recombination on the fluorescent compound.

Example 8

In Example 8, an example in which a luminescent film is applied to an organic EL element will be described. Note that a light emitting layer (a luminescent film) was formed by an evaporation method.

<Preparation of organic EL elements (8-1) to (8-9)>
(Formation of Anode)

An anode was prepared to a glass substrate (transparent substrate) of 50 mm×50 mm having a thickness of 0.7 mm on which ITO (indium tin oxide) was formed with a thickness of 150 mm After performing pattering, the above transparent substrate provided with the ITO transparent electrode was subjected to ultrasonic washing with isopropyl alcohol, followed by drying with desiccated nitrogen gas, and was subjected to UV ozone washing for 5 minutes. In each of the resistance heating boats for vapor deposition in the vacuum vapor deposition apparatus, the constituent material of each layer was filled in an optimum amount for device fabrication. The resistance heating boat was made of molybdenum or tungsten.

(Formation of Hole Injection Layer)

After reducing the pressure to a vacuum degree of $1 \times 10^4$ Pa, the resistance heating boat containing HI-1 was energized and heated to deposit it on the ITO transparent electrode at a vapor deposition rate of 0.1 nm/sec to result in forming a hole injection layer having a thickness of 10 nm.

(Formation of Hole Transport Layer)

Next, HT-1 was vapor-deposited at a deposition rate of 1.0 Å/sec to form a hole transport layer having a thickness of 30 nm.

(Formation of Light Emitting Layer)

Subsequently, the resistance heating boats each containing "a host compound", "a phosphorescent compound", and "a fluorescent compound" indicated in Table VIII were energized and heated. Co-evaporation was performed on the hole transport layer to make the host compound, the phosphorescent compound and the fluorescent compound each have a volume % shown in Table VIII at a vapor deposition rate of 0.8 Å/sec, 0.2 Å/sec, and 0.002 Å/sec respectively. Thus, a light emitting layer having a thickness of 40 nm was formed.

(Formation of Electron Transport Layer)

Next, a first electron transport layer and a second electron transport layer were formed as an electron transport layer on the light emitting layer. Specifically, HB-1 was vapor-deposited at a deposition rate of 1.0 Å/sec to form a first electron transport layer having a thickness of 30 nm. Further thereon, ET-1 was vapor-deposited at a deposition rate of 1.0 Å/sec to form a second electron transport layer having a thickness of 30 nm.

(Formation of Cathode)

Thereafter, lithium fluoride was evaporated to a layer thickness of 0.5 nm, and then aluminum was evaporated to a thickness of 100 nm to form a cathode.

(Sealing)

To the laminate body formed by the above steps, a sealing substrate was bonded using a commercially available roll laminating apparatus. As a sealing substrate, the following material was prepared. An adhesive layer having a layer thickness of 1.5 μm was provided on a flexible aluminum foil having a thickness of 30 μm (made by Toyo Aluminum K.K.) using a two-liquid reaction type urethane adhesive for dry lamination, then a polyethylene terephthalate (PET) film having a thickness of 12 μm was laminated.

A thermosetting adhesive as a sealing adhesive was uniformly applied with a thickness of 20 μm along the adhesive surface (gloss surface) of the aluminum foil of the sealing substrate using a dispenser. This was dried under a vacuum of 100 Pa or less for 12 hours. Further, the sealing substrate was moved to a nitrogen atmosphere having a dew point temperature of −80° C. or less and an oxygen concentration of 0.8 ppm and dried for 12 hours or more, and the moisture content of the sealing adhesive was adjusted to be 100 ppm or less.

As the thermosetting adhesive, an epoxy adhesive obtained by mixing the following (A) to (C) was used.

(A) Bisphenol A diglycidyl ether (DGEBA)

(B) Dicyandiamide (DICY)

(C) Epoxy adduct type curing accelerator

The sealing substrate was brought into close contact with the above laminate body and tightly sealed under a pressure bonding condition of a pressure roll temperature of 100° C., a pressure of 0.5 MPa, and a machine speed of 0.3 m/min using a pressure roll. As described above, each of the organic EL element (8-1) to (8-9) was manufactured.

«Preparation of Lighting Device (8-1) to (8-9)»

The non-light emitting surface of the organic EL element of the present invention was covered with a glass case, and a 300 μm thick glass substrate was employed as a sealing substrate. An epoxy based light curable type adhesive (LUXTRACK LC0629B produced by Toagosei Co., Ltd.) was employed in the periphery as a sealing material. The resulting one was superimposed on the aforesaid cathode to be brought into close contact with the aforesaid transparent support substrate, and curing and sealing were carried out via exposure of UV radiation onto the glass substrate side, whereby the lighting device having a configuration shown in FIG. 5 and FIG. 6 was formed.

«Evaluation»

The following evaluation was performed on the evaluation lighting devices.

(Measurement of Luminous Efficiency)

The measurement of the luminous efficiency (EQE) was performed at room temperature (25° C.) at a constant current density of 2.5 mA/cm$^2$, and each was measured using a spectroradiometer CS-2000 (manufactured by Konica Minolta Inc.). The emission luminance of the lighting device for evaluation was measured, and the light emission efficiency (external quantum efficiency) at the current value was determined. In Table VIII, the relative values of the luminous efficiency of the lighting devices (8-2) to (8-9) when the luminous efficiency of the illumination device (8-1) is 1.00 is shown in Table VIII.

(Half-Life)

For each evaluation lighting device, the luminance was measured using a spectral radiance meter CS-2000, and the time (LT50) at which the measured luminance was reduced by half was determined as the half-life. The driving conditions were a current value of 15 mA/cm$^2$. For each evaluation lighting device for the present invention (lighting devices (8-2) to (8-5) and (8-7) to (8-9)), comparative lighting devices (8-1) and (8-6) containing no fluorescent compound were produced, and the relative value (half-life: relative value) with the half-life of the comparative lighting device being 1.00 was obtained.

TABLE VIII

| Lighting Device No. | Organic EL Element No. | Phosphorescent compound Kind | Phosphorescent compound Concentration (volume %) | Host compound Kind | Host compound Concentration (volume %) | Fluorescent compound Kind | Fluorescent compound Concentration (volume %) | EQE (Relative value) | LT50 (Relative value) | Remarks |
|---|---|---|---|---|---|---|---|---|---|---|
| 8-1 | 8-1 | Dp-1 | 15 | H-1 | 85 | — | — | 1.00 | 1.00 | *1 |
| 8-2 | 8-2 | Dp-1 | 15 | H-1 | 82 | F-2 | 3 | 1.05 | 2.89 | *2 |
| 8-3 | 8-3 | Dp-1 | 15 | H-1 | 82 | F-5 | 3 | 1.11 | 3.37 | *2 |
| 8-4 | 8-4 | Dp-1 | 15 | H-3 | 75 | F-5 | 10 | 1.07 | 3.75 | *2 |
| 8-5 | 8-5 | Dp-1 | 90 | — | — | F-5 | 10 | 1.08 | 4.01 | *2 |
| 8-6 | 8-6 | Dp-2 | 15 | H-1 | 85 | — | — | 1.00 | 1.00 | *1 |
| 8-7 | 8-7 | Dp-2 | 15 | H-1 | 82 | F-8 | 3 | 1.01 | 1.22 | *2 |
| 8-8 | 8-8 | Dp-2 | 15 | H-1 | 82 | F-5 | 3 | 1.05 | 4.05 | *2 |
| 8-9 | 8-9 | Dp-2 | 15 | H-3 | 82 | F-5 | 3 | 1.08 | 6 22 | *2 |

*1: Comparative example
*2: Present invention

In the present invention in which a luminescent film to which a fluorescent compound was added was used as an element in a light emitting layer, improvement in EQE and improvement in element lifetime were confirmed as compared with the comparative example in which a luminescent film to which a fluorescent compound was not added was used as an element in a light emitting layer. In addition, the improvement of the element lifetime (LT50) was achieved along with the shortening of the emission decay lifetime ($\tau$), and the improvement of the element lifetime was achieved by lowering the lowest triplet excited states of the host compound used. In addition, it was confirmed that the fastness of the fluorescent material itself was improved when the fluorescent compound of F-8 to F-5 was used, and the lifetime was further greatly improved.

Example 9

Example 9 describes a case where a compound having a lower triplet energy level than that of a phosphorescent compound was used for an adjacent layer and a light emitting layer was formed by an evaporation method in manufacturing an organic EL element.

«Preparation of Lighting Device (9-1) to (9-6)»

Lighting device (9-1) to (9-6) for evaluation each were prepared in the same manner as used for the preparation in Example 8 except that the type and volume % of the host compound, the phosphorescent compound and the fluorescent compound were changed as shown in Table IX, and the material HB-1 used for the first electron transport layer (adjacent layer) was changed as indicated in Table IX. Each was changed as shown.

«Evaluation»

Evaluation was performed in the same manner as in Example 1 above. In Table IX, $\Delta T_1$ is as follows.

$\Delta T_1 = (T_1$ level of adjacent material$) - (T_1$ level of phosphorescent compound$)$

TABLE IX

| Lighting Device No. | Organic EL Element No. | Phosphorescent compound Kind | Phosphorescent compound Concentration (volume %) | T1 | Host compound Kind | Host compound Concentration (volume %) | Fluorescent compound Kind | Fluorescent compound Concentration (volume %) | Adjacent layer Kind | $\Delta T_1$ | EQE (Relative value) | LT50 (Relative value) | Remarks |
|---|---|---|---|---|---|---|---|---|---|---|---|---|---|
| 9-1 | 9-1 | Dp-1 | 15 | 2.90 | H-1 | 85 | — | — | HB-1 | +0.38 | 1.00 | 1.00 | Comparative example |
| 9-2 | 9-2 | Dp-1 | 15 | 2.90 | H-1 | 85 | — | — | HB-2 | −0.04 | 0.84 | 0.78 | Comparative example |
| 9-3 | 9-3 | Dp-1 | 15 | 2.90 | H-1 | 85 | — | — | HB-3 | −0.27 | 0.37 | 0.29 | Comparative example |
| 9-4 | 9-4 | Dp-1 | 15 | 2.90 | H-1 | 82 | F-2 | 3 | HB-2 | −0.04 | 1.05 | 1.37 | Present invention |
| 9-5 | 9-5 | Dp-1 | 15 | 2.90 | H-1 | 82 | F-5 | 3 | HB-2 | −0.04 | 1.05 | 1.51 | Present invention |
| 9-6 | 9-6 | Dp-1 | 15 | 2.90 | H-1 | 82 | F-5 | 3 | HB-3 | −0.27 | 1.01 | 1.55 | Present invention |

In the comparative example in which the fluorescent compound is not added to the light emitting layer, the exciton deactivation is caused by Dexter transfer from the triplet energy level of the phosphorescent compound to the triplet energy level of the adjacent layer compound to cause a decrease in EQE. On the other hand, in the present invention in which the fluorescent compound is added to the light emitting layer and the exciton is transferred from the phosphorescent compound to the fluorescent compound in the light emitting layer at a high speed to the triplet energy level of the phosphorescent compound. As a result, the influence of the triplet energy level of the adjacent layer compound is suppressed, and the improvement of EQE and the improvement of the device life (LT50) are confirmed. In addition, the improvement of the device lifetime (LT50) was achieved by lowering the lowest triplet excited states of the adjacent layer compound used, thereby further improving the element lifetime.

Example 10

Example 10 describes a case where a compound having a triplet energy level relatively high than that of a phosphorescent compound is used in an adjacent layer and a light emitting layer is formed by an evaporation method in preparation an organic EL element.
<Preparation of Organic EL Elements and Lighting Devices (10-1) to (10-5)>
Organic EL devices (10-1) to (10-5) were produced in the same manner as used for the preparation in Example 8, except that the types and volume % of the host compound, phosphorescent compound, and fluorescent compound were changed as shown in Table X, and the material HB-1 used for the first electron transport layer (adjacent layer) was changed as shown in Table X. Thereafter, evaluation lighting devices (10-1) to (10-5) were produced using the respective organic EL elements in the same manner as used for the preparation in Example 8.
«Evaluation»
Evaluation was performed in the same manner as in Example 1 above.
In Table X, $\Delta T_1$ is as follows.

$\Delta T_1 = (T_1$ level of adjacent material$) - (T_1$ level of phosphorescent compound$)$ triplet energy level of the adjacent layer compound to cause a decrease in EQE. On the other hand, in the present invention in which the fluorescent compound is added to the light emitting layer and the exciton is transferred to the adjacent layer at a higher speed than the triplet energy level of the phosphorescent compound. As a result, the influence of the triplet energy level of the adjacent layer compound is suppressed by the exciton transfer from the phosphorescent compound to the fluorescent compound in the light emitting layer, and the improvement of EQE and the improvement of the device life (LT50) are confirmed. In addition, the improvement of the element lifetime (LT50) was achieved by lowering the lowest triplet excited states of the adjacent layer compounds used.

Example 11

In Example 11, a light emitting layer was formed by a coating method in manufacturing an organic EL device.
«Preparation of Organic EL Elements (11-1) to (11-7)»
As described in the following, an organic EL element of the bottom emission type was produced by sealing the laminated body of anode/hole injection layer/hole transport layer/light emitting layer/blocking layer/electron transport layer/electron injection layer/cathode.
(Preparation of Substrate)
First, on the entire surface of a polyethylene naphthalate film (hereinafter abbreviated as PEN) (manufactured by Teijin DuPont Films Co. Ltd.) on which the anode is to be formed, an atmospheric pressure plasma discharge treatment using an apparatus having the structure described in JP-A 2004-68143 was carried out to form an inorganic gas barrier layer made of $SiO_x$ having a thickness of 500 nm. In this way, a flexible substrate having gas barrier properties of an oxygen permeability of 0.001 mL/(m²·24 h) or less and a water vapor permeability of 0.001 g/(m²·24 h) or less was prepared.
(Anode)
ITO (indium tin oxide) having a thickness of 120 nm was formed on the above-described substrate by a sputtering method and patterned by a photolithography method. Thus, an anode was formed. The pattern was such that the area of the light emitting region was 5 cm×5 cm.

TABLE X

| Lighting Device No. | Organic EL Element No. | Phosphorescent compound Kind | Concentration (volume %) | T1 | Host compound Kind | Concentration (volume %) | Fluorescent compound Kind | Concentration (volume %) | Adjacent layer Kind | ΔT1 | EQE (Relative value) | LT50 (Relative value) | Remarks |
|---|---|---|---|---|---|---|---|---|---|---|---|---|---|
| 10-1 | 10-1 | Dp-2 | 15 | 2.79 | H-1 | 85 | — | — | HB-1 | +0.49 | 1.00 | 1.00 | Comparative example |
| 10-2 | 10-2 | Dp-2 | 15 | 2.79 | H-1 | 85 | — | — | HB-2 | +0.07 | 0.91 | 0.89 | Comparative example |
| 10-3 | 10-3 | Dp-2 | 15 | 2.79 | H-1 | 85 | — | — | HB-3 | −0.16 | 0.83 | 0.78 | Comparative example |
| 10-4 | 10-4 | Dp-2 | 15 | 2.79 | H-1 | 82 | F-5 | 3 | HB-2 | +0.07 | 1.12 | 1.67 | Present invention |
| 10-5 | 10-5 | Dp-2 | 15 | 2.79 | H-1 | 82 | F-5 | 3 | HB-3 | −0.16 | 1.11 | 1.88 | Present invention |

In the comparative example in which the fluorescent compound is not added to the light emitting layer, the exciton deactivation is caused by Dexter transfer from the triplet energy level of the phosphorescent compound to the (Hole Injection Layer)
The substrate on which the anode was formed was subjected to ultrasonic washing with isopropyl alcohol, followed by drying with desiccated nitrogen gas, and was subjected to UV ozone washing for 5 minutes. Then, a dispersion liquid of poly (3,4-ethylenedioxythiophene)/polystyrene sulfonate (PEDOT/PSS) was prepared in the same manner as in Example 16 of Japanese Patent No. 4,509,787. A 2 mass % solution prepared by diluting the above-described dispersion liquid with isopropyl alcohol was applied by a die coating method and followed by air dried to form a hole injection layer having a thickness of 40 nm.

(Hole Transport Layer)

Subsequently, the substrate on which the hole injection layer was formed was transferred under a nitrogen atmosphere using nitrogen gas (grade G1), and the coating solution for forming a hole transport layer having the following composition was coated by a spin coating method, and then dried at 130° C. for 30 minutes. Thus, a hole transport layer having a thickness of 30 nm was formed.

<Coating Solution for Forming Hole Transport Layer>

| | |
|---|---|
| Hole transport material HT-2 (weight average molecular weight Mw = 80000): | 10 parts by mass |
| Chlorobenzene: | 3000 parts by mass |

(Light Emitting Layer)

Next, the compounds shown in Table XI were used as the host compound, the phosphorescent compound and the fluorescent compound, and were dissolved in isopropyl acetate so as to have the mol % shown in Table XI, respectively, for forming the light emitting layer. A coating solution was formed, and the coating solution was applied to the substrate on which the hole transport layer was formed by spin coating, and dried at 120° C. for 30 minutes to form a 50 nm-thick light emitting layer having a thickness of 50 nm.

(Formation of Blocking Layer)

Subsequently, the substrate on which the light emitting layer was formed was coated by a spin coating method using a coating solution for forming a blocking layer having the following composition, followed by dried, at 80° C. for 30 minutes. Thus, a blocking layer (hole blocking layer) having a thickness of 10 nm was formed.

<Coating Solution for Forming Blocking Layer>

| | |
|---|---|
| HS-1: | 2 parts by mass |
| Isopropyl alcohol (IPA): | 1500 mass parts |
| 1H, 1H, 5H-octafluoropentanol (OFAO): | 500 mass parts |

(Formation of Electron Transport Layer)

Subsequently, the substrate on which the blocking layer was formed was coated by a die coating method at a coating rate of 5 m/min using a coating solution for forming an electron transport layer having the following composition, followed by air dried, and then kept at 80° C. for 30 minutes. Thus, an electron transport layer having a thickness of 30 nm was formed.

<Coating Solution for Forming Electron Transport Layer>

| | |
|---|---|
| ET-1: | 6 parts by mass |
| 2,2,3,3-Tetrafluoro-1-propanol : | 2000 parts by mass |

(Formation of Electron Injection Layer and Cathode)

Subsequently, the substrate was attached to a vacuum vapor deposition apparatus without exposure to the atmosphere. Also, molybdenum resistance heating boats each containing sodium fluoride and potassium fluoride were attached to the vacuum evaporation apparatus, and the vacuum chamber was reduced to $4 \times 10^{-5}$ Pa. Thereafter, the boat was energized and heated, and sodium fluoride was vapor-deposited on the electron transport layer at 0.02 nm/sec. Thus, a thin film having a thickness of 1 nm was formed. Similarly, potassium fluoride was vapor-deposited on the sodium fluoride thin film at 0.02 nm/sec. Thus, an electron injection layer with a layer thickness of 1.5 nm was formed. Subsequently, aluminum was vapor-deposited to form a cathode having a thickness of 100 nm.

(Sealing)

The laminated body formed by the above steps was closely adhered and arranged with a sealing substrate in the same manner as in Example 8, and was tightly sealed using a pressure roll. As described above, each organic EL element was manufactured. Thereafter, lighting devices (11-1) to (11-7) for evaluation were produced in the same manner as in Example 8 using each organic EL element.

«Evaluation»

Evaluation was performed in the same manner as in Example 8.

TABLE XI

| Lighting Device No. | Organic EL Element No. | Phosphorescent compound Kind | Phosphorescent compound Concentration (volume %) | Host compound Kind | Host compound Concentration (volume %) | Fluorescent compound Kind | Fluorescent compound Concentration (volume %) | EQE (Relative value) | LT50 (Relative value) | Remarks |
|---|---|---|---|---|---|---|---|---|---|---|
| 11-1 | 11-1 | Dp-2 | 10 | H-1 | 90 | — | — | 1.00 | 1.00 | *1 |
| 11-2 | 11-2 | Dp-2 | 10 | H-1 | 87 | F-1 | 3 | 1.02 | 2.35 | *2 |
| 11-3 | 11-3 | Dp-2 | 10 | H-1 | 87 | F-6 | 3 | 1.05 | 3.65 | *2 |
| 11-4 | 11-4 | Dp-5 | 10 | H-1 | 90 | — | — | 1.00 | 1.00 | *1 |
| 11-5 | 11-5 | Dp-5 | 10 | H-1 | 87 | F-1 | 3 | 1.04 | 1.65 | *2 |
| 11-6 | 11-6 | Dp-5 | 10 | H-1 | 87 | F-6 | 3 | 1.07 | 2.11 | *2 |
| 11-7 | 11-7 | Dp-5 | 10 | H-4 | 80 | F-6 | 10 | 1.05 | 2.95 | *2 |

*1: Comparative example
*2: Present invention

In the present invention in which a luminescent film to which a fluorescent compound was added was used as an element in a light emitting layer, improvement in EQE and improvement in element lifetime (LT50) were confirmed as compared with the comparative example in which a luminescent film to which a fluorescent compound was not added was used as an element in a light emitting layer. This is the same as in the case of luminescent film formation with an evaporation method. In addition, the improvement of the element lifetime (LT50) was achieved along with the shortening of the emission decay lifetime (t), and the improvement of the element lifetime (LT50) was achieved by lowering the lowest triplet excited states of the host compound used.

Example 12

«Preparation of Lighting Devices (12-1) to (12-24)»(Low barrier)

Each organic EL element was produced in the same manner as used for the preparation of organic EL elements (8-1) to (8-4) in Example (8) and organic EL elements (11-1) to (11-3) in Example (11), except that the functions of the sealing substrate (gas barrier layer) used for sealing the laminated body stacked to the cathode (thickness of the gas barrier layer, WVTR, OTR) were changed as shown in Table XII below. The non-light emitting surface of the organic EL device thus produced was covered with a glass case under an atmosphere of high purity nitrogen gas having a purity of 99.999% or more, and evaluation lighting devices (12-1) to (12-24) having the configurations shown in FIGS. 5 and 6 were produced.

«Evaluation»

The following evaluations were carried out to the above evaluation lighting devices.

(Evaluation of Dark Spot (DS))

Each lighting device was stored for 500 hours in an environment of 85° C. and 85% RH. Thereafter, a 1 mA/cm$^2$ current was applied to the respective lighting devices to emit light. Next, a part of the light emitting part of the lighting device was enlarged and photographed by using an optical microscope of 100 times (MS-804, a lens MP-ZE25-200, manufactured by MORITEX Corporation). Next, the photographed image was cut out in 2 mm squares, and the presence or absence of dark spot generation was observed for each image. The ratio of the area of dark spots generated to the area of light emission was determined from the observation results, and the dark spot resistance was evaluated according to the following criteria.

5: There is no occurrence of dark spots.

4: The area of dark spot generation is 0.1% or more and less than 1.0%.

3: The area of dark spot generation is 1.0% or more and less than 3.0%.

2: The area of dark spot generation is 3.0% or more and less than 6.0%.

1: The area of dark spot generation is 6.0% or more.

(Evaluation of Continuous Startup Stability (Half-Life and Luminous Efficiency)

The luminous efficiency and half-life of each lighting device were evaluated in the same manner as in Example 8 under an environment of 85° C. and 85% RH. In addition, the overlap integral value (J) of the obtained light emitting layer of each organic EL element was calculated in the same manner as in Example 1.

TABLE XII

| Lighting Device No. | Reference Organic EL Element No. | Thickness of gas barier layer (nm) | WVTR [g/(m$^2$·day)] | OTR [mL/(m$^2$·day·atm)] | J | DS (Dark Spot) evaluation | EQE (Relative value) | LT50 (Relative value) | Remarks |
|---|---|---|---|---|---|---|---|---|---|
| 12-1 | 8-1 | 300 × 10$^2$ | 1.00 × 10$^{-5}$ | 1.2 × 10$^{-5}$ | — | 5 | 1.00 | 1.00 | Comparative example |
| 12-2 | 8-2 | 300 × 10$^2$ | 1.00 × 10$^{-5}$ | 1.2 × 10$^{-5}$ | 2.5 × 10$^{14}$ | 5 | 1.05 | 2.89 | Present invention |
| 12-3 | 8-3 | 300 × 10$^2$ | 1.00 × 10$^{-5}$ | 1.2 × 10$^{-5}$ | 6.1 × 10$^{14}$ | 5 | 1.11 | 3.37 | Present invention |
| 12-4 | 8-4 | 300 × 10$^2$ | 1.00 × 10$^{-5}$ | 1.2 × 10$^{-5}$ | 6.1 × 10$^{14}$ | 5 | 1.07 | 3.75 | Present invention |
| 12-5 | 11-1 | 300 × 10$^2$ | 1.00 × 10$^{-5}$ | 1.2 × 10$^{-5}$ | — | 5 | 1.00 | 1.00 | Comparative example |
| 12-6 | 11-3 | 300 × 10$^2$ | 1.00 × 10$^{-5}$ | 1.2 × 10$^{-5}$ | 9.1 × 10$^{14}$ | 5 | 1.05 | 3.65 | Present invention |
| 12-7 | 8-1 | 500 | 1.00 × 10$^{-3}$ | 1.2 × 10$^{-3}$ | — | 2 | 1.00 | 0.65 | Comparative example |
| 12-8 | 8-2 | 500 | 1.00 × 10$^{-3}$ | 1.2 × 10$^{-3}$ | 2.5 × 10$^{14}$ | 5 | 1.05 | 2.85 | Present invention |
| 12-9 | 8-3 | 500 | 1.00 × 10$^{-3}$ | 1.2 × 10$^{-3}$ | 6.1 × 10$^{14}$ | 5 | 1.10 | 3.38 | Present invention |
| 12-10 | 8-4 | 500 | 1.00 × 10$^{-3}$ | 1.2 × 10$^{-3}$ | 6.1 × 10$^{14}$ | 5 | 1.06 | 3.77 | Present invention |
| 12-11 | 11-1 | 500 | 1.00 × 10$^{-3}$ | 1.2 × 10$^{-3}$ | — | 2 | 1.00 | 0.58 | Comparative example |
| 12-12 | 11-3 | 500 | 1.00 × 10$^{-3}$ | 1.2 × 10$^{-3}$ | 9.1 × 10$^{14}$ | 5 | 1.05 | 3.55 | Present invention |
| 12-13 | 8-1 | 200 | 1.00 × 10$^{-1}$ | 1.2 × 10$^{-1}$ | — | 1 | 0.78 | 0.24 | Comparative example |
| 12-14 | 8-2 | 200 | 1.00 × 10$^{-1}$ | 1.2 × 10$^{-1}$ | 2.5 × 10$^{14}$ | 4 | 1.02 | 2.32 | Present invention |
| 12-15 | 8-3 | 200 | 1.00 × 10$^{-1}$ | 1.2 × 10$^{-1}$ | 6.1 × 10$^{14}$ | 4 | 1.05 | 3.15 | Present invention |
| 12-16 | 8-4 | 200 | 1.00 × 10$^{-1}$ | 1.2 × 10$^{-1}$ | 6.1 × 10$^{14}$ | 5 | 1.03 | 3.22 | Present invention |
| 12-17 | 11-1 | 200 | 1.00 × 10$^{-1}$ | 1.2 × 10$^{-1}$ | — | 1 | 0.69 | 0.26 | Comparative example |
| 12-18 | 11-3 | 200 | 1.00 × 10$^{-1}$ | 1.2 × 10$^{-1}$ | 9.1 × 10$^{14}$ | 4 | 1.01 | 2.99 | Present invention |
| 12-19 | 8-1 | 50 | 1.00 | 1.2 | — | 1 | 0.41 | 0.11 | Comparative example |
| 12-20 | 8-2 | 50 | 1.00 | 1.2 | 2.5 × 10$^{14}$ | 3 | 1.01 | 1.35 | Present invention |
| 12-21 | 8-3 | 50 | 1.00 | 1.2 | 6.1 × 10$^{14}$ | 3 | 1.02 | 1.21 | Present invention |
| 12-22 | 8-4 | 50 | 1.00 | 1.2 | 6.1 × 10$^{14}$ | 4 | 1.03 | 1.33 | Present invention |
| 12-23 | 11-1 | 50 | 1.00 | 1.2 | — | 1 | 0.38 | 0.14 | Comparative example |
| 12-24 | 11-3 | 50 | 1.00 | 1.2 | 9.1 × 10$^{14}$ | 4 | 1.00 | 1.14 | Present invention |

As described above, when sealing with a gas barrier layer having a low gas barrier property, in the comparative example in which a fluorescent compound is not added, the EQE and the lifetime are greatly lowered by being affected by the atmosphere, whereas in the present invention in which a fluorescent compound is added, it becomes difficult to be affected by the atmosphere with the shortening of the emission decay lifetime (t), and the element performance can be maintained even when sealing with a gas barrier layer having a low gas barrier property.

INDUSTRIAL APPLICABILITY

The present invention can be applied to a luminescent film having excellent luminous efficiency, chromaticity, and element life, an organic electroluminescence element, and a method for manufacturing an organic electroluminescence element.

DESCRIPTION OF SYMBOLS $S_0$: Ground state
$S_1$: Singlet state
$T_1$: Lowest triplet excited state
a: Förster-type energy transfer
b: Dexter-type energy transfer
c: Radiationless deactivation
1: Display
3: Pixel
5: Scanning line
6: Data line
101: Organic EL element
102: Glass cover
105: Cathode
106: Organic EL layer (Light emitting unit)
107: Glass substrate having a transparent electrode
108: Nitrogen gas
109: Water catching agent
A: Display section
B: Control section

What is claimed is:

1. A luminescent film containing at least a phosphorescent compound and a fluorescent compound, wherein an overlap integral value of an emission spectrum of the phosphorescent compound and an absorption spectrum of the fluorescent compound satisfies the following Expression (1); in the emission spectrum of the luminescent film, light emission from the fluorescent compound accounts for 90% or more; and an absolute quantum yield (PLQE) of the luminescent film satisfies the following Expression (2), $J \geq 1.5 \times 10^{14}$   Expression (1):

in expression (1), J represents an overlap integral value of the emission spectrum of the phosphorescent complex and the absorption spectrum of the fluorescent compound; and PLQE (of a film containing a phosphorescent compound and a host compound)×0.9≤PLQE (of a film containing a phosphorescent compound and a fluorescent compound)   Expression (2):

in Expression (2), a lowest triplet excited state of the host compound is higher than a lowest triplet excited state of the phosphorescent compound, and does not inhibit the luminescence of the phosphorescent compound.

2. The luminescent film described in claim 1, wherein the overlap integral value of an emission spectrum of the phosphorescent compound and an absorption spectrum of the fluorescent compound satisfies the following Expression (3), $J \geq 6.0 \times 10^{14}$.   Expression (3):

3. The luminescent film described in claim 1, wherein the host compound has the lowest triplet excited state existing at a higher energy level than the lowest triplet excited state of the phosphorescent luminescent compound.

4. The luminescent film described in claim 1, wherein the host compound has the lowest triplet excited state existing at a lower energy level than the lowest triplet excited state of the phosphorescent luminescent compound.

5. The luminescent film described in claim 1 consisting of the phosphorescent compound and the fluorescent compound.

6. The luminescent film described in claim 1, wherein the fluorescent compound has an absolute quantum yield (PLQE) of 10% or more in a film consisted of the fluorescent compound.

7. The luminescent film described in claim 1, wherein the fluorescent compound is a compound having a structure represented by the following Formula (1), $X—(Y)_n$   Formula (1)

wherein X represents a n-conjugated condensed ring of 14π electron system or more; Y represents a deuterium atom, a halogen atom, a cyano group, a nitro group, a hydroxy group, a mercapto group, an alkyl group, cycloalkyl group, an alkenyl group, an alkynyl group, a heterocyclic group, an alkoxy group, a cycloalkoxy group, an aryloxy group, an alkylthio group, a cycloalkylthio group, an arylthio group, an alkoxycarbonyl group, an aryloxycarbonyl group, a sulfamoyl group, an acyl group, an acyloxy group, an amide group, a carbamoyl group, a ureido group, a sulfinyl group, an alkylsulfonyl group, an arylsulfonyl group, a heteroarylsulfonyl group, an amino group, a fluorinated hydrocarbon group, a triarylsilyl group, a diarylalkylsilyl group, an aryldialkylsilyl group, a trialkylsilyl group, a phosphate group, a phosphite group, a phosphono group, a phenyl group, provided that these group may further have a substituent; or a group having the structure represented by the following Formula (2) which may further have a substituent; at least one of Y is a group having a structure represented by the following Formula (2), when there are a plurality of Y, they may be different from each other; and n is an integer from 1 to the maximum number that can be substituted by X,

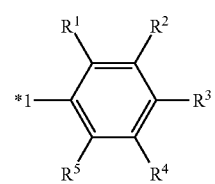

Formula (2)

wherein $R^1$ to $R^5$ each independently represent a hydrogen atom, a deuterium atom, a halogen atom, a cyano group, a nitro group, a hydroxy group, a mercapto group, an alkyl group, a cycloalkyl group, an alkenyl group, an alkynyl group, a heterocyclic group, an alkoxy group, a cycloalkoxy group, an aryloxy group, an alkylthio group, a cycloalkylthio group, an arylthio group, an alkoxycarbonyl group, an aryloxycarbonyl group, a sulfamoyl group, an acyl group, an acyloxy group, an amide group, a carbamoyl group, a ureido group, a sulfinyl group, an alkylsulfonyl group, an arylsulfonyl group, a heteroarylsulfonyl group, an amino group, a fluorinated hydrocarbon group, a triarylsilyl group, a diarylalkylsilyl group, an aryldialkylsilyl group, trialkylsilyl group, a phosphate group, a phosphite group, or a phosphono group, provided that these groups may further have a substituent, at least one of $R^1$ and $R^5$ is a group having a structure represented by the following Formula (3) or (4); and *1 represents a binding site to X,

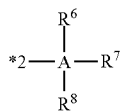

Formula (3)

wherein A represents a carbon atom or a silicon atom, $R^6$ to $R^8$ each independently represent the same group as $R^1$ to $R^5$ in Formula (2), provided that at least one of $R^6$ to $R^8$ is an alkyl group having 1 or more carbon atoms; and *2 represents a bonding site with an adjacent atom,

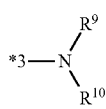

Formula (4)

wherein $R^9$ and $R^{10}$ each independently represent the same group as $R^1$ to $R^5$ in Formula (2), provided that at least one of $R^1$ to $R^5$ is an alkyl group having 1 or more carbon atoms; *3 represents a bonding site with an adjacent atom; in R1 to R10 in Formulas (2) to (4), adjacent groups may be bonded to each other to form an aliphatic ring.

8. The luminescent film described in claim 1, wherein the phosphorescent compound is a compound having a structure represented by the following Formula (5),

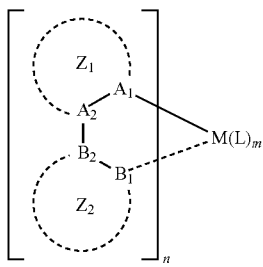

Formula (5)

wherein M represents iridium (Ir) or platinum (Pt); $A_1$, $A_2$, $B_1$ and $B_2$ each independently represent a carbon atom or a nitrogen atom; a ring $Z_1$ represents a 6-membered aromatic hydrocarbon ring, or a 5- or 6-membered aromatic heterocyclic ring formed with $A_1$ and $A_2$, or an aromatic condensed ring containing at least one of the aforesaid rings; a ring $Z_2$ represents a 5- or 6-membered aromatic heterocyclic ring formed with $B_1$ and B2, or an aromatic condensed ring containing at least one of the aforesaid rings; the carbon atoms of the ring $Z_1$ and the ring $Z_2$ may be carbene carbon atoms; among a bond between $A_1$ and M, and a bond between $B_1$ and M, one is a coordinate bond and the other is a covalent bond; the ring $Z_1$ and the ring $Z_2$ each independently may have a substituent; the substituent of the ring $Z_1$ and the substituent of the ring $Z_{12}$ may be bonded to form a condensed ring structure, and ligands represented by the ring $Z_1$ and the ring $Z_2$ may be linked to each other; L represents a monoanionic bidentate ligand coordinated to M, and L may have a substituent; m represents an integer of 0 to 2, n represents an integer of 1 to 3, when M represents iridium (Ir), m+n is 3, and when m represents platinum (Pt), m+n is 2, when m or n is 2 or more, the ligands represented by the ring $Z_1$ and the ring $Z_2$, or L may be the same or different; and the ligands represented by the ring $Z_1$ and the ring $Z_2$ may be linked to L.

9. The luminescent film described in claim 1, wherein the phosphorescent compound is a compound having a structure represented by the following Formula (6),

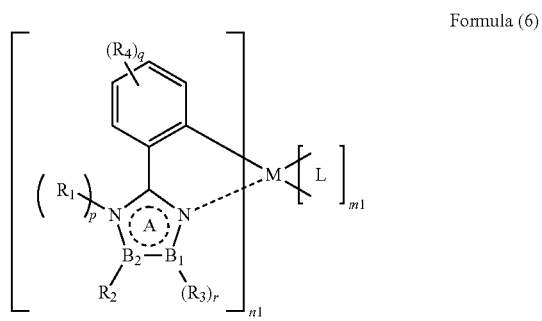

Formula (6)

wherein a ring A represents a triazole ring; $B_1$ and $B_2$ each represent a carbon atom or a nitrogen atom; $R_1$ represents a substituent, and p represents an integer of 0 or 1; $R_2$ represents a substituent; $R_3$ represents a hydrogen atom or a substituent, and r represents an integer of 0 or 1; $R_4$ represents a substituent, and q represents an integer of 1 to 4; M represents iridium (Ir) or platinum (Pt); L represents any ligand capable of coordinating with M; n1 represents an integer of 1 to 3; and ml represents an integer of 0 to 2.

10. An organic electroluminescent element having a light emitting layer made of the luminescent film described in claim 1.

11. The organic electroluminescent element described in claim 10, wherein a lowest triplet energy of a material used in a layer adjacent to the light emitting layer is lower than the lowest triplet excited state of the phosphorescent compound contained in the light emitting layer.

12. The organic electroluminescent element described in claim 10, sealed with a gas barrier layer having a water vapor permeability in the range of 0.001 to 1 g/(m²·day) determined by a method based on JIS K 7129-1992 and an oxygen permeability in the range of 0.001 to 1 mL/(m²·day·atm) determined by a method based on JIS K 7126-1987.

13. A method of manufacturing an organic electroluminescence element described claim 10, wherein the luminescent film is formed with a dry process.

14. A method of manufacturing an organic electroluminescence element described in claim 10, wherein the luminescent film is formed with a wet process.

* * * * *